United States Patent
Stoessel

(10) Patent No.: US 12,178,124 B2
(45) Date of Patent: Dec. 24, 2024

(54) COMPOUNDS THAT CAN BE USED IN AN ORGANIC ELECTRONIC DEVICE AS ACTIVE COMPOUNDS

(71) Applicant: Merck Patent GmbH, Darmstadt (DE)

(72) Inventor: Philipp Stoessel, Frankfurt am Main (DE)

(73) Assignee: Merck KGAA, Darmstadt (DE)

( * ) Notice: Subject to any disclaimer, the term of this patent is extended or adjusted under 35 U.S.C. 154(b) by 775 days.

(21) Appl. No.: 17/281,166

(22) PCT Filed: Sep. 24, 2019

(86) PCT No.: PCT/EP2019/075593
§ 371 (c)(1),
(2) Date: Mar. 29, 2021

(87) PCT Pub. No.: WO2020/064666
PCT Pub. Date: Apr. 2, 2020

(65) Prior Publication Data
US 2021/0384443 A1    Dec. 9, 2021

(30) Foreign Application Priority Data

Sep. 27, 2018  (EP) .................................... 18197197

(51) Int. Cl.
| H10K 85/60 | (2023.01) |
| H10K 50/11 | (2023.01) |
| H10K 50/15 | (2023.01) |
| H10K 101/10 | (2023.01) |

(52) U.S. Cl.
CPC ....... *H10K 85/6572* (2023.02); *H10K 85/624* (2023.02); *H10K 85/626* (2023.02); *H10K 85/633* (2023.02); *H10K 85/636* (2023.02); *H10K 85/654* (2023.02); *H10K 85/6574* (2023.02); *H10K 85/6576* (2023.02); *H10K 50/11* (2023.02); *H10K 50/15* (2023.02); *H10K 2101/10* (2023.02)

(58) Field of Classification Search
CPC ............ H10K 85/56572; C07D 221/02; C07D 221/18; C07D 221/22
See application file for complete search history.

(56) References Cited

U.S. PATENT DOCUMENTS

| 4,539,507 A | 9/1985 | Vanslyke et al. |
| 5,151,629 A | 9/1992 | Vanslyke |
| 7,875,408 B2 * | 1/2011 | Hoffnagle ............. G03F 7/0382 430/905 |
| 11,322,696 B2 * | 5/2022 | Stoessel ............... H10K 85/342 |
| 11,711,976 B2 * | 7/2023 | Stoessel ............... H10K 85/654 |
| 2016/0226003 A1 | 8/2016 | Stoessel et al. |
| 2016/0365520 A1 | 12/2016 | Stoessel et al. |

FOREIGN PATENT DOCUMENTS

| EP | 0676461 A2 | 10/1995 |
| JP | 2016-533386 A | 10/2016 |
| JP | 2017-503856 A | 2/2017 |
| JP | 2018-510903 A | 4/2018 |
| WO | 98/27136 A1 | 6/1998 |
| WO | 2014/094960 A1 | 6/2014 |
| WO | 2014/094961 A1 | 6/2014 |
| WO | 2015/036078 A1 | 3/2015 |
| WO | 2015/104045 A1 | 7/2015 |
| WO | 2015/117718 A1 | 8/2015 |
| WO | 2016/124304 A1 | 8/2016 |
| WO | 2018/041769 A1 | 3/2018 |
| WO | 2018/054798 A1 | 3/2018 |
| WO | 2018/069197 A1 | 4/2018 |
| WO | 2018/069273 A1 | 4/2018 |
| WO | 2018/087346 A1 | 5/2018 |

OTHER PUBLICATIONS

International Preliminary Report on Patentability received for PCT Patent Application No. PCT/EP2019/075593, mailed on Apr. 8, 2021, 13 pages. (7 pages of English Translation and 6 pages of Original Document).

International Search Report and Written Opinion received for PCT Patent Application No. PCT/EP2019/075593, mailed on Nov. 26, 2019, 16 pages. (7 pages of English Translation and 9 pages of Original Document).

Li G et al. "Synthesis. structural characterization. and skeletal rearrangement of dibenzo tricyclo [3.3.0.0,]-1,2,5,6 tetrasubstituted octanes" Tetrahedron Letters, vol. 45, 2004, pp. 8399-8402.

* cited by examiner

*Primary Examiner* — Amanda C. Walke
(74) *Attorney, Agent, or Firm* — David K. Benson

(57) ABSTRACT

The invention relates to compounds that can be used in an organic electronic device as an active compound, in particular for use in electronic devices. The invention further relates to a method for producing the compounds according to the invention, and to electronic devices comprising same.

13 Claims, No Drawings

COMPOUNDS THAT CAN BE USED IN AN ORGANIC ELECTRONIC DEVICE AS ACTIVE COMPOUNDS

CROSS-REFERENCE TO RELATED APPLICATIONS

This application is a national stage application (under 35 U.S.C. § 371) of PCT/EP2019/075593, filed Sep. 24, 2019, which claims benefit of European Application No. 18197197.9 filed Sep. 27, 2018, both of which are incorporated herein by reference in their entirety.

The present invention relates to compounds, especially for use in electronic devices. The invention further relates to a process for preparing the compounds of the invention and to electronic devices comprising these compounds.

The structure of organic electroluminescent devices (OLEDs) in which organic semiconductors are used as functional materials is described, for example, in U.S. Pat. Nos. 4,539,507, 5,151,629, EP 0676461 and WO 98/27136. Emitting materials used are frequently organometallic complexes which exhibit phosphorescence. For quantum-mechanical reasons, up to four times the energy efficiency and power efficiency is possible using organometallic compounds versus phosphorescent emitters. In general terms, there is still a need for improvement in OLEDs, especially also in OLEDs which exhibit phosphorescence, for example with regard to efficiency, operating voltage and lifetime. Also known are organic electroluminescent devices comprising fluorescent emitters or emitters that exhibit TADF (thermally activated delayed fluorescence).

The properties of organic electroluminescent devices are not only determined by the emitters used. Also of particular significance here are especially the other materials used, such as host/matrix materials, hole blocker materials, electron transport materials, hole transport materials and electron or exciton blocker materials. Improvements to these materials can lead to distinct improvements to electroluminescent devices.

According to the prior art, compounds having bi- or tricyclic ring systems are used especially for preparation of metal complexes that show phosphorescence. These compounds especially serve as ligand in the corresponding complexes. This prior art especially includes documents WO 2014/094960 A1, WO 2014/094961 A1, WO 2015/104045 A1, WO 2015/117718 A1 and WO 2016/124304. Matrix materials, electron transport materials, hole transport materials, fluorescent emitters or emitters that exhibit TADF (thermally activated delayed fluorescence) are not set out in these documents.

Moreover, document WO 2015/036078 discloses heterocyclic compounds that can be used inter alia as matrix materials, electron transport materials or hole transport materials. Most of these compounds comprise a bicyclic ring system fused to a pyridine or pyridazine structure, to which an aromatic or heteroaromatic ring system is fused in turn.

In general terms, in the case of these materials, for example for use as matrix materials, hole conductor materials or electron transport materials, there is still a need for improvement, particularly in relation to the lifetime, but also in relation to the efficiency and operating voltage of the device. Moreover, the compounds should have high color purity.

It is a further object of the present invention to provide compounds which are suitable for use in an organic electronic device, especially in an organic electroluminescent device, as fluorescent emitters or emitters that exhibit TADF (thermally activated delayed fluorescence), and which lead to good device properties when used in this device, and to provide the corresponding electronic device.

It is therefore an object of the present invention to provide compounds which are suitable for use in an organic electronic device, especially in an organic electroluminescent device, and which lead to good device properties when used in this device, and to provide the corresponding electronic device.

It is a particular object of the present invention to provide compounds which lead to a high lifetime, good efficiency and low operating voltage. Particularly the properties of the matrix materials, the hole conductor materials or the electron transport materials too have an essential influence on the lifetime and efficiency of the organic electroluminescent device.

A further problem addressed by the present invention can be considered that of providing compounds suitable for use in a phosphorescent or fluorescent OLED, especially as a matrix material. More particularly, a problem addressed by the present invention is that of providing matrix materials suitable for red-, yellow- and green-phosphorescing OLEDs.

In addition, the compounds, especially when they are used as matrix materials, as hole conductor materials or as electron transport materials in organic electroluminescent devices, should lead to devices having excellent color purity.

Moreover, the compounds should be processable in a very simple manner, and especially exhibit good solubility and film formation. For example, the compounds should exhibit elevated oxidation stability and an improved glass transition temperature.

A further object can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, particular compounds that are described in detail hereinafter solve these problems and eliminate the disadvantage from the prior art. The use of the compounds leads to very good properties of organic electronic devices, especially of organic electroluminescent devices, especially with regard to lifetime, efficiency and operating voltage. The present invention therefore provides electronic devices, especially organic electroluminescent devices, comprising compounds of this kind, and the corresponding preferred embodiments.

The present invention therefore provides a compound usable as active compound an organic electronic device, characterized in that the compound has at least one aromatic or heteroaromatic ring system which has 5 to 60 carbon atoms and is fused to an aliphatic polycyclic ring system having at least 3 rings.

It may preferably be the case that the largest cycle of the aliphatic polycyclic ring system having at least 3 rings has not more than 14, preferably not more than 12, more preferably not more than 10 and especially preferably not more than 7 atoms in the corresponding ring.

It may further be the case that the ring via which the aliphatic polycyclic ring system having at least 3 rings is fused to the aromatic or heteroaromatic ring system having 5 to 60 carbon atoms comprises six ring atoms and at least two nonadjacent nitrogen atoms.

It may further be the case that the ring via which the aliphatic polycyclic ring system having at least 3 rings is fused to the aromatic or heteroaromatic ring system having 5 to 60 carbon atoms comprises six ring atoms and no nitrogen atom.

It may further be the case that the ring via which the aliphatic polycyclic ring system having at least 3 rings is fused to the aromatic or heteroaromatic ring system having 5 to 60 carbon atoms comprises six ring atoms and at least one nitrogen atom and no further ring system is fused to that ring.

Active compounds are generally the organic or inorganic materials introduced between anode and cathode, for example in an organic electronic device, especially in an organic electroluminescent device, for example charge injection, charge transport or charge blocker materials, but especially emission materials and matrix materials.

The compound usable as active compound an organic electronic device may preferably be selected from the group consisting of fluorescent emitters, phosphorescent emitters, emitters that exhibit TADF (thermally activated delayed fluorescence), host materials, electron transport materials, exciton blocker materials, electron injection materials, hole conductor materials, hole injection materials, n-dopants, p-dopants, wide band gap materials, electron blocker materials and/or hole blocker materials. Preference is given here to fluorescent emitters, emitters that exhibit TADF (thermally activated delayed fluorescence), host materials, electron transport materials, exciton blocker materials, electron injection materials, hole conductor materials, hole injection materials, n-dopants, p-dopants, wide bandgap materials, electron blocker materials and/or hole blocker materials.

In a preferred configuration, the compounds of the invention may comprise at least one structure of the formulae (I) to (XVIII)

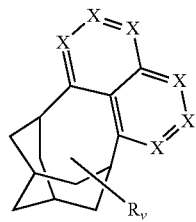

Formula (I)

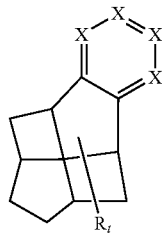

Formula (II)

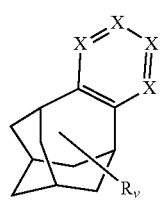

Formula (III)

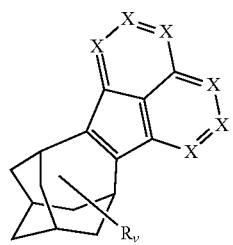

Formula (IV)

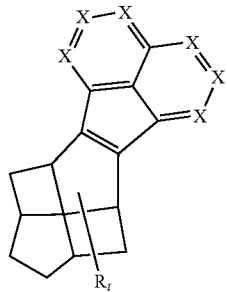

Formula (V)

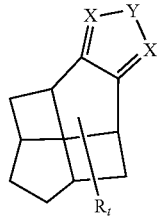

Formula (VI)

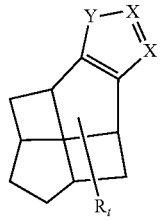

Formula (VII)

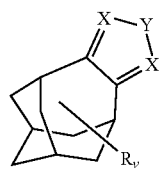

Formula (VIII)

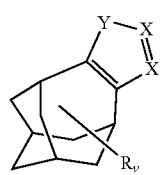

Formula (IX)

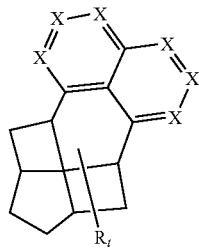

Formula (X)

-continued

Formula (XI)
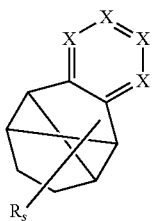

Formula (XII)
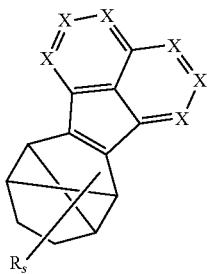

Formula (XIII)
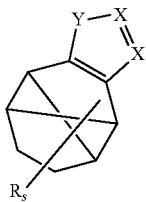

Formula (XIV)
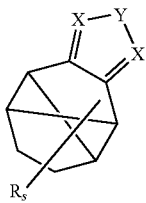

Formula (XV)
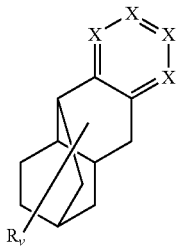

Formula (XVI)
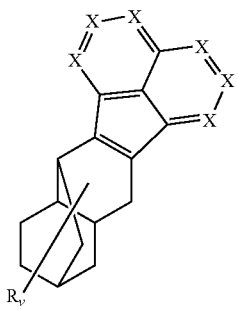

-continued

Formula (XVII)
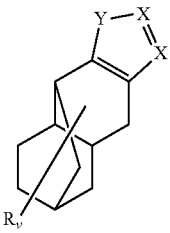

Formula (XVIII)
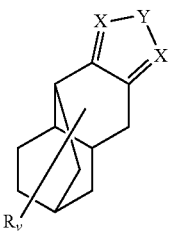

where the symbols used are as follows:

Y is the same or different at each instance and is O, S, $C(R)_2$, CArR, $C(Ar)_2$, $Si(Ar)_2$, SiArR or $Si(R)_2$, NR or NAr, preferably O, S, NAr, more preferably NAr;

X is the same or different at each instance and is N or CR, preferably CR;

R is the same or different at each instance and is H, D, OH, F, Cl, Br, I, CN, $NO_2$, $N(Ar)_2$, $N(R^1)_2$, $C(=O)N(Ar)_2$, $C(=O)N(R^1)_2$, $Si(Ar)_3$, $Si(R^1)_3$, $B(OAr)_2$, $B(OR^1)_2$, $C(=O)Ar$, $C(=O)R^1$, $P(=O)(Ar)_2$, $P(=O)(R^1)_2$, $S(=O)Ar$, $S(=O)R^1$, $S(=O)_2Ar$, $S(=O)_2R^1$, $OSO_2Ar$, $OSO_2R^1$, a straight-chain alkyl, alkoxy or thioalkoxy group having 1 to 20 carbon atoms or an alkenyl or alkynyl group having 2 to 20 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more $R^1$ radicals, where one or more nonadjacent $CH_2$ groups may be replaced by $R^1C=CR^1$, C≡C, $Si(R^1)_2$, C=O, $NR^1$, O, S or $CONR^1$, or an aromatic or heteroaromatic ring system which has 5 to 40 aromatic ring atoms and may be substituted in each case by one or more $R^1$ radicals, or an aryloxy or heteroaryloxy group which has 5 to 40 aromatic ring atoms and may be substituted by one or more $R^1$ radicals; at the same time, two R radicals together may also form a mono- or polycyclic, aliphatic or aromatic or heteroaromatic ring system;

Ar is the same or different at each instance and is an aromatic or heteroaromatic ring system which has 5 to 60 aromatic ring atoms and may be substituted by one or more $R^1$ radicals; at the same time, it is possible for two Ar radicals bonded to the same silicon atom, nitrogen atom, phosphorus atom or boron atom also to be joined to one another by a single bond or a bridge selected from $B(R^1)$, $C(R^1)_2$, $Si(R^1)_2$, C=O, $C=NR^1$, $C=C(R^1)_2$, O, S, S=O, $SO_2$, $N(R^1)$, $P(R^1)$ and $P(=O)R^1$;

$R^1$ is the same or different at each instance and is H, D, OH, F, Cl, Br, I, CN, $NO_2$, $N(Ar^1)_2$, $N(R^2)_2$, $C(=O)Ar^1$, $C(=O)R^2$, $P(=O)(Ar^1)_2$, $P(Ar^1)_2$, $B(Ar^1)_2$, $B(OR^2)_2$, $Si(Ar^1)_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl or alkynyl group having 2 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-C(=O)O-$, $-C(=O)NR^2-$, $NR^2$, $P(=O)(R^2)$, $-O-$, $-S-$, $SO$ or $SO_2$ and where one or more hydrogen atoms may be replaced by D, F, Cl, Br, I, CN or $NO_2$, or an aromatic or heteroaromatic ring system which has 5 to 40 aromatic ring atoms, each of which may be substituted by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a combination of these systems; at the same time, two or more, preferably adjacent $R^1$ radicals together may form a mono- or polycyclic, aliphatic or aromatic or heteroaromatic ring system;

$Ar^1$ is the same or different at each instance and is an aromatic or heteroaromatic ring system which has 5 to 30 aromatic ring atoms and may be substituted by one or more, preferably nonaromatic $R^2$ radicals; at the same time, it is possible for two $Ar^1$ radicals bonded to the same silicon atom, nitrogen atom, phosphorus atom or boron atom also to be joined to one another by a single bond or a bridge selected from $B(R^2)$, $C(R^2)_2$, $Si(R^2)_2$, $C=O$, $C=NR^2$, $C=C(R^2)_2$, O, S, $S=O$, $SO_2$, $N(R^2)$, $P(R^2)$ and $P(=O)R^2$;

$R^2$ is the same or different at each instance and is H, D, F, Cl, Br, I, CN, $B(OR^3)_2$, $NO_2$, $C(=O)R^3$, $CR^3=C(R^3)_2$, $C(=O)OR^3$, $C(=O)N(R^3)_2$, $Si(R^3)_3$, $P(R^3)_2$, $B(R^3)_2$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $-R^3C=CR^3-$, $-C\equiv C-$, $Si(R^3)_2$, $Ge(R^3)_2$, $Sn(R^3)_2$, $C=O$, $C=S$, $C=NR^3$, $-C(=O)O-$, $-C(=O)NR^3-$, $NR^3$, $P(=O)(R^3)$, $-O-$, $-S-$, $SO$ or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^3$ radicals, or an aryloxy or heteroaryloxy group which has 5 to 40 aromatic ring atoms and may be substituted by one or more $R^3$ radicals, or a combination of these systems; at the same time, two or more, preferably adjacent substituents $R^2$ together may also form a mono- or polycyclic, aliphatic or aromatic or heteroaromatic ring system;

$R^3$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, two or more preferably adjacent substituents $R^3$ together may also form a mono- or polycyclic, aliphatic or aromatic or heteroaromatic ring system;

the index s is 0, 1, 2, 3, 4, 5 or 6, preferably 0, 1, 2, 3 or 4, more preferably 0, 1 or 2;

the index t is 0, 1, 2, 3, 4, 5, 6, 7 or 8, preferably 0, 1, 2, 3 or 4, more preferably 0, 1 or 2;

the index v is 0, 1, 2, 3, 4, 5, 6, 7, 8 or 9, preferably 0, 1, 2, 3 or 4, more preferably 0, 1 or 2.

Adjacent carbon atoms in the context of the present invention are carbon atoms bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

The wording that two or more radicals together may form a ring, in the context of the present description, should be understood to mean, inter alia, that the two radicals are joined to one another by a chemical bond with formal elimination of two hydrogen atoms. This is illustrated by the following scheme:

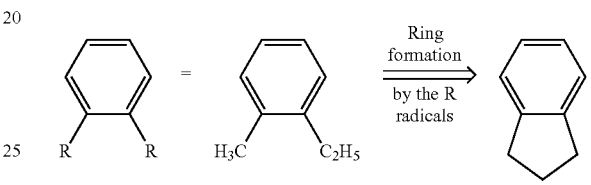

In addition, however, the abovementioned wording shall also be understood to mean that, if one of the two radicals is hydrogen, the second radical binds to the position to which the hydrogen atom was bonded, forming a ring. This shall be illustrated by the following scheme:

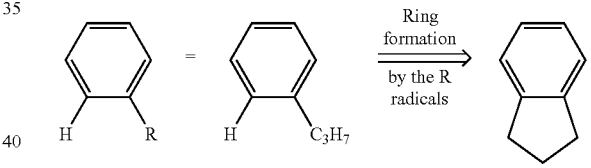

A fused aryl group, a fused aromatic ring system or a fused heteroaromatic ring system in the context of the present invention is a group in which two or more aromatic groups are fused, i.e. annelated, to one another along a common edge, such that, for example, two carbon atoms belong to the at least two aromatic or heteroaromatic rings, as, for example, in naphthalene. By contrast, for example, fluorene is not a fused aryl group in the context of the present invention, since the two aromatic groups in fluorene do not have a common edge. Corresponding definitions apply to heteroaryl groups and to fused ring systems which may but need not also contain heteroatoms.

If two or more, preferably adjacent R, $R^1$, $R^2$ and/or $R^3$ radicals together form a ring system, the result may be a monocyclic or polycyclic, aliphatic, aromatic or heteroaromatic ring system.

An aryl group in the context of this invention contains 6 to 60 carbon atoms, preferably 6 to 40 carbon atoms, more preferably 6 to 30 carbon atoms; a heteroaryl group in the context of this invention contains 2 to 60 carbon atoms, preferably 2 to 40 carbon atoms, more preferably 2 to 30 carbon atoms, and at least one heteroatom, with the proviso that the sum total of carbon atoms and heteroatoms is at least 5. The heteroatoms are preferably selected from N, O and/or S. Here, an aryl group or heteroaryl group is understood to mean either a simple aromatic ring, i.e. benzene, or a simple heteroaromatic ring, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 60 carbon atoms, preferably 6 to 40 carbon atoms, more preferably 6 to 30 carbon atoms, in the ring system. A heteroaromatic ring system in the context of this invention contains 1 to 60 carbon atoms, preferably 1 to 40 carbon atoms, more preferably 1 to 30 carbon atoms, and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for a plurality of aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$ to $C_{20}$-alkyl group in which individual hydrogen atoms or $CH_2$ groups may also be replaced by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5 to 60, preferably 5-40, aromatic ring atoms, more preferably 5 to 30 aromatic ring atoms, and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is also given to compounds having structures of the formulae (I) to (XVIII) in which not more than two X groups per ring are N, preferably all X groups in a ring are CR, and preferably at least one, more preferably at least two, of the X groups per ring are selected from C—H and C-D.

In a further configuration, preference is given to compounds having structures of the formulae (I) to (XVIII) in which two X groups per ring are N, where these X groups are nonadjacent.

Furthermore, preference is given to compounds having structures of formulae (I) to (XVIII) in which not more than four, preferably not more than two, X groups are N, and more preferably all the X groups are CR, where preferably not more than four, more preferably not more than three and especially preferably not more than two of the CR groups that X represents are not the CH group.

In a further configuration, preference is given to compounds having structures of the formulae (I) to (XVIII) in which two X groups are N, where these X groups are nonadjacent.

The compounds of the invention may preferably comprise at least one structure of the formulae (Ia) to (XVIIIa)
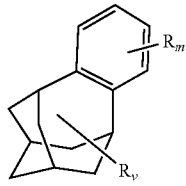
Formula (Ia)
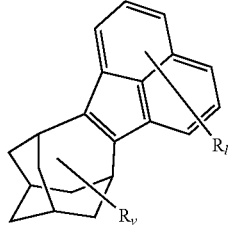
Formula (IIa)
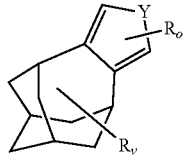
Formula (IIIa)
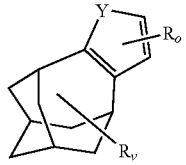
Formula (IVa)
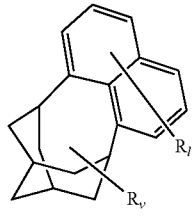
Formula (Va)
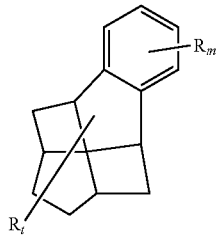
Formula (VIa)
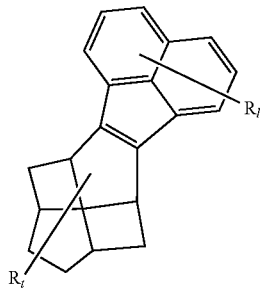
Formula (VIIa)
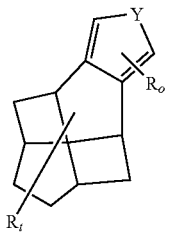
Formula (VIIIa)
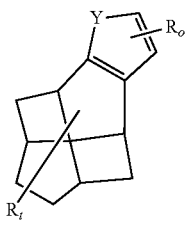
Formula (IXa)
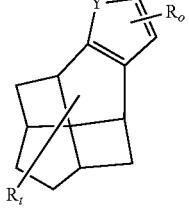
Formula (Xa)
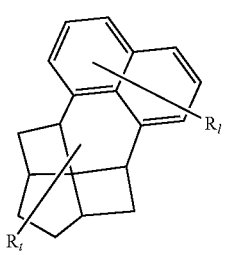
Formula (XIa)
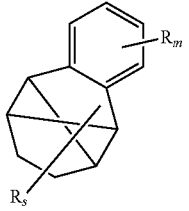
Formula (XIIa)
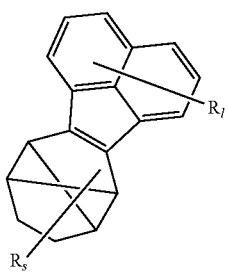
Formula (XIII)
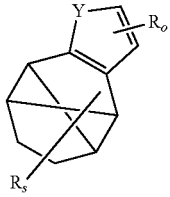
Formula (XIV)
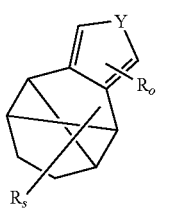

-continued

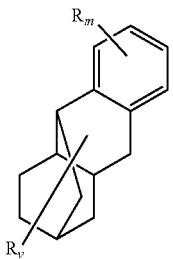

Formula (XVa)

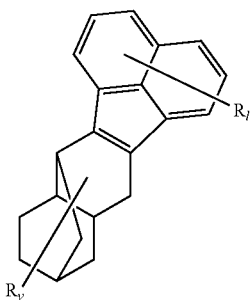

Formula (XVIa)

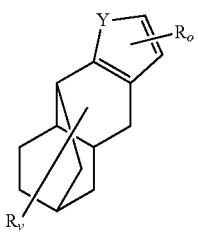

Formula (XVIIa)

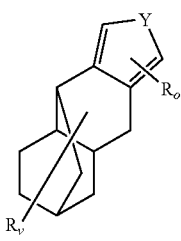

Formula (XVIIIa)

where the symbols Y, R, v, t and s have the definition set out above, especially for formulae (I) to (XVIII), the index o is 0, 1 or 2, preferably 0 or 1, the index n is 0, 1, 2, or 3, preferably 0, 1 or 2, and the index m is 0, 1, 2, 3 or 4, preferably 0, 1 or 2, and the index l is 0, 1, 2, 3, 4, 5 or 6, preferably 0, 1 or 2, where Y is preferably O, S, NR or NAr, more preferably NAr.

In addition, in the structures of the formulae (Ia) to (XVIIIa), it may be the case that the sum total of the indices v, t, s, o, n, m and l is not more than 6, preferably not more than 4 and more preferably not more than 2.

When X is CR or when the aromatic and/or heteroaromatic groups are substituted by substituents R, these substituents R are preferably selected from the group consisting of H, D, F, CN, N(Ar)$_2$, C(=O)Ar, P(=O)(Ar)$_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more R$^1$ radicals, where one or more nonadjacent CH$_2$ groups may be replaced by O and where one or more hydrogen atoms may be replaced by D or F, an aromatic or heteroaromatic ring system which has 5 to 24 aromatic ring atoms and may be substituted in each case by one or more R$^1$ radicals, but is preferably unsubstituted, or an aralkyl or heteroaralkyl group which has 5 to 25 aromatic ring atoms and may be substituted by one or more R$^1$ radicals; at the same time, it is optionally possible for two substituents R preferably bonded to adjacent carbon atoms to form a monocyclic or polycyclic, aliphatic, aromatic or heteroaromatic ring system which may be substituted by one or more R$^1$ radicals; where the Ar group has the definition given above, especially for formulae (I) to (XVIII).

More preferably, these substituents R are selected from the group consisting of H, D, F, CN, N(Ar)$_2$, a straight-chain alkyl group having 1 to 8 carbon atoms, preferably having 1, 2, 3 or 4 carbon atoms, or a branched or cyclic alkyl group having 3 to 8 carbon atoms, preferably having 3 or 4 carbon atoms, or an alkenyl group having 2 to 8 carbon atoms, preferably having 2, 3 or 4 carbon atoms, each of which may be substituted by one or more R$^1$ radicals, but is preferably unsubstituted, or an aromatic or heteroaromatic ring system which has 5 to 24 aromatic ring atoms, preferably 6 to 18 aromatic ring atoms, more preferably 6 to 13 aromatic ring atoms, and may be substituted in each case by one or more nonaromatic R$^1$ radicals, but is preferably unsubstituted; at the same time, it is optionally possible for two substituents R$^1$ preferably bonded to adjacent carbon atoms to form a monocyclic or polycyclic aliphatic ring system which may be substituted by one or more R$^2$ radicals, but is preferably unsubstituted, where Ar may have the definition set out above.

Most preferably, the substituents R are selected from the group consisting of H and an aromatic or heteroaromatic ring system having 6 to 18 aromatic ring atoms, preferably having 6 to 13 aromatic ring atoms, each of which may be substituted by one or more nonaromatic R$^1$ radicals, but is preferably unsubstituted. Examples of suitable substituents R are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, 1-, 2-, 3- or 4-carbazolyl and indenocarbazolyl, each of which may be substituted by one or more R$^1$ radicals, but are preferably unsubstituted.

In addition, it may be the case that the substituents R of the heteroaromatic ring system of the formulae (I) to (XVIII) and/or (Ia) to (XVIIIa) do not form a fused aromatic or heteroaromatic ring system with the ring atoms of the aromatic or heteroaromatic ring system, preferably any fused ring system. This includes the formation of a fused ring system with possible substituents R$^1$, R$^2$, R$^3$ which may be bonded to the R$^1$ radicals.

In a further-preferred embodiment, it may be the case that the compound usable as active compound in an organic electronic device comprises at least two, preferably at least three, aliphatic polycyclic ring systems having at least 3 rings.

It may further be the case that the aromatic or heteroaromatic ring system having 5 to 60 carbon atoms to which an aliphatic polycyclic ring system having at least 3 rings is fused is selected from phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, pyrenyl, triazinyl, imidazolyl, benzimidazolyl, benzoxazolyl, benzothiazolyl, 1-, 2-, 3- or 4-carbazolyl, indenocarbazolyl, 1- or 2-naphthyl, anthracenyl, preferably 9-anthracenyl, phenanthrenyl and/or triphenylenyl, each of which may be substituted by one or more R and/or $R^1$ radicals, particular preference being given to phenyl, spirobifluorene, fluorene, dibenzofuran, dibenzothiophene, anthracene, phenanthrene, triphenylene groups.

In a further-preferred embodiment, it may be the case that the aliphatic polycyclic ring system which has at least 3 rings and is fused to an aromatic or heteroaromatic ring system having 5 to 60 carbon atoms forms a substructure of the formulae (N-1) to (N-6)

aliphatic polycyclic ring system having at least 3 rings is fused. The double bond shown in the structures of formulae (N-1) to (N-6) may be regarded here as part of the aromatic or heteroaromatic ring system having 5 to 60 carbon atoms to which the structure of one of the formulae (N-1) to (N-6) is fused.

It may further be the case that the aromatic or heteroaromatic ring system having 5 to 60 carbon atoms to which an aliphatic polycyclic ring system having at least 3 rings is fused forms a substructure of the formulae (Ar-1) to (Ar-66)

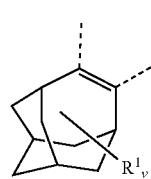

Formula (N-1)

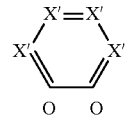

(Ar-1)

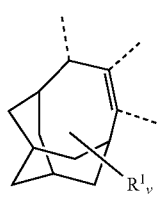

Formula (N-2)

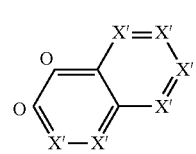

(Ar-2)

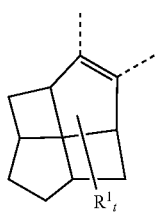

Formula (N-3)

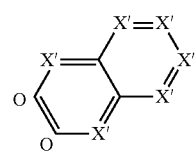

(Ar-3)

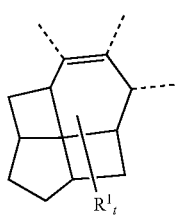

Formula (N-4)

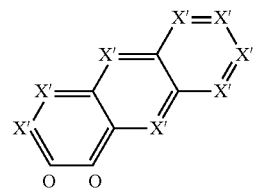

(Ar-4)

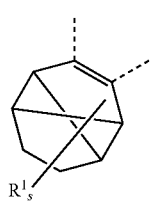

Formula (N-5)

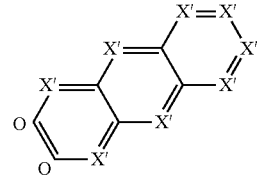

(Ar-5)

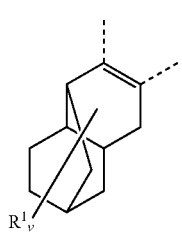

Formula (N-6)

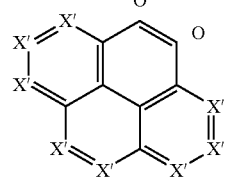

(Ar-6)

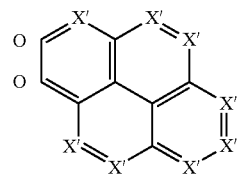

(Ar-7)

where the symbols $R^1$, v, t and s have the definition given above, especially for formulae (I) to (XVIII), and the dotted lines represent the bonds of the aromatic or heteroaromatic ring system having 5 to 60 carbon atoms to which the

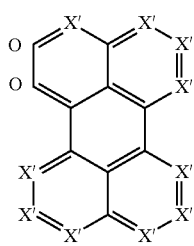 (Ar-8)
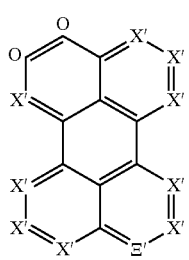 (Ar-9)
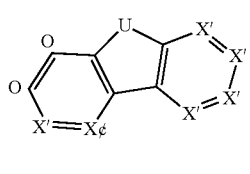 (Ar-10)
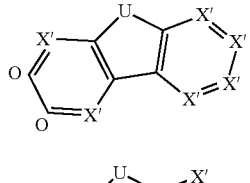 (Ar-11)
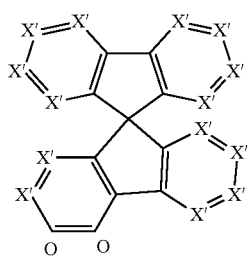 (Ar-12)
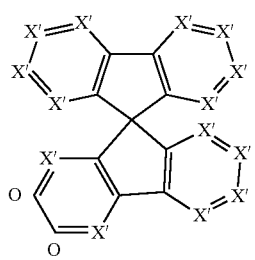 (Ar-13)
(Ar-14)
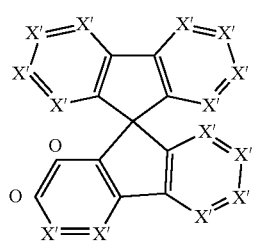 (Ar-15)
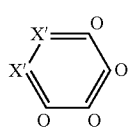 (Ar-16)
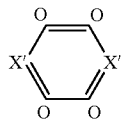 (Ar-17)
(Ar-18)
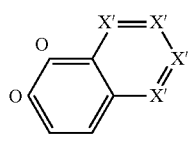 (Ar-19)
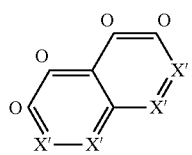 (Ar-20)
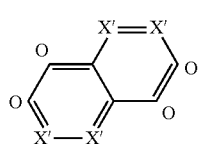 (Ar-21)
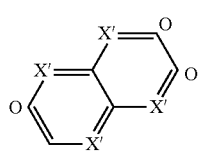 (Ar-22)
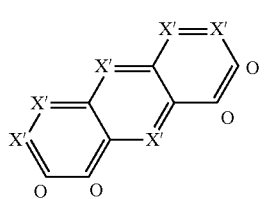 (Ar-23)

(Ar-24)
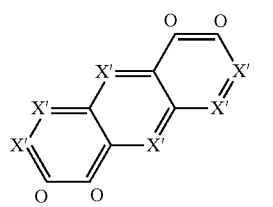
(Ar-25)
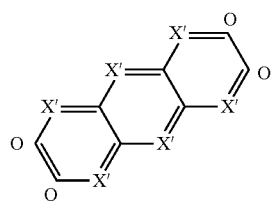
(Ar-26)
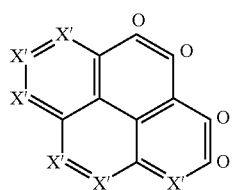
(Ar-27)
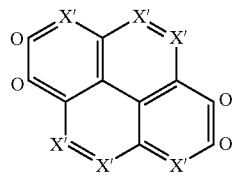
(Ar-28)
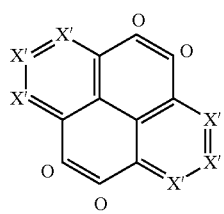
(Ar-29)
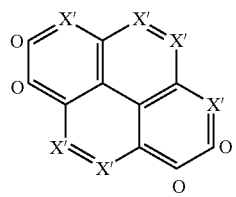
(Ar-30)
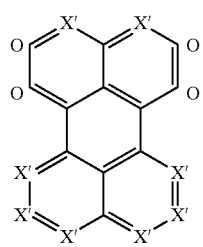
(Ar-31)
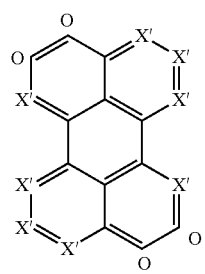
(Ar-32)
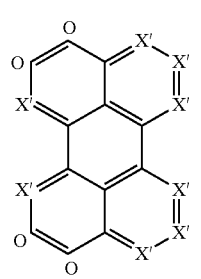
(Ar-33)
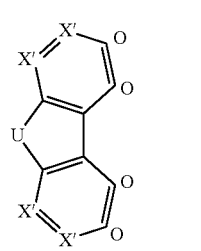
(Ar-34)
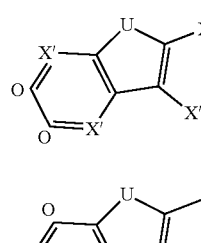
(Ar-35)
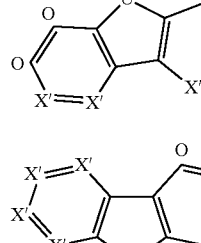
(Ar-36)
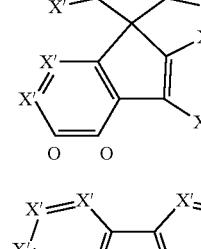
(Ar-37)
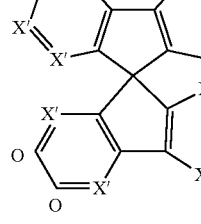

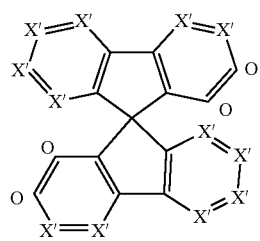 (Ar-38)
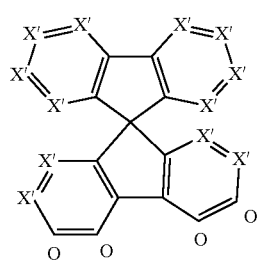 (Ar-39)
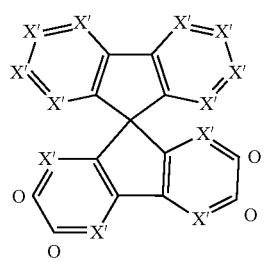 (Ar-40)
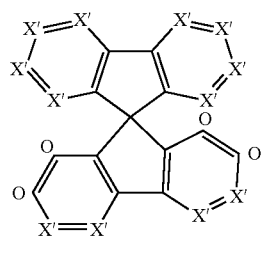 (Ar-41)
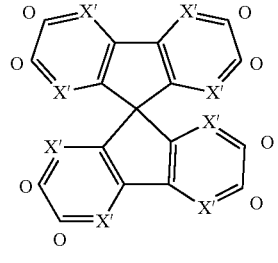 (Ar-42)
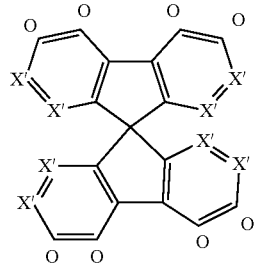 (Ar-43)
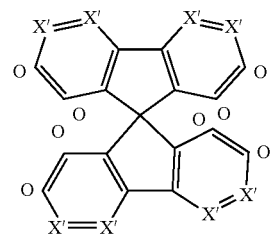 (Ar-44)
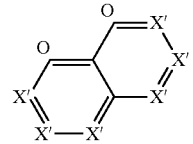 (Ar-45)
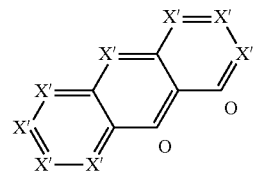 (Ar-46)
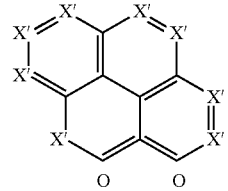 (Ar-47)
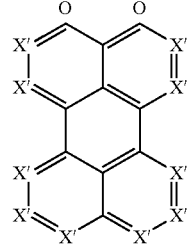 (Ar-48)
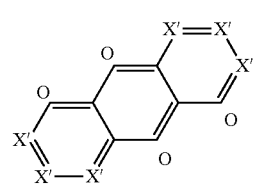 (Ar-49)
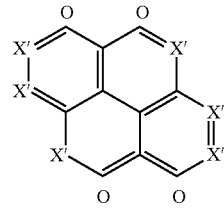 (Ar-50)

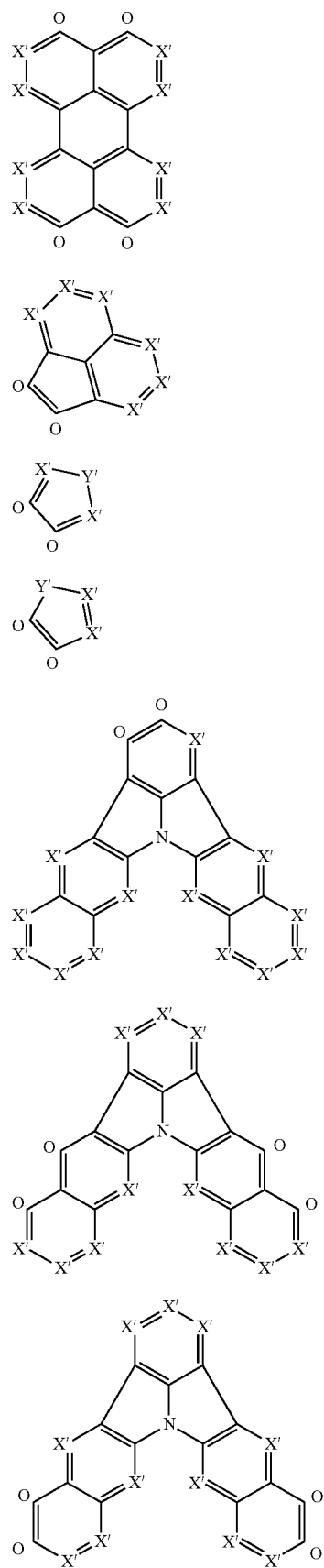

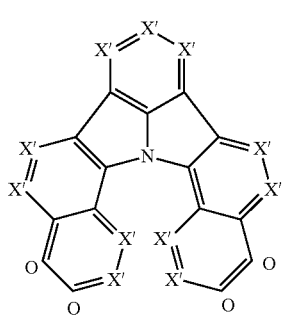
(Ar-63)

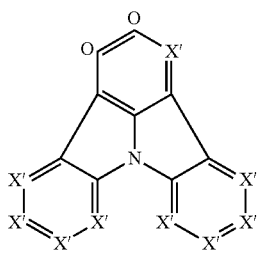
(Ar-64)

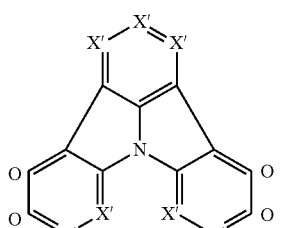
(Ar-65)

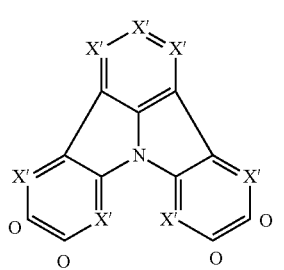
(Ar-66)

where X' is N or CR$^1$, preferably CR$^1$, Y' is selected from O, S, C(R$^1$)$_2$, Si(R$^1$)$_2$, NR$^1$ and NAr$^1$, preferably O, S, NAr$^1$, more preferably NAr$^1$, U is selected from O, S, C(R$^1$)$_2$, N(R$^1$), B(R$^1$), Si(R$^1$)$_2$, C=O, S=O, SO$_2$, P(R$^1$) and P(=O) R$^1$, where R$^1$ has the definition set out above, especially for formulae (I) to (XVIII), and the aliphatic polycyclic ring system having at least 3 rings binds to the aromatic or heteroaromatic ring system having 5 to 60 carbon atoms at the respective positions identified by o to form a ring. Preference is given here to structures of the formulae (Ar-2) to (Ar-66) and particular preference to structures of the formulae (Ar-4) to (Ar-15) and (Ar-23) to (Ar-44).

Preference is also given to compounds having substructures of the formulae (Ar-1) to (Ar-66) in which not more than two X' groups per ring are N, preferably all X' groups in a ring are CR$^1$, and preferably at least one, more preferably at least two, of the X' groups per ring are selected from C—H and C-D.

In a further configuration, preference is given to compounds having structures of the formulae (I) to (XVIII) in which two X' groups per ring are N, where these X' groups are nonadjacent.

Furthermore, preference is given to compounds having substructures of formulae (Ar-1) to (Ar-66) in which not more than four, preferably not more than two, X' groups are N, and more preferably all the X' groups are CR$^1$, where preferably not more than four, more preferably not more than three and especially preferably not more than two of the CR$^1$ groups that X' represents are not the CH group.

In a further configuration, preference is given to compounds having substructures of the formulae (Ar-1) to (Ar-66) in which two X' groups are N, where these X groups are nonadjacent.

In yet a further configuration, preference is given to compounds having substructures of the formulae (Ar-55) to (Ar-66) in which preferably not more than two X' groups are N.

In a preferred embodiment, preference is given inter alia to the combinations according to the following table:

| Substructure of the formula | Substructure of the formula | Number of X' groups that are N, where these X groups are nonadjacent | Number of X' groups that are CR$^1$, where the CR$^1$ group is not the CH group |
|---|---|---|---|
| N-1 | Ar-1 | 0 | 0 to 4, preferably 1 or 2, more preferably 1 |
| N-3 | Ar-1 | 0 | 0 to 4, preferably 1 or 2, more preferably 1 |
| N-5 | Ar-1 | 0 | 0 to 4, preferably 1 or 2, more preferably 1 |
| N-6 | Ar-1 | 0 | 0 to 4, preferably 1 or 2, more preferably 1 |
| N-1 | Ar-1 | 2 | 0 to 2, preferably 1 or 2, more preferably 1 |
| N-3 | Ar-1 | 2 | 0 to 2, preferably 1 or 2, more preferably 1 |
| N-5 | Ar-1 | 2 | 0 to 2, preferably 1 or 2, more preferably 1 |
| N-6 | Ar-1 | 2 | 0 to 2, preferably 1 or 2, more preferably 1 |
| N-1 | Ar-2 | 0 | 0 to 4, preferably 1 or 2, more preferably 1 |
| N-3 | Ar-2 | 0 | 0 to 4, preferably 1 or 2, more preferably 1 |
| N-5 | Ar-2 | 0 | 0 to 4, preferably 1 or 2, more preferably 1 |
| N-6 | Ar-2 | 0 | 0 to 4, preferably 1 or 2, more preferably 1 |
| N-1 | Ar-2 | 2 | 0 to 2, preferably 1 or 2, more preferably 1 |
| N-3 | Ar-2 | 2 | 0 to 2, preferably 1 or 2, more preferably 1 |
| N-5 | Ar-2 | 2 | 0 to 2, preferably 1 or 2, more preferably 1 |
| N-6 | Ar-2 | 2 | 0 to 2, preferably 1 or 2, more preferably 1 |
| N-1 | Ar-3 | 0 | 0 to 4, preferably 1 or 2, more preferably 1 |
| N-3 | Ar-3 | 0 | 0 to 4, preferably 1 or 2, more preferably 1 |
| N-5 | Ar-3 | 0 | 0 to 4, preferably 1 or 2, more preferably 1 |
| N-6 | Ar-3 | 0 | 0 to 4, preferably 1 or 2, more preferably 1 |
| N-1 | Ar-3 | 2 | 0 to 2, preferably 1 or 2, more preferably 1 |
| N-3 | Ar-3 | 2 | 0 to 2, preferably 1 or 2, more preferably 1 |
| N-5 | Ar-3 | 2 | 0 to 2, preferably 1 or 2, more preferably 1 |
| N-6 | Ar-3 | 2 | 0 to 2, preferably 1 or 2, more preferably 1 |
| N-1 | Ar-4 | 0 | 0 to 4, preferably 1, 2 or 3, more preferably 2 |
| N-3 | Ar-4 | 0 | 0 to 4, preferably 1, 2 or 3, more preferably 2 |

-continued

| Substructure of the formula | Substructure of the formula | Number of X' groups that are N, where these X groups are nonadjacent | Number of X' groups that are CR[1], where the CR[1] group is not the CH group |
|---|---|---|---|
| N-5 | Ar-4 | 0 | 0 to 4, preferably 1, 2 or 3, more preferably 2 |
| N-6 | Ar-4 | 0 | 0 to 4, preferably 1, 2 or 3, more preferably 2 |
| N-1 | Ar-4 | 2 | 0 to 2, preferably 1 or 2, more preferably 2 |
| N-3 | Ar-4 | 2 | 0 to 2, preferably 1 or 2, more preferably 2 |
| N-5 | Ar-4 | 2 | 0 to 2, preferably 1 or 2, more preferably 2 |
| N-6 | Ar-4 | 2 | 0 to 2, preferably 1 or 2, more preferably 2 |
| N-1 | Ar-5 | 0 | 0 to 4, preferably 1, 2 or 3, more preferably 2 |
| N-3 | Ar-5 | 0 | 0 to 4, preferably 1, 2 or 3, more preferably 2 |
| N-5 | Ar-5 | 0 | 0 to 4, preferably 1, 2 or 3, more preferably 2 |
| N-6 | Ar-5 | 0 | 0 to 4, preferably 1, 2 or 3, more preferably 2 |
| N-1 | Ar-5 | 2 | 0 to 2, preferably 1 or 2, more preferably 2 |
| N-3 | Ar-5 | 2 | 0 to 2, preferably 1 or 2, more preferably 2 |
| N-5 | Ar-5 | 2 | 0 to 2, preferably 1 or 2, more preferably 2 |
| N-6 | Ar-5 | 2 | 0 to 2, preferably 1 or 2, more preferably 2 |
| N-1 | Ar-6 | 0 | 0 to 4, preferably 1 or 2, more preferably 1 |
| N-3 | Ar-6 | 0 | 0 to 4, preferably 1 or 2, more preferably 1 |
| N-5 | Ar-6 | 0 | 0 to 4, preferably 1 or 2, more preferably 1 |
| N-6 | Ar-6 | 0 | 0 to 4, preferably 1 or 2, more preferably 1 |
| N-1 | Ar-6 | 2 | 0 to 2, preferably 1 or 2, more preferably 1 |
| N-3 | Ar-6 | 2 | 0 to 2, preferably 1 or 2, more preferably 1 |
| N-5 | Ar-6 | 2 | 0 to 2, preferably 1 or 2, more preferably 1 |
| N-6 | Ar-6 | 2 | 0 to 2, preferably 1 or 2, more preferably 1 |
| N-1 | Ar-7 | 0 | 0 to 4, preferably 1 or 2, more preferably 1 |
| N-3 | Ar-7 | 0 | 0 to 4, preferably 1 or 2, more preferably 1 |
| N-5 | Ar-7 | 0 | 0 to 4, preferably 1 or 2, more preferably 1 |
| N-6 | Ar-7 | 0 | 0 to 4, preferably 1 or 2, more preferably 1 |
| N-1 | Ar-7 | 2 | 0 to 2, preferably 1 or 2, more preferably 1 |
| N-3 | Ar-7 | 2 | 0 to 2, preferably 1 or 2, more preferably 1 |
| N-5 | Ar-7 | 2 | 0 to 2, preferably 1 or 2, more preferably 1 |
| N-6 | Ar-7 | 2 | 0 to 2, preferably 1 or 2, more preferably 1 |
| N-1 | Ar-8 | 0 | 0 to 4, preferably 1 or 2, more preferably 1 |
| N-3 | Ar-8 | 0 | 0 to 4, preferably 1 or 2, more preferably 1 |
| N-5 | Ar-8 | 0 | 0 to 4, preferably 1 or 2, more preferably 1 |
| N-6 | Ar-8 | 0 | 0 to 4, preferably 1 or 2, more preferably 1 |
| N-1 | Ar-8 | 2 | 0 to 2, preferably 1 or 2, more preferably 1 |
| N-3 | Ar-8 | 2 | 0 to 2, preferably 1 or 2, more preferably 1 |
| N-5 | Ar-8 | 2 | 0 to 2, preferably 1 or 2, more preferably 1 |
| N-6 | Ar-8 | 2 | 0 to 2, preferably 1 or 2, more preferably 1 |
| N-1 | Ar-9 | 0 | 0 to 4, preferably 1 or 2, more preferably 1 |
| N-3 | Ar-9 | 0 | 0 to 4, preferably 1 or 2, more preferably 1 |
| N-5 | Ar-9 | 0 | 0 to 4, preferably 1 or 2, more preferably 1 |
| N-6 | Ar-9 | 0 | 0 to 4, preferably 1 or 2, more preferably 1 |
| N-1 | Ar-9 | 2 | 0 to 2, preferably 1 or 2, more preferably 1 |
| N-3 | Ar-9 | 2 | 0 to 2, preferably 1 or 2, more preferably 1 |
| N-5 | Ar-9 | 2 | 0 to 2, preferably 1 or 2, more preferably 1 |
| N-6 | Ar-9 | 2 | 0 to 2, preferably 1 or 2, more preferably 1 |
| N-1 | Ar-10 | 0 | 0 to 4, preferably 1 or 2, more preferably 1 |
| N-3 | Ar-10 | 0 | 0 to 4, preferably 1 or 2, more preferably 1 |
| N-5 | Ar-10 | 0 | 0 to 4, preferably 1 or 2, more preferably 1 |
| N-6 | Ar-10 | 0 | 0 to 4, preferably 1 or 2, more preferably 1 |
| N-1 | Ar-10 | 2 | 0 to 2, preferably 1 or 2, more preferably 1 |
| N-3 | Ar-10 | 2 | 0 to 2, preferably 1 or 2, more preferably 1 |
| N-5 | Ar-10 | 2 | 0 to 2, preferably 1 or 2, more preferably 1 |
| N-6 | Ar-10 | 2 | 0 to 2, preferably 1 or 2, more preferably 1 |
| N-1 | Ar-11 | 0 | 0 to 4, preferably 1 or 2, more preferably 1 |
| N-3 | Ar-11 | 0 | 0 to 4, preferably 1 or 2, more preferably 1 |
| N-5 | Ar-11 | 0 | 0 to 4, preferably 1 or 2, more preferably 1 |
| N-6 | Ar-11 | 0 | 0 to 4, preferably 1 or 2, more preferably 1 |
| N-1 | Ar-11 | 2 | 0 to 2, preferably 1 or 2, more preferably 1 |
| N-3 | Ar-11 | 2 | 0 to 2, preferably 1 or 2, more preferably 1 |
| N-5 | Ar-11 | 2 | 0 to 2, preferably 1 or 2, more preferably 1 |
| N-6 | Ar-11 | 2 | 0 to 2, preferably 1 or 2, more preferably 1 |
| N-1 | Ar-12 | 0 | 0 to 4, preferably 1 or 2, more preferably 1 |
| N-3 | Ar-12 | 0 | 0 to 4, preferably 1 or 2, more preferably 1 |
| N-5 | Ar-12 | 0 | 0 to 4, preferably 1 or 2, more preferably 1 |
| N-6 | Ar-12 | 0 | 0 to 4, preferably 1 or 2, more preferably 1 |
| N-1 | Ar-12 | 2 | 0 to 2, preferably 1 or 2, more preferably 1 |
| N-3 | Ar-12 | 2 | 0 to 2, preferably 1 or 2, more preferably 1 |
| N-5 | Ar-12 | 2 | 0 to 2, preferably 1 or 2, more preferably 1 |
| N-6 | Ar-12 | 2 | 0 to 2, preferably 1 or 2, more preferably 1 |
| N-1 | Ar-13 | 0 | 0 to 4, preferably 1 or 2, more preferably 1 |
| N-3 | Ar-13 | 0 | 0 to 4, preferably 1 or 2, more preferably 1 |
| N-5 | Ar-13 | 0 | 0 to 4, preferably 1 or 2, more preferably 1 |

| Substructure of the formula | Substructure of the formula | Number of X' groups that are N, where these X groups are nonadjacent | Number of X' groups that are CR$^1$, where the CR$^1$ group is not the CH group |
|---|---|---|---|
| N-6 | Ar-13 | 0 | 0 to 4, preferably 1 or 2, more preferably 1 |
| N-1 | Ar-13 | 2 | 0 to 2, preferably 1 or 2, more preferably 1 |
| N-3 | Ar-13 | 2 | 0 to 2, preferably 1 or 2, more preferably 1 |
| N-5 | Ar-13 | 2 | 0 to 2, preferably 1 or 2, more preferably 1 |
| N-6 | Ar-13 | 2 | 0 to 2, preferably 1 or 2, more preferably 1 |
| N-1 | Ar-14 | 0 | 0 to 4, preferably 1 or 2, more preferably 1 |
| N-3 | Ar-14 | 0 | 0 to 4, preferably 1 or 2, more preferably 1 |
| N-5 | Ar-14 | 0 | 0 to 4, preferably 1 or 2, more preferably 1 |
| N-6 | Ar-14 | 0 | 0 to 4, preferably 1 or 2, more preferably 1 |
| N-1 | Ar-14 | 2 | 0 to 2, preferably 1 or 2, more preferably 1 |
| N-3 | Ar-14 | 2 | 0 to 2, preferably 1 or 2, more preferably 1 |
| N-5 | Ar-14 | 2 | 0 to 2, preferably 1 or 2, more preferably 1 |
| N-6 | Ar-14 | 2 | 0 to 2, preferably 1 or 2, more preferably 1 |
| N-1 | Ar-15 | 0 | 0 to 4, preferably 1 or 2, more preferably 1 |
| N-3 | Ar-15 | 0 | 0 to 4, preferably 1 or 2, more preferably 1 |
| N-5 | Ar-15 | 0 | 0 to 4, preferably 1 or 2, more preferably 1 |
| N-6 | Ar-15 | 0 | 0 to 4, preferably 1 or 2, more preferably 1 |
| N-1 | Ar-15 | 2 | 0 to 2, preferably 1 or 2, more preferably 1 |
| N-3 | Ar-15 | 2 | 0 to 2, preferably 1 or 2, more preferably 1 |
| N-5 | Ar-15 | 2 | 0 to 2, preferably 1 or 2, more preferably 1 |
| N-6 | Ar-15 | 2 | 0 to 2, preferably 1 or 2, more preferably 1 |
| 2 * N-1 | Ar-16 | 0 | 0 to 2, preferably 1 or 2, more preferably 1 |
| 2 * N-3 | Ar-16 | 0 | 0 to 2, preferably 1 or 2, more preferably 1 |
| 2 * N-5 | Ar-16 | 0 | 0 to 2, preferably 1 or 2, more preferably 1 |
| 2 * N-6 | Ar-16 | 0 | 0 to 2, preferably 1 or 2, more preferably 1 |
| 2 * N-1 | Ar-17 | 0 | 0 to 2, preferably 1 or 2, more preferably 1 |
| 2 * N-3 | Ar-17 | 0 | 0 to 2, preferably 1 or 2, more preferably 1 |
| 2 * N-5 | Ar-17 | 0 | 0 to 2, preferably 1 or 2, more preferably 1 |
| 2 * N-6 | Ar-17 | 0 | 0 to 2, preferably 1 or 2, more preferably 1 |
| 3 * N-1 | Ar-18 | 0 | 0 |
| 3 * N-3 | Ar-18 | 0 | 0 |
| 3 * N-5 | Ar-18 | 0 | 0 |
| 3 * N-6 | Ar-18 | 0 | 0 |
| 2 * N-1 | Ar-19 | 0 | 0 to 4, preferably 1 or 2, more preferably 1 |
| 2 * N-3 | Ar-19 | 0 | 0 to 4, preferably 1 or 2, more preferably 1 |
| 2 * N-5 | Ar-19 | 0 | 0 to 4, preferably 1 or 2, more preferably 1 |
| 2 * N-6 | Ar-19 | 0 | 0 to 4, preferably 1 or 2, more preferably 1 |
| 2 * N-1 | Ar-19 | 2 | 0 to 4, preferably 1 or 2, more preferably 1 |
| 2 * N-3 | Ar-19 | 2 | 0 to 4, preferably 1 or 2, more preferably 1 |
| 2 * N-5 | Ar-19 | 2 | 0 to 4, preferably 1 or 2, more preferably 1 |
| 2 * N-6 | Ar-19 | 2 | 0 to 4, preferably 1 or 2, more preferably 1 |
| 2 * N-1 | Ar-20 | 0 | 0 to 4, preferably 1 or 2, more preferably 1 |
| 2 * N-3 | Ar-20 | 0 | 0 to 4, preferably 1 or 2, more preferably 1 |
| 2 * N-5 | Ar-20 | 0 | 0 to 4, preferably 1 or 2, more preferably 1 |
| 2 * N-6 | Ar-20 | 0 | 0 to 4, preferably 1 or 2, more preferably 1 |
| 2 * N-1 | Ar-20 | 2 | 0 to 4, preferably 1 or 2, more preferably 1 |
| 2 * N-3 | Ar-20 | 2 | 0 to 4, preferably 1 or 2, more preferably 1 |
| 2 * N-5 | Ar-20 | 2 | 0 to 4, preferably 1 or 2, more preferably 1 |
| 2 * N-6 | Ar-20 | 2 | 0 to 4, preferably 1 or 2, more preferably 1 |
| 2 * N-1 | Ar-21 | 0 | 0 to 4, preferably 1 or 2, more preferably 1 |
| 2 * N-3 | Ar-21 | 0 | 0 to 4, preferably 1 or 2, more preferably 1 |
| 2 * N-5 | Ar-21 | 0 | 0 to 4, preferably 1 or 2, more preferably 1 |
| 2 * N-6 | Ar-21 | 0 | 0 to 4, preferably 1 or 2, more preferably 1 |
| 2 * N-1 | Ar-21 | 2 | 0 to 4, preferably 1 or 2, more preferably 1 |
| 2 * N-3 | Ar-21 | 2 | 0 to 4, preferably 1 or 2, more preferably 1 |
| 2 * N-5 | Ar-21 | 2 | 0 to 4, preferably 1 or 2, more preferably 1 |
| 2 * N-6 | Ar-21 | 2 | 0 to 4, preferably 1 or 2, more preferably 1 |
| 2 * N-1 | Ar-22 | 0 | 0 to 4, preferably 1 or 2, more preferably 1 |
| 2 * N-3 | Ar-22 | 0 | 0 to 4, preferably 1 or 2, more preferably 1 |
| 2 * N-5 | Ar-22 | 0 | 0 to 4, preferably 1 or 2, more preferably 1 |
| 2 * N-6 | Ar-22 | 0 | 0 to 4, preferably 1 or 2, more preferably 1 |
| 2 * N-1 | Ar-22 | 2 | 0 to 4, preferably 1 or 2, more preferably 1 |
| 2 * N-3 | Ar-22 | 2 | 0 to 4, preferably 1 or 2, more preferably 1 |
| 2 * N-5 | Ar-22 | 2 | 0 to 4, preferably 1 or 2, more preferably 1 |
| 2 * N-6 | Ar-22 | 2 | 0 to 4, preferably 1 or 2, more preferably 1 |
| 2 * N-1 | Ar-23 | 0 | 0 to 4, preferably 1, 2 or 3, more preferably 2 |
| 2 * N-3 | Ar-23 | 0 | 0 to 4, preferably 1, 2 or 3, more preferably 2 |
| 2 * N-5 | Ar-23 | 0 | 0 to 4, preferably 1, 2 or 3, more preferably 2 |
| | Ar-23 | 0 | 0 to 4, preferably 1, 2 or 3, more preferably 2 |
| | Ar-23 | 2 | 0 to 2, preferably 1 or 2, more preferably 2 |
| | Ar-23 | 2 | 0 to 2, preferably 1 or 2, more preferably 2 |
| | Ar-23 | 2 | 0 to 2, preferably 1 or 2, more preferably 2 |
| | Ar-23 | 2 | 0 to 2, preferably 1 or 2, more preferably 2 |
| | Ar-24 | 0 | 0 to 4, preferably 1, 2 or 3, more preferably 2 |
| | Ar-24 | 0 | 0 to 4, preferably 1, 2 or 3, more preferably 2 |

| Substructure of the formula | Substructure of the formula | Number of X' groups that are N, where these X groups are nonadjacent | Number of X' groups that are CR$^1$, where the CR$^1$ group is not the CH group |
|---|---|---|---|
| | Ar-24 | 0 | 0 to 4, preferably 1, 2 or 3, more preferably 2 |
| | Ar-24 | 0 | 0 to 4, preferably 1, 2 or 3, more preferably 2 |
| | Ar-24 | 2 | 0 to 2, preferably 1 or 2, more preferably 2 |
| | Ar-24 | 2 | 0 to 2, preferably 1 or 2, more preferably 2 |
| | Ar-24 | 2 | 0 to 2, preferably 1 or 2, more preferably 2 |
| | Ar-24 | 2 | 0 to 2, preferably 1 or 2, more preferably 2 |
| | Ar-25 | 0 | 0 to 4, preferably 1, 2 or 3, more preferably 2 |
| | Ar-25 | 0 | 0 to 4, preferably 1, 2 or 3, more preferably 2 |
| | Ar-25 | 0 | 0 to 4, preferably 1, 2 or 3, more preferably 2 |
| | Ar-25 | 0 | 0 to 4, preferably 1, 2 or 3, more preferably 2 |
| | Ar-25 | 2 | 0 to 2, preferably 1 or 2, more preferably 2 |
| | Ar-25 | 2 | 0 to 2, preferably 1 or 2, more preferably 2 |
| | Ar-25 | 2 | 0 to 2, preferably 1 or 2, more preferably 2 |
| | Ar-25 | 2 | 0 to 2, preferably 1 or 2, more preferably 2 |
| | Ar-26 | 0 | 0 to 4, preferably 1 or 2, more preferably 1 |
| | Ar-26 | 0 | 0 to 4, preferably 1 or 2, more preferably 1 |
| | Ar-26 | 0 | 0 to 4, preferably 1 or 2, more preferably 1 |
| | Ar-26 | 0 | 0 to 4, preferably 1 or 2, more preferably 1 |
| | Ar-26 | 2 | 0 to 4, preferably 1 or 2, more preferably 1 |
| | Ar-26 | 2 | 0 to 4, preferably 1 or 2, more preferably 1 |
| | Ar-26 | 2 | 0 to 4, preferably 1 or 2, more preferably 1 |
| | Ar-26 | 2 | 0 to 4, preferably 1 or 2, more preferably 1 |
| | Ar-27 | 0 | 0 to 4, preferably 1 or 2, more preferably 1 |
| | Ar-27 | 0 | 0 to 4, preferably 1 or 2, more preferably 1 |
| | Ar-27 | 0 | 0 to 4, preferably 1 or 2, more preferably 1 |
| | Ar-27 | 0 | 0 to 4, preferably 1 or 2, more preferably 1 |
| | Ar-27 | 2 | 0 to 4, preferably 1 or 2, more preferably 1 |
| | Ar-27 | 2 | 0 to 4, preferably 1 or 2, more preferably 1 |
| | Ar-27 | 2 | 0 to 4, preferably 1 or 2, more preferably 1 |
| | Ar-27 | 2 | 0 to 4, preferably 1 or 2, more preferably 1 |
| | Ar-28 | 0 | 0 to 4, preferably 1 or 2, more preferably 1 |
| | Ar-28 | 0 | 0 to 4, preferably 1 or 2, more preferably 1 |
| | Ar-28 | 0 | 0 to 4, preferably 1 or 2, more preferably 1 |
| | Ar-28 | 0 | 0 to 4, preferably 1 or 2, more preferably 1 |
| | Ar-28 | 2 | 0 to 4, preferably 1 or 2, more preferably 1 |
| | Ar-28 | 2 | 0 to 4, preferably 1 or 2, more preferably 1 |
| | Ar-28 | 2 | 0 to 4, preferably 1 or 2, more preferably 1 |
| | Ar-28 | 2 | 0 to 4, preferably 1 or 2, more preferably 1 |
| | Ar-29 | 0 | 0 to 4, preferably 1 or 2, more preferably 1 |
| | Ar-29 | 0 | 0 to 4, preferably 1 or 2, more preferably 1 |
| | Ar-29 | 0 | 0 to 4, preferably 1 or 2, more preferably 1 |
| | Ar-29 | 0 | 0 to 4, preferably 1 or 2, more preferably 1 |
| | Ar-29 | 2 | 0 to 4, preferably 1 or 2, more preferably 1 |
| | Ar-29 | 2 | 0 to 4, preferably 1 or 2, more preferably 1 |
| | Ar-29 | 2 | 0 to 4, preferably 1 or 2, more preferably 1 |
| | Ar-29 | 2 | 0 to 4, preferably 1 or 2, more preferably 1 |
| | Ar-30 | 0 | 0 to 4, preferably 1 or 2, more preferably 1 |
| | Ar-30 | 0 | 0 to 4, preferably 1 or 2, more preferably 1 |
| | Ar-30 | 0 | 0 to 4, preferably 1 or 2, more preferably 1 |
| | Ar-30 | 0 | 0 to 4, preferably 1 or 2, more preferably 1 |
| | Ar-30 | 2 | 0 to 4, preferably 1 or 2, more preferably 1 |
| | Ar-30 | 2 | 0 to 4, preferably 1 or 2, more preferably 1 |
| | Ar-30 | 2 | 0 to 4, preferably 1 or 2, more preferably 1 |
| | Ar-30 | 2 | 0 to 4, preferably 1 or 2, more preferably 1 |
| | Ar-31 | 0 | 0 to 4, preferably 1 or 2, more preferably 1 |
| | Ar-31 | 0 | 0 to 4, preferably 1 or 2, more preferably 1 |
| | Ar-31 | 0 | 0 to 4, preferably 1 or 2, more preferably 1 |
| | Ar-31 | 0 | 0 to 4, preferably 1 or 2, more preferably 1 |
| | Ar-31 | 2 | 0 to 4, preferably 1 or 2, more preferably 1 |
| | Ar-31 | 2 | 0 to 4, preferably 1 or 2, more preferably 1 |
| | Ar-31 | 2 | 0 to 4, preferably 1 or 2, more preferably 1 |
| | Ar-31 | 2 | 0 to 4, preferably 1 or 2, more preferably 1 |
| | Ar-32 | 0 | 0 to 4, preferably 1 or 2, more preferably 1 |
| | Ar-32 | 0 | 0 to 4, preferably 1 or 2, more preferably 1 |
| | Ar-32 | 0 | 0 to 4, preferably 1 or 2, more preferably 1 |
| | Ar-32 | 0 | 0 to 4, preferably 1 or 2, more preferably 1 |
| | Ar-32 | 2 | 0 to 4, preferably 1 or 2, more preferably 1 |
| | Ar-32 | 2 | 0 to 4, preferably 1 or 2, more preferably 1 |
| | Ar-32 | 2 | 0 to 4, preferably 1 or 2, more preferably 1 |
| | Ar-32 | 2 | 0 to 4, preferably 1 or 2, more preferably 1 |
| | Ar-33 | 0 | 0 to 4, preferably 1 or 2, more preferably 1 |
| | Ar-33 | 0 | 0 to 4, preferably 1 or 2, more preferably 1 |
| | Ar-33 | 0 | 0 to 4, preferably 1 or 2, more preferably 1 |

| Substructure of the formula | Substructure of the formula | Number of X' groups that are N, where these X groups are nonadjacent | Number of X' groups that are CR$^1$, where the CR$^1$ group is not the CH group |
|---|---|---|---|
| | Ar-33 | 0 | 0 to 4, preferably 1 or 2, more preferably 1 |
| | Ar-33 | 2 | 0 to 4, preferably 1 or 2, more preferably 1 |
| | Ar-33 | 2 | 0 to 4, preferably 1 or 2, more preferably 1 |
| | Ar-33 | 2 | 0 to 4, preferably 1 or 2, more preferably 1 |
| | Ar-33 | 2 | 0 to 4, preferably 1 or 2, more preferably 1 |
| | Ar-34 | 0 | 0 to 4, preferably 1 or 2, more preferably 1 |
| | Ar-34 | 0 | 0 to 4, preferably 1 or 2, more preferably 1 |
| | Ar-34 | 0 | 0 to 4, preferably 1 or 2, more preferably 1 |
| | Ar-34 | 0 | 0 to 4, preferably 1 or 2, more preferably 1 |
| | Ar-34 | 2 | 0 to 4, preferably 1 or 2, more preferably 1 |
| | Ar-34 | 2 | 0 to 4, preferably 1 or 2, more preferably 1 |
| | Ar-34 | 2 | 0 to 4, preferably 1 or 2, more preferably 1 |
| | Ar-34 | 2 | 0 to 4, preferably 1 or 2, more preferably 1 |
| | Ar-35 | 0 | 0 to 4, preferably 1 or 2, more preferably 1 |
| | Ar-35 | 0 | 0 to 4, preferably 1 or 2, more preferably 1 |
| | Ar-35 | 0 | 0 to 4, preferably 1 or 2, more preferably 1 |
| | Ar-35 | 0 | 0 to 4, preferably 1 or 2, more preferably 1 |
| | Ar-35 | 2 | 0 to 4, preferably 1 or 2, more preferably 1 |
| | Ar-35 | 2 | 0 to 4, preferably 1 or 2, more preferably 1 |
| | Ar-35 | 2 | 0 to 4, preferably 1 or 2, more preferably 1 |
| | Ar-35 | 2 | 0 to 4, preferably 1 or 2, more preferably 1 |
| | Ar-36 | 0 | 0 to 4, preferably 1 or 2, more preferably 1 |
| | Ar-36 | 0 | 0 to 4, preferably 1 or 2, more preferably 1 |
| | Ar-36 | 0 | 0 to 4, preferably 1 or 2, more preferably 1 |
| | Ar-36 | 0 | 0 to 4, preferably 1 or 2, more preferably 1 |
| | Ar-36 | 2 | 0 to 4, preferably 1 or 2, more preferably 1 |
| | Ar-36 | 2 | 0 to 4, preferably 1 or 2, more preferably 1 |
| | Ar-36 | 2 | 0 to 4, preferably 1 or 2, more preferably 1 |
| | Ar-36 | 2 | 0 to 4, preferably 1 or 2, more preferably 1 |
| | Ar-36 | 0 | 0 to 4, preferably 1 or 2, more preferably 1 |
| | Ar-36 | 0 | 0 to 4, preferably 1 or 2, more preferably 1 |
| | Ar-36 | 0 | 0 to 4, preferably 1 or 2, more preferably 1 |
| | Ar-36 | 0 | 0 to 4, preferably 1 or 2, more preferably 1 |
| | Ar-36 | 2 | 0 to 4, preferably 1 or 2, more preferably 1 |
| | Ar-36 | 2 | 0 to 4, preferably 1 or 2, more preferably 1 |
| | Ar-36 | 2 | 0 to 4, preferably 1 or 2, more preferably 1 |
| | Ar-36 | 2 | 0 to 4, preferably 1 or 2, more preferably 1 |
| | Ar-37 | 0 | 0 to 4, preferably 1 or 2, more preferably 1 |
| | Ar-37 | 0 | 0 to 4, preferably 1 or 2, more preferably 1 |
| | Ar-37 | 0 | 0 to 4, preferably 1 or 2, more preferably 1 |
| | Ar-37 | 0 | 0 to 4, preferably 1 or 2, more preferably 1 |
| | Ar-37 | 2 | 0 to 4, preferably 1 or 2, more preferably 1 |
| | Ar-37 | 2 | 0 to 4, preferably 1 or 2, more preferably 1 |
| | Ar-37 | 2 | 0 to 4, preferably 1 or 2, more preferably 1 |
| | Ar-37 | 2 | 0 to 4, preferably 1 or 2, more preferably 1 |
| | Ar-38 | 0 | 0 to 4, preferably 1 or 2, more preferably 1 |
| | Ar-38 | 0 | 0 to 4, preferably 1 or 2, more preferably 1 |
| | Ar-38 | 0 | 0 to 4, preferably 1 or 2, more preferably 1 |
| | Ar-38 | 0 | 0 to 4, preferably 1 or 2, more preferably 1 |
| | Ar-38 | 2 | 0 to 4, preferably 1 or 2, more preferably 1 |
| | Ar-38 | 2 | 0 to 4, preferably 1 or 2, more preferably 1 |
| | Ar-38 | 2 | 0 to 4, preferably 1 or 2, more preferably 1 |
| | Ar-38 | 2 | 0 to 4, preferably 1 or 2, more preferably 1 |
| | Ar-39 | 0 | 0 to 4, preferably 1 or 2, more preferably 1 |
| | Ar-39 | 0 | 0 to 4, preferably 1 or 2, more preferably 1 |
| | Ar-39 | 0 | 0 to 4, preferably 1 or 2, more preferably 1 |
| | Ar-39 | 0 | 0 to 4, preferably 1 or 2, more preferably 1 |
| | Ar-39 | 2 | 0 to 4, preferably 1 or 2, more preferably 1 |
| | Ar-39 | 2 | 0 to 4, preferably 1 or 2, more preferably 1 |
| | Ar-39 | 2 | 0 to 4, preferably 1 or 2, more preferably 1 |
| | Ar-39 | 2 | 0 to 4, preferably 1 or 2, more preferably 1 |
| | Ar-40 | 0 | 0 to 4, preferably 1 or 2, more preferably 1 |
| | Ar-40 | 0 | 0 to 4, preferably 1 or 2, more preferably 1 |
| | Ar-40 | 0 | 0 to 4, preferably 1 or 2, more preferably 1 |
| | Ar-40 | 0 | 0 to 4, preferably 1 or 2, more preferably 1 |
| | Ar-40 | 2 | 0 to 4, preferably 1 or 2, more preferably 1 |
| | Ar-40 | 2 | 0 to 4, preferably 1 or 2, more preferably 1 |
| | Ar-40 | 2 | 0 to 4, preferably 1 or 2, more preferably 1 |
| | Ar-40 | 2 | 0 to 4, preferably 1 or 2, more preferably 1 |
| | Ar-41 | 0 | 0 to 4, preferably 1 or 2, more preferably 1 |
| | Ar-41 | 0 | 0 to 4, preferably 1 or 2, more preferably 1 |
| | Ar-41 | 0 | 0 to 4, preferably 1 or 2, more preferably 1 |
| | Ar-41 | 0 | 0 to 4, preferably 1 or 2, more preferably 1 |

| Substructure of the formula | Substructure of the formula | Number of X' groups that are N, where these X groups are nonadjacent | Number of X' groups that are CR$^1$, where the CR$^1$ group is not the CH group |
|---|---|---|---|
|  | Ar-41 | 2 | 0 to 4, preferably 1 or 2, more preferably 1 |
|  | Ar-41 | 2 | 0 to 4, preferably 1 or 2, more preferably 1 |
|  | Ar-41 | 2 | 0 to 4, preferably 1 or 2, more preferably 1 |
|  | Ar-41 | 2 | 0 to 4, preferably 1 or 2, more preferably 1 |
|  | Ar-42 | 0 | 0 to 4, preferably 1 or 2, more preferably 1 |
|  | Ar-42 | 0 | 0 to 4, preferably 1 or 2, more preferably 1 |
|  | Ar-42 | 0 | 0 to 4, preferably 1 or 2, more preferably 1 |
|  | Ar-42 | 0 | 0 to 4, preferably 1 or 2, more preferably 1 |
|  | Ar-42 | 2 | 0 to 4, preferably 1 or 2, more preferably 1 |
|  | Ar-42 | 2 | 0 to 4, preferably 1 or 2, more preferably 1 |
|  | Ar-42 | 2 | 0 to 4, preferably 1 or 2, more preferably 1 |
|  | Ar-42 | 2 | 0 to 4, preferably 1 or 2, more preferably 1 |
|  | Ar-43 | 0 | 0 to 4, preferably 1 or 2, more preferably 1 |
|  | Ar-43 | 0 | 0 to 4, preferably 1 or 2, more preferably 1 |
|  | Ar-43 | 0 | 0 to 4, preferably 1 or 2, more preferably 1 |
|  | Ar-43 | 0 | 0 to 4, preferably 1 or 2, more preferably 1 |
|  | Ar-43 | 2 | 0 to 4, preferably 1 or 2, more preferably 1 |
|  | Ar-43 | 2 | 0 to 4, preferably 1 or 2, more preferably 1 |
|  | Ar-43 | 2 | 0 to 4, preferably 1 or 2, more preferably 1 |
|  | Ar-43 | 2 | 0 to 4, preferably 1 or 2, more preferably 1 |
|  | Ar-44 | 0 | 0 to 4, preferably 1 or 2, more preferably 1 |
|  | Ar-44 | 0 | 0 to 4, preferably 1 or 2, more preferably 1 |
|  | Ar-44 | 0 | 0 to 4, preferably 1 or 2, more preferably 1 |
|  | Ar-44 | 0 | 0 to 4, preferably 1 or 2, more preferably 1 |
|  | Ar-44 | 2 | 0 to 4, preferably 1 or 2, more preferably 1 |
|  | Ar-44 | 2 | 0 to 4, preferably 1 or 2, more preferably 1 |
|  | Ar-44 | 2 | 0 to 4, preferably 1 or 2, more preferably 1 |
|  | Ar-44 | 2 | 0 to 4, preferably 1 or 2, more preferably 1 |
| N-2 | Ar-45 | 0 | 0 to 4, preferably 1 or 2, more preferably 1 |
| N-4 | Ar-45 | 0 | 0 to 4, preferably 1 or 2, more preferably 1 |
| N-2 | Ar-45 | 2 | 0 to 2, preferably 1 or 2, more preferably 1 |
| N-4 | Ar-45 | 2 | 0 to 2, preferably 1 or 2, more preferably 1 |
| N-2 | Ar-46 | 0 | 0 to 4, preferably 1 or 2, more preferably 1 |
| N-4 | Ar-46 | 0 | 0 to 4, preferably 1 or 2, more preferably 1 |
| N-2 | Ar-46 | 2 | 0 to 2, preferably 1 or 2, more preferably 1 |
| N-4 | Ar-46 | 2 | 0 to 2, preferably 1 or 2, more preferably 1 |
| N-2 | Ar-47 | 0 | 0 to 4, preferably 1 or 2, more preferably 1 |
| N-4 | Ar-47 | 0 | 0 to 4, preferably 1 or 2, more preferably 1 |
| N-2 | Ar-47 | 2 | 0 to 2, preferably 1 or 2, more preferably 1 |
| N-4 | Ar-47 | 2 | 0 to 2, preferably 1 or 2, more preferably 1 |
| N-2 | Ar-48 | 0 | 0 to 4, preferably 1 or 2, more preferably 1 |
| N-4 | Ar-48 | 0 | 0 to 4, preferably 1 or 2, more preferably 1 |
| N-2 | Ar-48 | 2 | 0 to 2, preferably 1 or 2, more preferably 1 |
| N-4 | Ar-48 | 2 | 0 to 2, preferably 1 or 2, more preferably 1 |
|  | Ar-49 | 0 | 0 to 4, preferably 1 or 2, more preferably 1 |
|  | Ar-49 | 0 | 0 to 4, preferably 1 or 2, more preferably 1 |
|  | Ar-49 | 2 | 0 to 4, preferably 1 or 2, more preferably 1 |
|  | Ar-49 | 2 | 0 to 4, preferably 1 or 2, more preferably 1 |
|  | Ar-50 | 0 | 0 to 4, preferably 1 or 2, more preferably 1 |
|  | Ar-50 | 0 | 0 to 4, preferably 1 or 2, more preferably 1 |
|  | Ar-50 | 2 | 0 to 4, preferably 1 or 2, more preferably 1 |
|  | Ar-50 | 2 | 0 to 4, preferably 1 or 2, more preferably 1 |
|  | Ar-51 | 0 | 0 to 4, preferably 1 or 2, more preferably 1 |
|  | Ar-51 | 0 | 0 to 4, preferably 1 or 2, more preferably 1 |
|  | Ar-51 | 2 | 0 to 4, preferably 1 or 2, more preferably 1 |
|  | Ar-51 | 2 | 0 to 4, preferably 1 or 2, more preferably 1 |
| N-1 | Ar-52 | 0 | 0 to 4, preferably 1 or 2, more preferably 1 |
| N-3 | Ar-52 | 0 | 0 to 4, preferably 1 or 2, more preferably 1 |
| N-5 | Ar-52 | 0 | 0 to 4, preferably 1 or 2, more preferably 1 |
| N-6 | Ar-52 | 0 | 0 to 4, preferably 1 or 2, more preferably 1 |
| N-1 | Ar-52 | 2 | 0 to 2, preferably 1 or 2, more preferably 1 |
| N-3 | Ar-52 | 2 | 0 to 2, preferably 1 or 2, more preferably 1 |
| N-5 | Ar-52 | 2 | 0 to 2, preferably 1 or 2, more preferably 1 |
| N-6 | Ar-52 | 2 | 0 to 2, preferably 1 or 2, more preferably 1 |
| N-1 | Ar-53 | 0 | 0 to 4, preferably 1 or 2, more preferably 1 |
| N-3 | Ar-53 | 0 | 0 to 4, preferably 1 or 2, more preferably 1 |
| N-5 | Ar-53 | 0 | 0 to 4, preferably 1 or 2, more preferably 1 |
| N-6 | Ar-53 | 0 | 0 to 4, preferably 1 or 2, more preferably 1 |
| N-1 | Ar-53 | 2 | 0 to 2, preferably 1 or 2, more preferably 1 |
| N-3 | Ar-53 | 2 | 0 to 2, preferably 1 or 2, more preferably 1 |
| N-5 | Ar-53 | 2 | 0 to 2, preferably 1 or 2, more preferably 1 |
| N-6 | Ar-53 | 2 | 0 to 2, preferably 1 or 2, more preferably 1 |
| N-1 | Ar-54 | 0 | 0 to 4, preferably 1, 2 or 3, more preferably 2 |

| Substructure of the formula | Substructure of the formula | Number of X' groups that are N, where these X groups are nonadjacent | Number of X' groups that are CR¹, where the CR¹ group is not the CH group |
|---|---|---|---|
| N-3 | Ar-54 | 0 | 0 to 4, preferably 1, 2 or 3, more preferably 2 |
| N-5 | Ar-54 | 0 | 0 to 4, preferably 1, 2 or 3, more preferably 2 |
| N-6 | Ar-54 | 0 | 0 to 4, preferably 1, 2 or 3, more preferably 2 |
| N-1 | Ar-54 | 2 | 0 to 2, preferably 1 or 2, more preferably 2 |
| N-3 | Ar-54 | 2 | 0 to 2, preferably 1 or 2, more preferably 2 |
| N-5 | Ar-54 | 2 | 0 to 2, preferably 1 or 2, more preferably 2 |
| N-6 | Ar-54 | 2 | 0 to 2, preferably 1 or 2, more preferably 2 |

The X' groups that are $CR^1$, where the $CR^1$ group is not the CH group, are preferably selected from hole conductor groups and/or electron conductor groups, where the electron conductor groups preferably comprise at least 2 nitrogen atoms in one six-membered ring or in two fused six-membered rings, more preferably selected from triazines and pyrimidines. Preference is further given to groups that promote TADF (thermally activated delayed fluorescence), according to the end use of the compounds of the invention.

Of the compounds set out above, preference is given especially to the compounds having fused, more preferably two-dimensionally fused, aromatic or heteroaromatic ring systems, for example compounds having substructures of the formulae (Ar-2) to (Ar-12), (Ar-19) to (Ar-35) and (Ar-45) to (Ar-54), more preferably (Ar-4) to (Ar-9), (Ar-23) to (Ar-32) and (Ar-46) to (Ar-54), especially preferably (Ar-4), (Ar-5), (Ar-23) to (Ar-25), (Ar-46) and (Ar-49).

In a further embodiment of the present invention, preference is given to compounds comprising fluorene, dibenzofuran, dibenzothiofuran, carbazole, spirobifluorene and similar structures, particularly, for example, compounds having substructures of the formulae (Ar-10) to (Ar-15) and (Ar-33) to (Ar-44), more preferably (Ar-13) to (Ar-15) and (Ar-36) to (Ar-44).

By way of clarity of the above combinations, it should be emphasized that, for example, the combination of a substructure N-1 with a substructure Ar-1 results in a compound of formula (I). Similarly, for example, the combination of a substructure N-2 with a substructure Ar-45 results in a structure of formula (V). The same applies to the further combinations.

It may further be the case that the aromatic or heteroaromatic ring system having 5 to 60 carbon atoms to which an aliphatic polycyclic ring system having at least 3 rings is fused forms a substructure of the formulae (Ar'-1) to (Ar'-65)

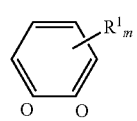
(Ar'-1)

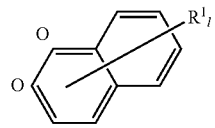
(Ar'-2)

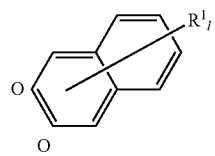
(Ar'-3)

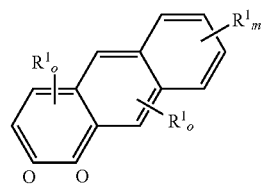
(Ar'-4)

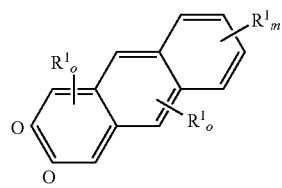
(Ar'-5)

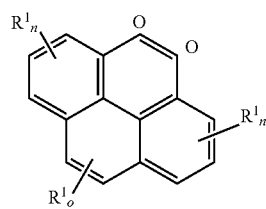
(Ar'-6)

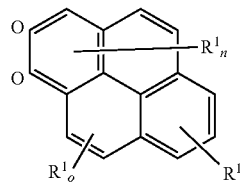
(Ar'-7)

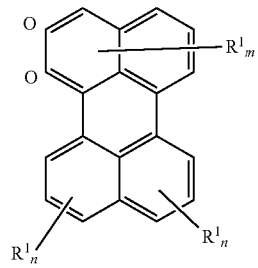
(Ar'-8)

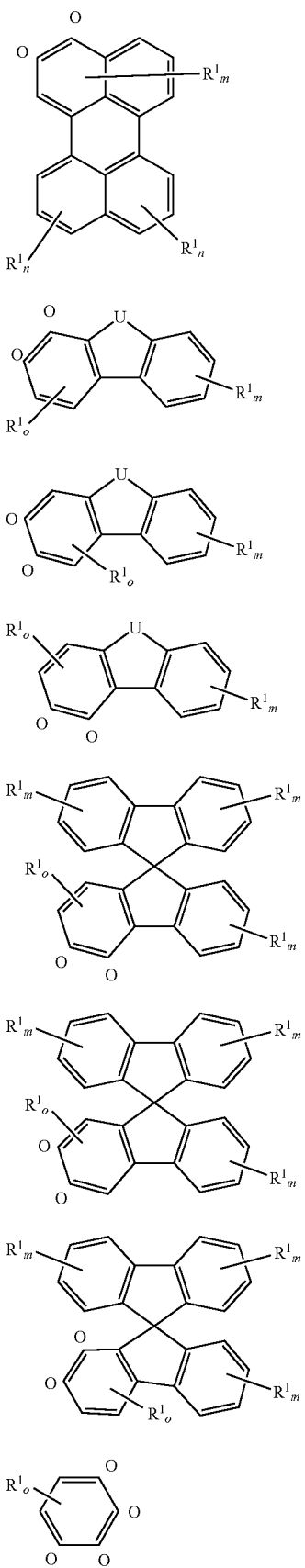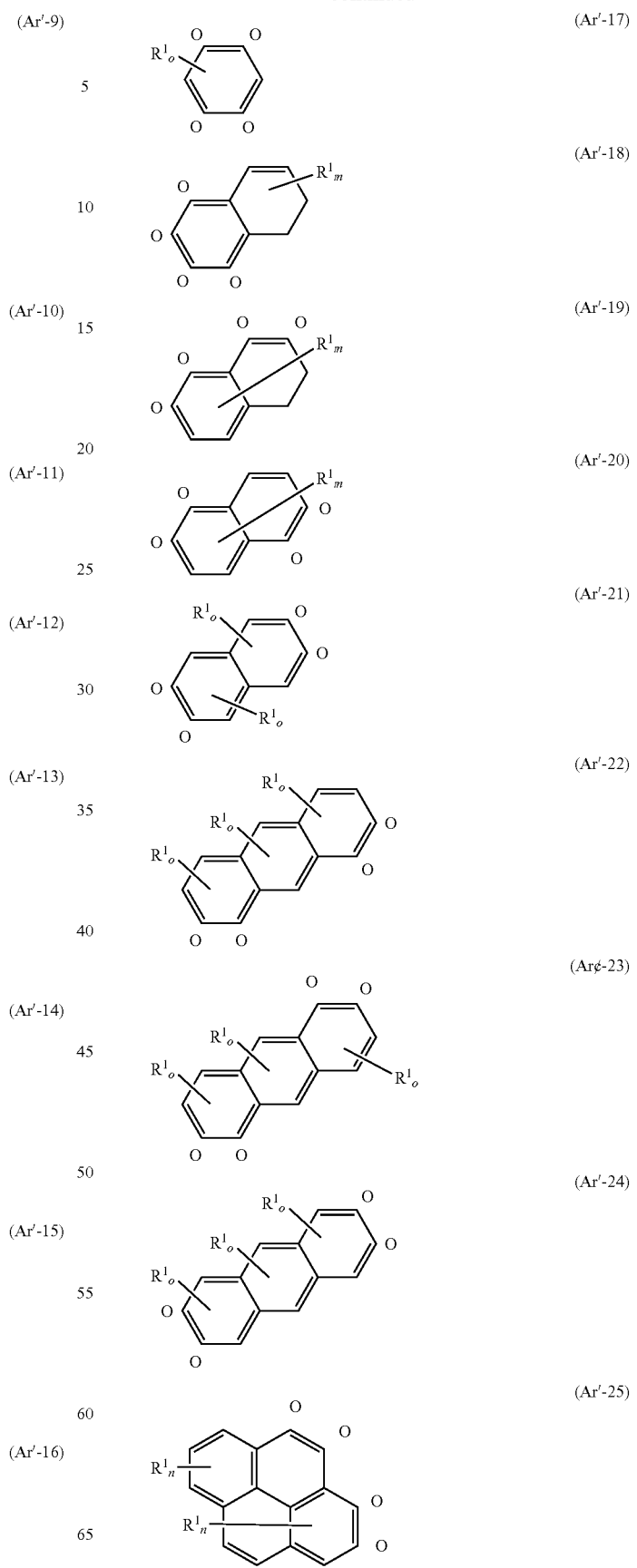

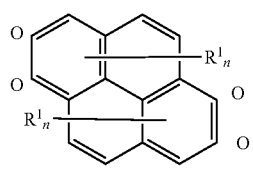
(Ar'-26)
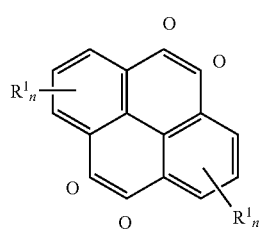
(Ar'-27)
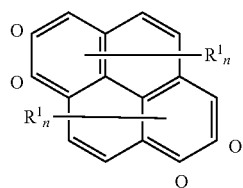
(Ar'-28)
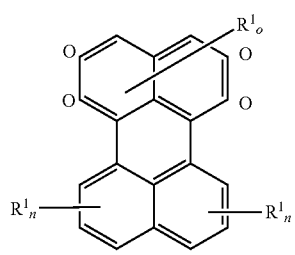
(Ar'-29)
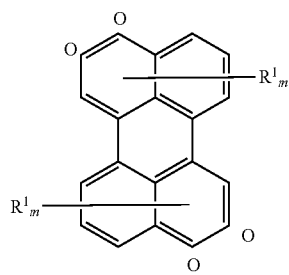
(Ar'-30)
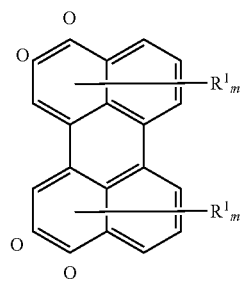
(Ar'-31)
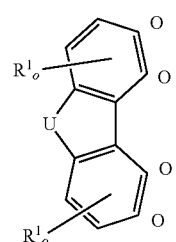
(Ar'-32)
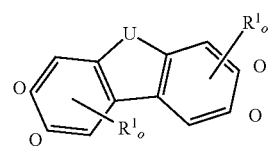
(Ar'-33)
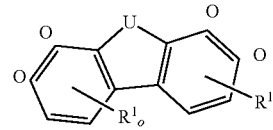
(Ar'-34)
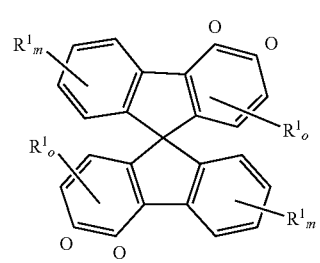
(Ar'-35)
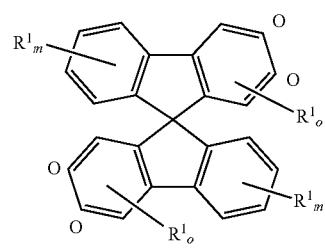
(Ar'-36)
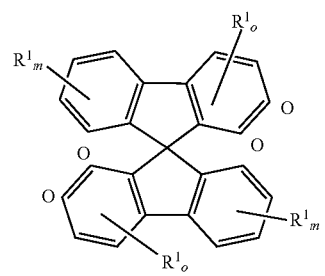
(Ar'-37)
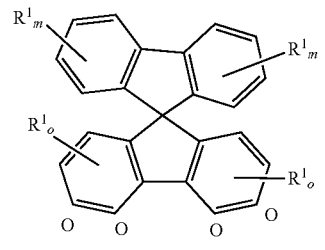
(Ar'-38)

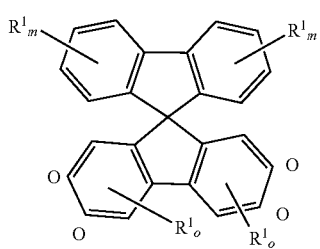
(Ar'-39)
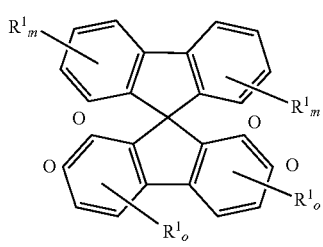
(Ar'-40)
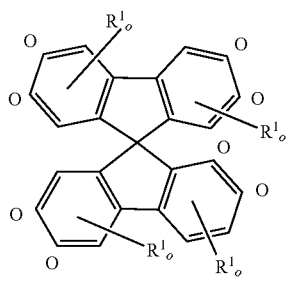
(Ar'-41)
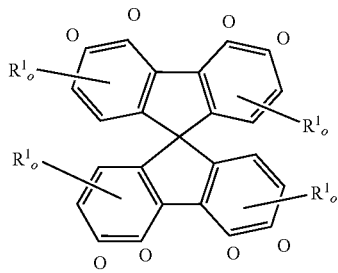
(Ar'-42)
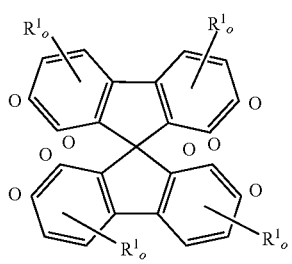
(Ar'-43)
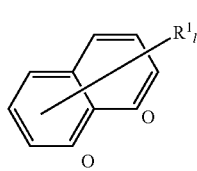
(Ar'-44)
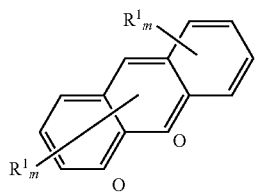
(Ar'-45)
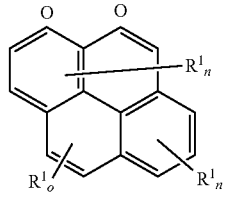
(Ar'-46)
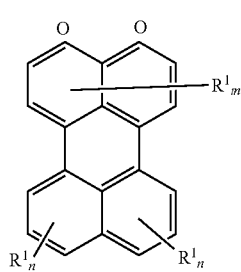
(Ar'-47)
(Ar'-48)
(Ar'-49)
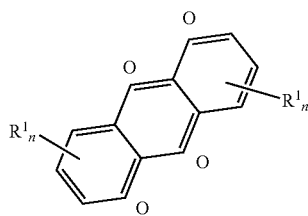
(Ar'-50)
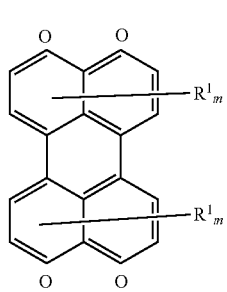
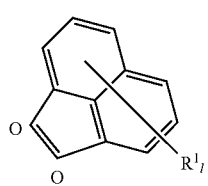
(Ar'-51)

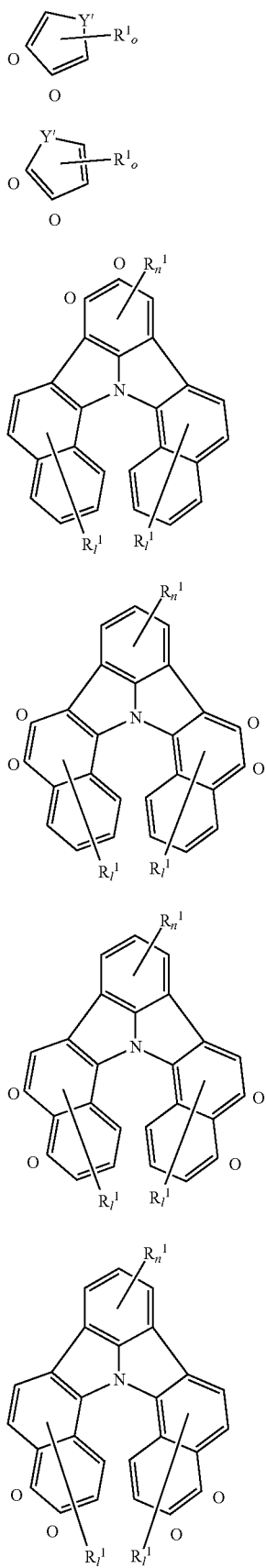
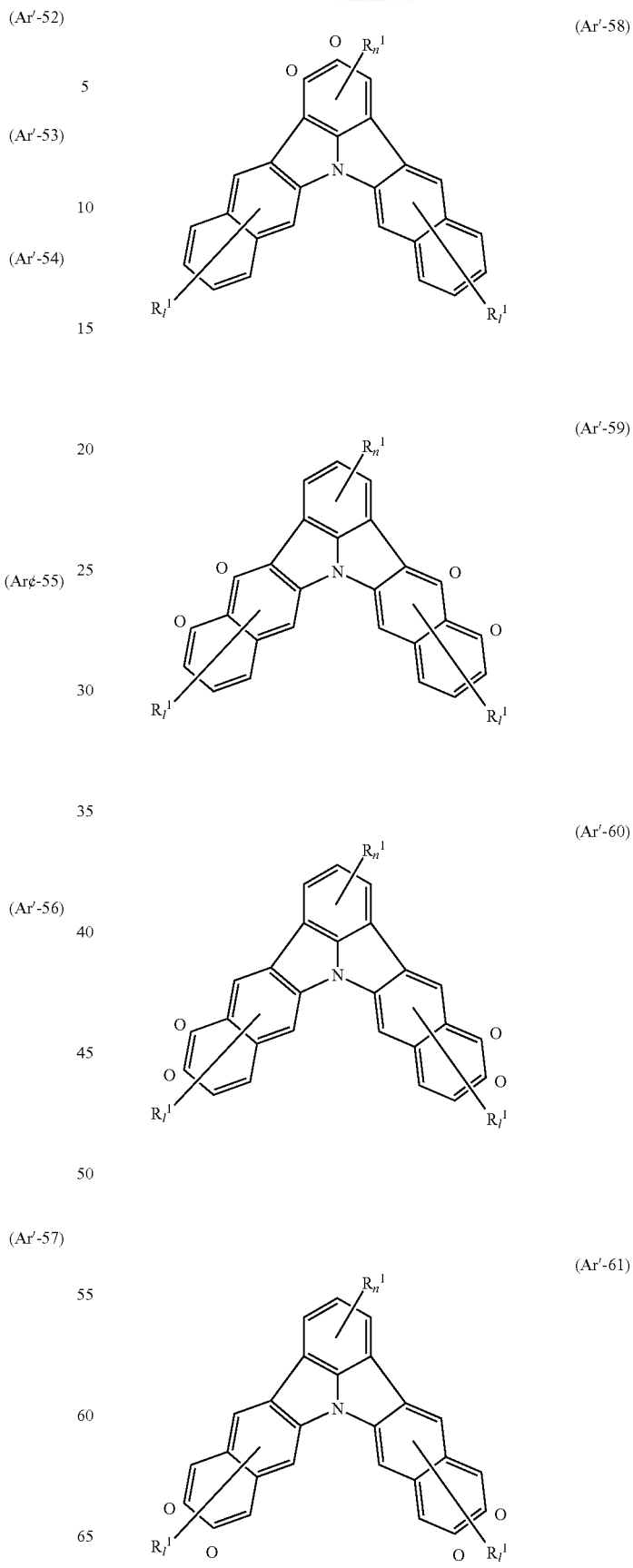

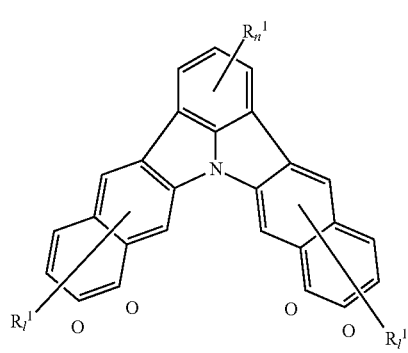
(Ar'-62)

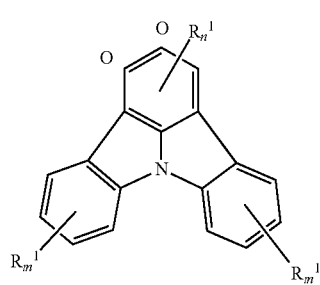
(Ar'-63)

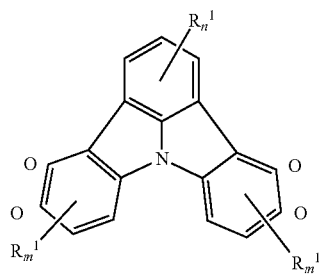
(Ar'-64)

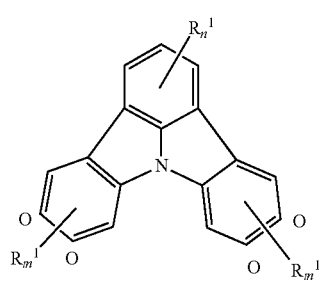
(Ar'-65)

where $R^1$ has the definition given above, especially for formulae (I) to (XVIII), and the symbols Y' and U have the definition given above, especially for formulae (Ar-1) to (Ar-65), the index o is 0, 1 or 2, preferably 0 or 1, the index n is 0, 1, 2 or 3, preferably 0, 1 or 2, and the index m is 0, 1, 2, 3 or 4, preferably 0, 1 or 2, and the index l is 0, 1, 2, 3, 4, 5 or 6, preferably 0, 1 or 2, and the aliphatic polycyclic ring system having at least 3 rings binds to the aromatic or heteroaromatic ring system having 5 to 60 carbon atoms at the respective positions identified by o to form a ring. Preference is given here to structures of the formulae (Ar'-2) to (Ar'-53) and particular preference to structures of the formulae (Ar'-4) to (Ar'-15) and (Ar'-22) to (Ar'-43).

In addition, in the substructures of the formulae (Ar'-1) to (Ar'-65), it may be the case that the sum total of the indices o, n, m and l is not more than 6, preferably not more than 4 and more preferably not more than 2.

Preference is further given to the substructures of the formulae (Ar'-54) to (Ar'-65).

In a preferred embodiment, preference is given inter alia to the combinations according to the following table:

| Substructure of the formula | Substructure of the formula | Index v, t and s in the substructures of the formulae (N-1) to (N-6) | Sum total of the indices o, n, m and l in the substructures of the formulae (Ar'-1) to (Ar'-53) |
|---|---|---|---|
| | N-1 | 0 to 6, preferably 0 to 3, more preferably 0 or 1 | 0 to 4, preferably 1 or 2, more preferably 1 |
| | N-3 | 0 to 6, preferably 0 to 3, more preferably 0 or 1 | 0 to 4, preferably 1 or 2, more preferably 1 |
| | N-5 | 0 to 6, preferably 0 to 3, more preferably 0 or 1 | 0 to 4, preferably 1 or 2, more preferably 1 |
| | N-6 | 0 to 6, preferably 0 to 3, more preferably 0 or 1 | 0 to 4, preferably 1 or 2, more preferably 1 |
| | N-1 | 0 | 0 to 2, preferably 1 or 2, more preferably 1 |
| | N-3 | 0 | 0 to 2, preferably 1 or 2, more preferably 1 |
| | N-5 | 0 | 0 to 2, preferably 1 or 2, more preferably 1 |
| | N-6 | 0 | 0 to 2, preferably 1 or 2, more preferably 1 |
| | N-1 | 0 to 6, preferably 0 to 3, more preferably 0 or 1 | 0 to 4, preferably 1 or 2, more preferably 1 |
| | N-3 | 0 to 6, preferably 0 to 3, more preferably 0 or 1 | 0 to 4, preferably 1 or 2, more preferably 1 |
| | N-5 | 0 to 6, preferably 0 to 3, more preferably 0 or 1 | 0 to 4, preferably 1 or 2, more preferably 1 |
| | N-6 | 0 to 6, preferably 0 to 3, more preferably 0 or 1 | 0 to 4, preferably 1 or 2, more preferably 1 |
| | N-1 | 0 | 0 to 2, preferably 1 or 2, more preferably 1 |
| | N-3 | 0 | 0 to 2, preferably 1 or 2, more preferably 1 |
| | N-5 | 0 | 0 to 2, preferably 1 or 2, more preferably 1 |
| | N-6 | 0 | 0 to 2, preferably 1 or 2, more preferably 1 |
| | N-1 | 0 to 6, preferably 0 to 3, more preferably 0 or 1 | 0 to 4, preferably 1 or 2, more preferably 1 |
| | N-3 | 0 to 6, preferably 0 to 3, more preferably 0 or 1 | 0 to 4, preferably 1 or 2, more preferably 1 |
| | N-5 | 0 to 6, preferably 0 to 3, more preferably 0 or 1 | 0 to 4, preferably 1 or 2, more preferably 1 |
| | N-6 | 0 to 6, preferably 0 to 3, more preferably 0 or 1 | 0 to 4, preferably 1 or 2, more preferably 1 |
| | N-1 | 0 | 0 to 2, preferably 1 or 2, more preferably 1 |
| | N-3 | 0 | 0 to 2, preferably 1 or 2, more preferably 1 |

-continued

| Substructure of the formula | Substructure of the formula | Index v, t and s in the substructures of the formulae (N-1) to (N-6) | Sum total of the indices o, n, m and l in the substructures of the formulae (Ar'-1) to (Ar'-53) |
|---|---|---|---|
| N-5 | | 0 | 0 to 2, preferably 1 or 2, more preferably 1 |
| N-6 | | 0 | 0 to 2, preferably 1 or 2, more preferably 1 |
| N-1 | | 0 to 6, preferably 0 to 3, more preferably 0 or 1 | 0 to 4, preferably 1 to 3, more preferably 2 |
| N-3 | | 0 to 6, preferably 0 to 3, more preferably 0 or 1 | 0 to 4, preferably 1 to 3, more preferably 2 |
| N-5 | | 0 to 6, preferably 0 to 3, more preferably 0 or 1 | 0 to 4, preferably 1 to 3, more preferably 2 |
| N-6 | | 0 to 6, preferably 0 to 3, more preferably 0 or 1 | 0 to 4, preferably 1 to 3, more preferably 2 |
| N-1 | | 0 | 0 to 3, preferably 1, 2 or 3, more preferably 2 |
| N-3 | | 0 | 0 to 3, preferably 1, 2 or 3, more preferably 2 |
| N-5 | | 0 | 0 to 3, preferably 1, 2 or 3, more preferably 2 |
| N-6 | | 0 | 0 to 3, preferably 1, 2 or 3, more preferably 2 |
| N-1 | | 0 to 6, preferably 0 to 3, more preferably 0 or 1 | 0 to 4, preferably 1 to 3, more preferably 2 |
| N-3 | | 0 to 6, preferably 0 to 3, more preferably 0 or 1 | 0 to 4, preferably 1 to 3, more preferably 2 |
| N-5 | | 0 to 6, preferably 0 to 3, more preferably 0 or 1 | 0 to 4, preferably 1 to 3, more preferably 2 |
| N-6 | | 0 to 6, preferably 0 to 3, more preferably 0 or 1 | 0 to 4, preferably 1 to 3, more preferably 2 |
| N-1 | | 0 | 0 to 3, preferably 1, 2 or 3, more preferably 2 |
| N-3 | | 0 | 0 to 3, preferably 1, 2 or 3, more preferably 2 |
| N-5 | | 0 | 0 to 3, preferably 1, 2 or 3, more preferably 2 |
| N-6 | | 0 | 0 to 3, preferably 1, 2 or 3, more preferably 2 |
| N-1 | | 0 to 6, preferably 0 to 3, more preferably 0 or 1 | 0 to 4, preferably 1 or 2, more preferably 1 |
| N-3 | | 0 to 6, preferably 0 to 3, more preferably 0 or 1 | 0 to 4, preferably 1 or 2, more preferably 1 |
| N-5 | | 0 to 6, preferably 0 to 3, more preferably 0 or 1 | 0 to 4, preferably 1 or 2, more preferably 1 |
| N-6 | | 0 to 6, preferably 0 to 3, more preferably 0 or 1 | 0 to 4, preferably 1 or 2, more preferably 1 |
| N-1 | | 0 | 0 to 2, preferably 1 or 2, more preferably 1 |
| N-3 | | 0 | 0 to 2, preferably 1 or 2, more preferably 1 |
| N-5 | | 0 | 0 to 2, preferably 1 or 2, more preferably 1 |
| N-6 | | 0 | 0 to 2, preferably 1 or 2, more preferably 1 |
| N-1 | | 0 to 6, preferably 0 to 3, more preferably 0 or 1 | 0 to 4, preferably 1 or 2, more preferably 1 |
| N-3 | | 0 to 6, preferably 0 to 3, more preferably 0 or 1 | 0 to 4, preferably 1 or 2, more preferably 1 |
| N-5 | | 0 to 6, preferably 0 to 3, more preferably 0 or 1 | 0 to 4, preferably 1 or 2, more preferably 1 |
| N-6 | | 0 to 6, preferably 0 to 3, more preferably 0 or 1 | 0 to 4, preferably 1 or 2, more preferably 1 |
| N-1 | | 0 | 0 to 2, preferably 1 or 2, more preferably 1 |
| N-3 | | 0 | 0 to 2, preferably 1 or 2, more preferably 1 |
| N-5 | | 0 | 0 to 2, preferably 1 or 2, more preferably 1 |
| N-6 | | 0 | 0 to 2, preferably 1 or 2, more preferably 1 |
| N-1 | | 0 to 6, preferably 0 to 3, more preferably 0 or 1 | 0 to 4, preferably 1 or 2, more preferably 1 |
| N-3 | | 0 to 6, preferably 0 to 3, more preferably 0 or 1 | 0 to 4, preferably 1 or 2, more preferably 1 |
| N-5 | | 0 to 6, preferably 0 to 3, more preferably 0 or 1 | 0 to 4, preferably 1 or 2, more preferably 1 |
| N-6 | | 0 to 6, preferably 0 to 3, more preferably 0 or 1 | 0 to 4, preferably 1 or 2, more preferably 1 |
| N-1 | | 0 | 0 to 2, preferably 1 or 2, more preferably 1 |
| N-3 | | 0 | 0 to 2, preferably 1 or 2, more preferably 1 |
| N-5 | | 0 | 0 to 2, preferably 1 or 2, more preferably 1 |

| Substructure of the formula | Substructure of the formula | Index v, t and s in the substructures of the formulae (N-1) to (N-6) | Sum total of the indices o, n, m and l in the substructures of the formulae (Ar'-1) to (Ar'-53) |
|---|---|---|---|
| N-6 | | 0 | 0 to 2, preferably 1 or 2, more preferably 1 |
| N-1 | | 0 to 6, preferably 0 to 3, more preferably 0 or 1 | 0 to 4, preferably 1 or 2, more preferably 1 |
| N-3 | | 0 to 6, preferably 0 to 3, more preferably 0 or 1 | 0 to 4, preferably 1 or 2, more preferably 1 |
| N-5 | | 0 to 6, preferably 0 to 3, more preferably 0 or 1 | 0 to 4, preferably 1 or 2, more preferably 1 |
| N-6 | | 0 to 6, preferably 0 to 3, more preferably 0 or 1 | 0 to 4, preferably 1 or 2, more preferably 1 |
| N-1 | | 0 | 0 to 2, preferably 1 or 2, more preferably 1 |
| N-3 | | 0 | 0 to 2, preferably 1 or 2, more preferably 1 |
| N-5 | | 0 | 0 to 2, preferably 1 or 2, more preferably 1 |
| N-6 | | 0 | 0 to 2, preferably 1 or 2, more preferably 1 |
| N-1 | | 0 to 6, preferably 0 to 3, more preferably 0 or 1 | 0 to 4, preferably 1 or 2, more preferably 1 |
| N-3 | | 0 to 6, preferably 0 to 3, more preferably 0 or 1 | 0 to 4, preferably 1 or 2, more preferably 1 |
| N-5 | | 0 to 6, preferably 0 to 3, more preferably 0 or 1 | 0 to 4, preferably 1 or 2, more preferably 1 |
| N-6 | | 0 to 6, preferably 0 to 3, more preferably 0 or 1 | 0 to 4, preferably 1 or 2, more preferably 1 |
| N-1 | | 0 | 0 to 2, preferably 1 or 2, more preferably 1 |
| N-3 | | 0 | 0 to 2, preferably 1 or 2, more preferably 1 |
| N-5 | | 0 | 0 to 2, preferably 1 or 2, more preferably 1 |
| N-6 | | 0 | 0 to 2, preferably 1 or 2, more preferably 1 |
| N-1 | | 0 to 6, preferably 0 to 3, more preferably 0 or 1 | 0 to 4, preferably 1 or 2, more preferably 1 |
| N-3 | | 0 to 6, preferably 0 to 3, more preferably 0 or 1 | 0 to 4, preferably 1 or 2, more preferably 1 |
| N-5 | | 0 to 6, preferably 0 to 3, more preferably 0 or 1 | 0 to 4, preferably 1 or 2, more preferably 1 |
| N-6 | | 0 to 6, preferably 0 to 3, more preferably 0 or 1 | 0 to 4, preferably 1 or 2, more preferably 1 |
| N-1 | | 0 | 0 to 2, preferably 1 or 2, more preferably 1 |
| N-3 | | 0 | 0 to 2, preferably 1 or 2, more preferably 1 |
| N-5 | | 0 | 0 to 2, preferably 1 or 2, more preferably 1 |
| N-6 | | 0 | 0 to 2, preferably 1 or 2, more preferably 1 |

| Substructure of the formula | Substructure of the formula | Index v, t and s in the substructures of the formulae (N-1) to (N-6) | Sum total of the indices o, n, m and l in the substructures of the formulae (Ar'-1) to (Ar'-53) | Substructure of the formula | Substructure of the formula | Index v, t and s in the substructures of the formulae (N-1) to (N-6) | Sum total of the indices o, n, m and l in the substructures of the formulae (Ar'-1) to (Ar'-53) |
|---|---|---|---|---|---|---|---|
| | | 0 to 6, preferably 0 to 3, more preferably 0 or 1 | 0 to 2, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 2, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 2, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 2, preferably 1 or 2, more preferably 1 | | | 0 to 6, preferably 0 to 3, more preferably 0 or 1 | 0 to 4, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 to 6, preferably 0 to 3, more preferably 0 or 1 | 0 to 2, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 2, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 2, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 2, preferably 1 or 2, more preferably 1 | | | 0 to 6, preferably 0 to 3, more preferably 0 or 1 | 0 to 4, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |

| Substructure of the formula | Substructure of the formula | Index v, t and s in the substructures of the formulae (N-1) to (N-6) | Sum total of the indices o, n, m and l in the substructures of the formulae (Ar'-1) to (Ar'-53) | Substructure of the formula | Substructure of the formula | Index v, t and s in the substructures of the formulae (N-1) to (N-6) | Sum total of the indices o, n, m and l in the substructures of the formulae (Ar'-1) to (Ar'-53) |
|---|---|---|---|---|---|---|---|
| | | 0 to 6, preferably 0 to 3, more preferably 0 or 1 | 0 to 4, preferably 1 to 3, more preferably 2 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 to 3, more preferably 2 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 to 3, more preferably 2 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 to 3, more preferably 2 | | | 0 to 6, preferably 0 to 3, more preferably 0 or 1 | 0 to 4, preferably 1 or 2, more preferably 1 |
| | | 0 | 0 to 3, preferably 1, 2 or 3, more preferably 2 | | | 0 | 0 to 2, preferably 1 or 2, more preferably 1 |
| | | 0 | 0 to 3, preferably 1, 2 or 3, more preferably 2 | | | 0 | 0 to 2, preferably 1 or 2, more preferably 1 |
| | | 0 | 0 to 3, preferably 1, 2 or 3, more preferably 2 | | | 0 | 0 to 2, preferably 1 or 2, more preferably 1 |
| | | 0 | 0 to 3, preferably 1, 2 or 3, more preferably 2 | | | 0 | 0 to 2, preferably 1 or 2, more preferably 1 |
| | | 0 to 6, preferably 0 to 3, more preferably 0 or 1 | 0 to 4, preferably 1 to 3, more preferably 2 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 to 3, more preferably 2 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 to 3, more preferably 2 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 to 3, more preferably 2 | | | 0 to 6, preferably 0 to 3, more preferably 0 or 1 | 0 to 4, preferably 1 or 2, more preferably 1 |
| | | 0 | 0 to 3, preferably 1, 2 or 3, more preferably 2 | | | 0 | 0 to 2, preferably 1 or 2, more preferably 1 |
| | | 0 | 0 to 3, preferably 1, 2 or 3, more preferably 2 | | | 0 | 0 to 2, preferably 1 or 2, more preferably 1 |
| | | 0 | 0 to 3, preferably 1, 2 or 3, more preferably 2 | | | 0 | 0 to 2, preferably 1 or 2, more preferably 1 |
| | | 0 | 0 to 3, preferably 1, 2 or 3, more preferably 2 | | | 0 | 0 to 2, preferably 1 or 2, more preferably 1 |
| | | 0 to 6, preferably 0 to 3, more preferably 0 or 1 | 0 to 4, preferably 1 to 3, more preferably 2 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 to 3, more preferably 2 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 to 3, more preferably 2 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 to 3, more preferably 2 | | | 0 to 6, preferably 0 to 3, more preferably 0 or 1 | 0 to 4, preferably 1 or 2, more preferably 1 |
| | | 0 | 0 to 3, preferably 1, 2 or 3, more preferably 2 | | | 0 | 0 to 2, preferably 1 or 2, more preferably 1 |
| | | 0 | 0 to 3, preferably 1, 2 or 3, more preferably 2 | | | 0 | 0 to 2, preferably 1 or 2, more preferably 1 |
| | | 0 | 0 to 3, preferably 1, 2 or 3, more preferably 2 | | | 0 | 0 to 2, preferably 1 or 2, more preferably 1 |
| | | 0 | 0 to 3, preferably 1, 2 or 3, more preferably 2 | | | 0 | 0 to 2, preferably 1 or 2, more preferably 1 |

-continued

| Substructure of the formula | Substructure of the formula | Index v, t and s in the substructures of the formulae (N-1) to (N-6) | Sum total of the indices o, n, m and l in the substructures of the formulae (Ar'-1) to (Ar'-53) |
|---|---|---|---|
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 | 0 to 2, preferably 1 or 2, more preferably 1 |

| Substructure of the formula | Substructure of the formula | Index v, t and s in the substructures of the formulae (N-1) to (N-6) | Sum total of the indices o, n, m and l in the substructures of the formulae (Ar'-1) to (Ar'-53) | Substructure of the formula | Substructure of the formula | Index v, t and s in the substructures of the formulae (N-1) to (N-6) | Sum total of the indices o, n, m and l in the substructures of the formulae (Ar'-1) to (Ar'-53) |
|---|---|---|---|---|---|---|---|
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 | | | 0 to 6, preferably 0 to 3, more preferably 0 or 1 | 0 to 4, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |
| | | 0 | 0 to 2, preferably 1 or 2, more preferably 1 | | | 0 | 0 to 2, preferably 1 or 2, more preferably 1 |

-continued

| Substructure of the formula | Substructure of the formula | Index v, t and s in the substructures of the formulae (N-1) to (N-6) | Sum total of the indices o, n, m and l in the substructures of the formulae (Ar'-1) to (Ar'-53) |
|---|---|---|---|
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 | 0 to 2, preferably 1 or 2, more preferably 1 |
| N-2 | | 0 to 6, preferably 0 to 3, more preferably 0 or 1 | 0 to 4, preferably 1 or 2, more preferably 1 |
| N-4 | | 0 to 6, preferably 0 to 3, more preferably 0 or 1 | 0 to 4, preferably 1 or 2, more preferably 1 |
| N-2 | | 0 to 6, preferably 0 to 3, more preferably 0 or 1 | 0 to 4, preferably 1 or 2, more preferably 1 |
| N-4 | | 0 | 0 to 2, preferably 1 or 2, more preferably 1 |
| N-2 | | 0 | 0 to 2, preferably 1 or 2, more preferably 1 |
| N-4 | | 0 to 6, preferably 0 to 3, more preferably 0 or 1 | 0 to 4, preferably 1 or 2, more preferably 1 |
| N-2 | | 0 to 6, preferably 0 to 3, more preferably 0 or 1 | 0 to 4, preferably 1 or 2, more preferably 1 |
| N-4 | | 0 | 0 to 2, preferably 1 or 2, more preferably 1 |

| Substructure of the formula | Substructure of the formula | Index v, t and s in the substructures of the formulae (N-1) to (N-6) | Sum total of the indices o, n, m and l in the substructures of the formulae (Ar'-1) to (Ar'-53) |
|---|---|---|---|
| N-2 | | 0 to 6, preferably 0 to 3, more preferably 0 or 1 | 0 to 4, preferably 1 or 2, more preferably 1 |
| N-4 | | 0 to 6, preferably 0 to 3, more preferably 0 or 1 | 0 to 4, preferably 1 or 2, more preferably 1 |
| N-2 | | 0 | 0 to 2, preferably 1 or 2, more preferably 1 |
| N-4 | | 0 | 0 to 2, preferably 1 or 2, more preferably 1 |
| N-2 | | 0 to 6, preferably 0 to 3, more preferably 0 or 1 | 0 to 4, preferably 1 or 2, more preferably 1 |
| N-4 | | 0 to 6, preferably 0 to 3, more preferably 0 or 1 | 0 to 4, preferably 1 or 2, more preferably 1 |
| N-2 | | 0 | 0 to 2, preferably 1 or 2, more preferably 1 |
| N-4 | | 0 | 0 to 2, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 | 0 to 2, preferably 1 or 2, more preferably 1 |
| | | 0 | 0 to 2, preferably 1 or 2, more preferably 1 |
| | | 0 to 6, preferably 0 to 3, more preferably 0 or 1 | 0 to 4, preferably 1 or 2, more preferably 1 |
| | | 0 to 6, preferably 0 to 3, more preferably 0 or 1 | 0 to 4, preferably 1 or 2, more preferably 1 |
| | | 0 | 0 to 2, preferably 1 or 2, more preferably 1 |
| | | 0 | 0 to 2, preferably 1 or 2, more preferably 1 |
| N-1 | | 0 to 6, preferably 0 to 3, more preferably 0 or 1 | 0 to 4, preferably 1 or 2, more preferably 1 |
| N-3 | | 0 to 6, preferably 0 to 3, more preferably 0 or 1 | 0 to 4, preferably 1 or 2, more preferably 1 |
| N-5 | | 0 to 6, preferably 0 to 3, more preferably 0 or 1 | 0 to 4, preferably 1 or 2, more preferably 1 |
| N-6 | | 0 to 6, preferably 0 to 3, more preferably 0 or 1 | 0 to 4, preferably 1 or 2, more preferably 1 |
| N-1 | | 0 | 0 to 2, preferably 1 or 2, more preferably 1 |
| N-3 | | 0 | 0 to 2, preferably 1 or 2, more preferably 1 |
| N-5 | | 0 | 0 to 2, preferably 1 or 2, more preferably 1 |
| N-6 | | 0 | 0 to 2, preferably 1 or 2, more preferably 1 |
| N-1 | | 0 to 6, preferably 0 to 3, more preferably 0 or 1 | 0 to 4, preferably 1 or 2, more preferably 1 |
| N-3 | | 0 to 6, preferably 0 to 3, more preferably 0 or 1 | 0 to 4, preferably 1 or 2, more preferably 1 |
| N-5 | | 0 to 6, preferably 0 to 3, more preferably 0 or 1 | 0 to 4, preferably 1 or 2, more preferably 1 |
| N-6 | | 0 to 6, preferably 0 to 3, more preferably 0 or 1 | 0 to 4, preferably 1 or 2, more preferably 1 |
| N-1 | | 0 | 0 to 2, preferably 1 or 2, more preferably 1 |
| N-3 | | 0 | 0 to 2, preferably 1 or 2, more preferably 1 |
| N-5 | | 0 | 0 to 2, preferably 1 or 2, more preferably 1 |
| N-6 | | 0 | 0 to 2, preferably 1 or 2, more preferably 1 |

The R$^1$ group in the above combinations, where the R$^1$ group is not the H group, are preferably selected from hole conductor groups and/or electron conductor groups, where the electron conductor groups preferably comprise at least 2 nitrogen atoms in one six-membered ring or in two fused six-membered rings, more preferably selected from triazines and pyrimidines. Preference is further given to groups that promote TADF (thermally activated delayed fluorescence), according to the end use of the compounds of the invention.

Of the compounds set out above, preference is given especially to the compounds having fused, more preferably two-dimensionally fused, aromatic or heteroaromatic ring systems, for example compounds having substructures of the formulae (Ar'-2) to (Ar'-12), (Ar'-18) to (Ar'-34) and (Ar'-44) to (Ar'-53), more preferably (Ar'-4) to (Ar'-9), (Ar'-22) to (Ar'-31) and (Ar'-45) to (Ar'-53), especially preferably (Ar'-4), (Ar'-5), (Ar'-22) to (Ar'-24), (Ar'-45) and (Ar'-48).

In a further embodiment of the present invention, preference is given to compounds comprising fluorene, dibenzofuran, dibenzothiofuran, carbazole, spirobifluorene and similar structures, particularly, for example, compounds having substructures of the formulae (Ar'-10) to (Ar'-15) and (Ar'-32) to (Ar'-43), more preferably (Ar'-13) to (Ar'-15) and (Ar'-35) to (Ar'-43).

In a further configuration, it may be the case that the compound usable as active compound an organic electronic device comprises a fused aromatic or heteroaromatic ring system having at least 2, preferably three, fused rings that may optionally be substituted.

In a further embodiment, it may be the case that the compound usable as active compound in an organic electronic device comprises a hole transport group, where, preferably, in a structure of the formulae (I) to (XVIII) and/or the formulae (Ia) to (XVIIIa), the Ar group present in a Y group or an R group comprises and preferably represents a hole transport group, or, in a structure of the formulae (N-1) to (N-6), (Ar-1) to (Ar-54) and/or (Ar'-1) to (Ar'-53), an $R^1$ group comprises and preferably represents a hole transport group. Hole transport groups are known in the technical field, and they preferably include triarylamine or carbazole groups.

It may preferably be the case that the hole transport group comprises a group and preferably is a group selected from the formulae (H-1) to (H-3)

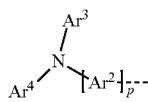

Formula (H-1)

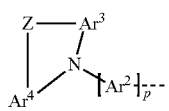

Formula (H-2)

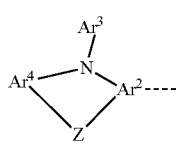

Formula (H-3)

where the dotted bond marks the position of attachment and $Ar^2$, $Ar^3$, $Ar^4$ are each independently an aryl group having 6 to 40 carbon atoms or a heteroaryl group having 3 to 40 carbon atoms, each of which may be substituted by one or more $R^1$ radicals;

p is 0 or 1, and

Z is a bond or $C(R^1)_2$, $Si(R^1)_2$, C=O, N—$R^1$, N—$Ar^1$, $BR^1$, $PR^1$, $PO(R^1)$, SO, $SO_2$, Se, O or S, preferably a bond or $C(R^1)_2$, N—$R^1$, O or S, where the symbols $Ar^1$ and $R^1$ have the definition given above, especially for formulae (I) to (XVIII). The substituents $R^1$ here in the structures of the formulae (H-1) to (H-3) should be replaced in structures of formulae (N-1) to (N-6), (Ar-1) to (Ar-54) and/or (Ar'-1) to (Ar'-53) by substituents $R^2$. In addition, the presence of an N—N bond is preferably ruled out.

It may additionally be the case that the hole transport group comprises a group and preferably is a group selected from the formulae (H-4) to (H-26)

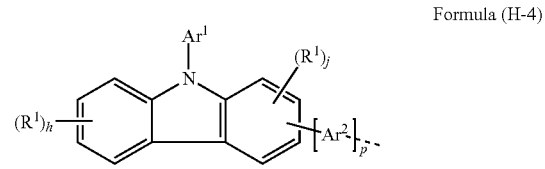

Formula (H-4)

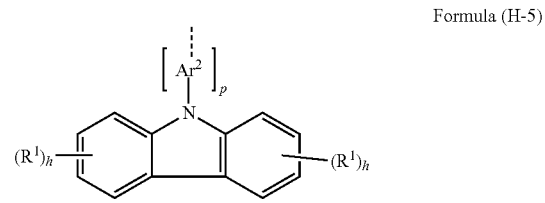

Formula (H-5)


Formula (H-6)


Formula (H-7)

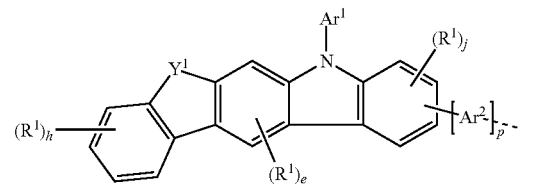

Formula (H-8)

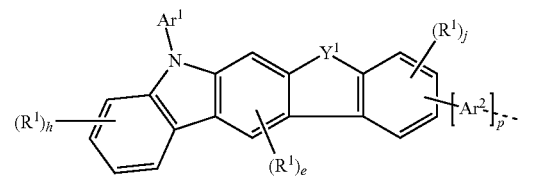

Formula (H-9)

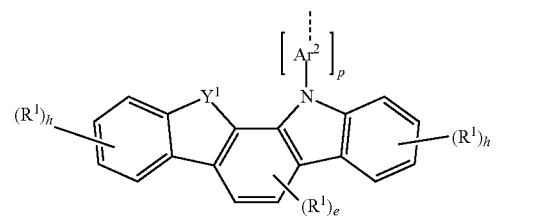

Formula (H-10)

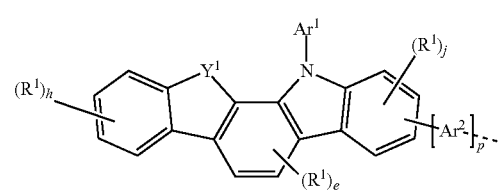

Formula (H-11)
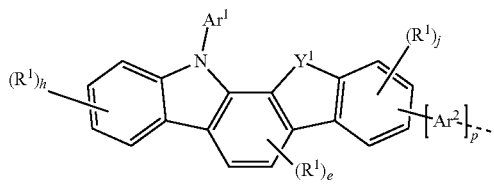
Formula (H-12)
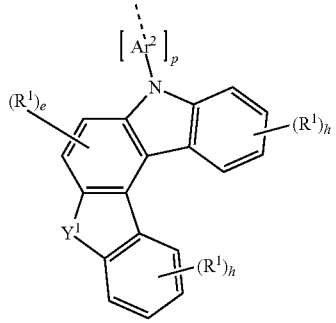
Formula (H-13)
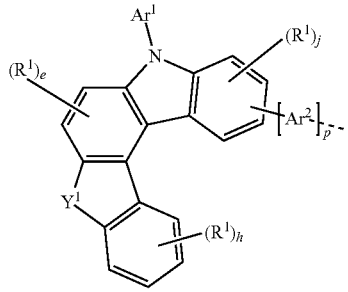
Formula (H-14)
Formula (H-15)
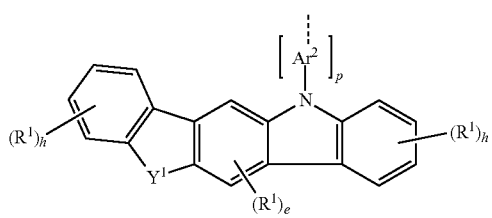
Formula (H-16)
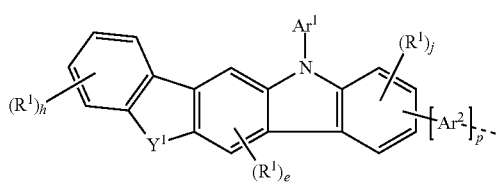
Formula (H-17)
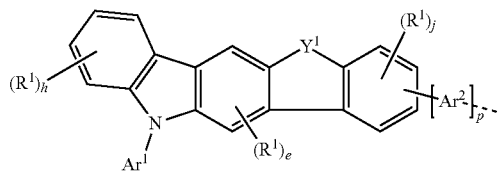
Formula (H-18)
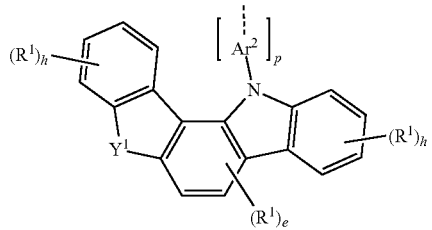
Formula (H-19)
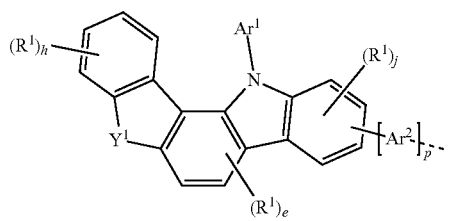
Formula (H-20)
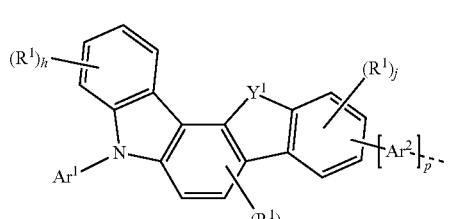
Formula (H-21)
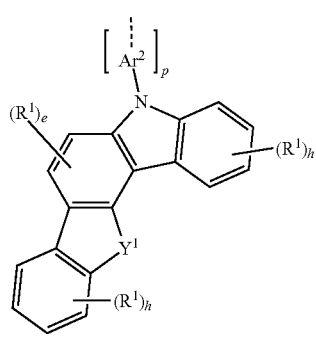
Formula (H-22)
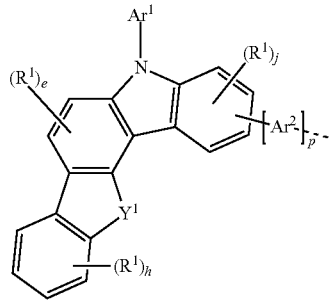

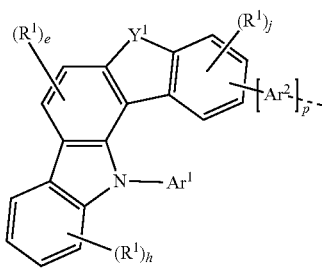

Formula (H-23)

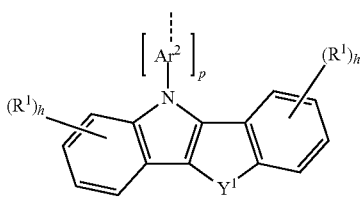

Formula (H-24)

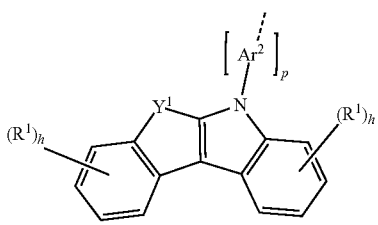

Formula (H-25)

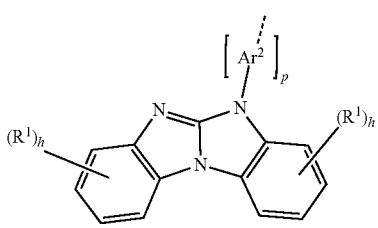

Formula (H-26)

where $Y^1$ is O, S, $C(R^1)_2$, $NR^1$ or $NAr^1$, the dotted bond marks the position of attachment, e is 0, 1 or 2, j is 0, 1, 2 or 3, h is the same or different at each instance and is 0, 1, 2, 3 or 4, p is 0 or 1, $Ar^1$ and $R^1$ have the definitions given above, especially for formulae (I) to (XVIII), and $Ar^2$ has the definitions given above, especially for formula (H-1) or (H-2). The substituents $R^1$ here in the structures of the formulae (H-3) to (H-26) should be replaced in structures of formulae (N-1) to (N-6), (Ar-1) to (Ar-54) and/or (Ar'-1) to (Ar'-53) by substituents $R^2$. In addition, the presence of an N—N bond is preferably ruled out.

The hole transport groups of the formulae (H-1) to (H-26) detailed above constitute preferred $R^1$ radicals of formulae (I) to (XVIII) or preferred embodiments of this formula, where in this case the $R^1$ groups detailed in the formulae (H-1) to (H-26) should be replaced by $R^2$ radicals.

It is clear from the above wording that, if the index is p=0, the corresponding $Ar^2$ group is absent and a bond is formed.

Preferably, the $Ar^2$ group may form through-conjugation with the aromatic or heteroaromatic radical or the nitrogen atom to which the $Ar^2$ group of the formulae (H-1) to (H-26) may be bonded.

In a further preferred embodiment of the invention, $Ar^2$ is an aromatic or heteroaromatic ring system which has 5 to 14 aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formulae (I) to (XVIII). More preferably, $Ar^2$ is an aromatic ring system having 6 to 10 aromatic ring atoms or a heteroaromatic ring system having 6 to 13 heteroaromatic ring atoms, each of which may be substituted by one or more $R^1$ radicals, but is preferably unsubstituted, where $R^1$ may have the definition given above, especially for formulae (I) to (XVIII).

Further preferably, the symbol $Ar^2$ shown in formulae (H-1) to (H-26) inter alia is an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded to the respective atom of the further group directly, i.e. via an atom of the aromatic or heteroaromatic group.

It may further be the case that the $Ar^2$ group shown in formulae (H-1) to (H-26) comprises an aromatic ring system having not more than two fused aromatic and/or heteroaromatic 6-membered rings; preferably it does not comprise any fused aromatic or heteroaromatic ring system with fused 6-membered rings. Accordingly, naphthyl structures are preferred over anthracene structures. In addition, fluorenyl, spirobifluorenyl, dibenzofuranyl and/or dibenzothienyl structures are preferred over naphthyl structures. Particular preference is given to structures having no fusion, for example phenyl, biphenyl, terphenyl and/or quaterphenyl structures.

It may further be the case that the $Ar^2$ group shown in formulae (H-1) to (H-26) inter alia has not more than 1 nitrogen atom, preferably not more than 2 heteroatoms, particularly preferably not more than one heteroatom and especially preferably no heteroatom.

In a further preferred embodiment of the invention, $Ar^3$ and/or $Ar^4$ are the same or different at each instance and are an aromatic or heteroaromatic ring system having 6 to 24 aromatic ring atoms, preferably 6 to 18 aromatic ring atoms, and are more preferably an aromatic ring system having 6 to 12 aromatic ring atoms or a heteroaromatic ring system having 6 to 13 aromatic ring atoms, each of which may be substituted by one or more $R^1$ radicals, but is preferably unsubstituted, where $R^1$ may have the definition given above, especially in formulae (I) to (XVIII).

In a further preferred embodiment, it may be the case that a compound usable as active compound in an organic electronic device comprises an electron transport group-comprising radical, where, preferably, in a structure of the formulae (I) to (XVIII) and/or the formulae (Ia) to (XVIIIa), the Ar group present in a Y group or an R group comprises and preferably represents an electron transport group-comprising radical, or, in a structure of the formulae (N-1) to (N-6), (Ar-1) to (Ar-54) and/or (Ar'-1) to (Ar'-53), an $R^1$ group comprises and preferably represents an electron transport group-comprising radical. Electron transport groups are widely known in the technical field and promote the ability of compounds to transport and/or conduct electrons.

In addition, surprising advantages are shown by compounds usable as active compound in an organic electronic device that comprise at least one structure selected from the group of the pyridines, pyrimidines, pyrazines, pyridazines, triazines, quinazolines, quinoxalines, quinolines, isoquinolines, imidazoles and/or benzimidazoles, particular preference being given to pyrimidines, triazines and quinazolines. These structures generally promote the ability of compounds to transport and/or to conduct electrons.

In a preferred configuration of the present invention, it may be the case that the electron transport group-comprising radical is a group that can be represented by the formula (QL)

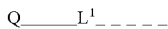   Formula (QL)

in which $L^1$ represents a bond or an aromatic or heteroaromatic ring system which has 5 to 40, preferably 5 to 30, aromatic ring atoms and may be substituted by one or more $R^1$ radicals, Q is an electron transport group, where $R^1$ has the definition given above, especially for formulae (I) to (XVIII), and the bond marks the position of attachment. The substituents $R^1$ here in the structure of the formula (QL) should be replaced in structures of formulae (N-1) to (N-6), (Ar-1) to (Ar-54) and/or (Ar'-1) to (Ar'-53) by substituents $R^2$.

Preferably, the $L^1$ group may form through-conjugation with the Q group and the atom, preferably the carbon or nitrogen atom, to which the $L^1$ group of formula (QL) is bonded. Through-conjugation of the aromatic or heteroaromatic systems is formed as soon as direct bonds are formed between adjacent aromatic or heteroaromatic rings. A further bond between the aforementioned conjugated groups, for example via a sulfur, nitrogen or oxygen atom or a carbonyl group, is not detrimental to conjugation. In the case of a fluorene system, the two aromatic rings are bonded directly, where the $sp^3$-hybridized carbon atom in position 9 does prevent fusion of these rings, but conjugation is possible since this $sp^3$-hybridized carbon atom in position 9 does not necessarily lie between the electron-transporting Q group and the atom via which the group of formula (QL) is bonded to further structural elements of a compound of the invention. In contrast, in the case of a second spirobifluorene structure, through-conjugation can be formed if the bond between the Q group and the aromatic or heteroaromatic radical to which the $L^1$ group of formula (QL) is bonded is via the same phenyl group in the spirobifluorene structure or via phenyl groups in the spirobifluorene structure that are bonded directly to one another and are in one plane. If the bond between the Q group and the aromatic or heteroaromatic radical to which the $L^1$ group of formula (QL) is bonded is via different phenyl groups in the second spirobifluorene structure bonded via the $sp^3$-hybridized carbon atom in position 9, the conjugation is interrupted.

In a further preferred embodiment of the invention, $L^1$ is a bond or an aromatic or heteroaromatic ring system which has 5 to 14 aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formulae (I) to (XVIII). More preferably, $L^1$ is an aromatic ring system having 6 to 10 aromatic ring atoms or a heteroaromatic ring system having 6 to 13 heteroaromatic ring atoms, each of which may be substituted by one or more $R^2$ radicals, but is preferably unsubstituted, where $R^2$ may have the definition given above, especially for formulae (I) to (XVIII).

Further preferably, the symbol $L^1$ shown in formula (QL) inter alia is the same or different at each instance and is a bond or an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded to the respective atom of the further group directly, i.e. via an atom of the aromatic or heteroaromatic group.

It may additionally be the case that the $L^1$ group shown in formula (QL) comprises an aromatic ring system having not more than two fused aromatic and/or heteroaromatic 6-membered rings, preferably does not comprise any fused aromatic or heteroaromatic ring system. Accordingly, naphthyl structures are preferred over anthracene structures. In addition, fluorenyl, spirobifluorenyl, dibenzofuranyl and/or dibenzothienyl structures are preferred over naphthyl structures.

Particular preference is given to structures having no fusion, for example phenyl, biphenyl, terphenyl and/or quaterphenyl structures.

Examples of suitable aromatic or heteroaromatic ring systems $L^1$ are selected from the group consisting of ortho-, meta- or para-phenylene, ortho-, meta- or para-biphenylene, terphenylene, especially branched terphenylene, quaterphenylene, especially branched quaterphenylene, fluorenylene, spirobifluorenylene, dibenzofuranylene, dibenzothienylene and carbazolylene, each of which may be substituted by one or more $R^1$ radicals, but are preferably unsubstituted.

It may further be the case that the $L^1$ group shown in formula (QL) inter alia has not more than 1 nitrogen atom, preferably not more than 2 heteroatoms, especially preferably not more than one heteroatom and more preferably no heteroatom.

Preferably, the Q group shown in the formula (QL) inter alia, or the electron transport group, may be selected from structures of the formulae (Q-1), (Q-2), (Q-4), (Q-4), (Q-5), (Q-6), (Q-7), (Q-8), (Q-9) and/or (Q-10)

Formula (Q-1)

Formula (Q-2)

Formula (Q-3)

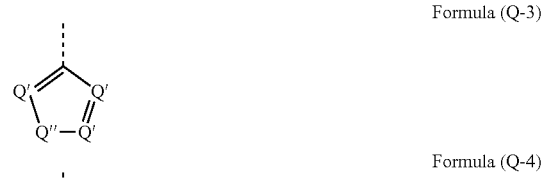

Formula (Q-4)

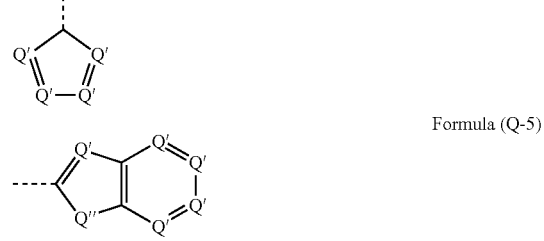

Formula (Q-5)

Formula (Q-6)

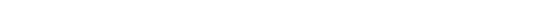

-continued

Formula (Q-7)

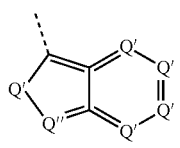

Formula (Q-8)

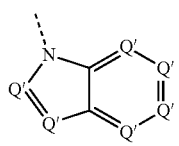

Formula (Q-9)

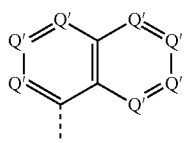

Formula (Q-10)

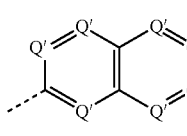

where the dotted bond marks the position of attachment,

Q' is the same or different at each instance and is $CR^1$ or N, and

Q" is $NR^1$, O or S;

where at least one Q' is N and $R^1$ is as defined above, especially in formulae (I) to (XVIII).

The substituents $R^1$ in the structures of the formulae (Q-1) to (Q-10) should be replaced in structures of formulae (N-1) to (N-6), (Ar-1) to (Ar-54) and/or (Ar'-1) to (Ar'-53) by substituents $R^2$.

In addition, the Q group shown in the formula (QL) inter alia, or the electron transport group, may preferably be selected from a structure of the formulae (Q-11), (Q-12), (Q-13), (Q-14) and/or (Q-15)

Formula (Q-11)

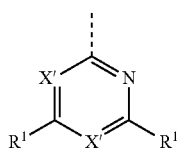

Formula (Q-12)

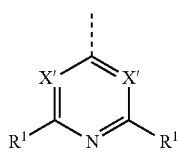

Formula (Q-13)

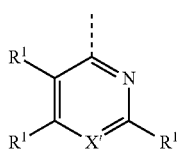

Formula (Q-14)

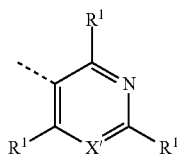

Formula (Q-15)

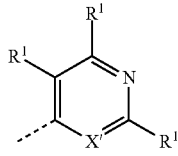

where the symbol $R^1$ has the definition given above for formulae (I) to (XVIII) inter alia, X' is N or $CR^1$ and the dotted bond marks the position of attachment, where X' is preferably a nitrogen atom. The substituents $R^1$ in the structures of the formulae (Q-11) to (Q-15) should be replaced in structures of formulae (N-1) to (N-6), (Ar-1) to (Ar-54) and/or (Ar'-1) to (Ar'-53) by substituents $R^2$.

In a further embodiment, the Q group shown in the formula (QL) inter alia, or the electron transport group, may be selected from structures of the formulae (Q-16), (Q-17), (Q-18), (Q-19), (Q-20), (Q-21) and/or (Q-22)

Formula (Q-16)

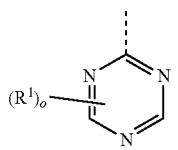

Formula (Q-17)

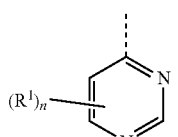

Formula (Q-18)

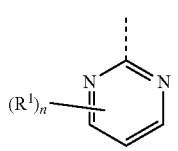

Formula (Q-19)

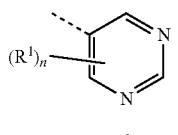

Formula (Q-20)

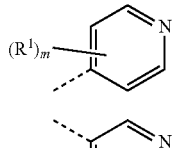

Formula (Q-21)

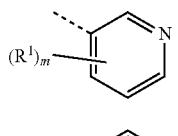

Formula (Q-22)

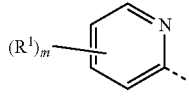

in which the symbol R¹ has the definition detailed above for formulae (I) to (XVIII) inter alia, the dotted bond marks the position of attachment and m is 0, 1, 2, 3 or 4, preferably 0, 1 or 2, n is 0, 1, 2 or 3, preferably 0, 1 or 2, and o is 0, 1 or 2, preferably 1 or 2. Preference is given here to the structures of the formulae (Q-16), (Q-17), (Q-18) and (Q-19). Moreover, the substituents R¹ in the structures of the formulae (Q-16) to (Q-22) should be replaced in structures of formulae (N-1) to (N-6), (Ar-1) to (Ar-54) and/or (Ar'-1) to (Ar¹-53) by substituents R².

In a further embodiment, the Q group shown in the formula (QL) inter alia, or the electron transport group, may be selected from structures of the formulae (Q-23), (Q-24) and/or (Q-25)

Formula (Q-23)

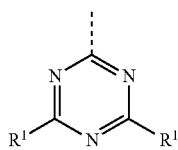

Formula (Q-24)

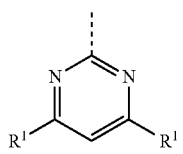

Formula (Q-25)

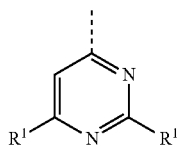

in which the symbol R¹ has the definition set out above for formulae (I) to (XVIII) inter alia, and the dotted bond marks the position of attachment. Moreover, the substituents R¹ in the structures of the formulae (Q-23) to (Q-25) should be replaced in structures of formulae (N-1) to (N-6), (Ar-1) to (Ar-54) and/or (Ar'-1) to (Ar'-53) by substituents R².

In a further embodiment, the Q group shown in the formula (QL) inter alia, or the electron transport group, may be selected from structures of the formulae (Q-26), (Q-27), (Q-28), (Q-29) and/or (Q-30)

Formula (Q-26)

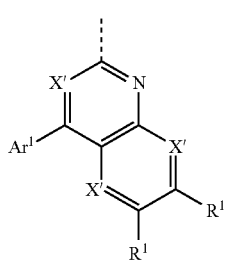

Formula (Q-27)

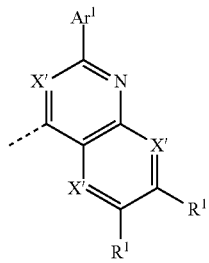

Formula (Q-28)

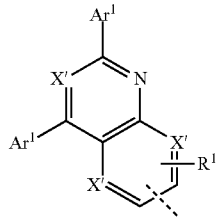

Formula (Q-29)

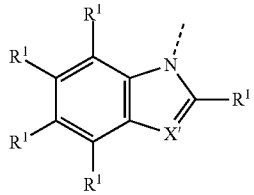

Formula (Q-30)

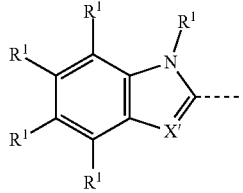

where symbols Ar¹ and R¹ have the definition given above for formulae (I) to (XVIII) inter alia, X' is N or CR¹ and the dotted bond marks the position of attachment. Preferably, in the structures of the formulae (Q-26), (Q-27) and (Q-28), exactly one X' is a nitrogen atom. Moreover, the substituents R¹ in the structures of the formulae (Q-26) to (Q-30) should be replaced in structures of formulae (N-1) to (N-6), (Ar-1) to (Ar-54) and/or (Ar'-1) to (Ar¹-53) by substituents R².

Preferably, the Q group shown in the formula (QL) inter alia, or the electron transport group, may be selected from structures of the formulae (Q-31), (Q-32), (Q-33), (Q-34), (Q-35), (Q-36), (Q-37), (Q-38), (Q-39), (Q-40), (Q-41), (Q-42), (Q-43) and/or (Q-44)

Formula (Q-31)

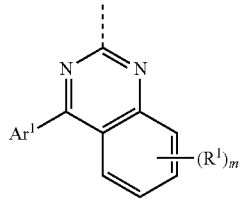

-continued

Formula (Q-32)
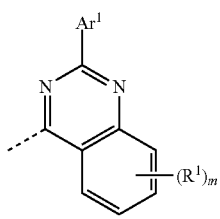

Formula (Q-33)
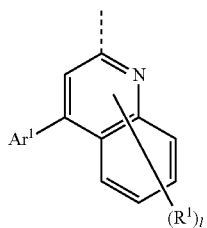

Formula (Q-34)
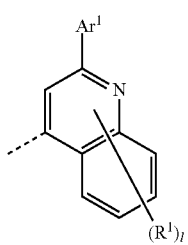

Formula (Q-35)
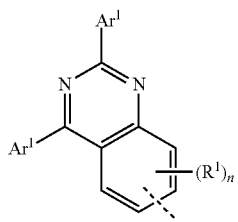

Formula (Q-36)
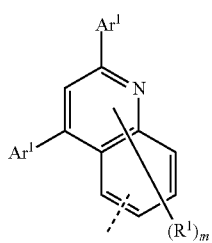

Formula (Q-37)
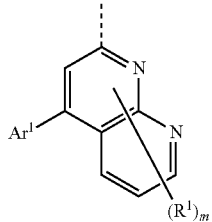

-continued

Formula (Q-38)
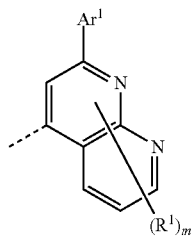

Formula (Q-39)
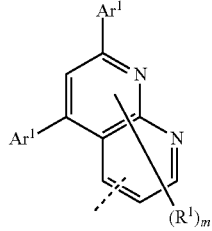

Formula (Q-40)
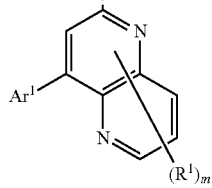

Formula (Q-41)
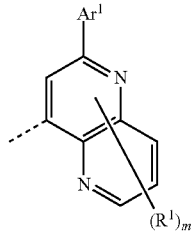

Formula (Q-42)
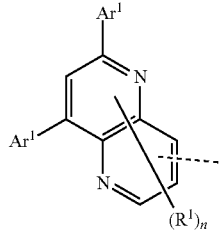

Formula (Q-43)

Formula (Q-44)
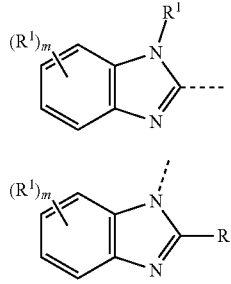

in which the symbols $Ar^1$ and $R^1$ have the definition set out above for formulae (I) to (XVIII) inter alia, the dotted bond marks the position of attachment and m is 0, 1, 2, 3 or 4, preferably 0, 1 or 2, n is 0, 1, 2 or 3, preferably 0 or 1, n is 0, 1, 2 or 3, preferably 0, 1 or 2, and l is 1, 2, 3, 4 or 5, preferably 0, 1 or 2. The substituents $R^1$ here in the structures of the formulae (Q-31) to (Q-44) should be replaced in structures of formulae (N-1) to (N-6), (Ar-1) to (Ar-54) and/or (Ar'-1) to (Ar'-53) by substituents $R^2$.

In a further preferred embodiment of the invention, $Ar^1$ is the same or different at each instance and is an aromatic or heteroaromatic ring system, preferably an aryl or heteroaryl radical having 5 to 24 aromatic ring atoms, preferably having 6 to 18 aromatic ring atoms, and is more preferably an aromatic ring system, preferably an aryl radical having 6 to 12 aromatic ring atoms, or a heteroaromatic ring system, preferably a heteroaryl group having 5 to 13 aromatic ring atoms, each of which may be substituted by one or more $R^2$ radicals, but is preferably unsubstituted, where $R^2$ may have the definition detailed above, especially in formulae (I) to (XVIII).

Preferably, the symbol $Ar^1$ is an aryl or heteroaryl radical, such that an aromatic or heteroaromatic group of an aromatic or heteroaromatic ring system is bonded directly, i.e. via an atom of the aromatic or heteroaromatic group, to the respective atom of the further group, for example a carbon or nitrogen atom of the (H-1) to (H-26) or (Q-26) to (Q-44) groups shown above.

Advantageously, $Ar^1$ in the formulae (H-1) to (H-26) or (Q-26) to (Q-44) is an aromatic ring system which has 6 to 12 aromatic ring atoms and may be substituted by one or more $R^2$ radicals, but is preferably unsubstituted, where $R^2$ may have the definition detailed above, especially for formulae (I) to (XVIII).

Preferably, the $R^1$ or $R^2$ radicals in the formulae (H-1) to (H-26) or (Q-1) to (Q-44) do not form a fused ring system with the ring atoms of the aryl group or heteroaryl group $Ar^1$, $Ar^2$, $Ar^3$ and/or $Ar^4$ to which the $R^1$ or $R^2$ radicals are bonded. This includes the formation of a fused ring system with possible substituents $R^2$, $R^3$ which may be bonded to the $R^1$ or $R^2$ radicals.

It may also be the case that the Ar, $Ar^1$, $Ar^2$, $Ar^3$ and/or $Ar^4$ group is selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, pyrenyl, triazinyl, imidazolyl, benzimidazolyl, benzoxazolyl, benzothiazolyl, 1-, 2-, 3- or 4-carbazolyl, indenocarbazolyl, 1- or 2-naphthyl, anthracenyl, preferably 9-anthracenyl, phenanthrenyl and/or triphenylenyl, each of which may be substituted by one or more $R^1$ and/or $R^2$ radicals, but are preferably unsubstituted, particular preference being given to phenyl, spirobifluorene, fluorene, dibenzofuran, dibenzothiophene, anthracene, phenanthrene, triphenylene groups.

When X or $X^1$ is $CR^1$ or when the aromatic and/or heteroaromatic groups are substituted by substituents $R^1$, these substituents $R^1$ are preferably selected from the group consisting of H, D, F, CN, $N(Ar^1)_2$, $C(=O)Ar^1$, $P(=O)(Ar^1)_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^2$ radicals, where one or more nonadjacent $CH_2$ groups may be replaced by O and where one or more hydrogen atoms may be replaced by D or F, an aromatic or heteroaromatic ring system which has 5 to 24 aromatic ring atoms and may be substituted in each case by one or more $R^2$ radicals, but is preferably unsubstituted, or an aralkyl or heteroaralkyl group which has 5 to 25 aromatic ring atoms and may be substituted by one or more $R^2$ radicals; at the same time, it is optionally possible for two substituents $R^1$ preferably bonded to adjacent carbon atoms to form a monocyclic or polycyclic, aliphatic, aromatic or heteroaromatic ring system which may be substituted by one or more $R^1$ radicals; where the $Ar^1$ group has the definition given above, especially for formulae (I) to (XVIII).

More preferably, these substituents $R^1$ are selected from the group consisting of H, D, F, CN, $N(Ar^1)_2$, a straight-chain alkyl group having 1 to 8 carbon atoms, preferably having 1, 2, 3 or 4 carbon atoms, or a branched or cyclic alkyl group having 3 to 8 carbon atoms, preferably having 3 or 4 carbon atoms, or an alkenyl group having 2 to 8 carbon atoms, preferably having 2, 3 or 4 carbon atoms, each of which may be substituted by one or more $R^2$ radicals, but is preferably unsubstituted, or an aromatic or heteroaromatic ring system which has 5 to 24 aromatic ring atoms, preferably 6 to 18 aromatic ring atoms, more preferably 6 to 13 aromatic ring atoms, and may be substituted in each case by one or more nonaromatic $R^1$ radicals, but is preferably unsubstituted; at the same time, two substituents $R^1$ preferably bonded to adjacent carbon atoms may optionally form a monocyclic or polycyclic aliphatic ring system which may be substituted by one or more $R^2$ radicals, but is preferably unsubstituted, where $Ar^1$ may have the definition set out above.

Most preferably, the substituents $R^1$ are selected from the group consisting of H or an aromatic or heteroaromatic ring system which has 6 to 18 aromatic ring atoms, preferably 6 to 13 aromatic ring atoms, and may be substituted in each case by one or more nonaromatic $R^2$ radicals, but is preferably unsubstituted. Examples of suitable substituents $R^1$ are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, 1-, 2-, 3- or 4-carbazolyl and indenocarbazolyl, each of which may be substituted by one or more $R^2$ radicals, but are preferably unsubstituted.

It may additionally be the case that the substituents $R^1$ of the heteroaromatic ring system of the formulae (I) to (XVIII), (Ia) to (XVIIIa), (N-1) to (N-6), (Ar-1) to (Ar-54) and/or (Ar'-1) to (Ar'-53) do not form a fused aromatic or heteroaromatic ring system with the ring atoms of the aromatic or heteroaromatic ring system, preferably any fused ring system. This includes the formation of a fused ring system with possible substituents $R^2$, $R^3$ which may be bonded to the $R^1$ radicals.

It may further be the case that, in a structure of formula (I) to (XVIII), (Ia) to (XVIIIa), (N-1) to (N-6), (Ar-1) to (Ar-54) and/or (Ar'-1) to (Ar'-53), at least one $R^1$ or $Ar^1$ radical is a group selected from the formulae ($R^1$-1) to ($R^1$-92), or, in a structure of formula (H-1) to (H-26), (Q-1) to (Q-44), at least one $Ar^1$ or $R^1$ radical, is a group selected from the formulae ($R^1$-1) to ($R^1$-92)

Formula ($R^1$-1)

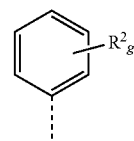

Formula (R¹-2)
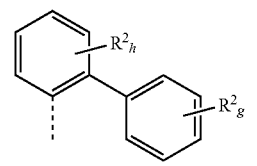
Formula (R¹-3)
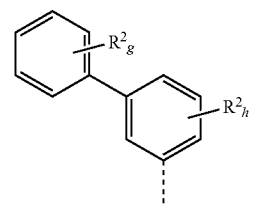
Formula (R¹-4)
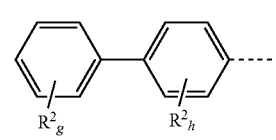
Formula (R¹-5)
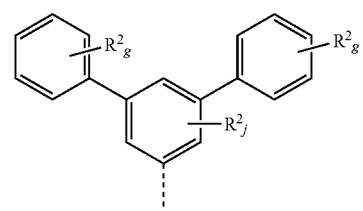
Formula (R¹-6)
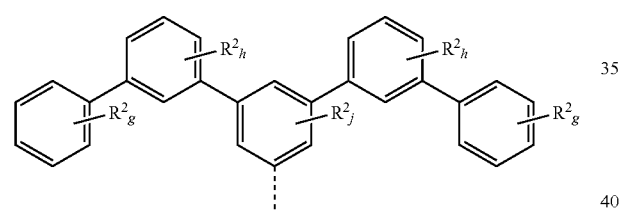
Formula (R¹-7)
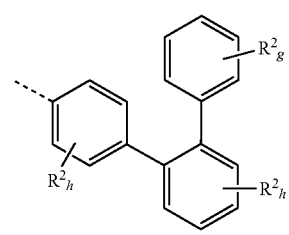
Formula (R¹-8)
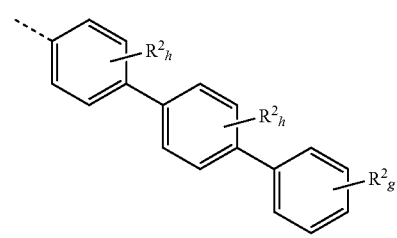
Formula (R¹-9)
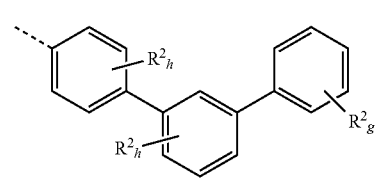
Formula (R¹-10)
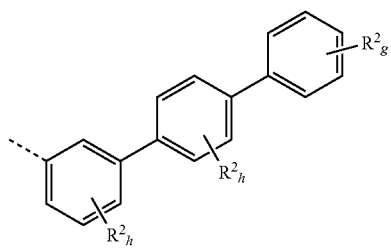
Formula (R¹-11)
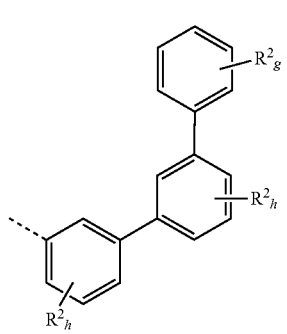
Formula (R¹-12)
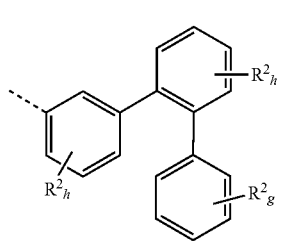
Formula (R¹-13)
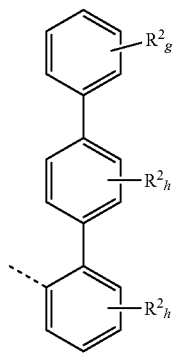
Formula (R¹-14)
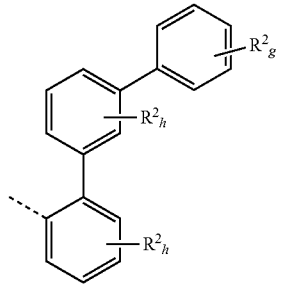

Formula (R¹-15)
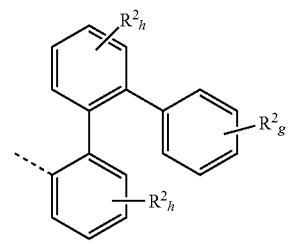
Formula (R¹-16)
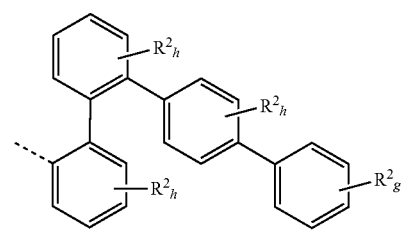
Formula (R¹-17)
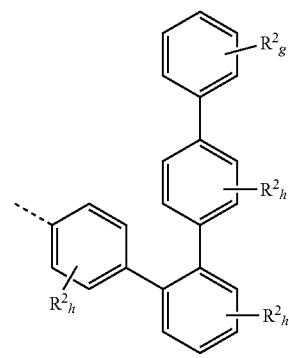
Formula (R¹-18)
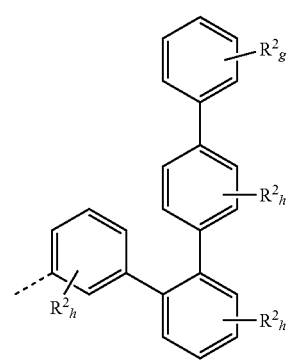
Formula (R¹-19)
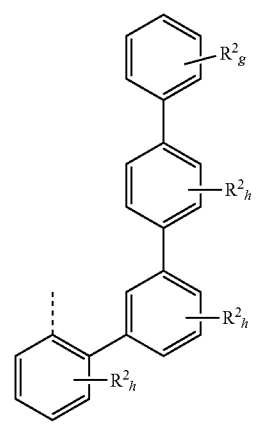
Formula (R¹-20)
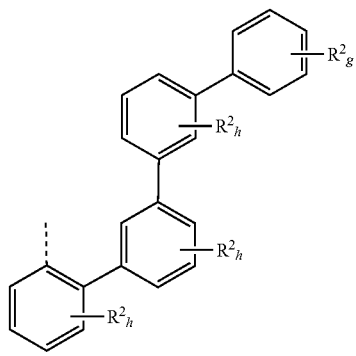
Formula (R¹-21)
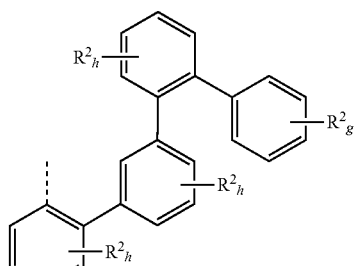
Formula (R¹-22)
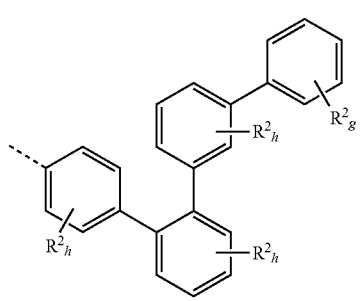
Formula (R¹-23)
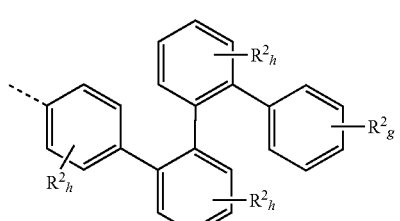
Formula (R¹-24)
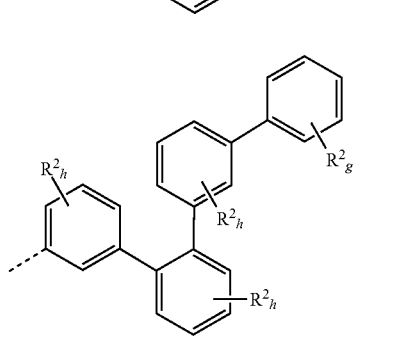

Formula (R¹-25)
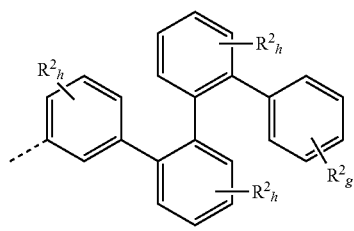
Formula (R¹-26)
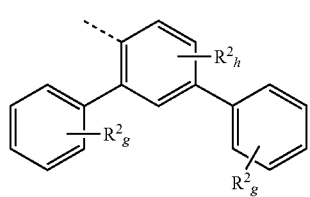
Formula (R¹-27)
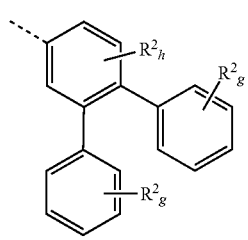
Formula (R¹-28)
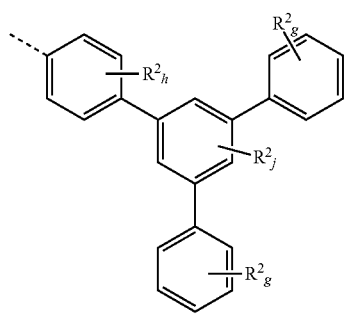
Formula (R¹-29)
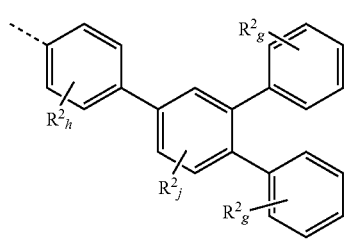
Formula (R¹-30)
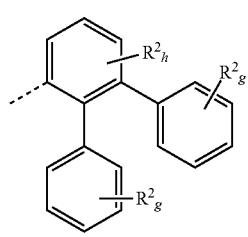
Formula (R¹-31)
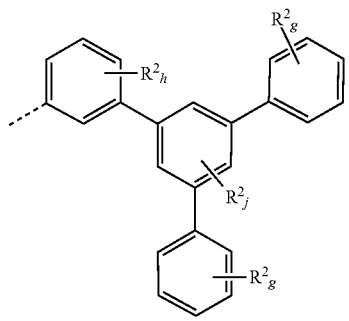
Formula (R¹-32)
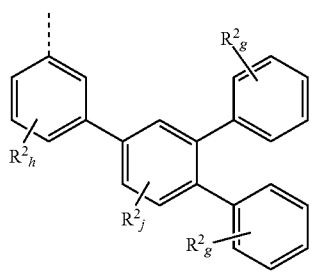
Formula (R¹-33)
Formula (R¹-34)
Formula (R¹-35)
Formula (R¹-36)
Formula (R¹-37)

-continued
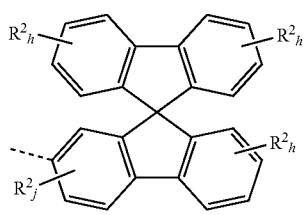
Formula (R1-38)
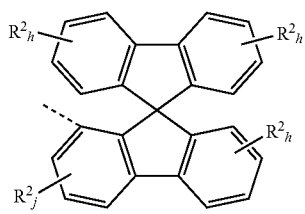
Formula (R1-39)
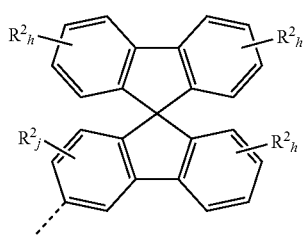
Formula (R1-40)
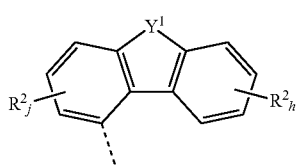
Formula (R1-41)
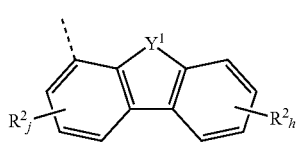
Formula (R1-42)
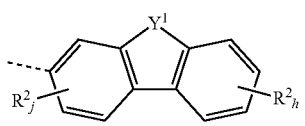
Formula (R1-43)
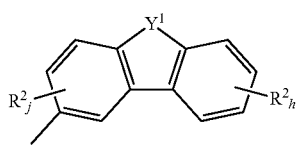
Formula (R1-44)
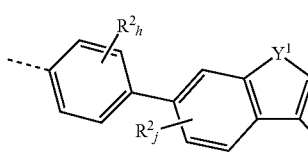
Formula (R1-45)
-continued
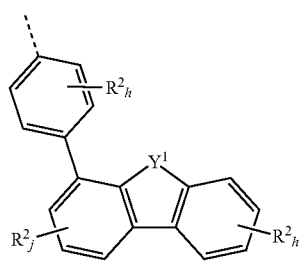
Formula (R1-46)
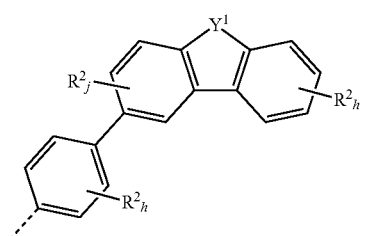
Formula (R1-47)
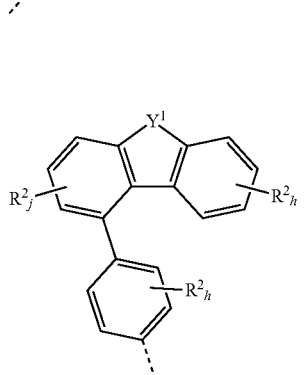
Formula (R1-48)
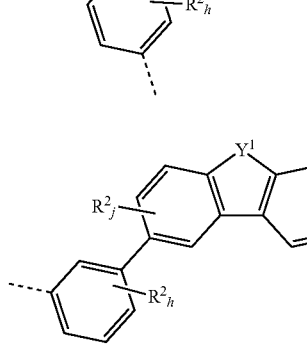
Formula (R1-49)
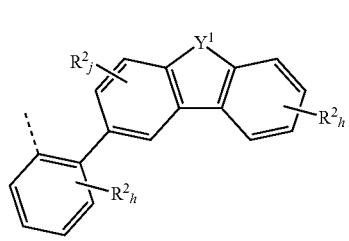
Formula (R1-50)
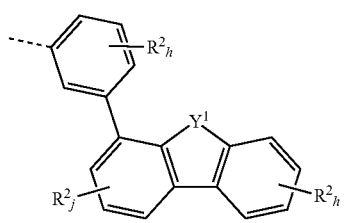
Formula (R1-51)

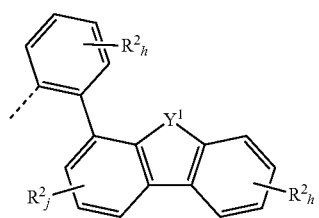
Formula (R¹-52)
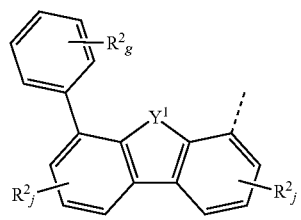
Formula (R¹-53)
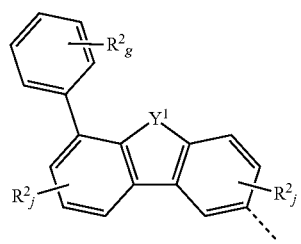
Formula (R¹-54)
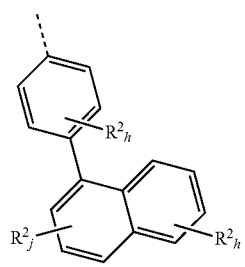
Formula (R¹-55)
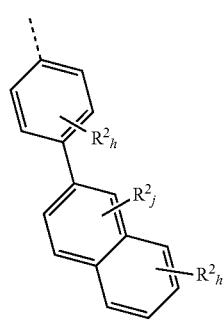
Formula (R¹-56)
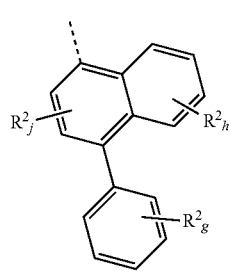
Formula (R¹-57)
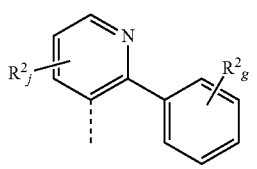
Formula (R¹-58)
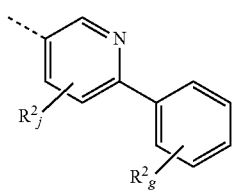
Formula (R¹-59)
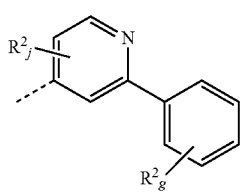
Formula (R¹-60)
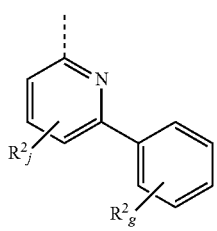
Formula (R¹-61)
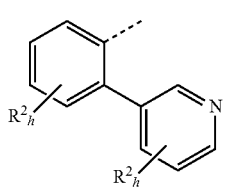
Formula (R¹-62)
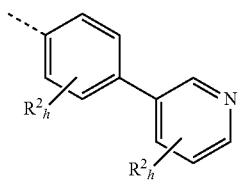
Formula (R¹-63)
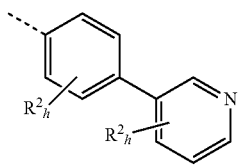
Formula (R¹-64)
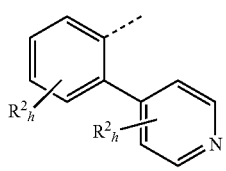
Formula (R¹-65)

91
-continued
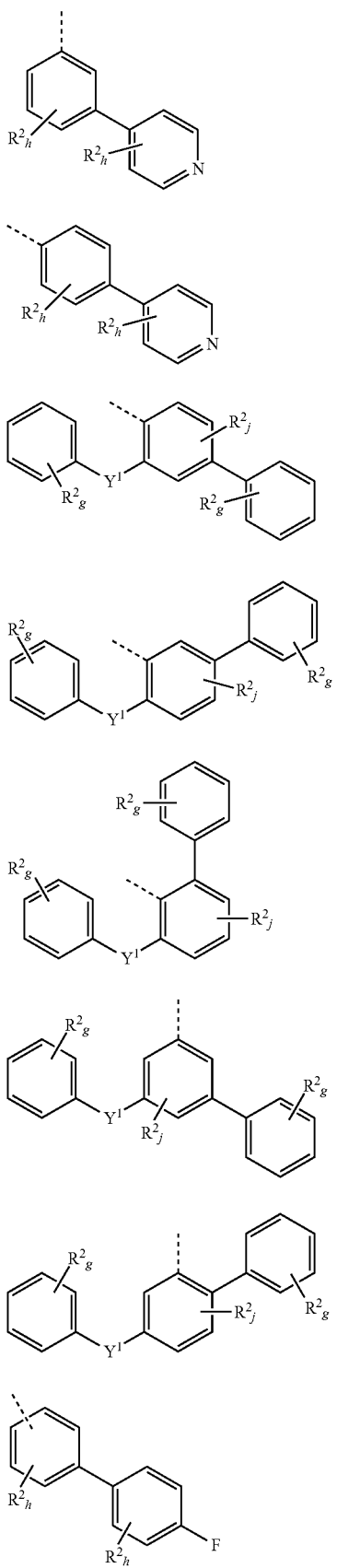
Formula (R¹-66)
Formula (R¹-67)
Formula (R¹-68)
Formula (R¹-69)
Formula (R¹-70)
Formula (R¹-71)
Formula (R¹-72)
Formula (R¹-73)
92
-continued
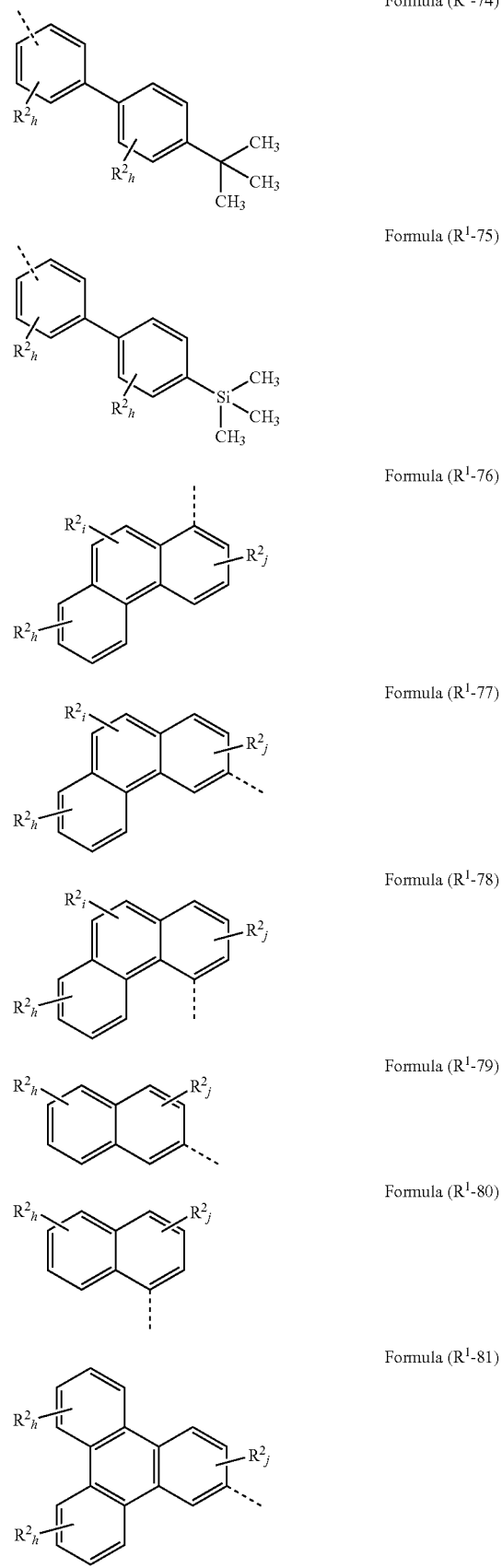
Formula (R¹-74)
Formula (R¹-75)
Formula (R¹-76)
Formula (R¹-77)
Formula (R¹-78)
Formula (R¹-79)
Formula (R¹-80)
Formula (R¹-81)

Formula (R¹-82)
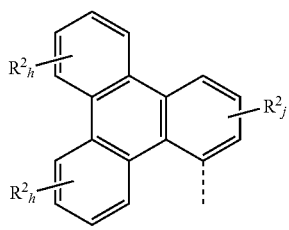

Formula (R¹-83)
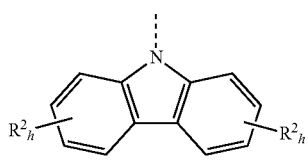

Formula (R¹-84)
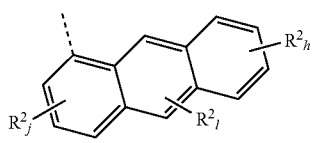

Formula (R¹-85)
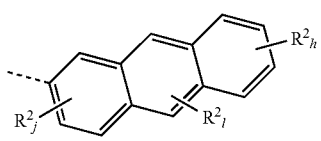

Formula (R¹-86)
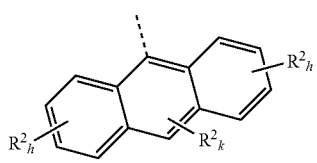

Formula (R¹-87)
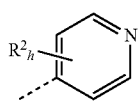

Formula (R¹-88)
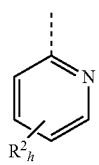

Formula (R¹-89)
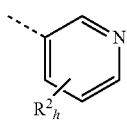

Formula (R¹-90)
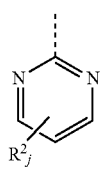

Formula (R¹-91)
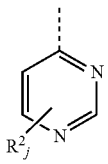

Formula (R¹-92)
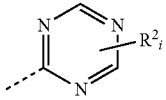

where the symbols used are as follows:

$Y^1$ is O, S or $NR^2$, preferably O or S;

k at each instance is independently 0 or 1;

i at each instance is independently 0, 1 or 2;

j at each instance is independently 0, 1, 2 or 3;

h at each instance is independently 0, 1, 2, 3 or 4;

g at each instance is independently 0, 1, 2, 3, 4 or 5;

$R^2$ may have the definition given above, especially for formulae (I) to (XVIII), and the dotted bond marks the position of attachment.

Preference is given here to the groups of the formulae $R^1$-1 to $R^1$-54, particular preference to the $R^1$-1, $R^1$-3, $R^1$-5, $R^1$-6, $R^1$-15, $R^1$-29, $R^1$-30, $R^1$-31, $R^1$-32, $R^1$-33, $R^1$-38, $R^1$-39, $R^1$-40, $R^1$-41, $R^1$-42, $R^1$-43, $R^1$-44 and/or $R^1$-45 groups.

It may preferably be the case that the sum total of the indices k, i, j, h and g in the structures of the formula ($R^1$-1) to ($R^1$-92) in each case is not more than 3, preferably not more than 2 and more preferably not more than 1.

Preferably, the $R^2$ radicals in the formulae ($R^1$-1) to ($R^1$-92) do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible substituents $R^3$ which may be bonded to the $R^2$ radicals.

The above-detailed radicals of the formulae ($R^1$-1) to ($R^1$-92) are preferred Ar radicals of formulae (I) to (XVIII) or $Ar^3$, $Ar^4$ radicals of formulae (H-1) to (H-3) or preferred embodiments of these formulae, where, in this case, the $R^2$ groups shown in the formulae ($R^1$-1) to ($R^1$-92) are to be replaced by $R^1$ radicals. The preferences detailed above with regard to the formulae ($R^1$-1) to ($R^1$-92) are correspondingly applicable.

Preference is given to compounds comprising at least one structure of the formulae (H-1) to (H-26) in which the $Ar^2$ group is a group selected from the formulae ($L^1$-1) to ($L^1$-108) and/or to compounds comprising structures of the formula (QL) in which the $L^1$ group is a bond or is a group selected from the formulae ($L^1$-1) to ($L^1$-108)

Formula ($L^1$-1)
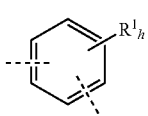

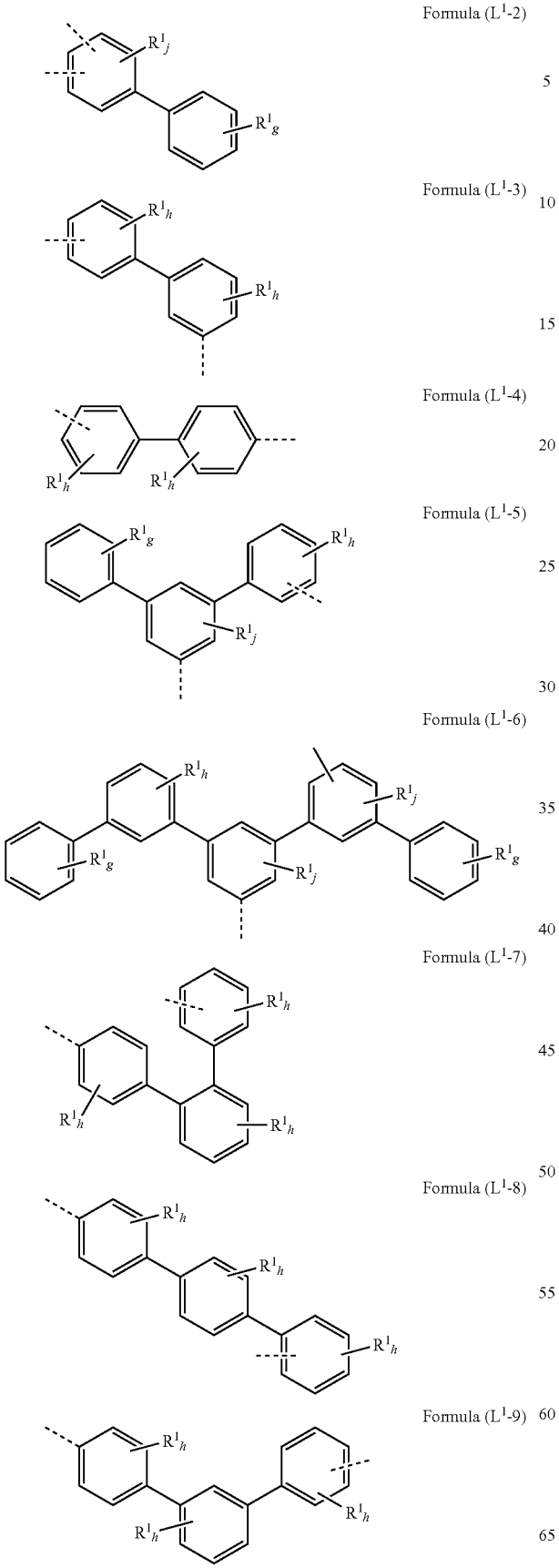
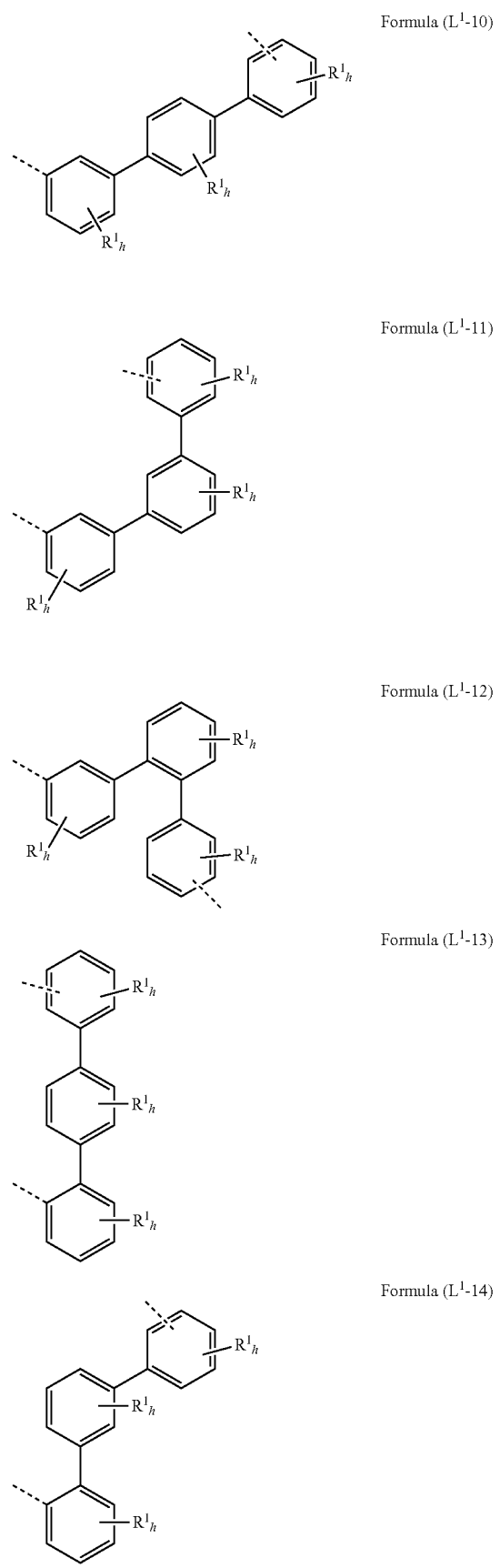

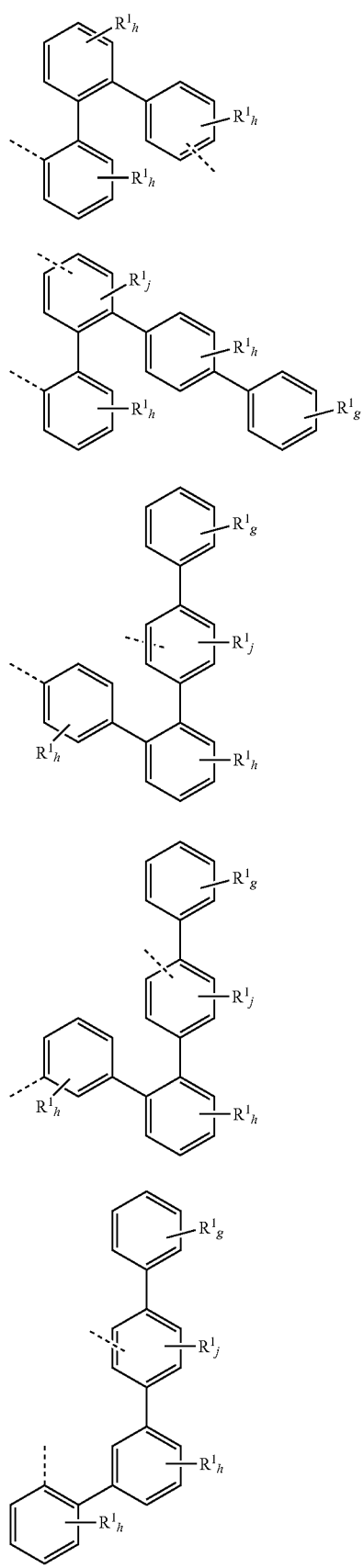
Formula (L¹-15)
Formula (L¹-16)
Formula (L¹-17)
Formula (L¹-18)
Formula (L¹-19)
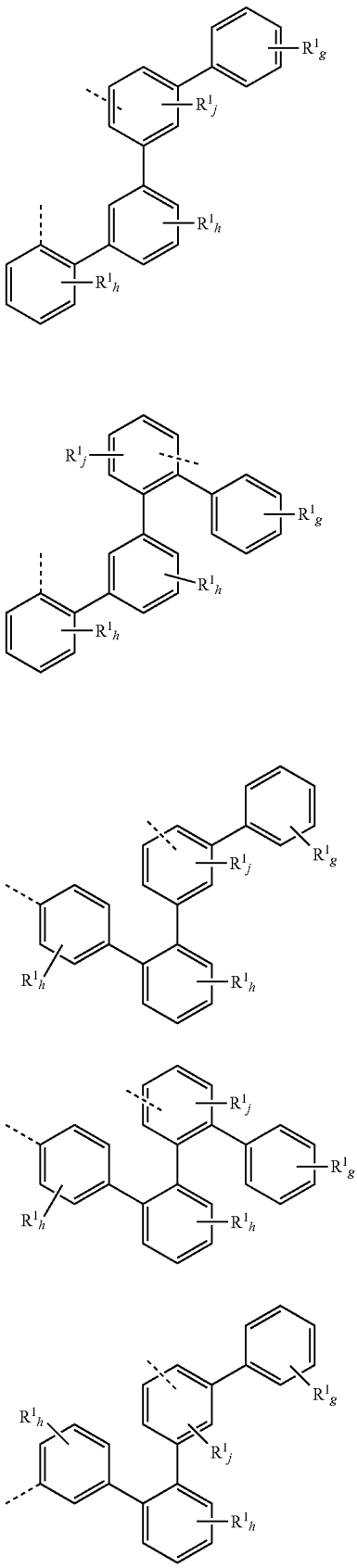
Formula (L¹-20)
Formula (L¹-21)
Formula (L¹-22)
Formula (L¹-23)
Formula (L¹-24)

-continued

Formula (L¹-25)

Formula (L¹-26)

Formula (L¹-27)

Formula (L¹-28)

Formula (L¹-29)

Formula (L¹-30)

Formula (L¹-31)

-continued

Formula (L¹-32)

Formula (L¹-33)

Formula (L¹-34)

Formula (L¹-35)

Formula (L¹-36)

Formula (L¹-37)

Formula (L¹-38)

Formula (L¹-39)

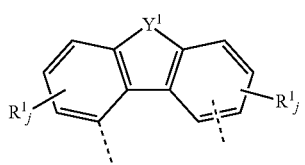
Formula (L¹-40)
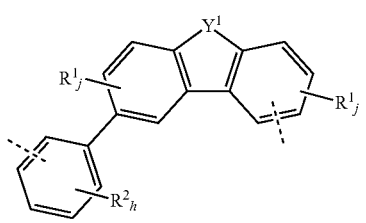
Formula (L¹-41)
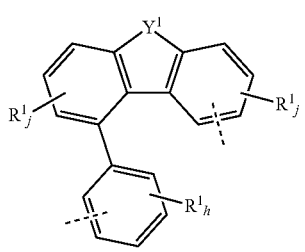
Formula (L¹-42)
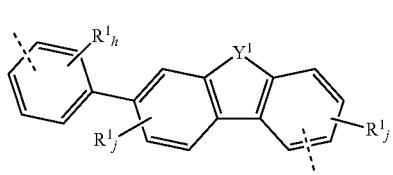
Formula (L¹-43)
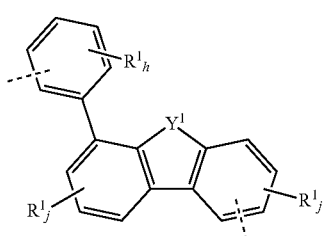
Formula (L¹-44)
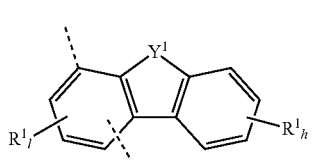
Formula (L1-45)
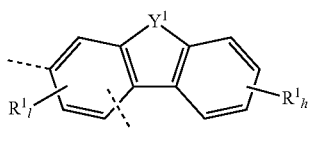
Formula (L¹-46)
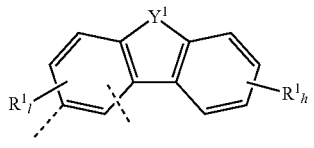
Formula (L¹-47)
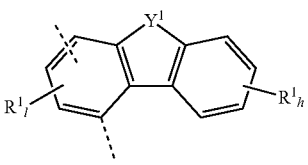
Formula (L¹-48)
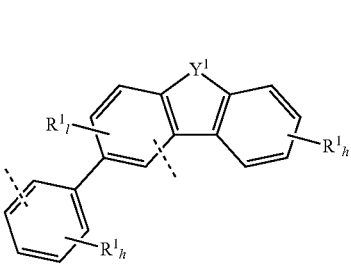
Formula (L¹-49)
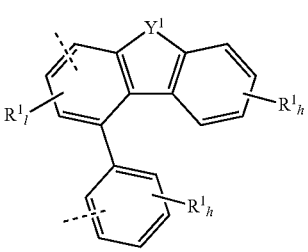
Formula (L¹-50)
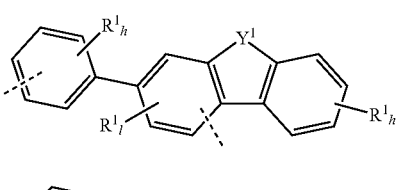
Formula (L¹-51)
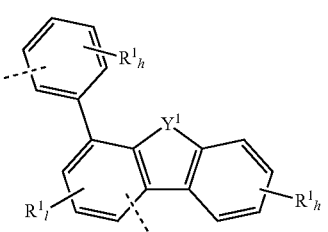
Formula (L¹-52)
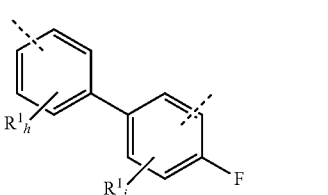
Formula (L¹-53)
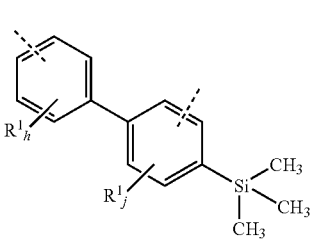
Formula (L¹-54)

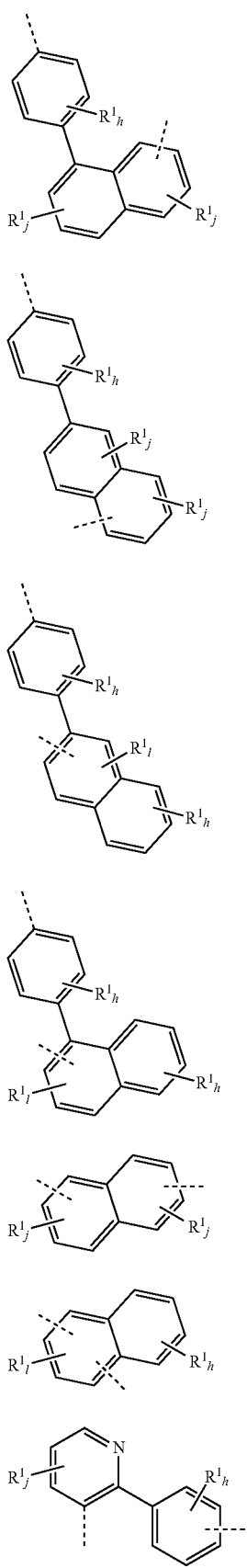
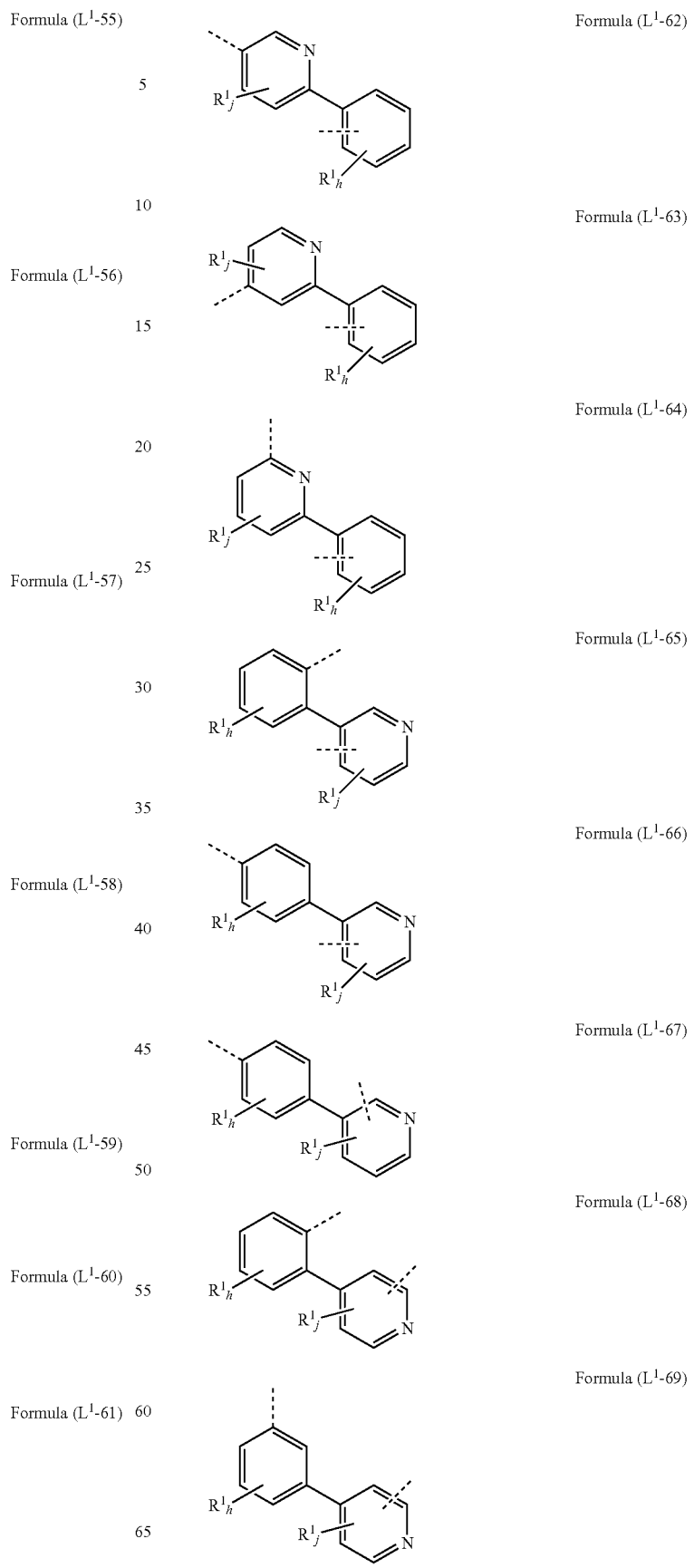

-continued

Formula (L¹-70)

Formula (L¹-71)

Formula (L¹-72)

Formula (L¹-73)

Formula (L¹-74)

Formula (L¹-75)

Formula (L¹-76)

Formula (L¹-77)

Formula (L¹-78)

Formula (L¹-79)

-continued

Formula (L¹-80)

Formula (L¹-81)

Formula (L¹-82)

Formula (L¹-83)

Formula (L¹-84)

Formula (L¹-85)

Formula (L¹-86)

Formula (L¹-87)

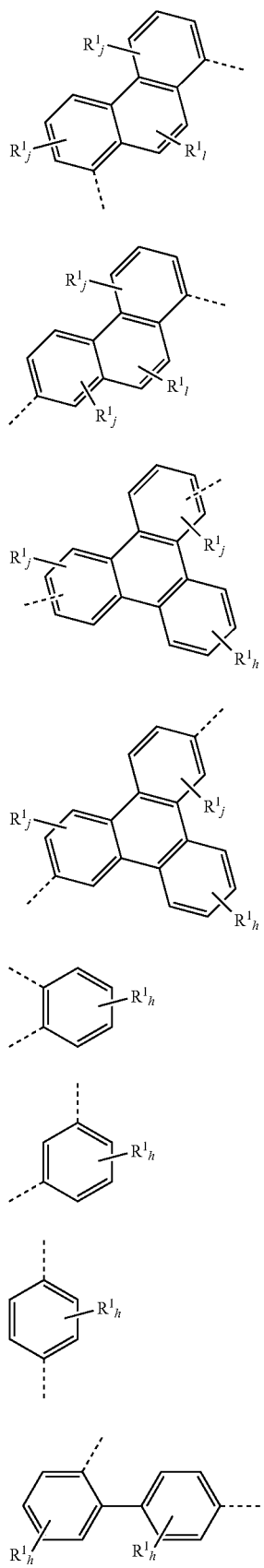
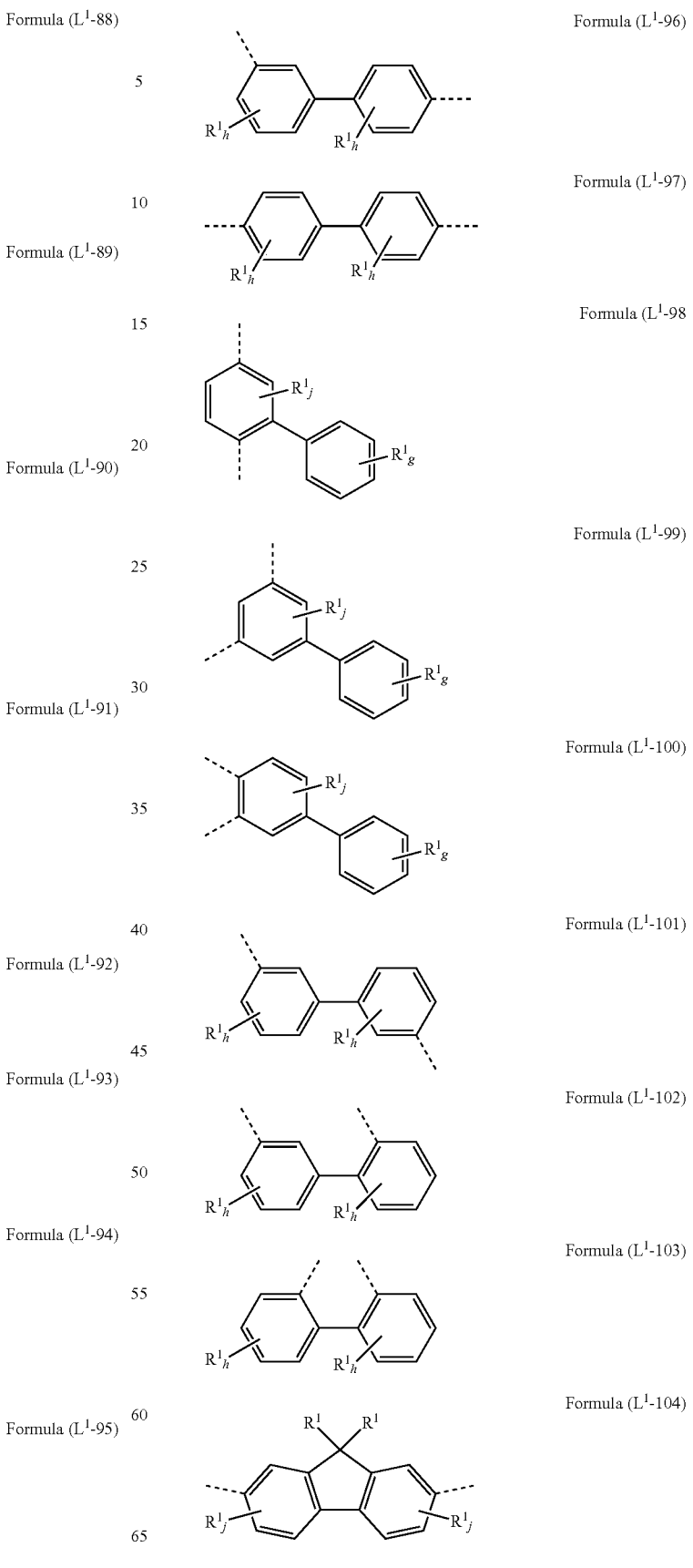

-continued

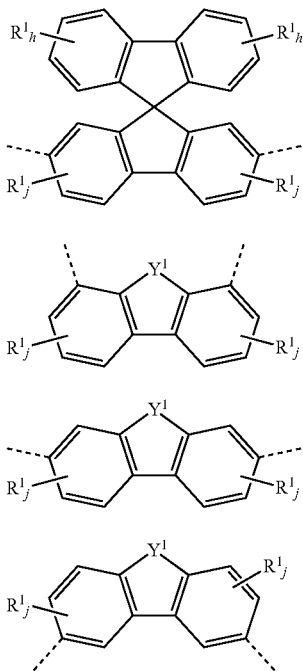

Formula (L¹-105)

Formula (L¹-106)

Formula (L¹-107)

Formula (L¹-108)

where the dotted bonds in each case mark the positions of attachment, the ' ' index k is 0 or 1, the index l is 0, 1 or 2, the index j at each instance is independently 0, 1, 2 or 3, the index h at each instance is independently 0, 1, 2, 3 or 4, the index g is 0, 1, 2, 3, 4 or 5; the symbol $Y^1$ is O, S or $NR^1$, preferably O or S; and the symbol $R^1$ has the definition given above, especially for formulae (I) to (XVIII).

It may preferably be the case that the sum total of the indices k, l, g, h and j in the structures of the formula ($L^1$-1) to ($L^1$-108) is at most 3 in each case, preferably at most 2 and more preferably at most 1.

Preferred compounds of the invention having a group of the formulae (H-1) to (H-26) comprise an $Ar^2$ group selected from one of the formulae ($L^1$-1) to ($L^1$-78) and/or ($L^1$-92) to ($L^1$-108), preferably of the formula ($L^1$-1) to ($L^1$-54) and/or ($L^1$-92) to ($L^1$-108), especially preferably of the formula ($L^1$-1) to ($L^1$-29) and/or ($L^1$-92) to ($L^1$-103). Advantageously, the sum total of the indices k, l, g, h and j in the structures of the formulae ($L^1$-1) to ($L^1$-78) and/or ($L^1$-92) to ($L^1$-108), preferably of the formula ($L^1$-1) to ($L^1$-54) and/or ($L^1$-92) to ($L^1$-108), especially preferably of the formula ($L^1$-1) to ($L^1$-29) and/or ($L^1$-92) to ($L^1$-103), may in each case be not more than 3, preferably not more than 2 and more preferably not more than 1.

Preferred compounds of the invention having a group of the formula (QL) comprise an $L^1$ group which represents a bond or which is selected from one of the formulae ($L^1$-1) to ($L^1$-78) and/or ($L^1$-92) to ($L^1$-108), preferably of the formula ($L^1$-1) to ($L^1$-54) and/or ($L^1$-92) to ($L^1$-108), especially preferably of the formula ($L^1$-1) to ($L^1$-29) and/or ($L^1$-92) to ($L^1$-103). Advantageously, the sum total of the indices k, l, g, h and j in the structures of the formulae ($L^1$-1) to ($L^1$-78) and/or ($L^1$-92) to ($L^1$-108), preferably of the formula ($L^1$-1) to ($L^1$-54) and/or ($L^1$-92) to ($L^1$-108), especially preferably of the formula ($L^1$-1) to ($L^1$-29) and/or ($L^1$-92) to ($L^1$-103), may in each case be not more than 3, preferably not more than 2 and more preferably not more than 1.

Preferably, the $R^2$ radicals in the formulae ($L^1$-1) to ($L^1$-108) do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible substituents $R^3$ which may be bonded to the $R^2$ radicals.

In a preferred configuration, compounds of the invention usable as active compound in an organic electronic device are selected from the group of the phenyls, fluorenes, indenofluorenes, spirobifluorenes, carbazoles, indenocarbazoles, indolocarbazoles, spirocarbazoles, pyrimidines, triazines, lactams, triarylamines, dibenzofurans, dibenzothienes, imidazoles, benzimidazoles, benzoxazoles, benzothiazoles, 5-arylphenanthridin-6-ones, 9,10-dehydrophenanthrenes, fluoranthenes, anthracenes, benzanthracenes, fluoradenes.

In a preferred configuration, compounds of the invention can be represented by structures of the formulae (I) to (XVIII) and/or the formulae (Ia) to (XVIIIa), or by a combination of the substructures of the formulae (N-1) to (N-6), (Ar-1) to (Ar-54) and/or (Ar'-1) to (Ar'-53). Preferably, compounds usable as active compound in an organic electronic device, preferably compounds comprising structures of the formulae (I) to (XVIII) and/or the formulae (Ia) to (XVIIIa), or the compounds obtainable by a combination of the substructures of the formulae (N-1) to (N-6), (Ar-1) to (Ar-54) and/or (Ar'-1) to (Ar'-53), have a molecular weight of not more than 5000 g/mol, preferably not more than 4000 g/mol, particularly preferably not more than 3000 g/mol, especially preferably not more than 2000 g/mol and very particularly preferably not more than 1200 g/mol.

In addition, it is a feature of preferred compounds of the invention that they are sublimable. These compounds generally have a molar mass of less than about 1200 g/mol.

When the compound of the invention is substituted by aromatic or heteroaromatic $R^1$ or $R^2$ groups, it is preferable when these do not have any aryl or heteroaryl groups having more than two aromatic six-membered rings fused directly to one another. More preferably, the substituents do not have any aryl or heteroaryl groups having six-membered rings fused directly to one another at all. The reason for this preference is the low triplet energy of such structures. Fused aryl groups which have more than two aromatic six-membered rings fused directly to one another but are nevertheless also suitable in accordance with the invention are phenanthrene and triphenylene, since these also have a high triplet level.

In the case of configuration of the compounds of the invention that are usable as active compound in an organic electronic device for use as fluorescent emitters or as blue OLED materials, preferred compounds may contain corresponding groups, for example fluorene, anthracene and/or pyrene groups which may be substituted by $R^1$ or $R^2$ groups or which are formed by corresponding substitution of the ($R^1$-1) to ($R^1$-95) groups, preferably ($R^1$-33) to ($R^1$-57) and ($R^1$-76) to ($R^1$-86), or ($L^1$-1) to ($L^1$-109), preferably ($L^1$-30) to ($L^1$-60) and ($L^1$-71) to ($L^1$-91), by the substituents $R^2$.

In a further preferred embodiment of the invention, $R^2$, for example in a structure of formulae (I) to (XVIII) and preferred embodiments of this structure or the structures where reference is made to these formulae, is the same or different at each instance and is selected from the group consisting of H, D, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

Preferably, the $R^2$ radicals do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible substituents $R^3$ which may be bonded to the $R^2$ radicals.

In a further preferred embodiment of the invention, $R^3$, for example in a structure of formulae (I) to (XVIII) and preferred embodiments of this structure or the structures where reference is made to these formulae, is the same or different at each instance and is selected from the group consisting of H, D, F, CN, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

In a further configuration of the present invention, preference is given to compounds that are obtained by a combination of the substructures N-1 and Ar-1, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of the substructures N-1 and Ar-1', where the sum total of the indices v, o and m is not more than 5, preferably not more than 3 and especially preferably 1, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of the substructures N-1 and Ar-4, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of the substructures N-1 and Ar-4', where the sum total of the indices v, o and m is not more than 5, preferably not more than 3 and especially preferably 2, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of the substructures N-1 and Ar-5, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of the substructures N-1 and Ar-5', where the sum total of the indices v, o and m is not more than 5, preferably not more than 3 and especially preferably 2, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of the substructures N-1 and Ar-10, where the U radical is $C(R^1)_2$ and a total of not more than 6, preferably not more than 4 and especially preferably not more than 2 radicals of the formula X' are not CH or CD, where the by the two $R^1$ radicals of the group defined by U are preferably derived from $R^1$-2 and together form a ring system to which there is preferably bonded in turn a structural element that can be obtained by a combination of the substructures N-1 and Ar-10, where these compounds have the following properties;

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of the substructures N-1 and Ar'-10, where the U radical is $C(R^1)_2$ and the sum total of the indices v, o and m is not more than 5, preferably not more than 3 and especially preferably 2, where the index v is especially preferably 0, where the by the two $R^1$ radicals of the group defined by U are preferably derived from $R^1$-2 and together form a ring system to which there is preferably bonded in turn a structural element that can be obtained by a combination of the substructures N-1 and Ar'-10, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of the substructures N-1 and Ar-10, where the U radical is $Si(R^1)_2$ and a total of not more than 6, preferably not more than 4 and especially preferably not more than 2 radicals of the formula X' are not CH or CD, where the by the two $R^1$ radicals of the group defined by U preferably form a structural element that can be obtained by a combination of the substructures N-1 and Ar-10, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of the substructures N-1 and Ar'-10, where the U radical is $Si(R^1)_2$ and the sum total of the indices v, o and m is not more than 5, preferably not more than 3 and especially preferably 2, where the index v is especially preferably 0, where the by the two $R^1$ radicals of the group defined by U preferably form a structural element that can be obtained by a combination of the substructures N-1 and Ar'-10, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of the substructures N-1 and Ar-11, where the U radical is $C(R^1)_2$ and a total of not more than 6, preferably not more than 4 and especially preferably not more than 2 radicals of the formula X' are not CH or CD, where the by the two $R^1$ radicals of the group defined by U are preferably derived from $R^1$-2 and together form a ring system to which there is preferably bonded in turn a structural element that can be obtained by a combination of the substructures N-1 and Ar-11, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of the substructures N-1 and Ar'-11, where the U radical is $C(R^1)_2$ and the sum total of the indices v, o and m is not more than 5, preferably not more than 3 and especially preferably 2, where the index v is especially preferably 0, where the by the two $R^1$ radicals of the group defined by U are preferably derived from $R^1$-2 and together form a ring system to which there is preferably bonded in turn a structural element that can be obtained by a combination of the substructures N-1 and Ar'-11, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of the substructures N-1 and Ar-11, where the U radical is $Si(R^1)_2$ and a total of not more than 6, preferably not more than 4 and especially preferably not more than 2 radicals of the formula X' are not CH or CD, where the by the two $R^1$ radicals of the group defined by U preferably form a structural element that can be obtained by a combination of the substructures N-1 and Ar-11, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of the substructures N-1 and Ar'-11, where the U radical is $Si(R^1)_2$ and the sum total of the indices v, o and m is not more than 5, preferably not more than 3 and especially preferably 2, where the index v is especially preferably 0, where the by the two $R^1$ radicals of the group defined by U preferably form a structural element that can be obtained by a combination of the substructures N-1 and Ar'-11, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of the substructures N-1 and Ar-12, where the U radical is $C(R^1)_2$ and a total of not more than 6, preferably not more than 4 and especially preferably not more than 2 radicals of the formula X' are not CH or CD, where the by the two $R^1$ radicals of the group defined by U are preferably derived from $R^1$-2 and together form a ring system to which there is preferably bonded in turn a structural element that can be obtained by a combination of the substructures N-1 and Ar-12, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of the substructures N-1 and Ar'-12, where the U radical is $C(R^1)_2$ and the sum total of the indices v, o and m is not more than 5, preferably not more than 3 and especially preferably 2, where the index v is especially preferably 0, where the by the two $R^1$ radicals of the group defined by U are preferably derived from $R^1$-2 and together form a ring system to which there is preferably bonded in turn a structural element that can be obtained by a combination of the substructures N-1 and Ar'-12, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of the substructures N-1 and Ar-10, where the U radical is $Si(R^1)_2$ and a total of not more than 6, preferably not more than 4 and especially preferably not more than 2 radicals of the formula X' are not CH or CD, where the by the two $R^1$ radicals of the group defined by U preferably form a structural element that can be obtained by a combination of the substructures N-1 and Ar-10, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |

-continued

| $R^1$, not H or D | preferably | preferably one $R^1$ | more preferably |
|---|---|---|---|
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of the substructures N-1 and Ar'-12, where the U radical is $Si(R^1)_2$ and the sum total of the indices v, o and m is not more than 5, preferably not more than 3 and especially preferably 2, where the index v is especially preferably 0, where the by the two $R^1$ radicals of the group defined by U preferably form a structural element that can be obtained by a combination of the substructures N-1 and Ar'-12, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of the substructures N-1 and Ar-13, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of the substructures N-1 and Ar-13', where the sum total of the indices v, o and m is not more than 5, preferably not more than 3 and especially preferably 1, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of the substructures N-1 and Ar-14, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of the substructures N-1 and Ar-14', where the sum total of the indices v, o and m is not more than 5, preferably not more than 3 and especially preferably 1, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of the substructures N-1 and Ar-15, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of the substructures N-1 and Ar-15', where the sum total of the indices v, o and m is not more than 5, preferably not more than 3 and especially preferably 1, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |

-continued

| $R^1$, not H or D | preferably | At least one $R^1$ | preferably |
|---|---|---|---|
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-23, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-22', where the sum total of the indices v, o and m is not more than 5, preferably not more than 3 and especially preferably 2, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-24, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-23', where the sum total of the indices v, o and m is not more than 5, preferably not more than 3 and especially preferably 2, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-25, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-24', where the sum total of the indices v, o and m is not more than 5, preferably not more than 3 and especially preferably 2, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-33, where the U radical is $C(R^1)_2$ and a total of not more than 6, preferably not more than 4 and especially preferably not more than 2 radicals of the formula X' are not CH or CD, where the by the two $R^1$ radicals of the group defined by U are preferably derived from $R^1$-2 and together form a ring system to which there is preferably bonded in turn a structural element that can be obtained by a combination of two substructures N-1 and one substructure Ar-33, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of two substructures N-1 and one substructure Ar'-32, where the U radical is $C(R^1)_2$ and the sum total of the indices v, o and m is not more than 5, preferably not more than 3 and especially preferably 2, where the index v is especially preferably 0, where the by the two $R^1$ radicals of the group defined by U are preferably derived from $R^1$-2 and together form a ring system to which there is preferably bonded in turn a structural element that can be obtained by a combination of two substructures N-1 and one substructure Ar'-32, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of two substructures N-1 and one substructure Ar'-33, where the U radical is $Si(R^1)_2$ and a total of not more than 6, preferably not more than 4 and especially preferably not more than 2 radicals of the formula X' are not CH or CD, where the by the two $R^1$ radicals of the group defined by U preferably form a structural element that can be obtained by a combination of two substructures N-1 and one substructure Ar'-33, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of two substructures N-1 and one substructure Ar'-32, where the U radical is $Si(R^1)_2$ and the sum total of the indices v, o and m is not more than 5, preferably not more than 3 and especially preferably 2, where the index v is especially preferably 0, where the by the two $R^1$ radicals of the group defined by U preferably form a structural element that can be obtained by a combination of two substructures N-1 and one substructure Ar'-32, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of two substructures N-1 and one substructure Ar-34, where the U radical is $C(R^1)_2$ and a total of not more than 6, preferably not more than 4 and especially preferably not more than 2 radicals of the formula X' are not CH or CD, where the by the two $R^1$ radicals of the group defined by U are preferably derived from $R^1$-2 and together form a ring system to which there is preferably bonded in turn a structural element that can be obtained by a combination of two substructures N-1 and one substructure Ar-34, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of two substructures N-1 and one substructure Ar'-33, where the U radical is $C(R^1)_2$ and the sum total of the indices v, o and m is not more than 5, preferably not more than 3 and especially preferably 2, where the index v is especially preferably 0, where the by the two $R^1$ radicals of the group defined by U are preferably derived from $R^1$-2 and together form a ring system to which there is preferably bonded in turn a structural element that can be obtained by a combination of two substructures N-1 and one substructure Ar'-33, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |

| $R^1$, not H or D | preferably | preferably one $R^1$ | more preferably |
|---|---|---|---|
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of two substructures N-1 and one substructure Ar-34, where the U radical is $Si(R^1)_2$ and a total of not more than 6, preferably not more than 4 and especially preferably not more than 2 radicals of the formula X' are not CH or CD, where the by the two $R^1$ radicals of the group defined by U preferably form a structural element that can be obtained by a combination of two substructures N-1 and one substructure Ar-34, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of two substructures N-1 and one substructure Ar'-33, where the U radical is $Si(R^1)_2$ and the sum total of the indices v, o and m is not more than 5, preferably not more than 3 and especially preferably 2, where the index v is especially preferably 0, where the by the two $R^1$ radicals of the group defined by U preferably form a structural element that can be obtained by a combination of two substructures N-1 and one substructure Ar'-33, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of two substructures N-1 and one substructure Ar-35, where the U radical is $C(R^1)_2$ and a total of not more than 6, preferably not more than 4 and especially preferably not more than 2 radicals of the formula X' are not CH or CD, where the by the two $R^1$ radicals of the group defined by U are preferably derived from $R^1$-2 and together form a ring system to which there is preferably bonded in turn a structural element that can be obtained by a combination of two substructures N-1 and one substructure Ar-35, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of two substructures N-1 and one substructure Ar'-34, where the U radical is $C(R^1)_2$ and the sum total of the indices v, o and m is not more than 5, preferably not more than 3 and especially preferably 2, where the index v is especially preferably 0, where the by the two $R^1$ radicals of the group defined by U are preferably derived from $R^1$-2 and together form a ring system to which there is preferably bonded in turn a structural element that can be obtained by a combination of two substructures N-1 and Ar'-34, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of two substructures N-1 and one substructure Ar-35, where the U radical is $Si(R^1)_2$ and a total of not more than 6, preferably not more than 4 and especially preferably not more than 2 radicals of the formula X' are not CH or CD, where the by the two $R^1$ radicals of the group defined by U preferably form a structural element that can be obtained by a combination of two substructures N-1 and one substructure Ar-35, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |

| $R^1$, not H or D | preferably | preferably one $R^1$ | more preferably |
|---|---|---|---|
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of two substructures N-1 and one substructure Ar'-34, where the U radical is $Si(R^1)_2$ and the sum total of the indices v, o and m is not more than 5, preferably not more than 3 and especially preferably 2, where the index v is especially preferably 0, where the by the two $R^1$ radicals of the group defined by U preferably form a structural element that can be obtained by a combination of two substructures N-1 and one substructure N-1 and Ar'-34, where these compounds have the following properties:

| $R^1$, not H or D | preferably | preferably one $R^1$ | more preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |
| $R^1$-1 to $R^1$-95 | $R^1$-1 to $R^1$-54 | — | — |
| $R^1$-1 to $R^1$-4 | $R^1$-1 | — | — |

In a further configuration of the present invention, preference is given to compounds that are obtained by a combination of two substructures N-1 and one substructure Ar-36, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-35', where the sum total of the indices v, o and m is not more than 5, preferably not more than 3 and especially preferably 1, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-37, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-36', where the sum total of the indices v, o and m is not more than 5, preferably not more than 3 and especially preferably 1, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-38, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-37', where the sum total of the indices v, o and m is not more than 5, preferably not more than 3 and especially preferably 1, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-39, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-38', where the sum total of the indices v, o and m is not more than 5, preferably not more than 3 and especially preferably 1, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-40, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of two substructures N-1 and one substructure Ar-39', where the sum total of the indices v, o and m is not more than 5, preferably not more than 3 and especially preferably 1, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of four substructures N-1 and one substructure Ar-41, where a total of not more than 6, preferably not more than 4 and especially preferably not more than 2 radicals of the formula X' are not CH or CD, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of four substructures N-1 and one substructure Ar-40', where the sum total of the indices v, o and m is not more than 5, preferably not more than 3 and especially preferably 1, where the index v is especially preferably 0, which have the following properties:

| $R^1$, not H or D | preferably | At least one $R^1$ | preferably |
|---|---|---|---|
| $R^1$-1 to $R^1$-95 | $R^1$-1 to $R^1$-54 | H-1 to H-26 | H1 |
| $R^1$-1 to $R^1$-95 | $R^1$-1 to $R^1$-54 | H-1 to H-26 | H4 or H-5 |
| $R^1$-1 to $R^1$-4 | $R^1$-1 | $R^1$-1 to $R^1$-54 | H1 |
| $R^1$-1 to $R^1$-4 | $R^1$-1 | H-1 to H-26 | H4 or H-5 |
| $R^1$-1 to $R^1$-95 | $R^1$-1 to $R^1$-54 | QL | Q-11 to Q-19, Q-23 to Q-28, Q-31 to Q-42 |
| $R^1$-1 to $R^1$-4 | $R^1$-1 | QL | Q-11 to Q-19 |

In a further configuration of the present invention, preference is given to compounds that are obtained by a combination of four substructures N-1 and one substructure Ar-42, where a total of not more than 6, preferably not more than 4 and especially preferably not more than 2 radicals of the formula X' are not CH or CD, which have the following properties:

| R¹, not H or D | preferably | At least one R¹ | preferably |
|---|---|---|---|
| R¹-1 to R¹-95 | R¹-1 to R¹-54 | H-1 to H-26 | H1 |
| R¹-1 to R¹-95 | R¹-1 to R¹-54 | H-1 to H-26 | H4 or H-5 |
| R¹-1 to R¹-4 | R¹-1 | R¹-1 to R¹-54 | H1 |
| R¹-1 to R¹-4 | R¹-1 | H-1 to H-26 | H4 or H-5 |
| R¹-1 to R¹-95 | R¹-1 to R¹-54 | QL | Q-11 to Q-19, Q-23 to Q-28, Q-31 to Q-42 |
| R¹-1 to R¹-4 | R¹-1 | QL | Q-11 to Q-19 |

In a further configuration of the present invention, preference is given to compounds that are obtained by a combination of four substructures N-1 and one substructure Ar-41', where the sum total of the indices v, o and m is not more than 5, preferably not more than 3 and especially preferably 1, where the index v is especially preferably 0, which have the following properties:

| R¹, not H or D | preferably | At least one R¹ | preferably |
|---|---|---|---|
| R¹-1 to R¹-95 | R¹-1 to R¹-54 | H-1 to H-26 | H1 |
| R¹-1 to R¹-95 | R¹-1 to R¹-54 | H-1 to H-26 | H4 or H-5 |
| R¹-1 to R¹-4 | R¹-1 | R¹-1 to R¹-54 | H1 |
| R¹-1 to R¹-4 | R¹-1 | H-1 to H-26 | H4 or H-5 |
| R¹-1 to R¹-95 | R¹-1 to R¹-54 | QL | Q-11 to Q-19, Q-23 to Q-28, Q-31 to Q-42 |
| R¹-1 to R¹-4 | R¹-1 | QL | Q-11 to Q-19 |

In a further configuration of the present invention, preference is given to compounds that are obtained by a combination of four substructures N-1 and one substructure Ar-43, where a total of not more than 6, preferably not more than 4 and especially preferably not more than 2 radicals of the formula X' are not CH or CD, which have the following properties:

| R¹, not H or D | preferably | At least one R¹ | preferably |
|---|---|---|---|
| R¹-1 to R¹-95 | R¹-1 to R¹-54 | H-1 to H-26 | H1 |
| R¹-1 to R¹-95 | R¹-1 to R¹-54 | H-1 to H-26 | H4 or H-5 |
| R¹-1 to R¹-4 | R¹-1 | R¹-1 to R¹-54 | H1 |
| R¹-1 to R¹-4 | R¹-1 | H-1 to H-26 | H4 or H-5 |
| R¹-1 to R¹-95 | R¹-1 to R¹-54 | QL | Q-11 to Q-19, Q-23 to Q-28, Q-31 to Q-42 |
| R¹-1 to R¹-4 | R¹-1 | QL | Q-11 to Q-19 |

In a further configuration of the present invention, preference is given to compounds that are obtained by a combination of four substructures N-1 and one substructure Ar-42', where the sum total of the indices v, o and m is not more than 5, preferably not more than 3 and especially preferably 1, where the index v is especially preferably 0, which have the following properties:

| R¹, not H or D | preferably | At least one R¹ | preferably |
|---|---|---|---|
| R¹-1 to R¹-95 | R¹-1 to R¹-54 | H-1 to H-26 | H1 |
| R¹-1 to R¹-95 | R¹-1 to R¹-54 | H-1 to H-26 | H4 or H-5 |
| R¹-1 to R¹-4 | R¹-1 | R¹-1 to R¹-54 | H1 |
| R¹-1 to R¹-4 | R¹-1 | H-1 to H-26 | H4 or H-5 |
| R¹-1 to R¹-95 | R¹-1 to R¹-54 | QL | Q-11 to Q-19, Q-23 to Q-28, Q-31 to Q-42 |
| R¹-1 to R¹-4 | R¹-1 | QL | Q-11 to Q-19 |

It may further be the case that the compound usable as active compound in an organic electronic device is not in direct contact with a metal atom, and is preferably not a ligand for a metal complex.

Examples of suitable compounds of the invention are the structures of the following formulae 1 to 108 shown below:

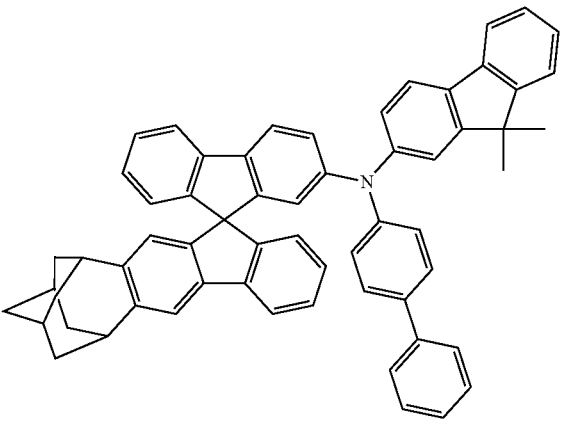

Formula 1

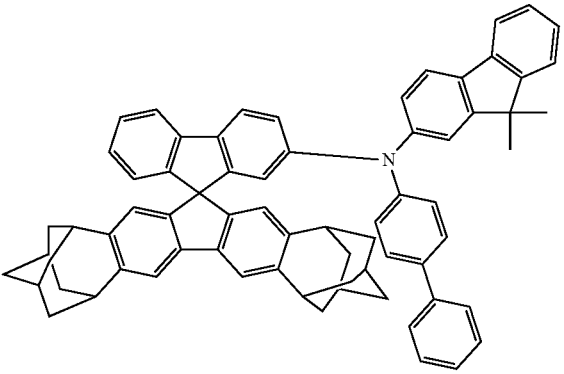

Formula 2

Formula 3
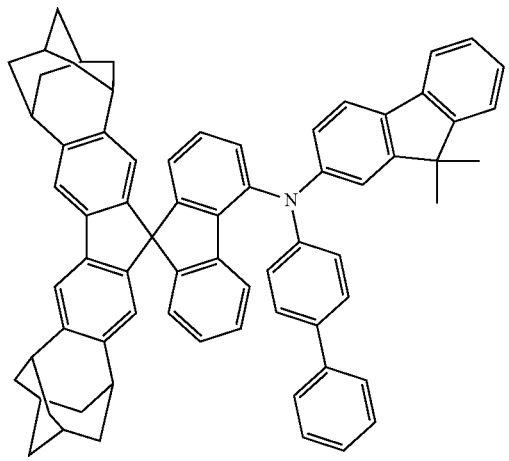
Formula 4
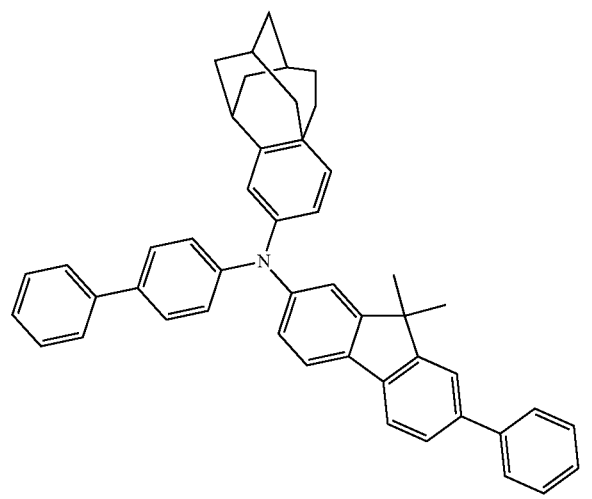
Formula 5
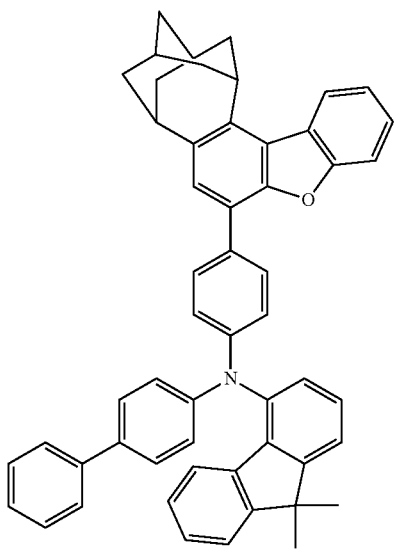
Formula 6
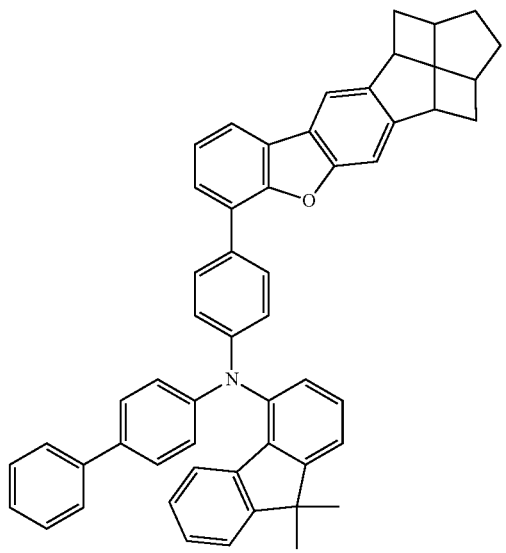
Formula 7
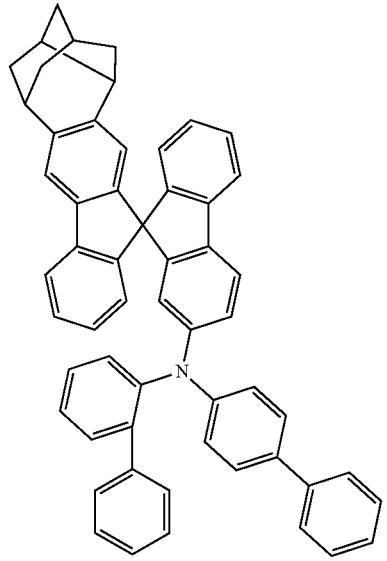

Formula 8
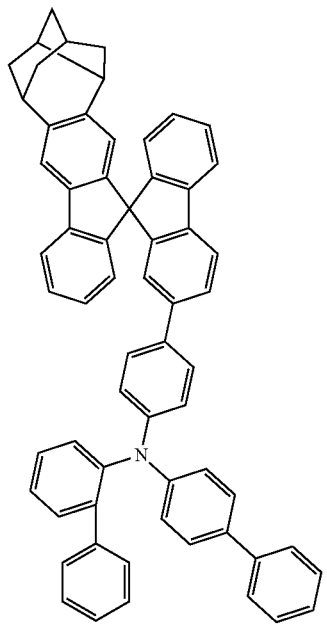
Formula 9
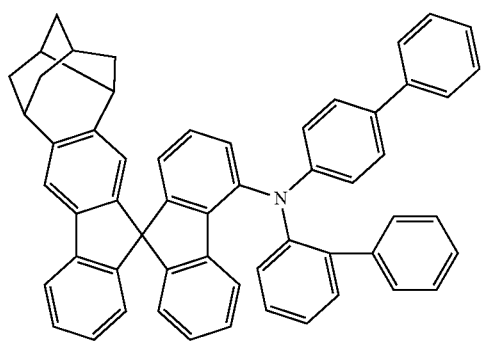
Formula 10
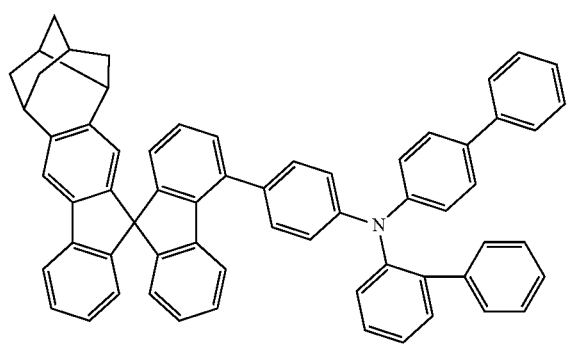
Formula 11
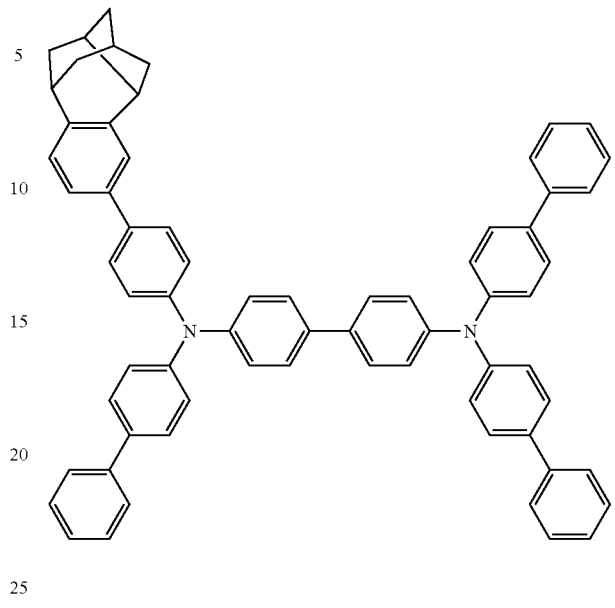
Formula 12
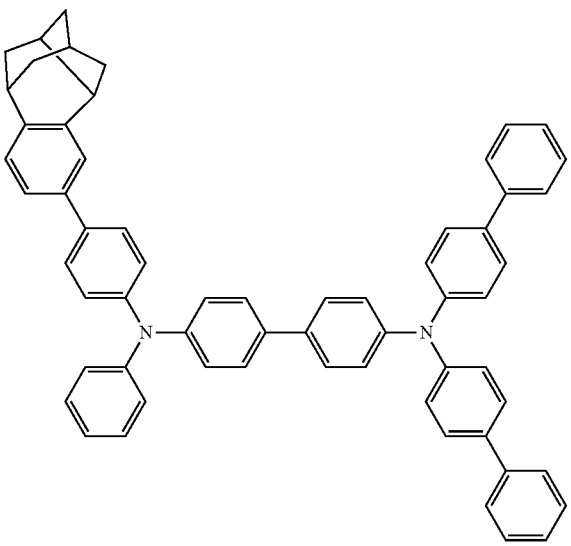

Formula 13
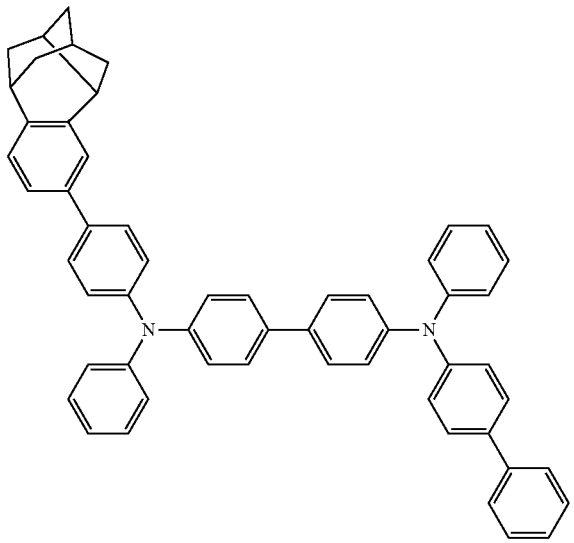
Formula 14
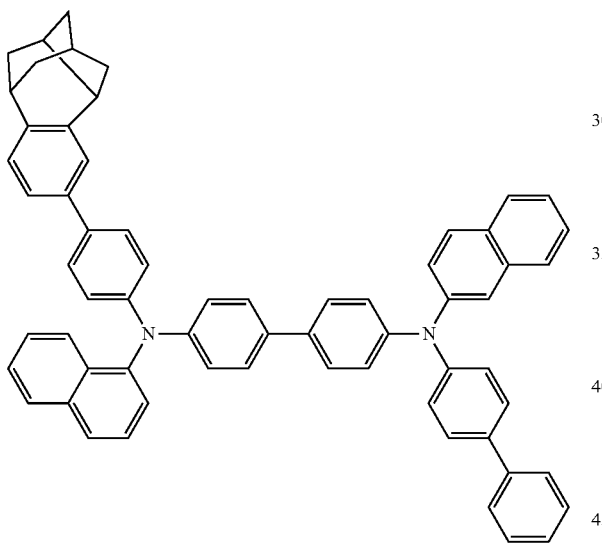
Formula 15
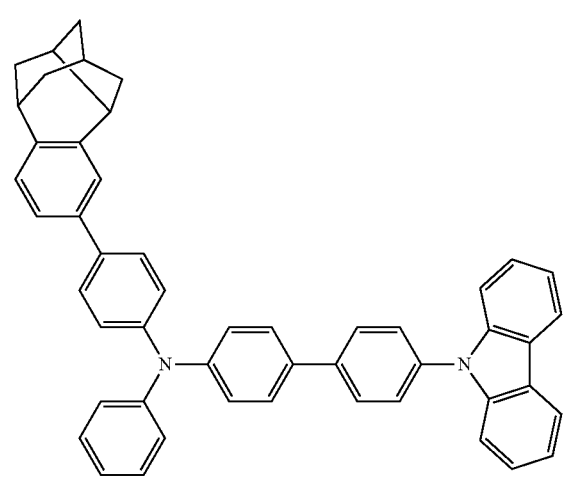
Formula 16
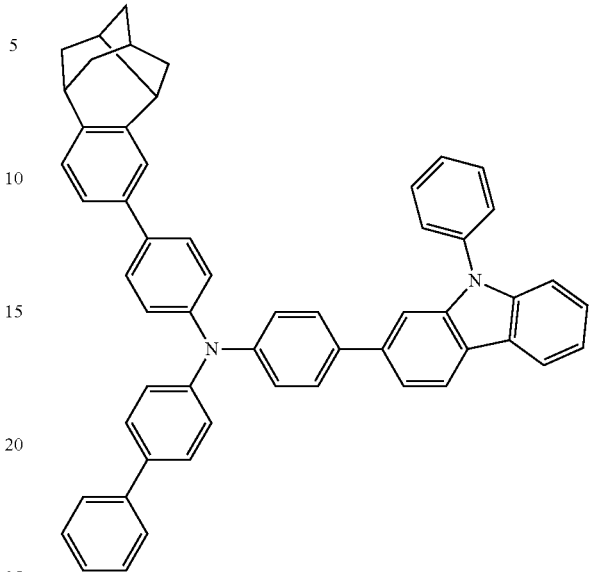
Formula 17
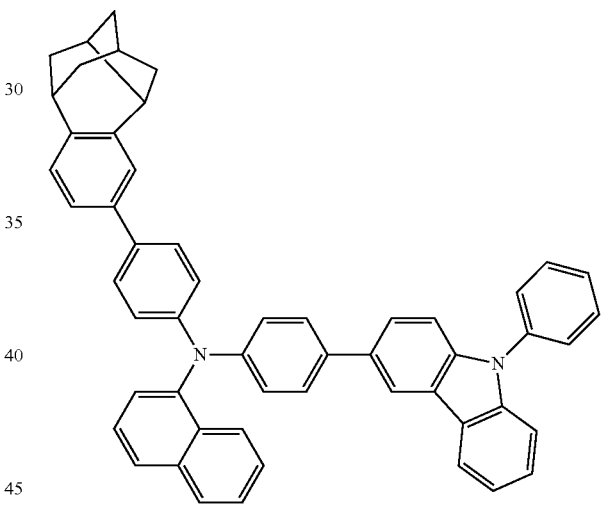
Formula 18
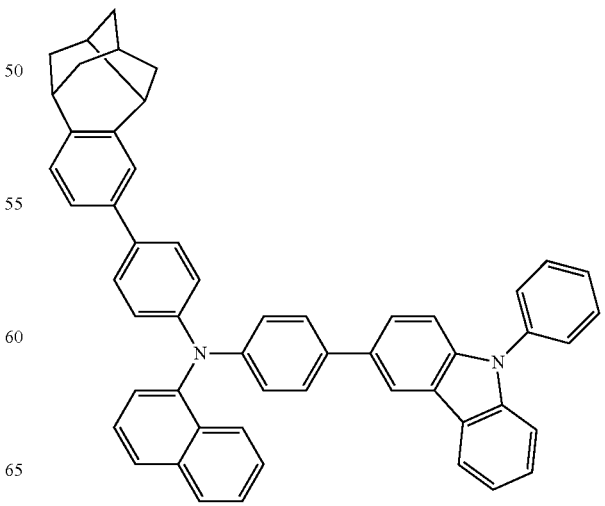

Formula 19
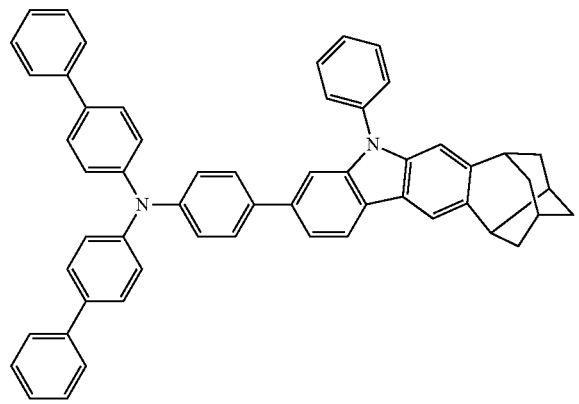
Formula 20
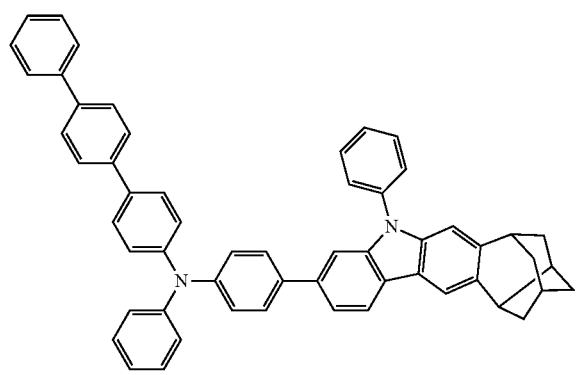
Formula 21
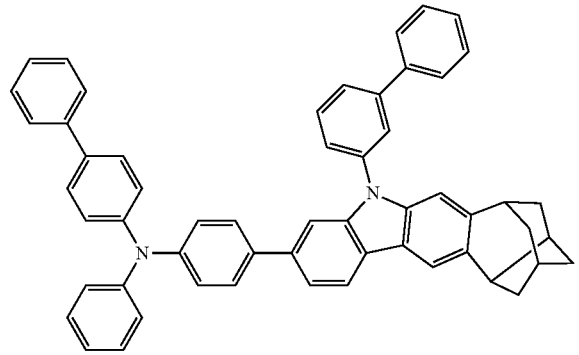
Formula 22
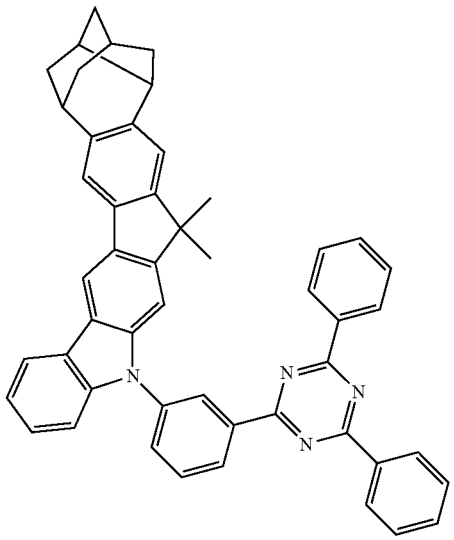
Formula 23
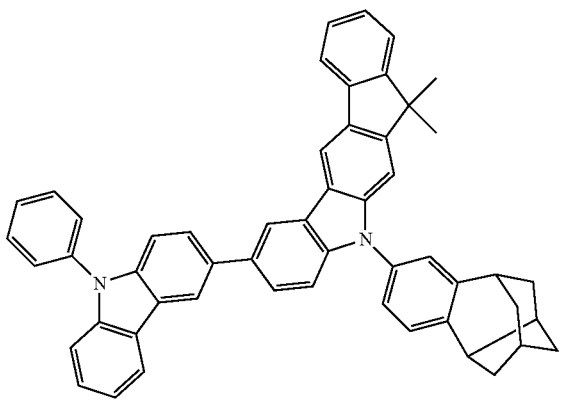
Formula 24
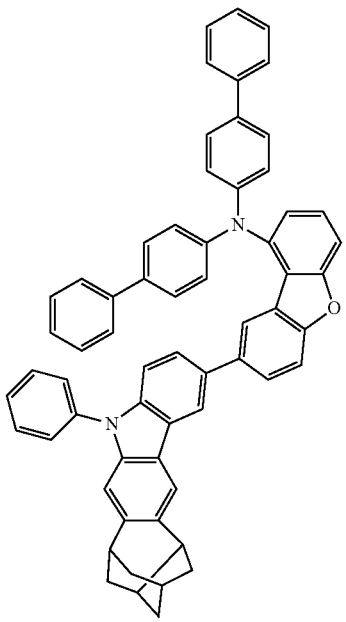

Formula 25
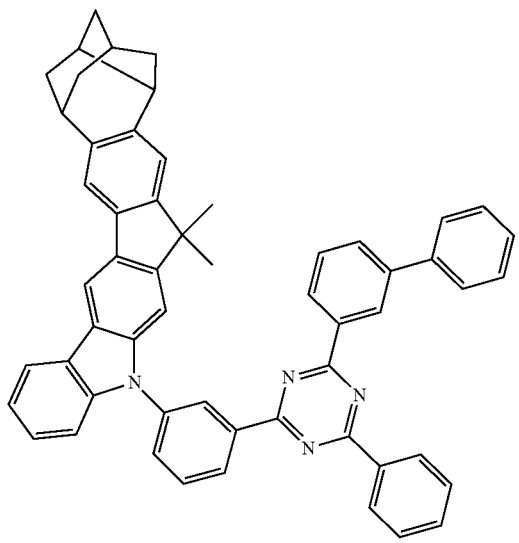
Formula 26
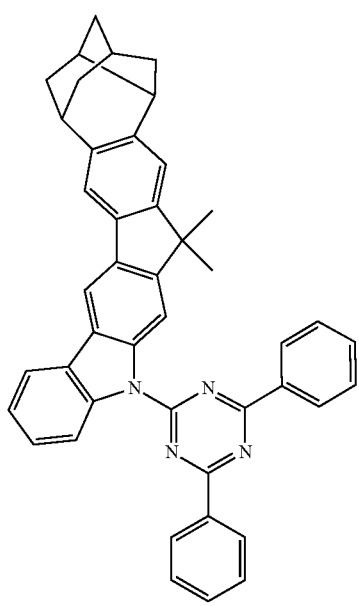
Formula 27
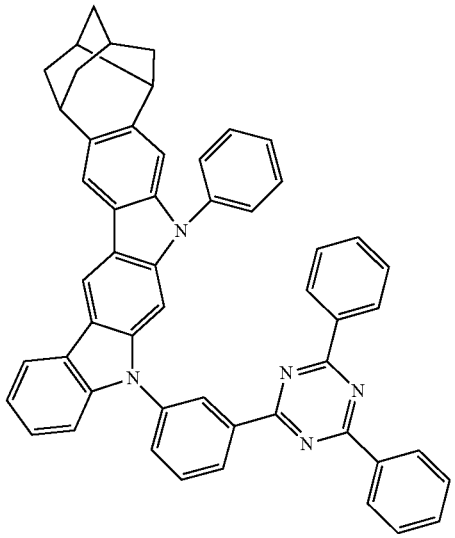
Formula 28
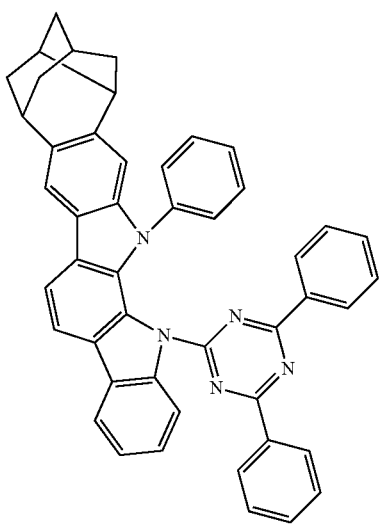
Formula 29

Formula 29
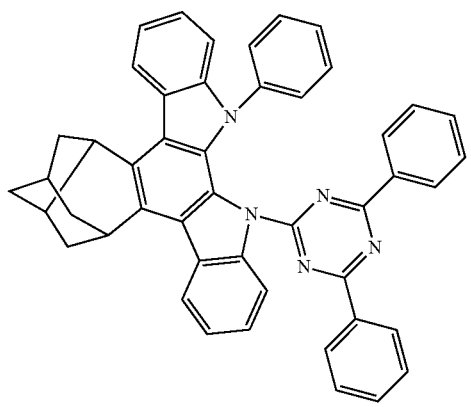
Formula 30
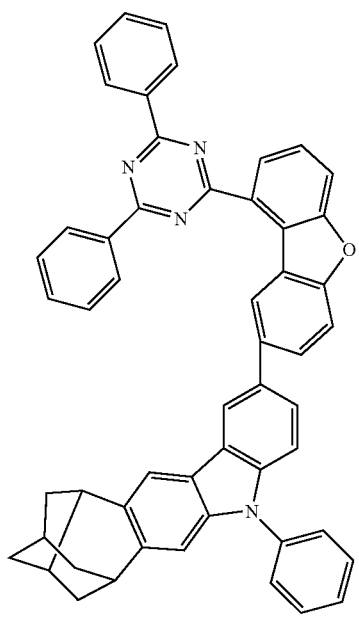
Formula 31
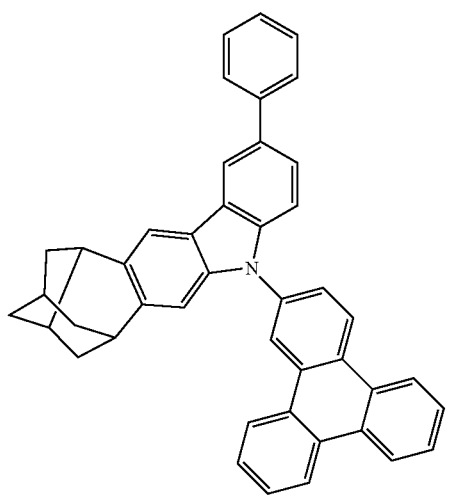
Formula 33
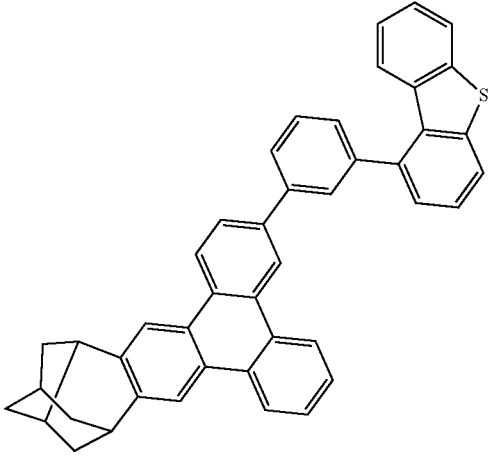
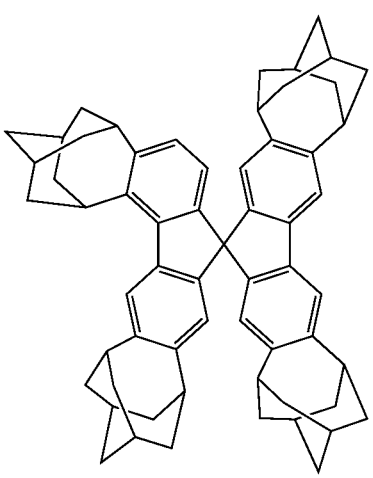
Formula 35
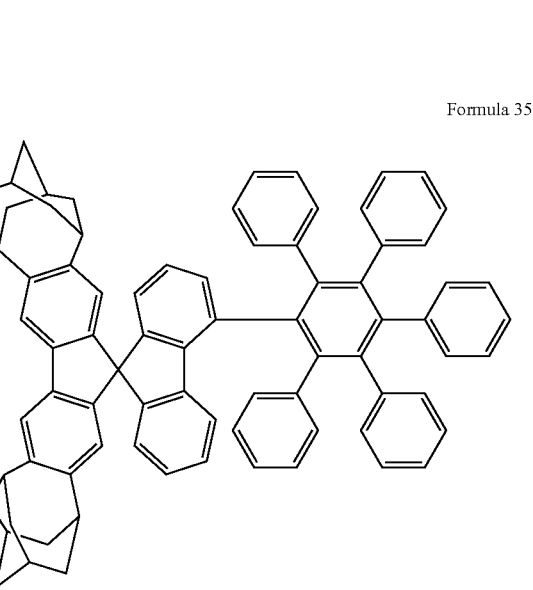

Formula 36
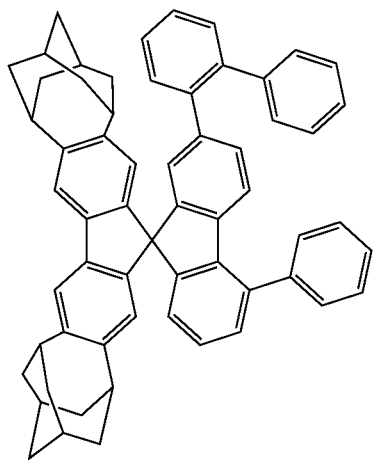
Formula 37
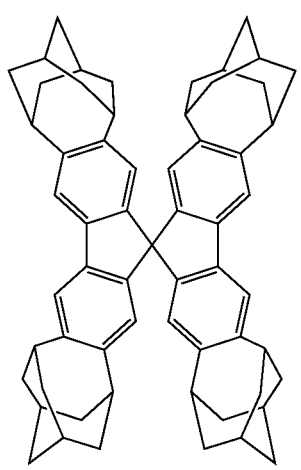
Formula 38
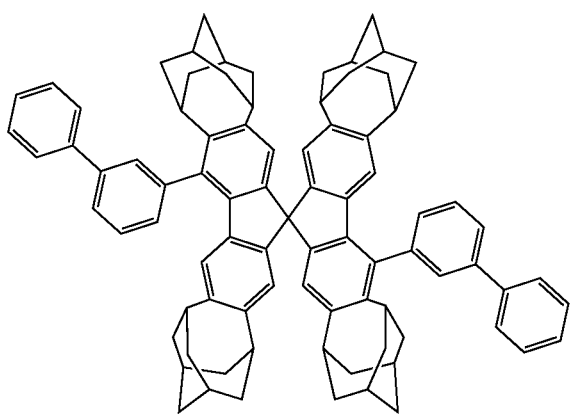
Formula 39
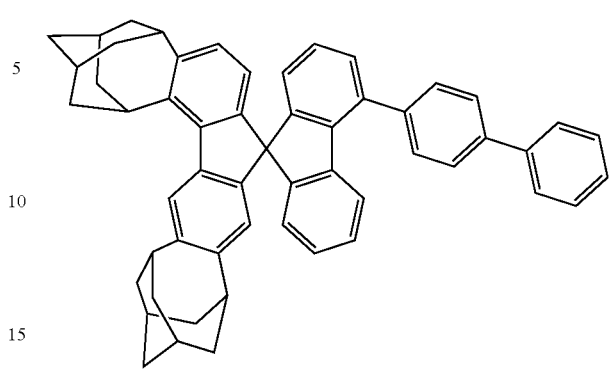
Formula 40
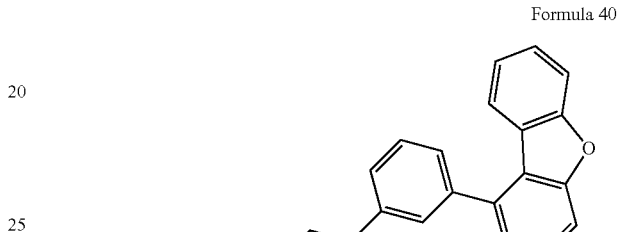
Formula 41
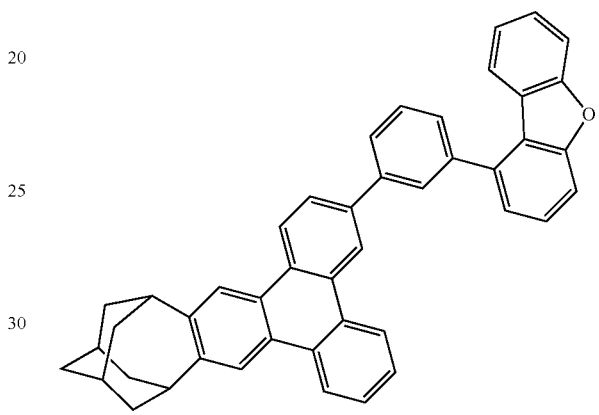
Formula 42
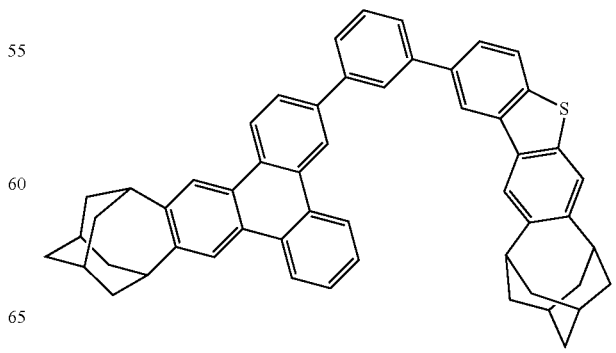

Formula 43
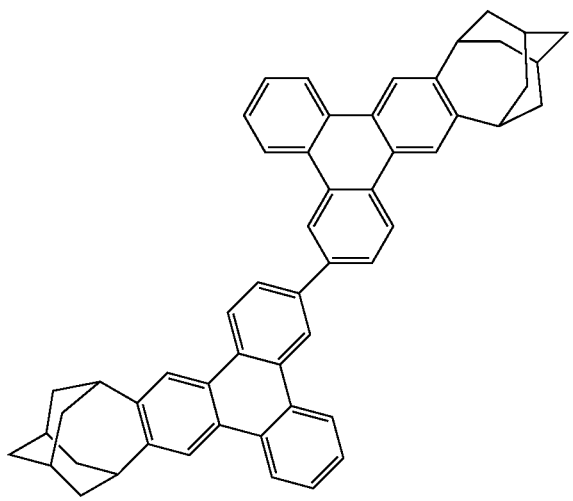
Formula 44
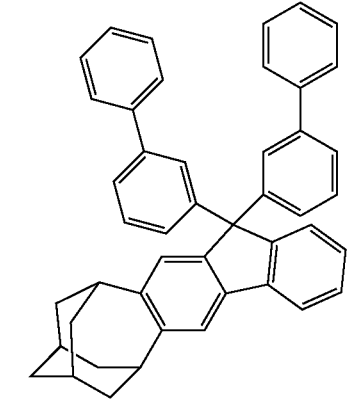
Formula 45
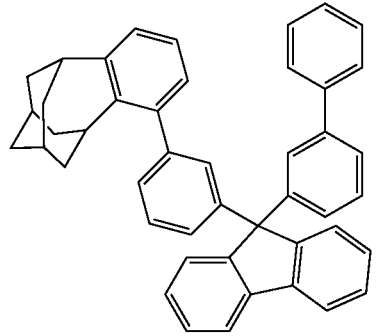
Formula 46
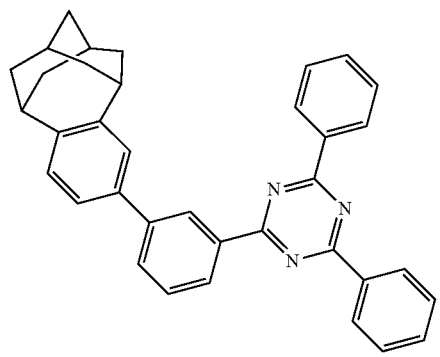
Formula 47
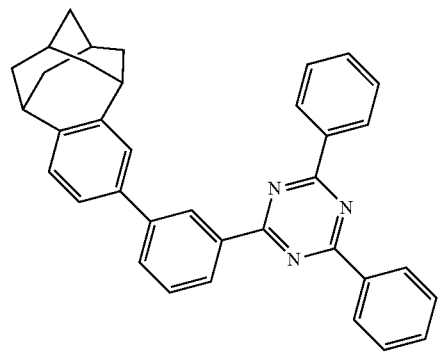
Formula 48
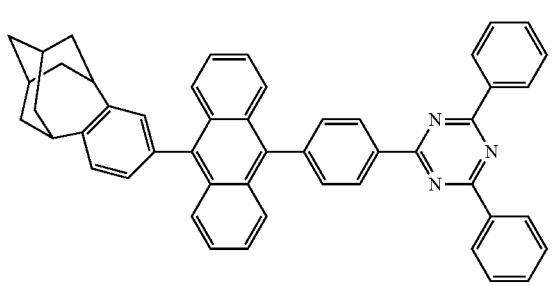
Formula 49
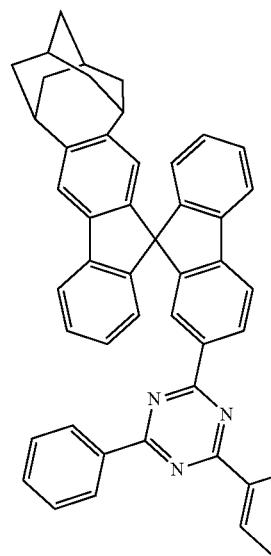

Formula 50
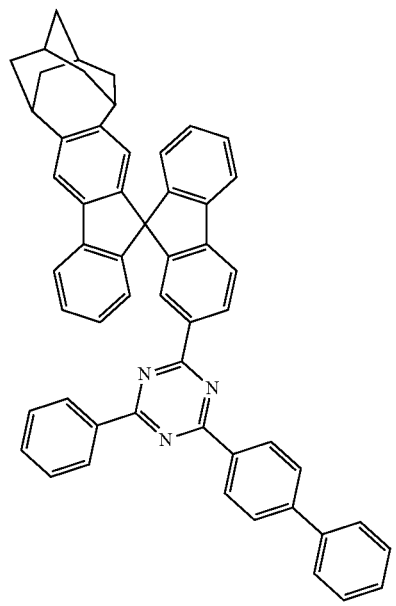
Formula 51
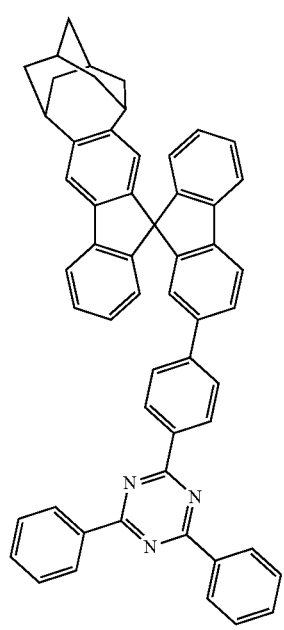
Formula 52
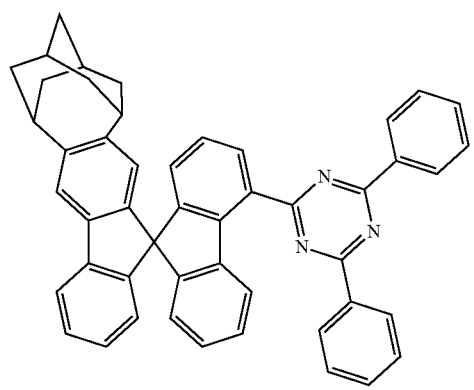
Formula 53
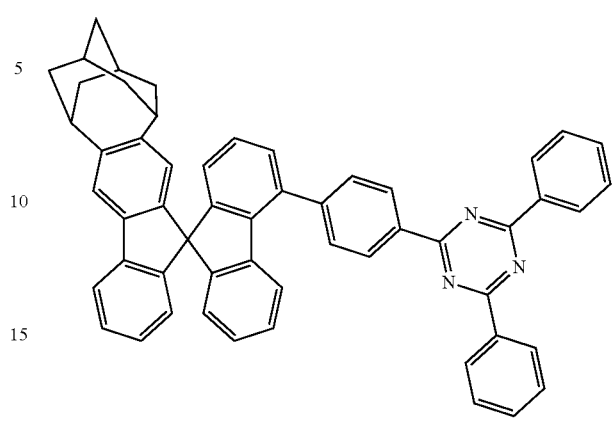
Formula 54
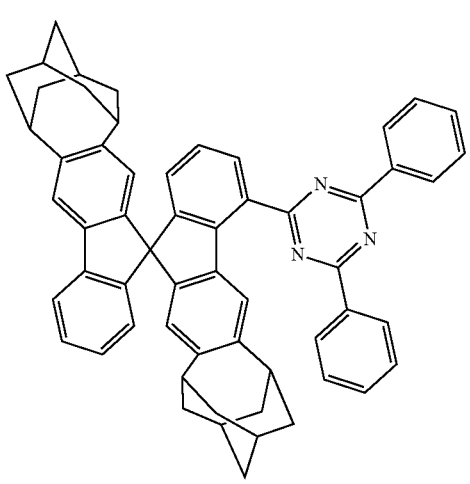
Formula 55
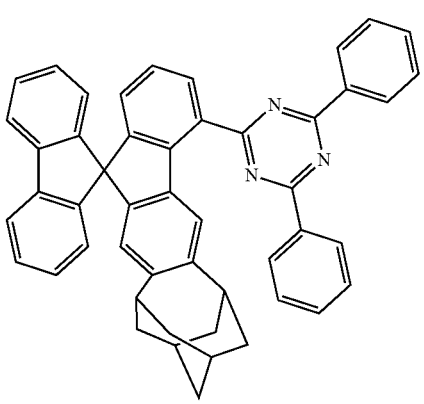

Formula 56
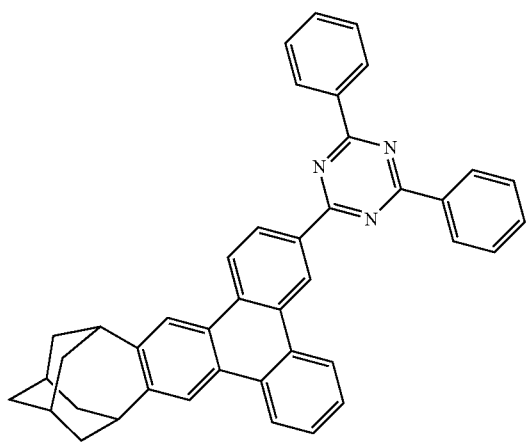
Formula 57
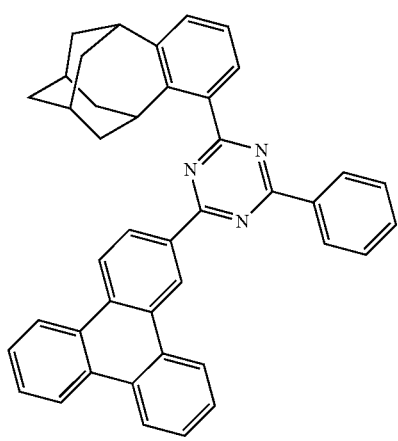
Formula 58
Formula 59
Formula 60
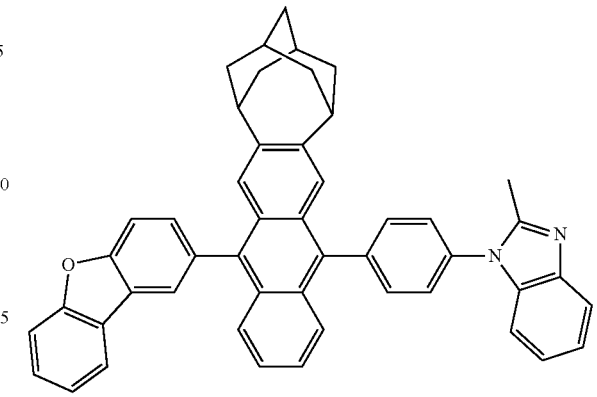
Formula 61
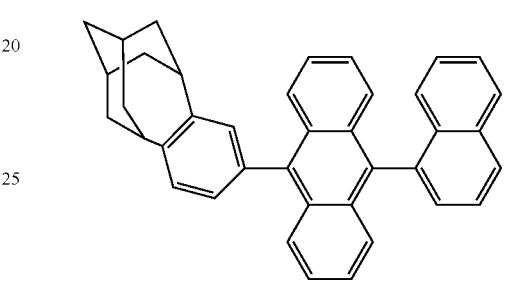
Formula 62
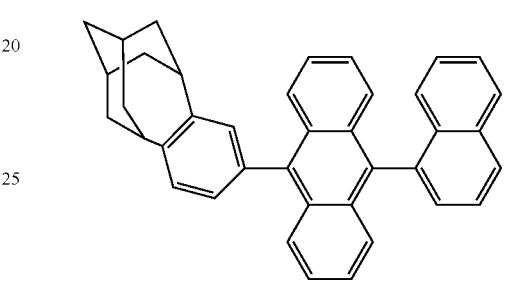
Formula 63
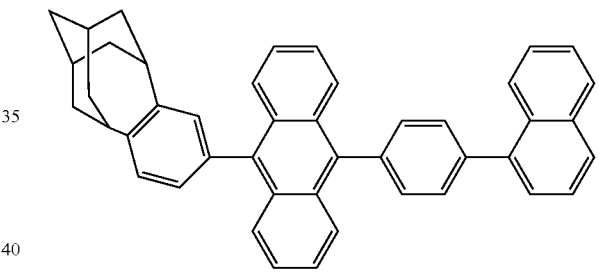
Formula 64
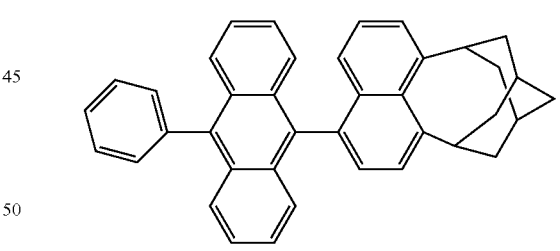

-continued
Formula 65
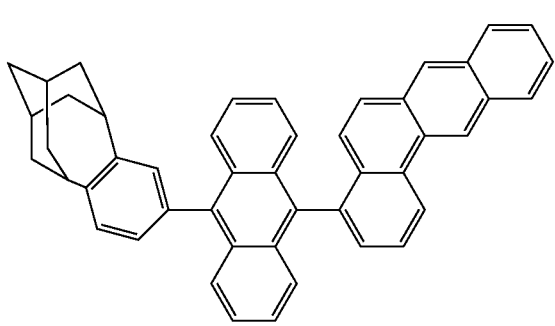
Formula 66
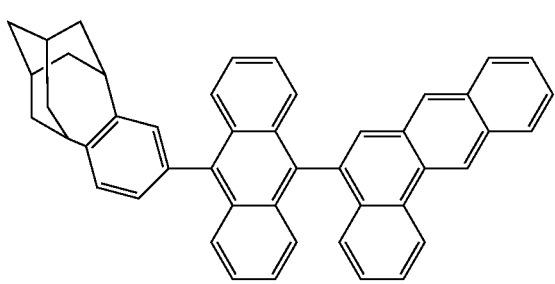
Formula 67
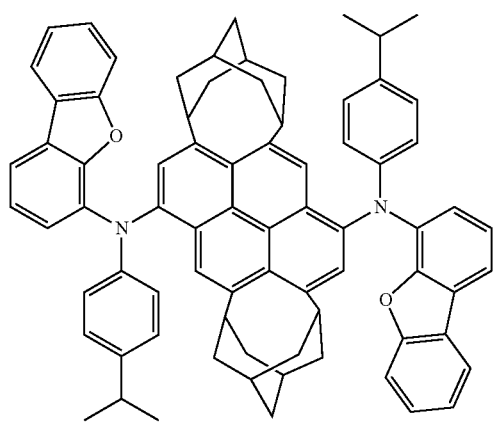
Formula 68
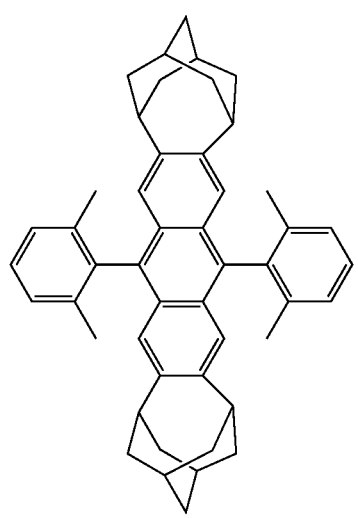
-continued
Formula 69
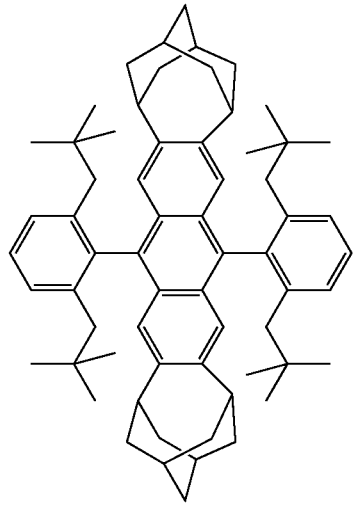
Formula 70
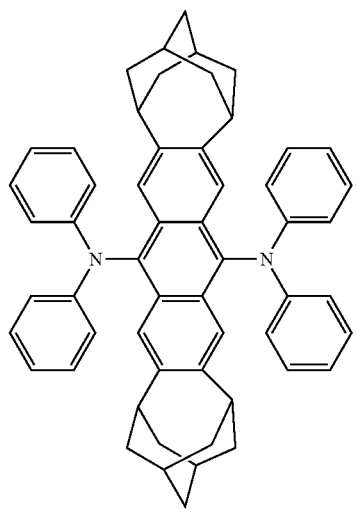
Formula 71

Formula 72
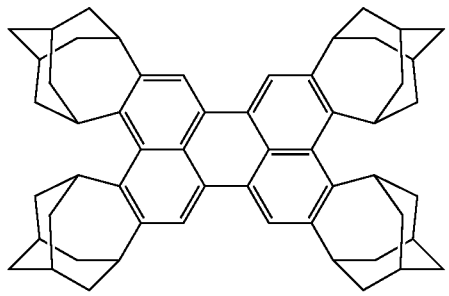
Formula 73
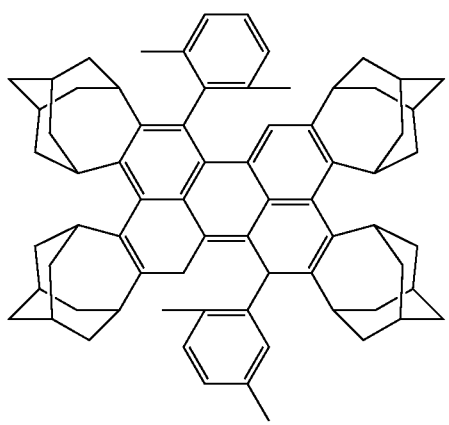
Formula 74
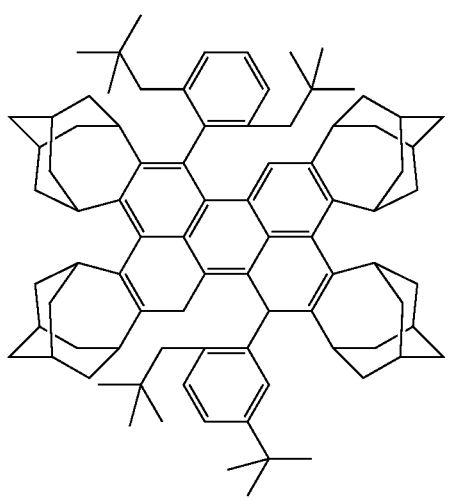
Formula 75
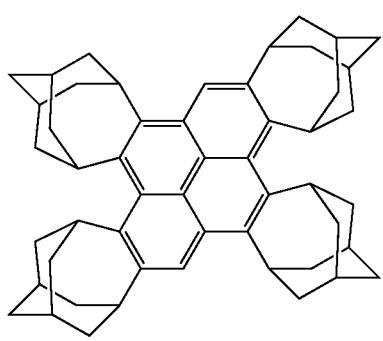
Formula 76
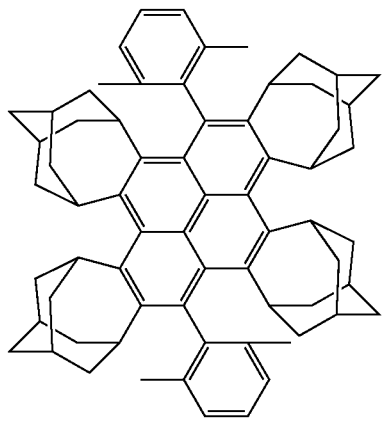
Formula 77
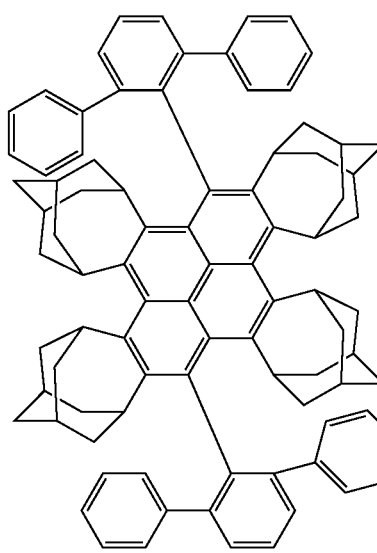
Formula 78
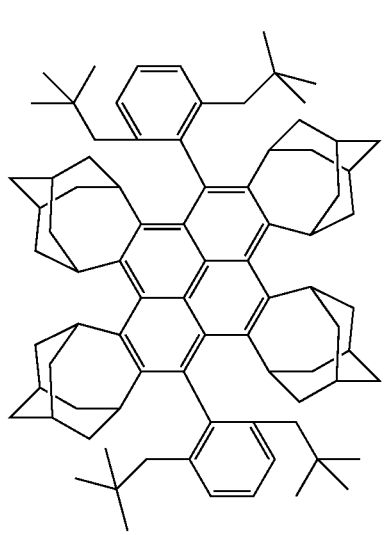

-continued
Formula 79
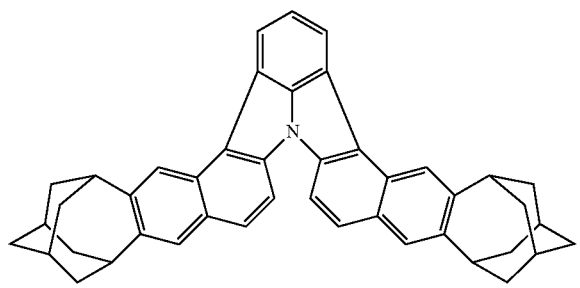
Formula 80
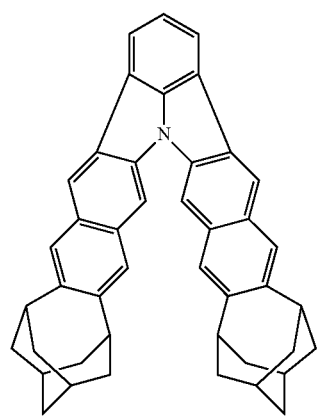
Formula 81
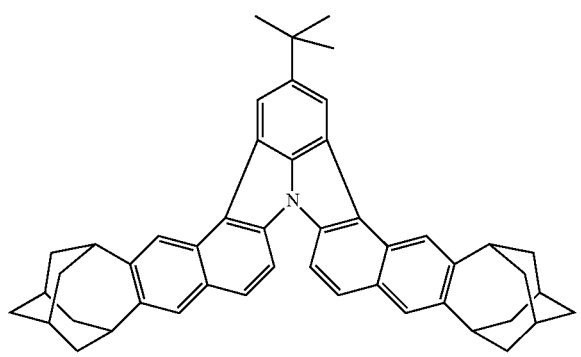
-continued
Formula 82
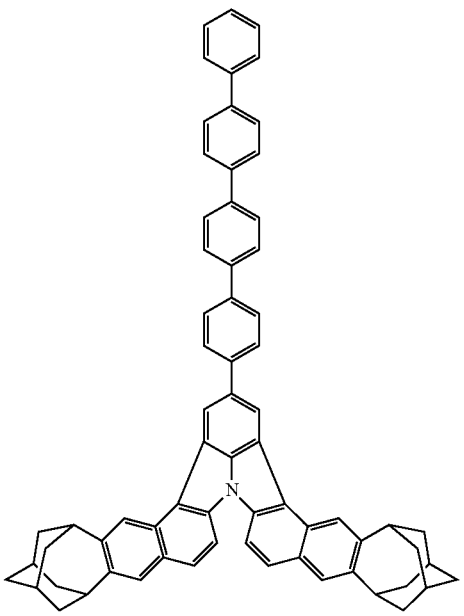
Formula 83
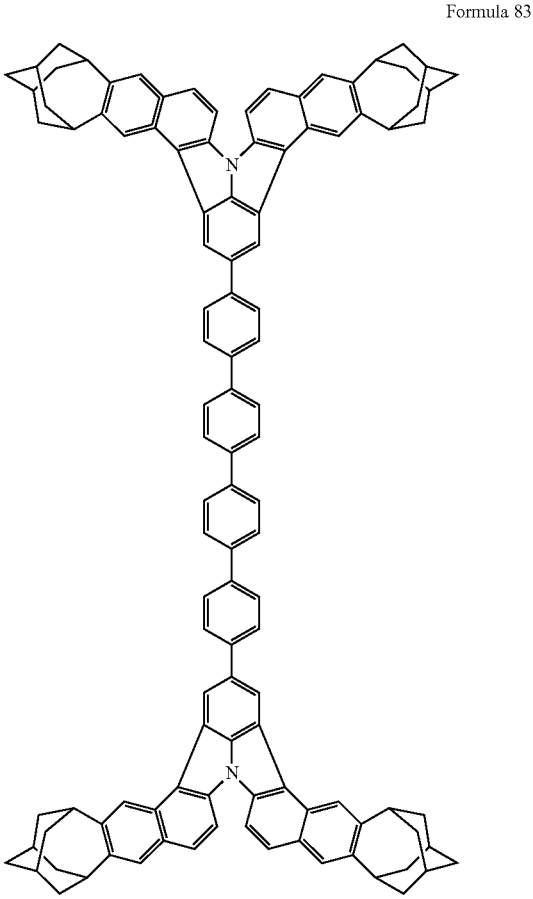

Formula 84
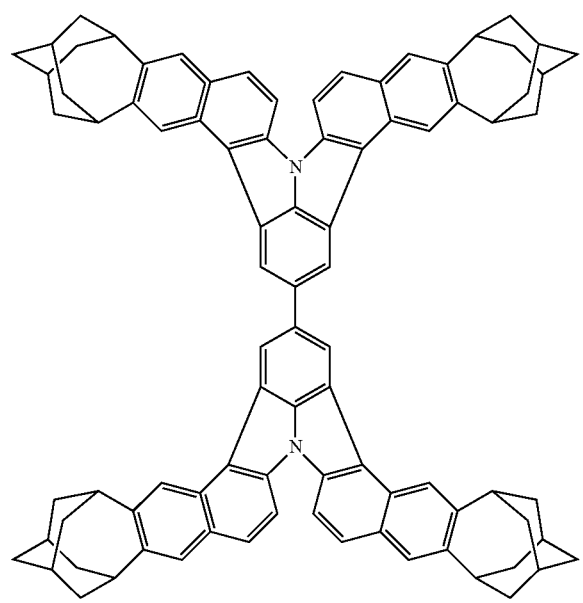
Formula 86
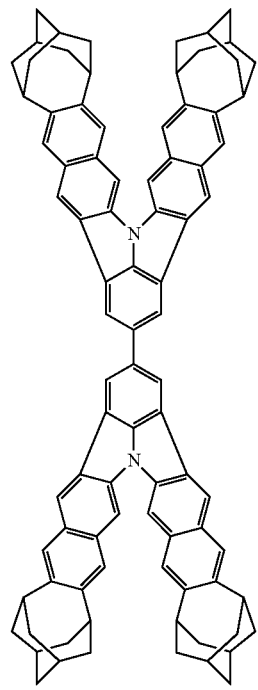
Formula 85
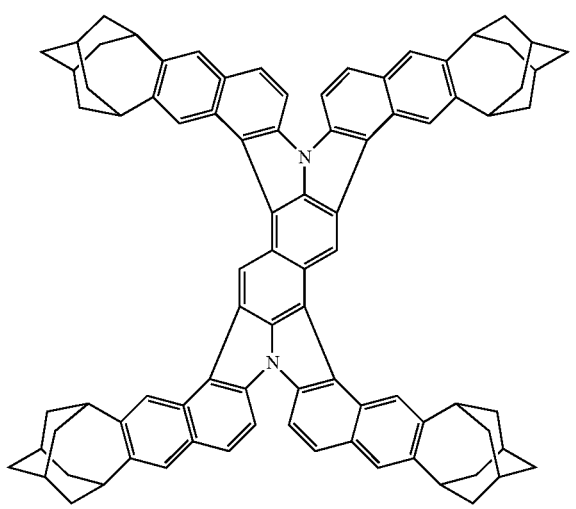
Formula 87
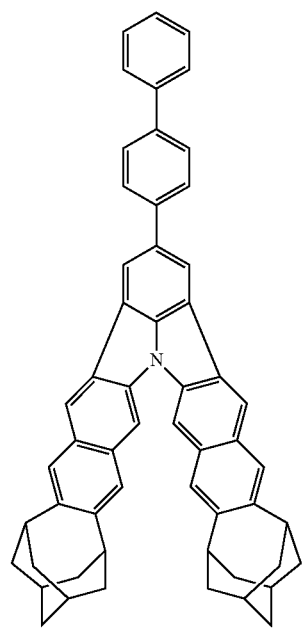

159
-continued
Formula 88
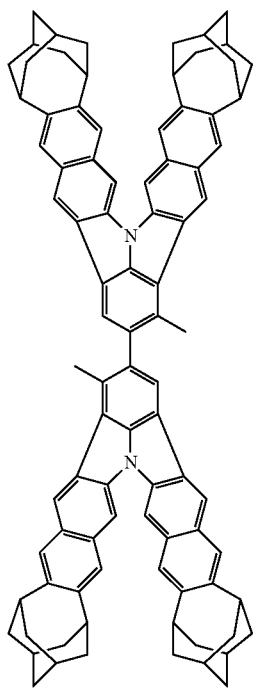
Formula 89
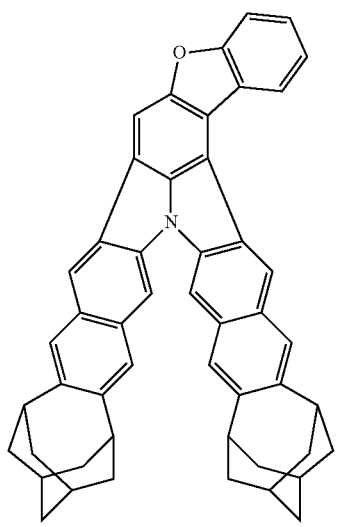
160
-continued
Formula 90
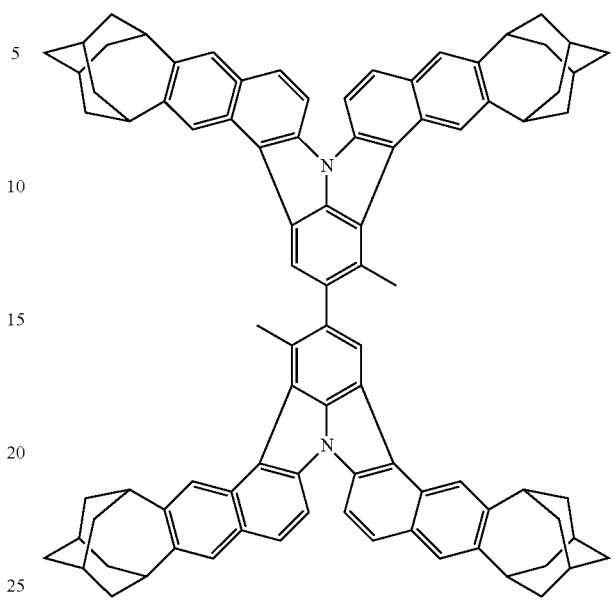
Formula 91
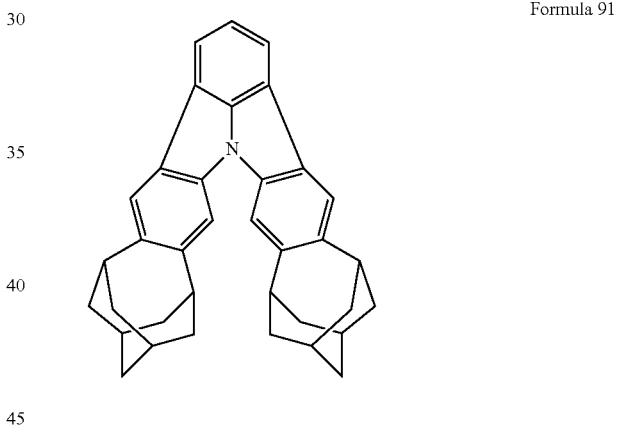
Formula 92
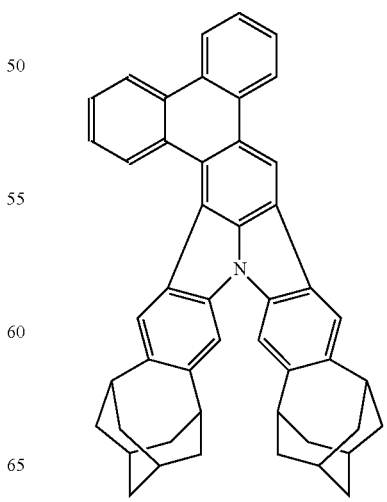

-continued
Formula 93
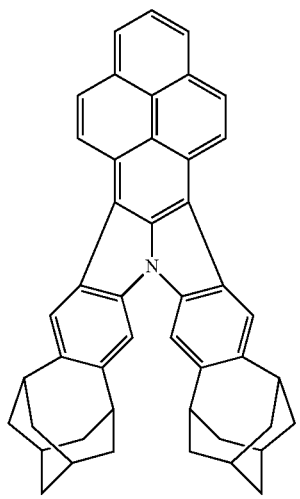
Formula 94
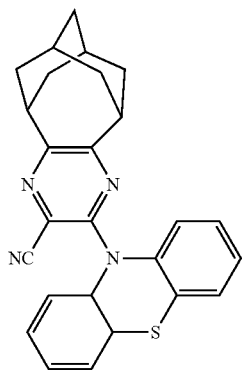
Formula 95
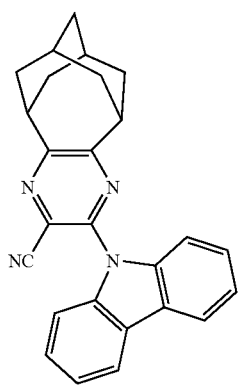
-continued
Formula 96
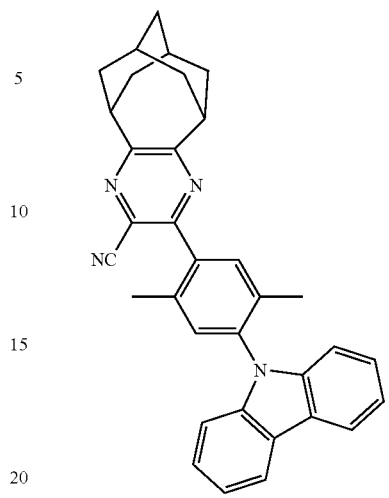
Formula 97
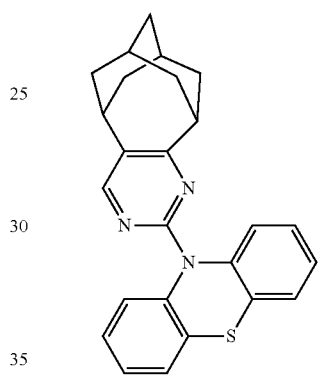
Formula 98
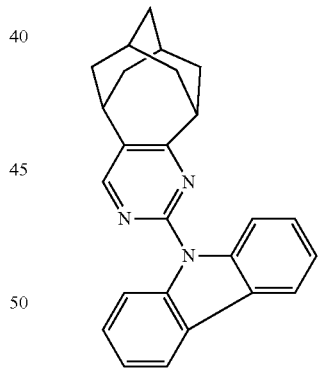
Formula 99
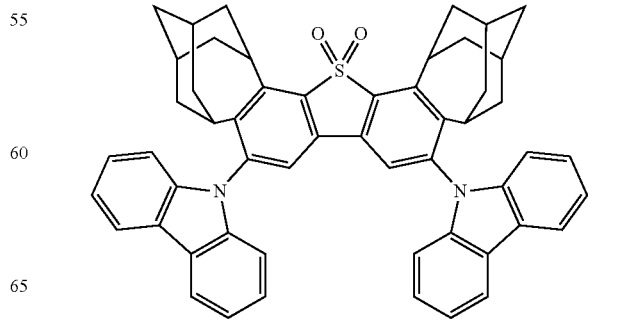

-continued
Formula 100
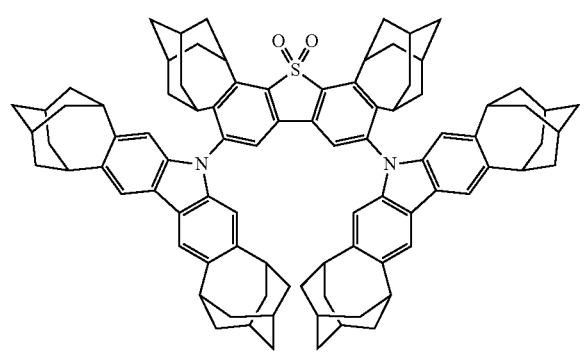
Formula 101
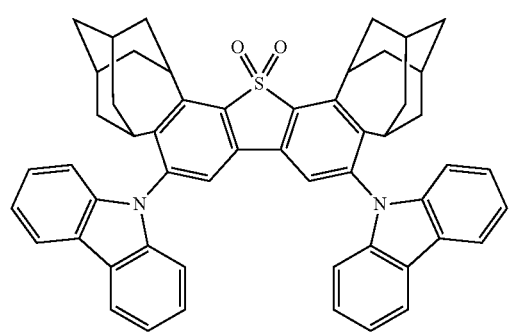
Formula 102
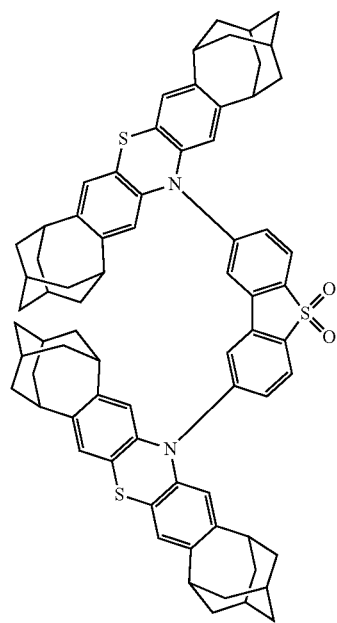
-continued
Formula 103
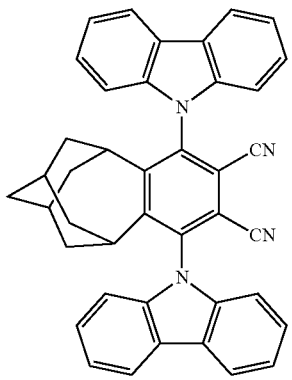
Formula 104
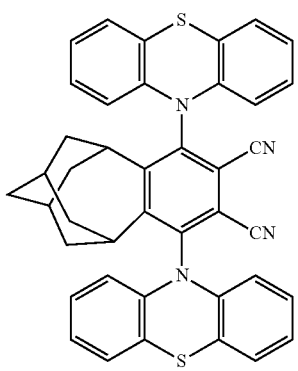
Formula 105
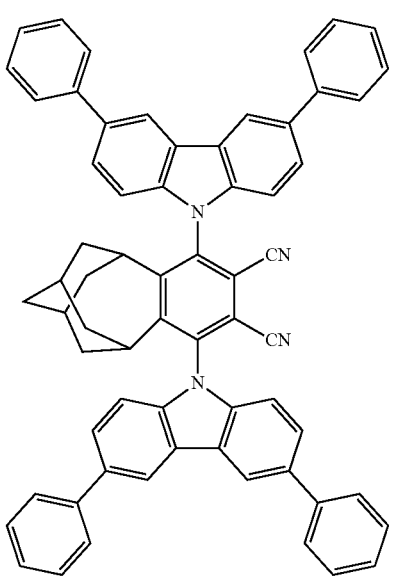
Formula 106
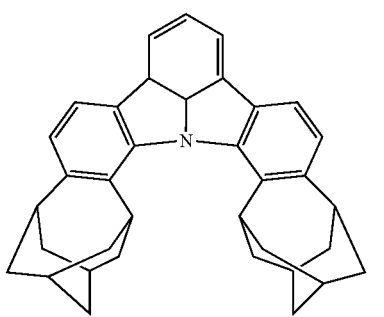

Formula 107

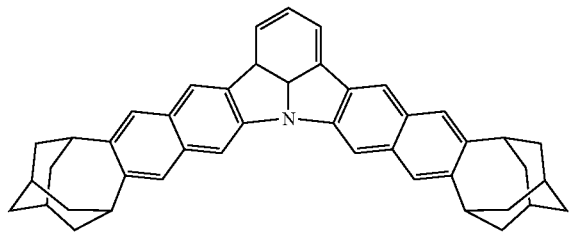

Formula 108

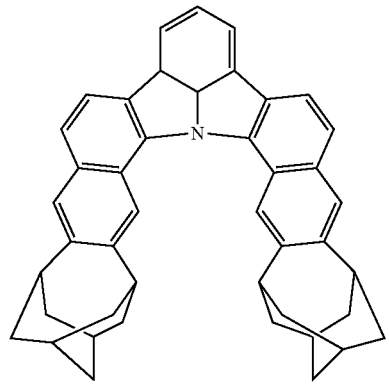

The structures of the formulae 1 to 18 are suitable inter alia as hole ' ' conductor materials (HTM) and possibly as electron blocker materials (EBM). The structures of the formulae 1 to 33 are suitable inter alia as triplet matrix material (TMM), especially for phosphorescent emitters, and as matrix material for TADF compounds. The structures of the formulae 34 to 45 are especially suitable as wide bandgap materials. The structures of the formulae 46 to 60 are especially suitable as electron transport materials (ETM) or as electron-conducting triplet matrix material (eTMM). The structures of the formulae 61 to 67 are especially suitable as matrix materials fluorescent emitters (SMB). The structures of the formulae 67 to 93 are especially suitable as fluorescent emitters (SEB). The structures of the formulae 94 to 105 are especially suitable as emitters that exhibit TADF (thermally activated delayed fluorescence) and as TADF compound in hyperfluorescences.

Preferred embodiments of compounds of the invention are recited specifically in the examples, these compounds being usable alone or in combination with further compounds for all purposes of the invention.

Provided that the conditions specified in claim 1 are met, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds of the invention, preferably compounds comprising structures of the formulae (I) to (XVIII), in which, in a coupling reaction, a compound comprising at least one aliphatic polycyclic ring system having at least 3 rings is joined to a compound comprising at least one aromatic or heteroaromatic group.

Suitable compounds comprising at least one aliphatic polycyclic ring system having at least 3 rings are in many cases commercially available, with the starting compounds detailed in the examples being obtainable by known processes, and so reference is made thereto.

These compounds can be reacted with further compounds comprising at least one aromatic or heteroaromatic group by known coupling reactions, the necessary conditions for this purpose being known to the person skilled in the art, and detailed specifications in the examples assisting the person skilled in the art in conducting these reactions.

Particularly suitable and preferred coupling reactions which all lead to C—C bond formation and/or C—N bond formation are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

The principles of the preparation processes detailed above are known in principle from the literature for similar compounds and can be adapted easily by the person skilled in the art to the preparation of the compounds of the invention. Further information can be found in the examples.

It is possible by these processes, if necessary followed by purification, for example recrystallization or sublimation, to obtain the compounds of the invention comprising structures of formulae (I) to (XVIII) in high purity, preferably more than 99% (determined by means of $^1$H NMR and/or HPLC).

The compounds of the invention may also have suitable substituents, for example by relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, such that the compounds are soluble at room temperature in toluene or xylene, for example, in sufficient concentration to be able to process the compounds from solution. These soluble compounds are of particularly good suitability for processing from solution, for example by printing methods. In addition, it should be emphasized that the compounds of the invention comprising at least one structure of the formulae (I) to (XVIII) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds and polymers of the invention may be used in the form of a crosslinked or uncrosslinked layer.

The invention therefore further provides oligomers, polymers or dendrimers containing one or more of the above-detailed structures of the formulae (I) to (XVIII) or compounds of the invention, wherein there are one or more bonds of the compounds of the invention or of the structures of the formulae (I) to (XVIII) to the polymer, oligomer or dendrimer. According to the linkage of the structures of the formulae (I) to (XVIII) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formulae (I) to (XVIII) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

Additionally of particular interest are compounds of the invention which feature a high glass transition temperature. In this connection, in particular, compounds of the invention that are usable as active compound in an organic electronic device are preferably compounds comprising structures of the formulae (I) to (XVIII) and/or the formulae (Ia) to (XVIIIa), or the compounds obtainable by a combination of the substructures of the formulae (N-1) to (N-6), (Ar-1) to (Ar-54) and/or (Ar'-1) to (Ar'-53), or the preferred embodiments recited above and hereinafter that have a glass transition temperature of at least 70° C., more preferably of at least 110° C., even more preferably of at least 125° C. and especially preferably of at least 150° C., determined to DIN 51005 (2005-08 version).

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound, for example a fluorescent dopant, a phosphorescent dopant or a compound that exhibits TADF (thermally activated delayed fluorescence), especially a phosphorescent dopant, and/or a further matrix material. This further compound may also be polymeric.

The present invention therefore still further provides a composition comprising a compound of the invention and at least one further organically functional material. Functional materials are generally the organic or inorganic materials introduced between the anode and cathode. Preferably, the organically functional material is selected from the group consisting of fluorescent emitters, phosphorescent emitters, emitters that exhibit TADF (thermally activated delayed fluorescence), host materials, electron transport materials, electron injection materials, hole conductor materials, hole injection materials, electron blocker materials, hole blocker materials, wide band gap materials and n-dopants.

The present invention therefore also relates to a composition comprising at least one compound of the invention, preferably a compound comprising structures of formulae (I) to (XVIII) or the preferred embodiments recited above and hereinafter, and at least one further matrix material. According to a particular aspect of the present invention, the further matrix material has hole-transporting properties.

The present further provides a composition comprising at least one compound of the invention, preferably a compound comprising at least one structure of formulae (I) to (XVIII) or the preferred embodiments recited above and hereinafter, and at least one wide bandgap material, a wide bandgap material being understood to mean a material in the sense of the disclosure of U.S. Pat. No. 7,294,849. These systems exhibit exceptional advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state ST of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31 G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31 G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

$$HOMO(eV)=((HEh*27.212)-0.9899)/1.1206$$

$$LUMO(eV)=((LEh*27.212)-2.0041)/1.385$$

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09 W" (Gaussian Inc.) and Q-Chem4.1 (Q-Chem, Inc.).

The present invention also relates to a composition comprising at least one compound comprising structures of formulae (I) to (XVIII) or the preferred embodiments recited above and hereinafter and at least one phosphorescent emitter, the term "phosphorescent emitters" also being understood to mean phosphorescent dopants.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in matrix systems, preferably mixed matrix systems, are the preferred phosphorescent dopants specified hereinafter.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent compounds.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2016124304, WO 2017032439, WO 2018019687, WO 2018019688, WO 2018041769, WO 2018054798, WO 2018069196, WO 2018069197, WO 2018069273.

In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Explicit examples of phosphorescent dopants are adduced in the following table:

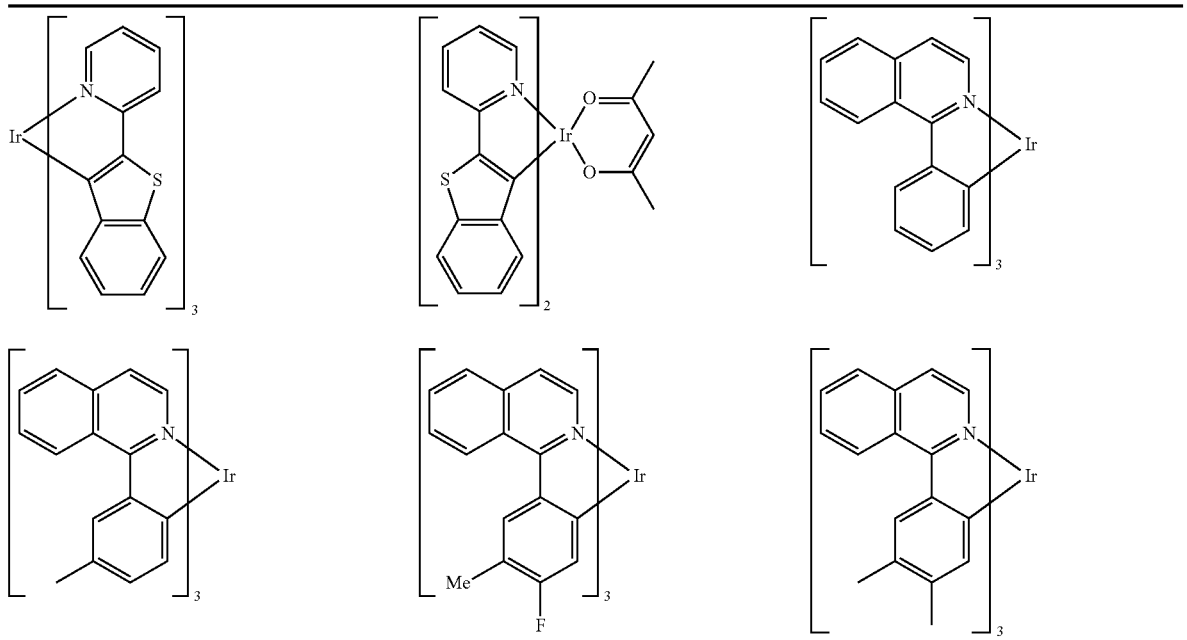

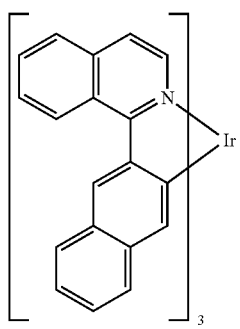
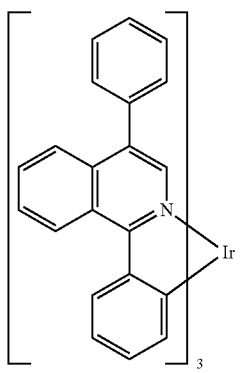
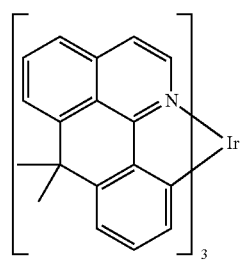
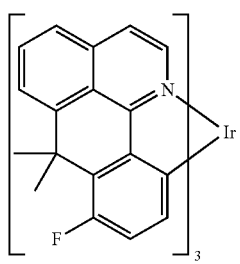
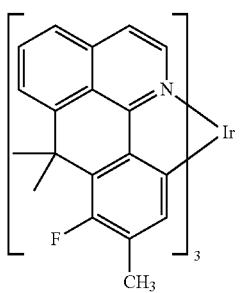
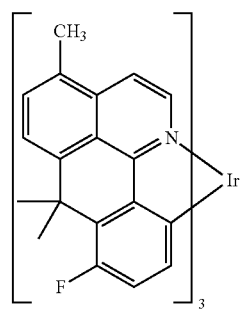
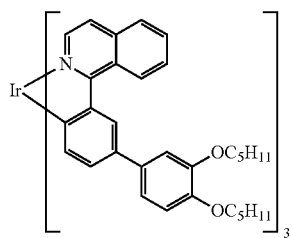
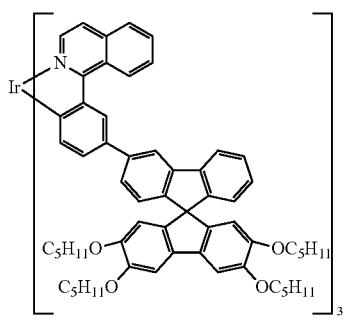
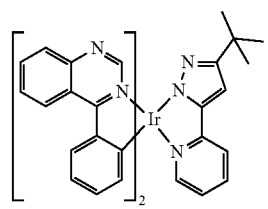
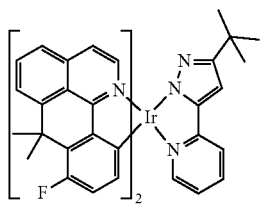
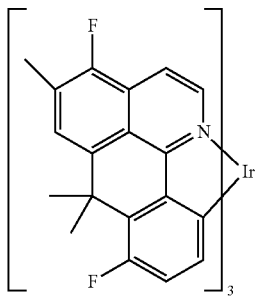
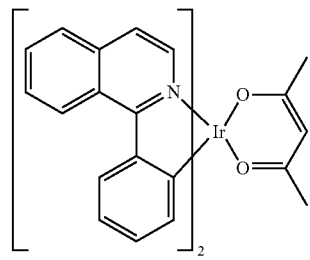
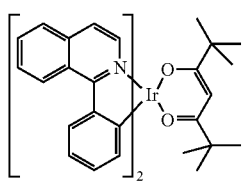
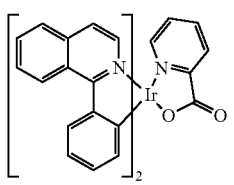
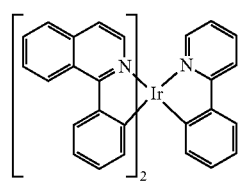

-continued
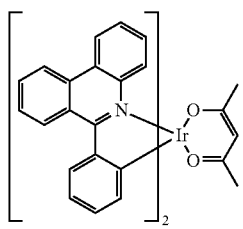 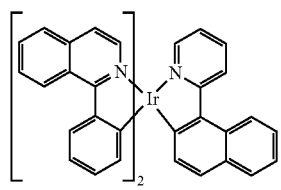 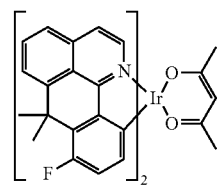
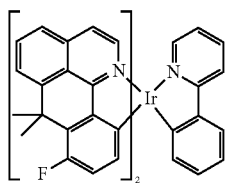 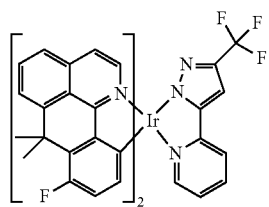 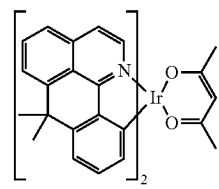
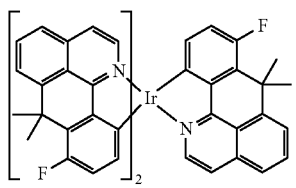 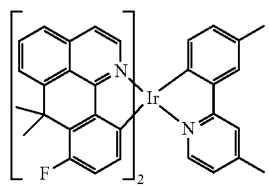 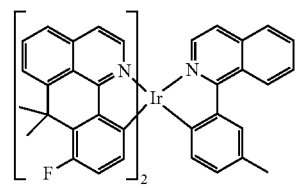
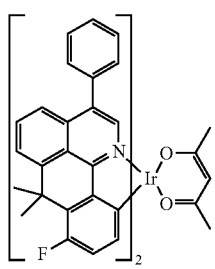 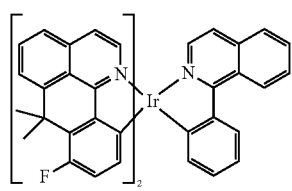 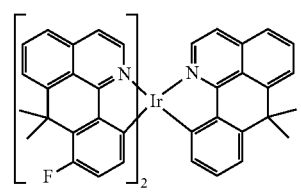
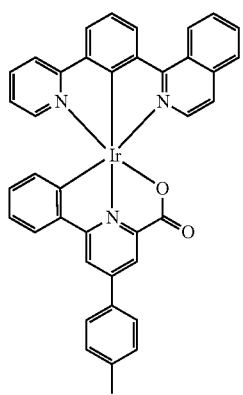 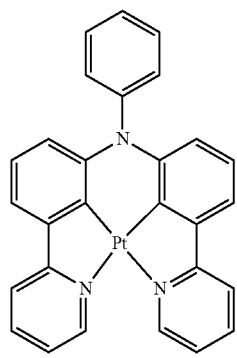 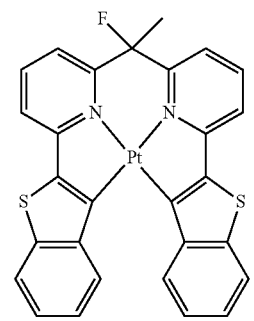

-continued
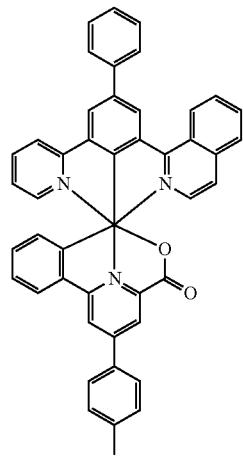 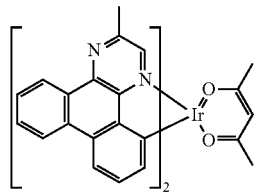 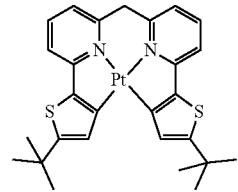
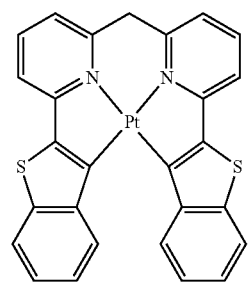 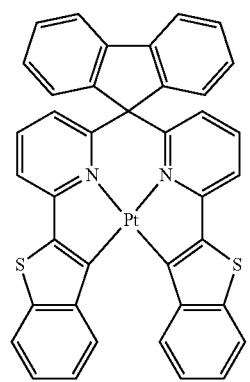 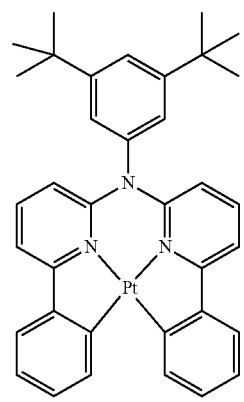
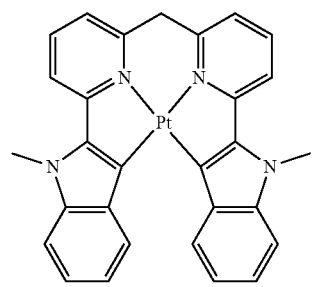 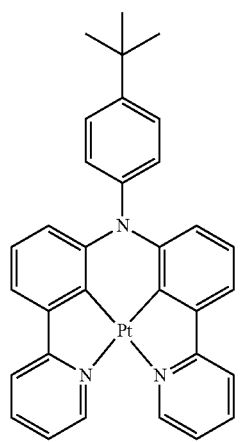 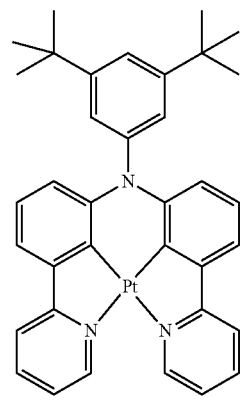

-continued
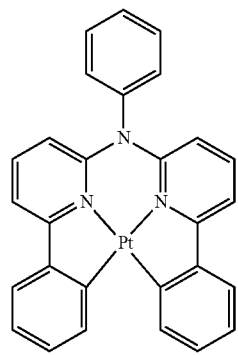
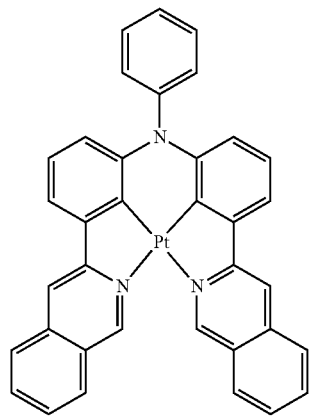
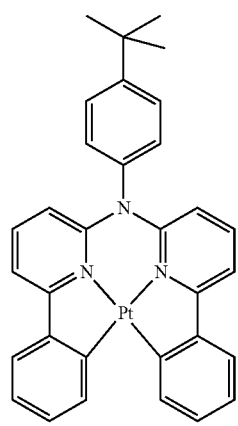
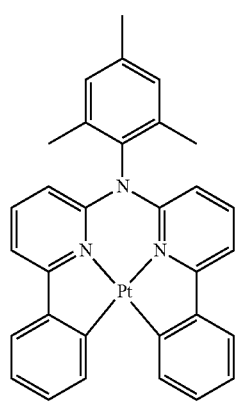
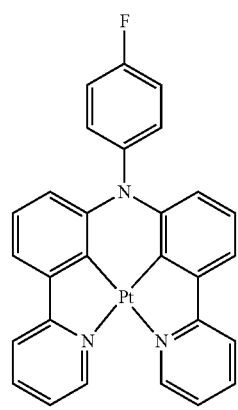
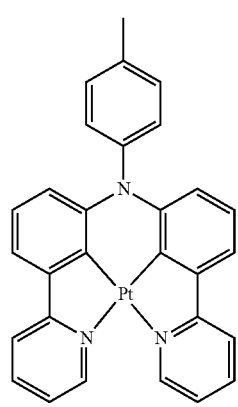
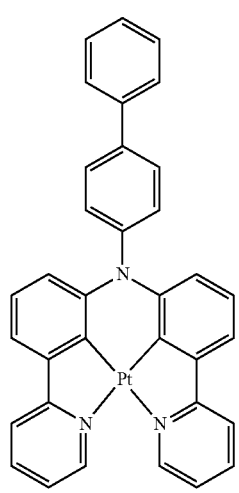
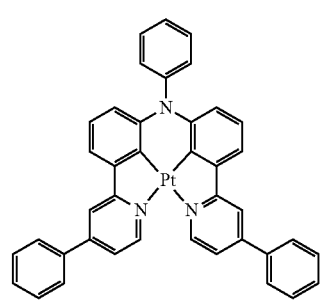

-continued
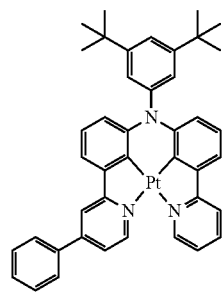
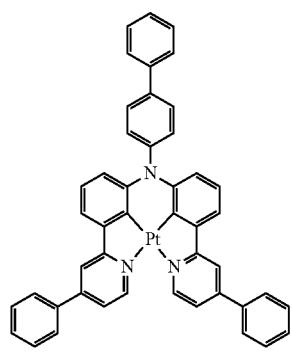
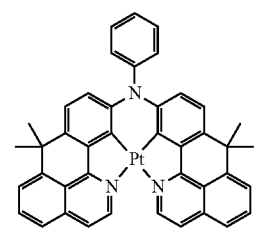
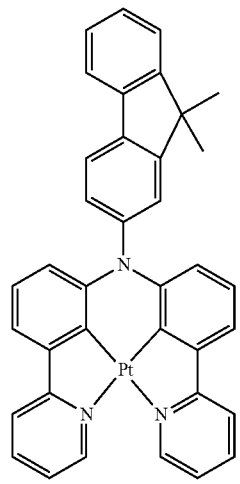
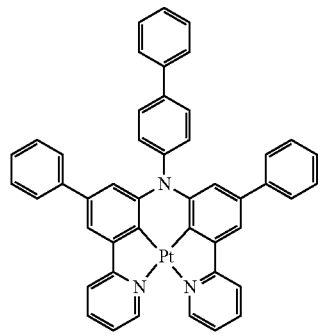
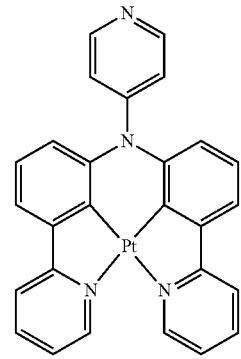
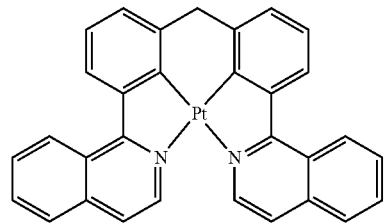
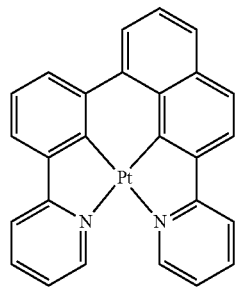
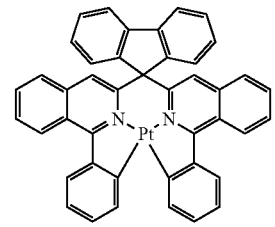
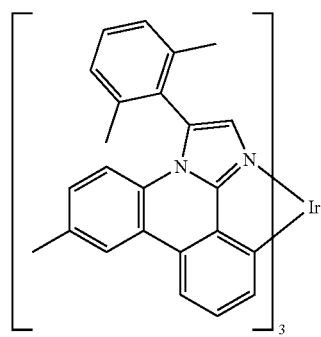
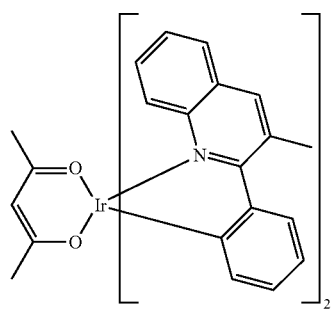
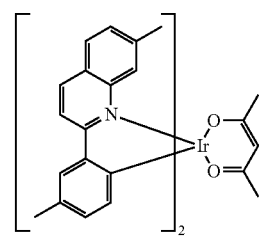

-continued
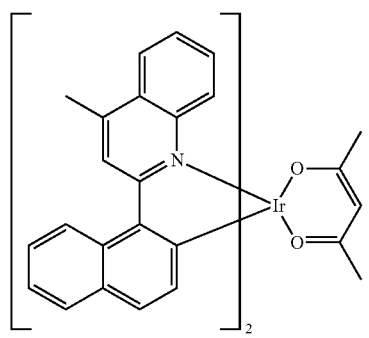
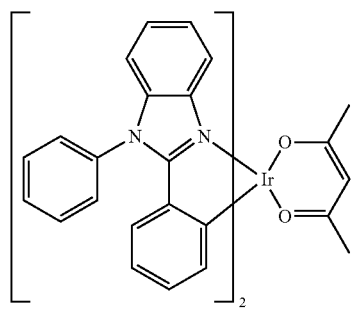
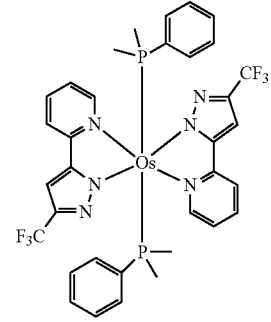
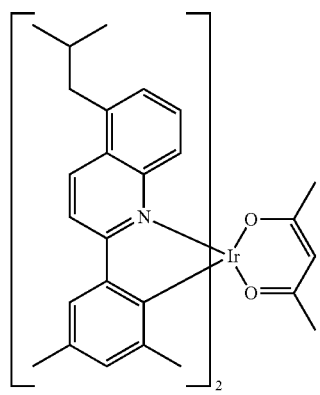
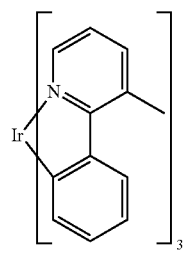
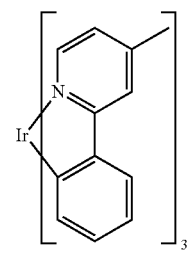
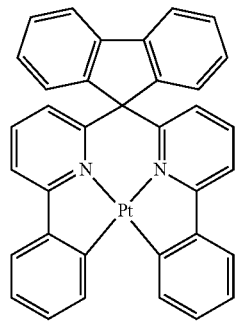
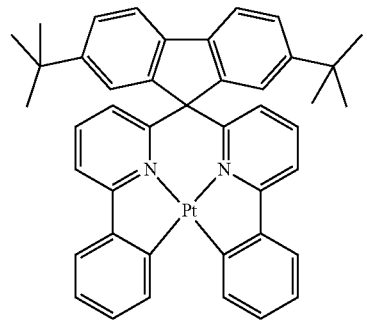
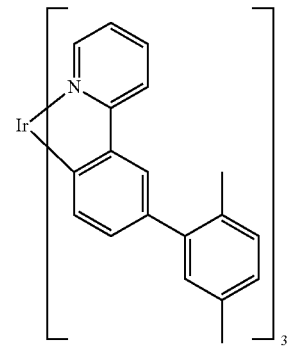
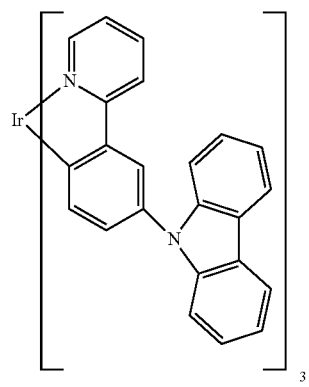
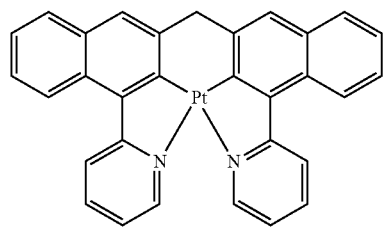
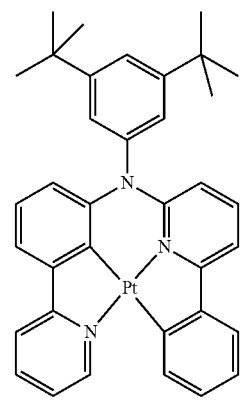

-continued
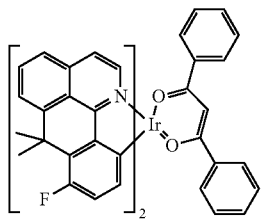
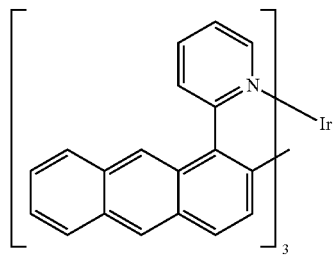
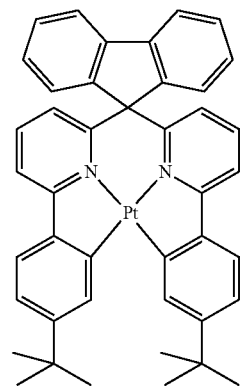
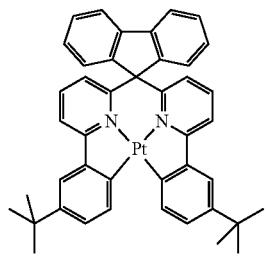
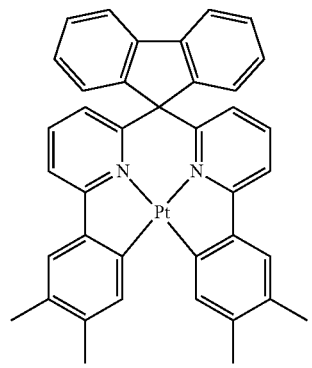
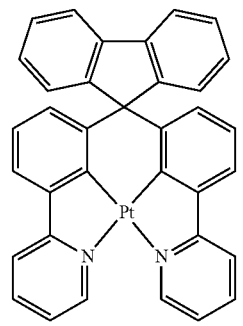
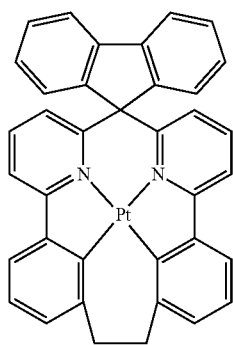
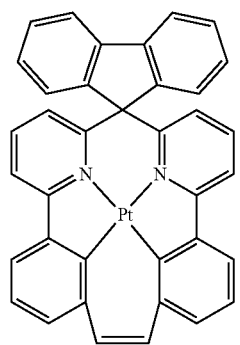
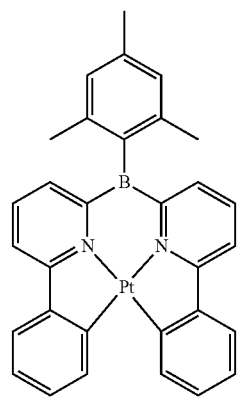
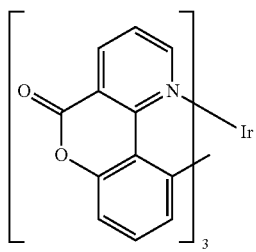
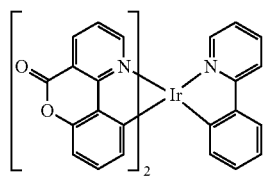
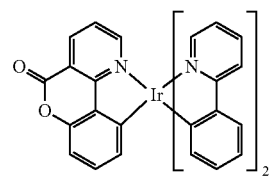

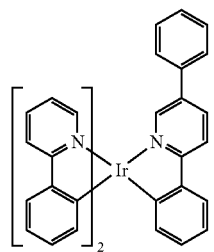
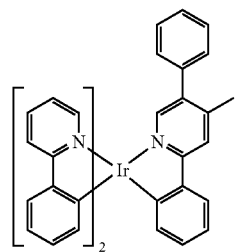
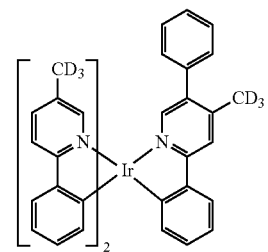
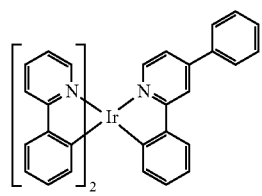
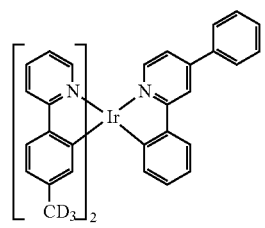
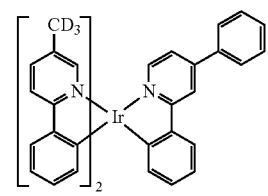
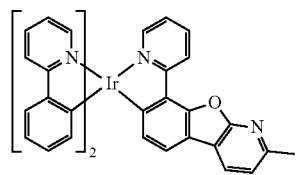
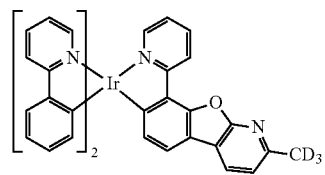
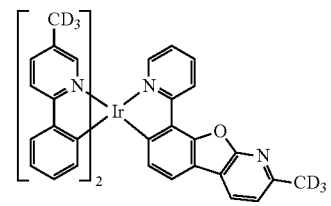
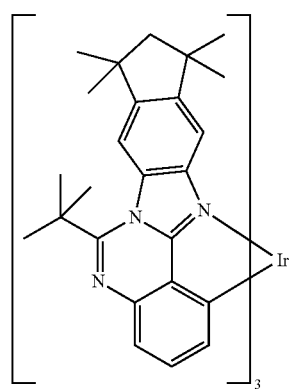
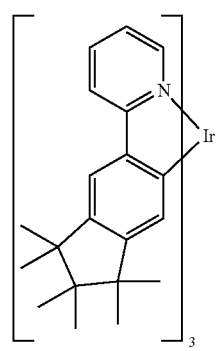
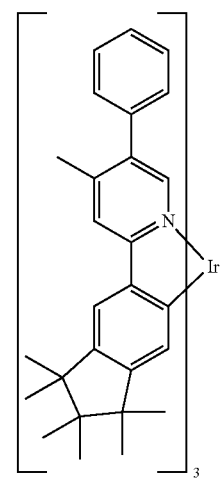
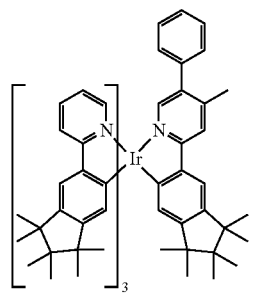
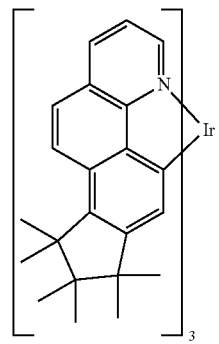
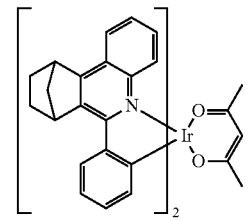

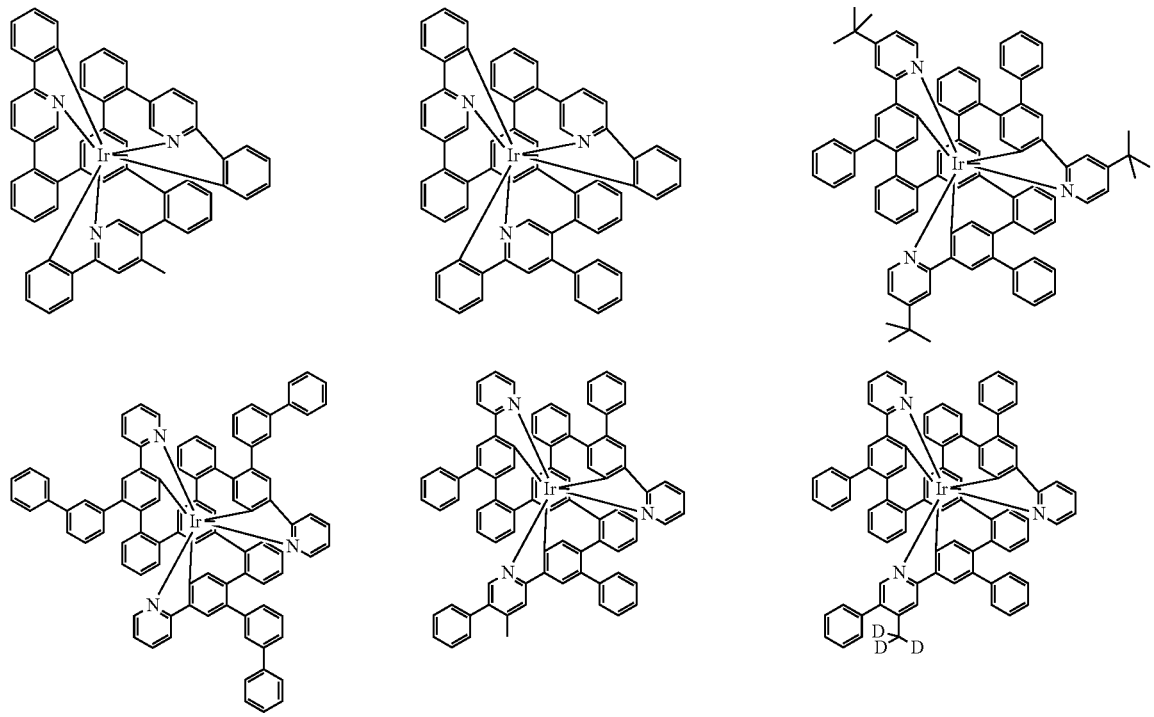

The above-described compounds comprising structures of the formulae (I) to (XVIII) or the above-detailed preferred embodiments can preferably be used as active component in an electronic device. An electronic device is understood to mean any device comprising anode, cathode and at least one layer between anode and cathode, said layer comprising at least one organic or organometallic compound. The electronic device of the invention thus comprises anode, cathode and at least one intervening layer containing at least one compound comprising structures of the formula (I). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices (D. M. Koller et al., *Nature Photonics* 2008, 1-4), preferably organic electroluminescent devices (OLEDs, PLEDs), especially phosphorescent OLEDs, containing at least one compound comprising structures of the formula (I) in at least one layer. Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. Preference is further given to tandem OLEDs as well. The system may also be a hybrid system wherein one or more layers fluoresce and one or more other layers phosphoresce.

In a preferred embodiment of the invention, the organic electroluminescent device contains the compound of the invention, preferably a compound comprising structures of formulae (I) to (XVIII) or the above-detailed preferred embodiments as matrix material, preferably as electron-conducting matrix material, in one or more emitting layers, preferably in combination with a further matrix material, preferably a hole-conducting matrix material. In a further preferred embodiment of the invention, the further matrix material is an electron-transporting compound. In yet a further preferred embodiment, the further matrix material is a compound having a large band gap which is not involved to a significant degree, if at all, in the hole and electron transport in the layer. An emitting layer comprises at least one emitting compound.

In a further particularly preferred embodiment of the present invention, an organic electroluminescent device of the invention comprises the compound of the invention, preferably a compound comprising structures or formulae (I) to (XVIII) or the above-detailed preferred embodiments in a hole conductor layer or an electron conductor layer.

Suitable matrix materials which can be used in combination with the compounds of formulae (I) to (XVIII) or according to the preferred embodiments are aromatic ketones, aromatic phosphine oxides or aromatic sulfoxides or sulfones, for example according to WO 2004/013080, WO 2004/093207, WO 2006/005627 or WO 2010/006680, triarylamines, especially monoamines, for example according to WO 2014/015935, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, lactams, for example according to WO 2011/116865, WO 2011/137951 or WO 2013/064206, 4-spirocarbazole derivatives, for example according to WO 2014/094963 or WO 2015/192939, or dibenzofuran derivatives, for example according to WO 2015/169412, WO 2016/015810, WO 2016/023608 or the as yet unpublished applications EP16158460.2 and EP16159829.7. It is likewise possible for a further phosphorescent emitter which emits at a shorter wavelength than the actual emitter to be present as co-host in the mixture.

Preferred co-host materials are triarylamine derivatives, especially monoamines, indenocarbazole derivatives, 4-spirocarbazole derivatives, lactams and carbazole derivatives.

Preferred triarylamine derivatives which are used as co-host materials together with the compounds of the invention are selected from the compounds of the following formula (TA-1):

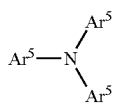

Formula (TA-1)

where $Ar^5$ is the same or different at each instance and is an aromatic or heteroaromatic ring system which has 6 to 40 carbon atoms and may be substituted in each case by one or more $R^2$ radicals, where two or more adjacent $R^2$ substituents may optionally form a mono- or polycyclic, aliphatic ring system which may be substituted by one or more $R^3$ radicals, where the symbol $R^2$ is as defined above, especially for formulae (I) to (XVIII). Preferably, $Ar^5$ is the same or different at each instance and is an aryl or heteroaryl group which has 5 to 24 and preferably 5 to 12 aromatic ring atoms, and which may be substituted in each case by one or more $R^2$ radicals, but is preferably unsubstituted.

Examples of suitable $Ar^5$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, indenocarbazolyl, 1-, 2-, 3- or 4-dibenzothienyl and 1-, 2-, 3- or 4-carbazolyl, each of which may be substituted by one or more $R^2$ radicals, but are preferably unsubstituted.

Preferably, the $Ar^5$ groups are the same or different at each instance and are selected from the abovementioned $R^1$-1 to $R^1$-92 groups, more preferably $R^1$-1 to $R^1$-54.

In a preferred embodiment of the compounds of the formula (TA-1), at least one $Ar^5$ group is selected from a biphenyl group, which may be an ortho-, meta- or para-biphenyl group. In a further preferred embodiment of the compounds of the formula (TA-1), at least one $Ar^5$ group is selected from a fluorene group or spirobifluorene group, where these groups may each be bonded to the nitrogen atom in the 1, 2, 3 or 4 position. In yet a further preferred embodiment of the compounds of the formula (TA-1), at least one $Ar^5$ group is selected from a phenylene or biphenyl group, where the group is an ortho-, meta- or para-bonded group, substituted by a dibenzofuran group, a dibenzothiophene group or a carbazole group, especially a dibenzofuran group, where the dibenzofuran or dibenzothiophene group is bonded to the phenylene or biphenyl group via the 1, 2, 3 or 4 position and where the carbazole group is bonded to the phenylene or biphenyl group via the 1, 2, 3 or 4 position or via the nitrogen atom.

In a particularly preferred embodiment of the compounds of the formula (TA-1), one $Ar^5$ group is selected from a fluorene or spirobifluorene group, especially a 4-fluorene or 4-spirobifluorene group, and one $Ar^5$ group is selected from a biphenyl group, especially a para-biphenyl group, or a fluorene group, especially a 2-fluorene group, and the third $Ar^5$ group is selected from a para-phenylene group or a para-biphenyl group, substituted by a dibenzofuran group, especially a 4-dibenzofuran group, or a carbazole group, especially an N-carbazole group or a 3-carbazole group.

Preferred indenocarbazole derivatives which are used as co-host materials together with the compounds of the invention are selected from the compounds of the following formula (TA-2):

Formula (TA-2)

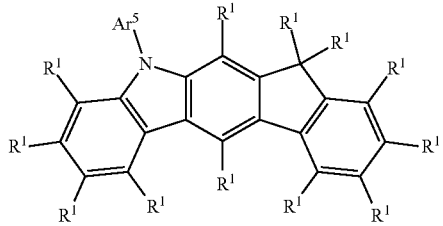

where $Ar^5$ and $R^1$ have the definitions listed above, especially for formulae (I) and/or (TA-1). Preferred embodiments of the $Ar^5$ group are the above-listed structures $R^1$-1 to $R^1$-92, more preferably $R^1$-1 to $R^1$-54.

A preferred embodiment of the compounds of the formula (TA-2) is the compounds of the following formula (TA-2a):

Formula (Ta-2a)

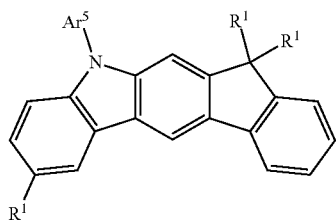

where $Ar^5$ and $R^1$ have the definitions listed above, especially for formulae (I) and/or (TA-1). The two $R^1$ groups bonded to the indeno carbon atom here are preferably the same or different and are an alkyl group having 1 to 4 carbon atoms, especially methyl groups, or an aromatic ring system having 6 to 12 carbon atoms, especially phenyl groups. More preferably, the two $R^1$ groups bonded to the indeno carbon atom are methyl groups.

Further preferably, the substituent $R^1$ bonded to the indenocarbazole base skeleton in formula (TA-2a) is H or a carbazole group which may be bonded to the indenocarbazole base skeleton via the 1, 2, 3 or 4 position or via the nitrogen atom, especially via the 3 position.

Preferred 4-spirocarbazole derivatives which are used as co-host materials together with the compounds of the invention are selected from the compounds of the following formula (TA-3):

Formula (TA-3)

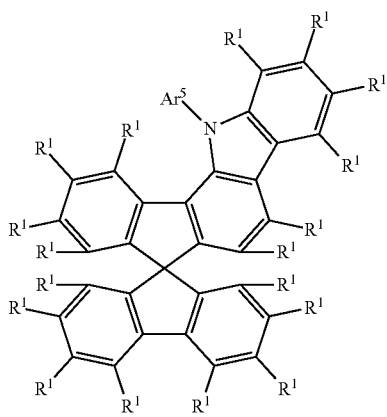

where $Ar^5$ and $R^1$ have the definitions listed above, especially for formulae (I) and/or (TA-1). Preferred embodiments of the $Ar^5$ group are the above-listed structures $R^1$-1 to $R^1$-92, more preferably $R^1$-1 to $R^1$-54.

A preferred embodiment of the compounds of the formula (TA-3) is the compounds of the following formula (TA-3a):

Formula (TA-3a)

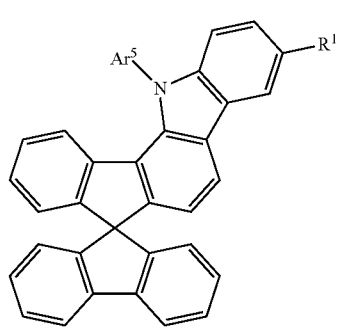

where $Ar^5$ and $R^1$ have the definitions listed above, especially for formulae (I) and/or (TA-1). Preferred embodiments of the $Ar^5$ group are the above-listed structures $R^1$-1 to $R^1$-92, more preferably $R^1$-1 to $R^1$-54.

Preferred lactams which are used as co-host materials together with the compounds of the invention are selected from the compounds of the following formula (LAC-1):

Formula (LAC-1)

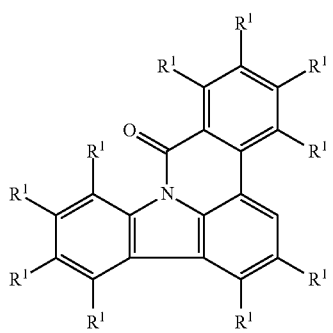

where $R^1$ has the definition listed above, especially for formula (I).

A preferred embodiment of the compounds of the formula (LAC-1) is the compounds of the following formula (LAC-1a):

Formula (LAC-1a)

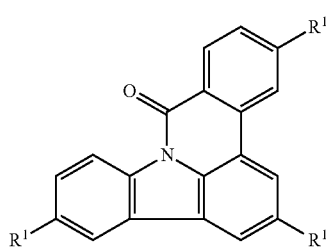

where $R^1$ has the definition given above, especially for formulae (I) or (XVIII). $R^1$ here is preferably the same or different at each instance and is H or an aromatic or heteroaromatic ring system which has 5 to 40 aromatic ring atoms and may be substituted by one or more $R^2$ radicals, where $R^2$ may have the definition given above, especially for formulae (I) to (XVIII). Most preferably, the substituents $R^1$ are selected from the group consisting of H and an aromatic or heteroaromatic ring system which has 6 to 18 aromatic ring atoms, preferably 6 to 13 aromatic ring atoms, and may be substituted in each case by one or more nonaromatic $R^2$ radicals, but is preferably unsubstituted. Examples of suitable substituents $R^1$ are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted. Suitable $R^1$ structures here are the same structures as depicted above for R-1 to R-79, more preferably $R^1$-1 to $R^1$-51.

It may also be preferable to use a plurality of different matrix materials as a mixture, especially at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, it is possible to use a compound of the invention comprising structures of formulae (I) to (XVIII), in a preferred embodiment, as matrix material in an emission layer of an organic electronic device, especially in an organic electroluminescent device, for example in an OLED or OLEC. In this case, the matrix material containing compound comprising structures of formulae (I) to (XVIII) or the preferred embodiments recited above and hereinafter is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compounds comprising structures of formulae (I) to (XVIII) or the preferred embodiments recited above and hereinafter are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfil(s) other functions. The two different matrix materials may be present here in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more electron-conducting layers, as electron-conducting compound.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $CS_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/ $NiO_x$, Al/$PtO_x$) may also be preferred. For some applications, at least one of the electrodes has to be transparent or partly transparent in order to enable either the irradiation of the organic material (O-SC) or the emission of light (OLED/ PLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapor deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example M. S. Arnold et al., *Appl. Phys. Lett.* 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device, can also be produced as a hybrid system by applying one or more layers from solution and applying one or more other layers by vapor deposition. For example, it is possible to apply an emitting layer comprising a compound of the invention comprising structures of formulae (I) to (XVIII) and a matrix material from solution, and to apply a hole blocker layer and/or an electron transport layer thereto by vapor deposition under reduced pressure.

These methods are known in general terms to those skilled in the art and can be applied without difficulty to electronic devices, especially organic electroluminescent devices comprising compounds of the invention comprising structures of formulae (I) to (XVIII) or the above-detailed preferred embodiments.

The electronic devices of the invention, especially organic electroluminescent devices, are notable for one or more of the following surprising advantages over the prior art:

1. Electronic devices, especially organic electroluminescent devices, comprising compounds, oligomers, polymers or dendrimers of the invention usable as active compound in an organic electronic device or the preferred embodiments recited above and hereinafter, especially as electron-conducting materials and/or hole conductor materials or as matrix materials, have a very good lifetime.
2. Electronic devices, especially organic electroluminescent devices, comprising compounds, oligomers, polymers ordendrimers of the invention that are usable as active compound in an organic electronic device, or the preferred embodiments recited above and hereinafter, especially as electron transport materials, hole conductor materials and/or as host materials, have excellent efficiency. More particularly, efficiency is distinctly higher compared to analogous compounds that do not contain an aliphatic polycyclic ring system which has at least 3 rings and is fused to an aromatic or heteroaromatic ring system having 5 to 60 carbon atoms. The effect of the compounds, oligomers, polymers or dendrimers of the invention that are usable as active compound in an organic electronic device, or the preferred embodiments recited above and hereinafter, is a low operating voltage when used in electronic devices. In this context, these compounds especially bring about low roll-off, i.e. a small drop in power efficiency of the device at high luminances.
3. Electronic devices, especially organic electroluminescent devices, comprising compounds, oligomers, polymers ordendrimers usable as active compound in an organic electronic device, or the preferred embodiments recited above and hereinafter, as electron transport materials, hole conductor materials and/or as host materials, have excellent color purity.
4. The compounds, oligomers, polymers or dendrimers of the invention that are usable as active compound in an organic electronic device, or the preferred embodiments recited above and hereinafter, exhibit very high thermal and photochemical stability and lead to compounds having a very long lifetime.
5. With compounds, oligomers, polymers or dendrimers that are usable as active compound in an organic electronic device, or the preferred embodiments recited above and hereinafter, it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
6. Compounds, oligomers, polymers or dendrimers that are usable as active compound in an organic electronic device, or the preferred embodiments recited above and hereinafter, have excellent glass film formation.
7. Compounds, oligomers, polymers or dendrimers that are usable as active compound in an organic electronic device, or the preferred embodiments recited above and hereinafter, form very good films from solutions.

These abovementioned advantages are not accompanied by a deterioration in the further electronic properties.

The compounds and mixtures of the invention are suitable for use in an electronic device. An electronic device is understood here to mean a device containing at least one layer containing at least one organic compound. The component may, however, also comprise inorganic materials or else layers formed entirely from inorganic materials.

The present invention therefore further provides for the use of the compounds or mixtures of the invention in an electronic device, especially in an organic electroluminescent device.

The present invention still further provides for the use of a compound of the invention and/or of an oligomer, polymer or dendrimer of the invention in an electronic device as fluorescent emitter, emitter that exhibits TADF (thermally activated delayed fluorescence), host material, electron transport material, electron injection material, hole-conducting material, hole injection material, electron blocker material, hole blocker material and/or wide bandgap material, preferably as fluorescent emitter (singlet emitter), host material, hole-conducting material and/or electron transport material.

The present invention still further provides an electronic device comprising at least one of the above-detailed compounds or mixtures of the invention. In this case, the preferences detailed above for the compound also apply to the electronic devices. More preferably, the electronic device is selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices (D. M. Koller et al., Nature Photonics 2008, 1-4), preferably organic electroluminescent devices (OLEDs, PLEDs), especially phosphorescent OLEDs.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art will therefore be able, without exercising inventive skill, to use all the materials known for organic electroluminescent devices in combination with the compounds of the invention that are usable as active compound in an organic electronic device, preferably compounds comprising structures of the formulae (I) to (XVIII) and/or the formulae (Ia) to (XVIIIa), or the compounds obtainable by a combination of the substructures of the formulae (N-1) to (N-6), (Ar-1) to (Ar-54) and/or (Ar'-1) to (Ar'-53), or according to the preferred embodiments.

The compounds of the invention generally have very good properties on use in organic electroluminescent devices. Especially in the case of use of the compounds of the invention in organic electroluminescent devices, the lifetime is significantly better compared to similar compounds according to the prior art. At the same time, the further properties of the organic electroluminescent device, especially the efficiency and voltage, are likewise better or at least comparable.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in more detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature. In the case of compounds that can display multiple tautomeric forms, one tautomeric form is shown representatively.

1) Synthesis of the Synthons S

Example S1

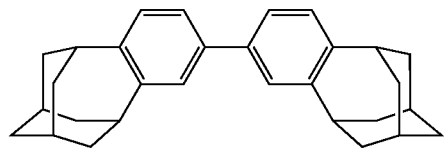 [SMILES: c1cc2c(cc1-c1ccc3c(c1)C1CC4CC(CC3C4)C1)C1CC3CC(CC2C3)C1]

A well-stirred mixture of 27.2 g (100 mmol) of 2-bromo-6,7,8,9,10,11-hexahydro-5,9:7,11-dimethano-5H-benzocyclononene [1801624-97-4], 32.4 g (100 mmol) of 2-(6,7,8,9,10,11-hexahydro-5,9:7,11-dimethano-5H-benzocyclononen-2-yl)-4,4,5,5-tetramethyl-1,3,2-dioxaborolane [1801624-63-4], 63.7 g (300 mmol) of tripotassium phosphate, 1.83 g (6 mmol) of tri-o-tolylphosphine, 225 mg (1 mmol) of palladium(II) acetate, 350 ml of toluene, 80 ml of dioxane and 300 ml of water is heated under reflux for 16 h. After cooling, the organic phase is separated from the aqueous phase and washed once with 300 ml of water and once with 300 ml of saturated sodium chloride solution, and then dried over magnesium sulfate. The desiccant is filtered off using a silica gel bed in the form of a toluene slurry, and the filtrate is concentrated to dryness. The glassy residue is recrystallized from iso-propanol. Yield: 30.8 g (78 mmol) 78%. Purity by $^1$H MMR about 97%.

In an analogous manner, it is possible to prepare the following compounds:

| Ex. | Reactants Bromide Ketone/electrophile | Product | Yield |
|---|---|---|---|
| S10 | 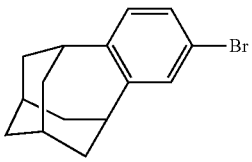 [1801624-97-4] 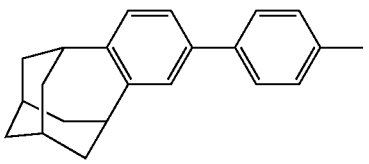 [SMILES: Cc1ccc(-c2ccc3c(c2)C2CC4CC(CC3C4)C2)cc1] [195062-57-8] | 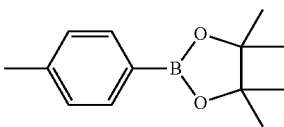 | 81% |
| S11 | 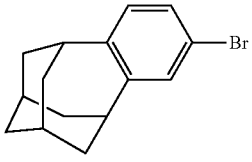 [1801624-97-4] 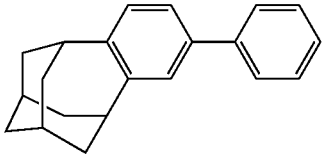 [SMILES: c1ccc(-c2ccc3c(c2)C2CC4CC(CC3C4)C2)cc1] [24388-23-6] | 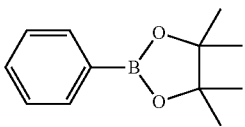 | 78% |

Example S2

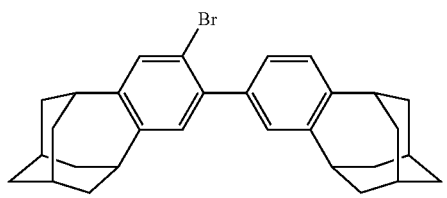 [SMILES: Brc1cc2c(cc1-c1ccc3c(c1)C1CC4CC(CC3C4)C1)C1CC3CC(CC2C3)C1]

To a well-stirred solution of 39.5 g (100 mmol) of S1 in 500 ml of dichloromethane is added dropwise, in the dark over the course of 3 h, a mixture of 3.1 ml (120 mmol) of bromine and 100 ml of dichloromethane. After the addition has ended, the mixture is stirred under reflux for 4 h and at room temperature for 8 h. 200 ml of sat. sodium sulfite solution is added to destroy excess bromine, and the organic phase is separated off, washed with 500 ml of water and 300 ml of sat. sodium hydrogencarbonate solution, and dried over magnesium sulfate. The desiccant is filtered off, the filtrate is concentrated to dryness and the red viscous residue is recrystallized from about 500 ml of iso-propanol. Yield: 32.7 g (69 mmol) 69%. Purity by $^1$H MMR about 95%.

The following compound can be prepared analogously:

| Ex. | Reactants Bromide Ketone/ electrophile | Product | Yield |
|---|---|---|---|
| S12 | S10 | 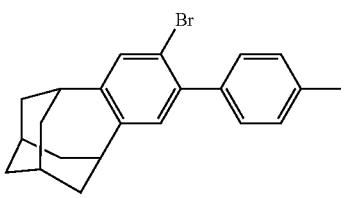 [SMILES: Cc1ccc(-c2cc3c(cc2Br)C2CC4CC(C2)CC3C4)cc1] | 46% |

Example S3

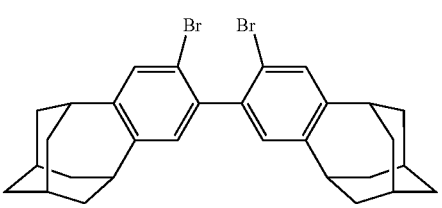 [SMILES: Brc1cc2c(cc1-c1cc3c(cc1Br)C1CC4CC(C1)CC3C4)C1CC3CC(CC2C3)C1]

Preparation analogous to S2, except that 6.4 ml (240 mmol) of bromine is used. Also added to the solution of S1 dichloromethane is 100 mg of iron powder. Yield: 33.7 g (61 mmol) 61%. Purity by $^1$H NMR about 97%.

The following compound can be prepared analogously:

| Ex. | Reactants Bromide Ketone/ electrophile | Product | Yield |
|---|---|---|---|
| S13 | S11 | 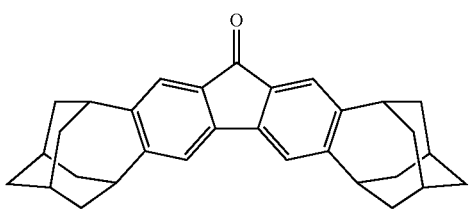 [SMILES: O=C1c2cc3c(cc2-c2cc4c(cc21)C1CC2CC(C1)CC4C2)C1CC2CC(CC3C2)C1] | 43% |

Example S4

To a well-stirred solution, cooled to −78° C., of 27.6 g (50 mmol) of S3 in 500 ml of THF is added dropwise 65.6 ml (105 mmol) of n-BuLi in hexane, 1.6 M, and the mixture is stirred for a further 30 min. A mixture of 5.1 ml (55 mmol) of dimethylcarbamoyl chloride [79-44-7] (caution: toxic, carcinogenic) and 50 ml of THF is slowly added dropwise, and the mixture is stirred for a further 30 min and then allowed to gradually warm up to room temperature. After 2 h at room temperature, 200 ml of sat. ammonium chloride solution is added, the mixture is extended with 300 ml of ethyl acetate, the aqueous phase is separated off and the organic phase is concentrated to dryness. The residue is taken up in 250 ml of dichloromethane (DCM), washed three times with 300 ml of water and once with 300 ml of sat. sodium chloride solution, and dried over magnesium sulfate. The desiccant is filtered off, the filtrate is concentrated to dryness under reduced pressure, and the residue is recrystallized from acetonitrile. Yield: 18.1 g (43 mmol) 85%, Purity by $^1$H NMR about 97%, Example S5

To a well-stirred solution, cooled to −78° C., of 47.4 g (100 mmol) of S2 in 500 ml of THF is added dropwise 85.6 ml (105 mmol) of n-BuLi in hexane, 1.8 M, and the mixture is stirred for a further 3 h. Then a solution of 27.2 g (105 mmol) of 2-bromo-9-fluorenone [3096-58-3] in 300 ml of THF is slowly added dropwise, and the mixture is stirred for a further 30 min and then allowed to gradually warm up to room temperature. After 2 h at room temperature, the THF is removed under reduced pressure, the residue is taken up in 500 ml of glacial acetic acid, 30 ml of conc, hydrochloric acid is added, and the mixture is heated under reflux for 3 h. The mixture is left to cool down to 80° C., 500 ml of water is slowly added dropwise, and the precipitated product is filtered off with suction while the mixture is still warm, washed with 100 ml of water and then three times with 100 ml each time of methanol, and dried under reduced pressure. Yield: 56.8 g (89 mmol) 89%. Purity by $^1$H MMR about 97%.

In an analogous manner, it is possible to prepare the compounds below.

| Ex. | Reactants Bromide Ketone/electrophile | Product | Yield |
|---|---|---|---|
| S6 | S2 [14348-75-5] | 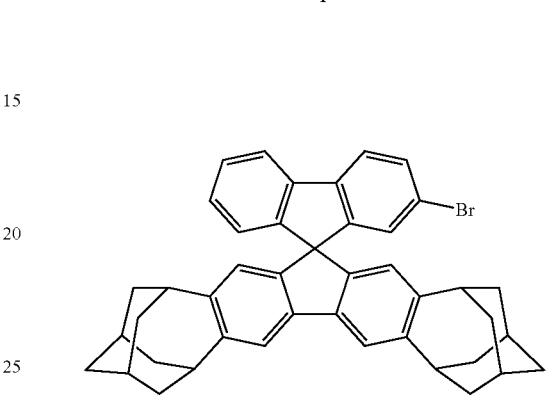 | 86% |

-continued

| Ex. | Reactants Bromide Ketone/electrophile | Product | Yield |
|---|---|---|---|
| S7 | Br-C6H4-C6H4-Br [13029-09-9] S4 | (structure) | 79% |
| S8 | S3 fluorenone [486-25-9] | (structure) | 83% |
| S9 | S3 S4 | (structure) | 80% |
| S15 | S12 2-bromofluorenone [3096-56-3] | (structure) | 78% |

Example S20

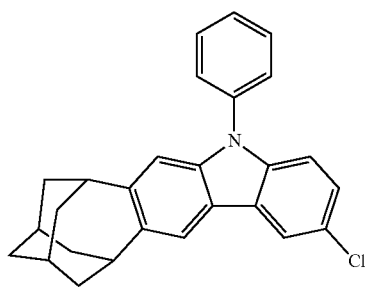 [SMILES: Clc1ccc2c(c1)c1cc3c(cc1n2-c1ccccc1)C1CC2CC(CC3C2)C1]

A well-stirred mixture of 28.3 g (100 mmol) of (2-bromo-4-chlorophenyl)phenylamine [2149611-39-0], 32.4 g (100 mmol) of 2-(6,7,8,9,10,11-hexahydro-5,9:7,11-dimethano-5H-benzocyclononen-2-yl)-4,4,5,5-tetramethyl-1,3,2-dioxaborolane [1801624-63-4], 63.7 g (300 mmol) of tripotassium phosphate, 1.83 g (6 mmol) of tri-o-tolyl-phosphine, 225 mg (1 mmol) of palladium(II) acetate, 350 ml of toluene, 60 ml of dioxane and 300 ml of water is heated under reflux for 16 h. After cooling, the organic phase is separated from the aqueous phase and washed once with 300 ml of water and once with 300 ml of saturated sodium chloride solution, and then dried over magnesium sulfate. The desiccant is filtered off using a silica gel bed in the form of a toluene slurry, and the filtrate is concentrated to dryness. The residue is recrystallized from acetonitrile with addition of a little ethyl acetate. The secondary amine thus obtained is dissolved in 300 ml of DMF, 45.4 g (250 mmol) of copper(II) acetate and 2.24 g (10 mmol) of palladium(II) acetate are added, and the mixture is stirred at for 4 h. The DMF is largely removed under reduced pressure, the residue is taken up in 500 ml of DCM, 300 ml of conc. ammonia solution is added, the mixture is stirred at room temperature for 1 h, and the organic phase is separated off and washed three times with 100 ml of conc. ammonia solution and once with sat. sodium chloride solution, and dried over magnesium sulfate. The magnesium sulfate is filtered off using a silica gel bed in the form of a DCM slurry, the filtrate is concentrated to dryness, and the residue is recrystallized from acetonitrile/eethyl acetate. Yield: 18.7 g (47 mmol) 47%. Purity by $^1$H NMR about 95%.

Example S25

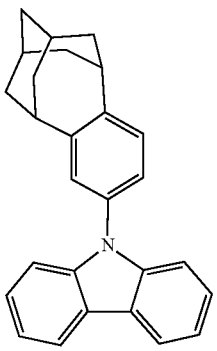 [SMILES: c1ccc2c(c1)c1ccccc1n2-c1ccc2c(c1)C1CC3CC(CC2C3)C1]

A well-stirred mixture of 27.2 g (100 mmol) of 2-bromo-6,7,8,9,10,11-hexahydro-5,9:7,11-dimethano-5H-benzocyc-lononene [1801624-97-4], 18.4 g (110 mmol) of carbazole [86-74-8], 41.5 g (300 mmol) of potassium carbonate, 1.9 g (10 mmol) of copper(I) iodide [7681-65-4], 100 g of glass beads (diameter 3 mm) and 300 ml of dimethylacetamide is heated under reflux for 30 h. While the mixture is still warm, the salts are filtered off with suction by means of a Celite bed in the form of a dimethylacetamide slurry, the filtrate is concentrated to dryness, the residue is taken up in 300 ml of DCM and filtered through a silica gel column (10×30 cm), and the core fraction is extracted. The evaluate is freed of the DCM under reduced pressure; the residue is recrystallized of acetonitrile. Yield: 33.4 g (88 mmol) 88%. Purity by $^1$H NMR about 99%.

Example S26

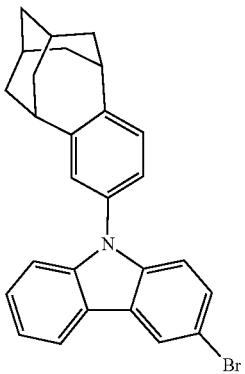 [SMILES: Brc1ccc2c(c1)c1ccccc1n2-c1ccc2c(c1)C1CC3CC(CC2C3)C1]

To a well-stirred solution, cooled to 0° C., of 38.0 g (100 mmol) of S25 in 500 ml of DCM is added dropwise, in the dark, a solution of 17.8 g (100 mmol) of N-bromosuccin-imide in 300 ml of dichloromethane, and then the mixture is stirred at room temperature for a further 12 h. The reaction solution is washed once with 200 ml of sat. sodium hydrogencarbonate solution, three times with 200 ml each time of water and once with 200 ml of sat. sodium chloride solution, and then dried over magnesium sulfate. The desiccant is filtered off, the filtrate is concentrated and the residue is chromatographed by flash chromatography (Combi-Flash Torrent from A. Semrau). Yield: 33.0 g (72 mmol) 72%. Purity by $^1$H NMR about 95%.

Example S30

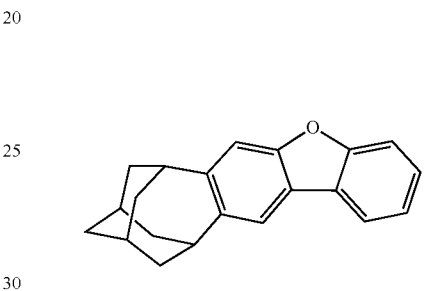

A well-stirred mixture of 17.3 g (100 mmol) of 2-brom-ophenol [95-96-7], 32.4 g (100 mmol) of 2-(6,7,8,9,10,11-hexahydro-5,9:7,11-dimethano-5H-benzocyclononen-2-yl)-4,4,5,5-tetramethyl-1,3,2-dioxaborolane [1801624-63-4], 63.7 g (300 mmol) of tripotassium phosphate, 1.83 g (6 mmol) of tri-o-tolyl-phosphine, 225 mg (1 mmol) of palladium(II) acetate, 350 ml of toluene, 60 ml of ethanol and 300 ml of water is heated under reflux for 16 h. After cooling, 60 ml of 10 N aqueous HCl is added, the organic phase is separated from the aqueous phase and washed once with 300 ml of water and once with 300 ml of saturated sodium chloride solution, and then dried over magnesium sulfate. The desiccant is filtered off using a silica gel bed in the form of a toluene slurry, and the filtrate is concentrated to dryness. The residue is recrystallized from iso-propanol with addition of a little ethyl acetate. The phenol thus obtained is dissolved in 800 ml of mesitylene, and the well-stirred solution is admixed with 27.8 g (200 mmol) of potassium carbonate, 100 g of 3 A molecular sieve, 9.3 g (50 mmol) of sodium 2,4,6-trimethylbenzoate [32642-28-7], 1.82 g (10 mmol) of 4,5-diazafluoren-9-one [50890-67-0], 4.26 g (10 mmol) of 1,3-bis[2,8-bis(1-methylethyl)phenyl]-1H-imidazolium chloride [250235-32-6] and 1.12 g (5 mmol) of palladium (II) acetate, and then the mixture is heated to 120° C. with introduction of a gentle stream or air for 16 h. While the mixture is still warm, it is filtered with suction through a silica gel bed in the form of a mesitylene slurry, the mesitylene is removed under reduced pressure, and the residue is recrystallized from acetonitrile. Yield: 15.6 g (54 mmol) 54%.
Purity by $^1$H NMR about 95%.

Example S31

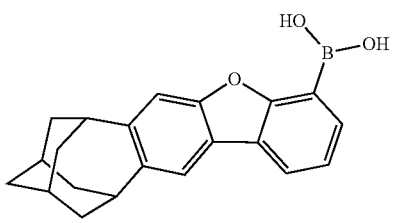 [SMILES: OB(O)c1cccc2c1oc1cc3c(cc12)C1CC2CC(CC3C2)C1]

To a well-stirred mixture, cooled to −78° C., of 33.2 g (100 mmol) of S30 and 500 ml of THF is added dropwise 65.6 ml (105 mmol) of n-BuLi in hexane, 1.6 M, and the mixture is stirred at −78° C. for 60 min and then at −40° C. for 30 min. After cooling again to −78° C., a mixture of 20.7 g (110 mmol) of triisopropyl borate [5419-55-8] and 50 ml of THF is added rapidly with good stirring, and the mixture is stirred for a further 30 min. The reaction mixture is allowed to warm up to room temperature, 100 ml of sat. ammonium chloride solution is added, the mixture is stirred for a further 15 min, and the organic phase is separated off, extended with 500 ml of ethyl acetate and washed three times with 300 ml each time of water and once with 200 ml of sat. sodium chloride solution. The organic phase is concentrated to dryness under reduced pressure and the residue is recrystallized from acetonitrile with addition of a little water. Yield: 18.9 g (57 mmol), 57%. Purity by $^1$H NMR about 95%.

Example S35

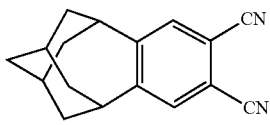 [SMILES: N#Cc1cc2c(cc1C#N)C1CC3CC(CC2C3)C1]

A well-stirred mixture of 35.6 g (100 mmol) of 2,3-dibromo-6,7,8,9,10,11-hexahydro-5,9:7,11-dimethano-5H-benzocyclononene [1801624-66-7], 26.9 g (300 mmol) of copper(I) cyanide, 50 g of glass beads (diameter 3 mm) and 300 of NMP is heated to 170° C. for 18 h. While the mixture is still warm, it is filtered with suction through a Celite bed in the form of an NMP slurry, the filtrate is concentrated to dryness under reduced pressure and the residue is extracted by stirring in 300 ml of boiling MeOH. The crude product is extracted twice with hot acetonitrile. Yield: 15.0 g (60 mmol) 60%. Purity by $^1$H NMR about 95%.

Example S36

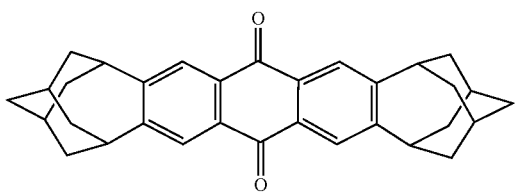 [SMILES: O=C1c2cc3c(cc2C(=O)c2cc4c(cc21)C1CC2CC(C1)CC4C2)C1CC2CC(CC3C2)C1]

To a well-stirred solution, cooled to −100° C., of 35.6 g (100 mmol) of 2,3-dibromo-6,7,8,9,10,11-hexahydro-5,9:7,11-dimethano-5H-benzocyclononene [1801624-66-7] in 1000 ml of THF is added dropwise 235 ml (400 mmol) of t-BuLi, 1.7 M in pentane, and the mixture is stirred for a further 30 min. Then a solution of 24.8 g (100 mmol) of S35 in 300 ml of THF is slowly added dropwise, and the mixture is stirred for a further 1 h, allowed to warm up to room temperature and quenched by addition of 50 ml of methanol. The THF is removed under reduced pressure, the residue is taken up in 300 ml of NMP, 30 ml of conc. hydrochloric acid is added, and the mixture is heated to about 150° C. for 4 h. After cooling, the mixture is extended with 500 ml of ethyl acetate, and the organic phase is washed three times with 500 ml each time of water and once with 300 ml of sat. sodium chloride solution, and dried over magnesium sulfate. The desiccant is filtered off, the filtrate is concentrated to dryness under reduced pressure, and the yellow residue is recrystallized twice from acetonitrile. Yield: 19.4 g (43 mmol) 43%. Purity by $^1$H NMR about 95%.

In an analogous manner, it is possible to prepare the compounds below.

| Ex. | Reactants | Product | Yield |
|---|---|---|---|
| S37 | S35<br>[583-53-9] | 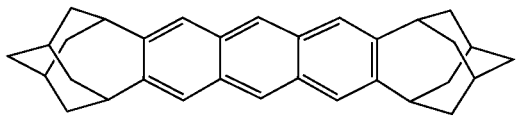 [SMILES: c1c2c(cc3cc4cc5c(cc4cc13)C1CC3CC(C1)CC5C3)C1CC3CC(CC2C3)C1] | 47% |

Example S38

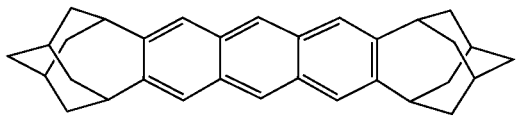 [SMILES: c1c2c(cc3cc4cc5c(cc4cc13)C1CC3CC(C1)CC5C3)C1CC3CC(CC2C3)C1]

To a suspension of 44.9 g (100 mmol) of S36 in 500 ml of glacial acetic acid are added 100 ml of aqueous hydriodic acid (57% by weight) and 200 ml of aqueous hypophosphorous acid (50% by weight), and the mixture is heated under reflux for 18 h. The precipitated solids are filtered off with suction, washed five times with 300 ml each time of hot water, and extracted by stirring with 300 ml of hot ethanol, washed with another 300 ml of hot ethanol and dried under reduced pressure. Yield: 38.6 g (92 mmol) 92%. Purity by $^1$H NMR about 95%.

The following compounds can be prepared analogously:

| Ex. | Reactants | Product | Yield |
|---|---|---|---|
| S39 | S37 |  | 72% |

Example S40

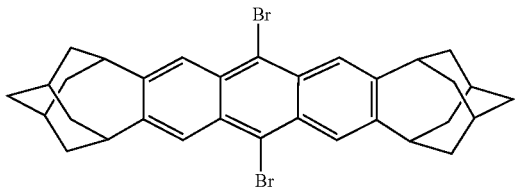 [SMILES: Brc1c2cc3c(cc2c(Br)c2cc4c(cc12)C1CC2CC(C1)CC4C2)C1CC2CC(CC3C2)C1]

To a solution of 41.9 g (100 mmol) of S38 in 500 ml of dichloromethane is added in portions, with good stirring and in the dark, 19.6 g (110 mmol) of N-bromosuccinimide, and the mixture is stirred at room temperature for 6 h. The reaction mixture is washed once with 300 ml of sat. sodium hydrogencarbonate solution, three times with 300 ml each time of water and once with 300 ml of sat. sodium chloride solution, and dried over magnesium sulfate. The desiccant is filtered off, the filtrate is concentrated to dryness and the solids are crystallized from acetonitrile/ethyl acetate. Yield: 50.2 g (87 mmol) 87%. Purity by $^1$H NMR about 98%.

The following compounds can be prepared analogously:

| Ex. | Reactants | Product | Yield |
|---|---|---|---|
| S41 | S37 | ![structure] | 84% |

2) Synthesis of the Amines A

Example A1

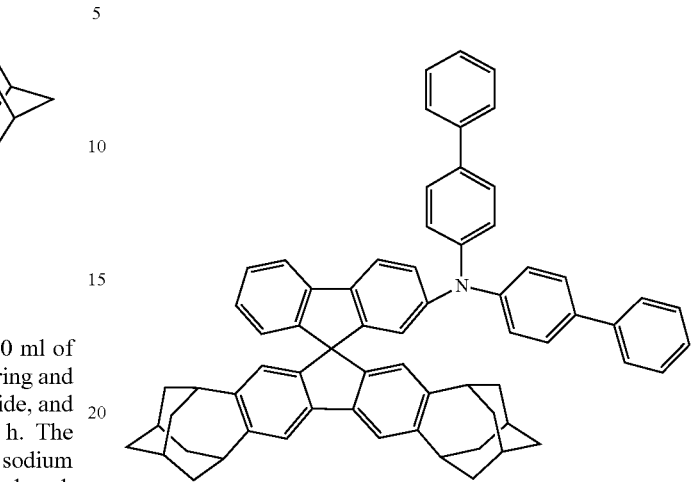

To a solution of 63.6 g (100 mmol) of S5 and 38.6 g (120 mmol) of bis-p-biphenylamine [102113-98-4] in 500 ml of toluene are added 4.0 ml (4.0 mmol) of a 1.0 M tri-tert-butylphosphine solution in toluene, 449 mg (2 mmol) of palladium acetate and 16.0 g of sodium tert-butoxide (166 mmol), and the mixture was heated under reflux for 3 h. The reaction mixture is cooled down to room temperature, extended with toluene and filtered through a Celite bed. The filtrate is concentrated under reduced pressure and the residue is crystallized from ethyl acetate/n-heptane. The crude product is extracted three times with hot acetonitrile and purified by zone sublimation under reduced pressure twice (p~$10^{-5}$ mbar, T~310° C.). Yield: 63.1 g (72 mmol), 72%, Purity by HPLC>99.9%.

The following compounds can be prepared analogously:

| Ex. | Reactants | Product | Yield |
|---|---|---|---|
| A2 | S5 [32228-99-2] | ![structure] | 70% |

| Ex. | Reactants | Product | Yield |
|---|---|---|---|
| A3 | S5 [1322090-81-2] | | 68% |
| A4 | S5 [1372775-52-4] | | 75% |
| A5 | S5 [897671-69-1] | | 73% |

-continued
| Ex. | Reactants | Product | Yield |
|---|---|---|---|
| A6 | S5 [1421789-16-3] | | 65% |
| A7 | S5 [1644054-07-8] | | 69% |
| A8 | S5 [955959-89-4] | | 74% |
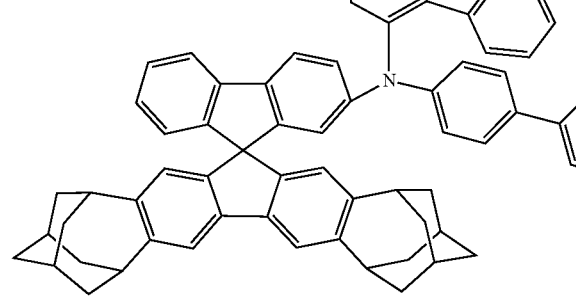

| Ex. | Reactants | Product | Yield |
|---|---|---|---|
| A9 | S5 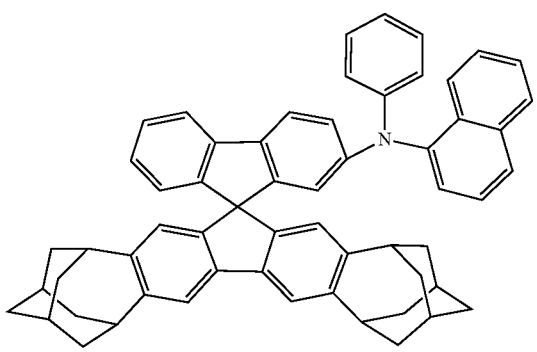 [SMILES: c1ccc(N(c2ccc3c(c2)C2(c4ccccc4-3)c3cc4c(cc3-c3cc5c(cc32)C2CC3CC(CC5C3)C2)C2CC3CC(C2)CC4C3)c2cccc3ccccc23)cc1] [90-30-2] | | 74% |
| A10 | S5 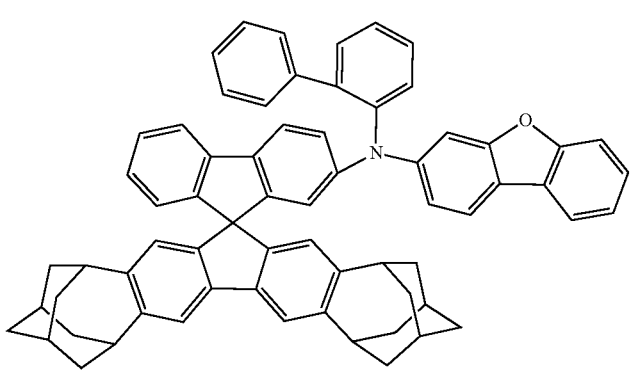 [SMILES: c1ccc(-c2ccccc2N(c2ccc3c(c2)C2(c4ccccc4-3)c3cc4c(cc3-c3cc5c(cc32)C2CC3CC(CC5C3)C2)C2CC3CC(C2)CC4C3)c2ccc3c(c2)oc2ccccc23)cc1] [1427556-44-2] | | 70% |
| A11 | S6 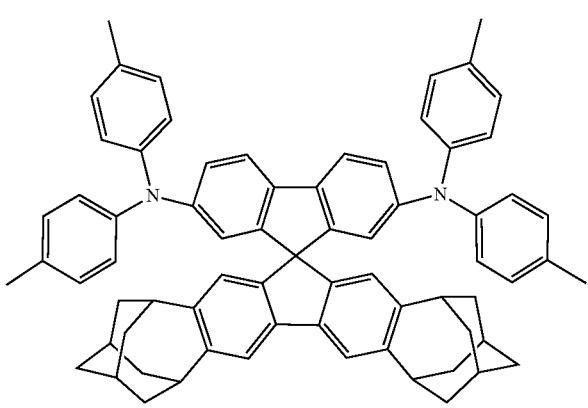 [620-93-9] | | 66% |
| A12 | S6 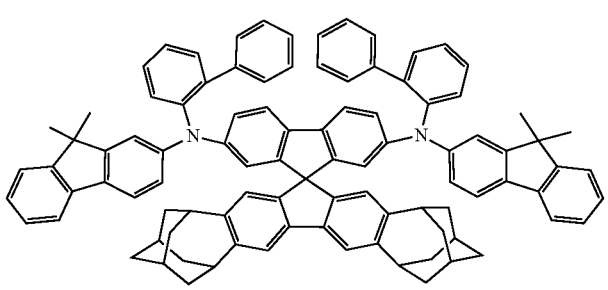 [SMILES: CC1(C)c2ccccc2-c2ccc(N(c3ccc4c(c3)C3(c5cc(N(c6ccc7c(c6)C(C)(C)c6ccccc6-7)c6ccccc6-c6ccccc6)ccc5-4)c4cc5c(cc4-c4cc6c(cc43)C3CC4CC(CC6C4)C3)C3CC4CC(C3)CC5C4)c3ccccc3-c3ccccc3)cc21] [1198395-24-2] | | 61% |

| Ex. | Reactants | Product | Yield |
|---|---|---|---|
| A13 | S7 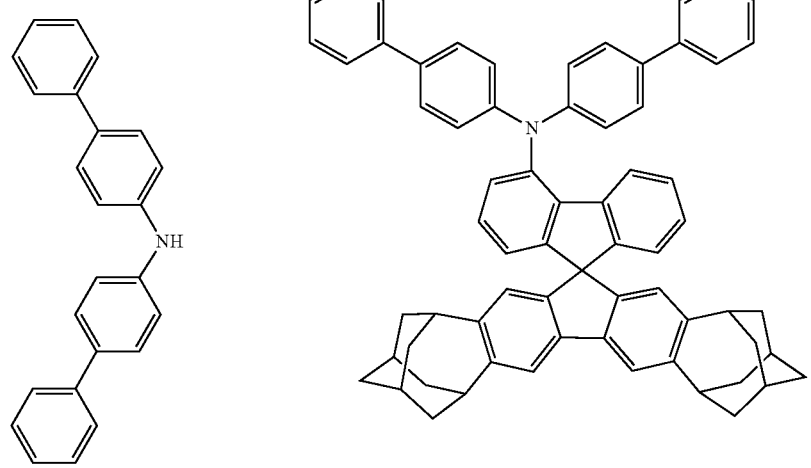 [102113-98-4] | | 78% |
| A14 | S7 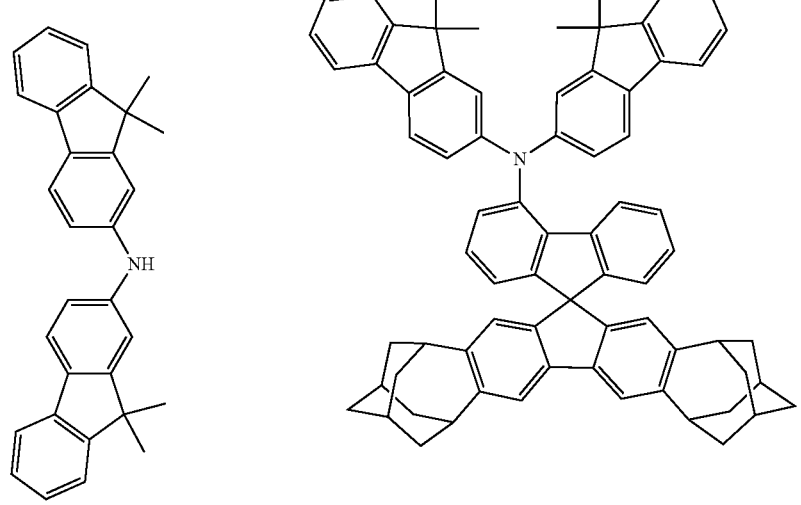 [500717-23-7] | | 75% |

| Ex. | Reactants | Product | Yield |
|---|---|---|---|
| A15 | S7 | 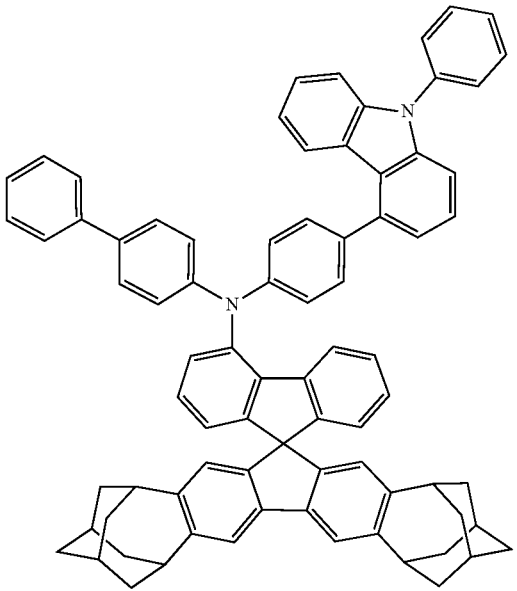 [SMILES: c1ccc(-c2ccc(N(c3ccc(-c4cccc5c4c4ccccc4n5-c4ccccc4)cc3)c3cccc4c3-c3ccccc3C43c4cc5c(cc4-c4cc6c(cc43)C3CC4CC(CC6C4)C3)C3CC4CC(C3)CC5C4)cc2)cc1] [1629995-09-0] | 71% |
| A16 | S7 | 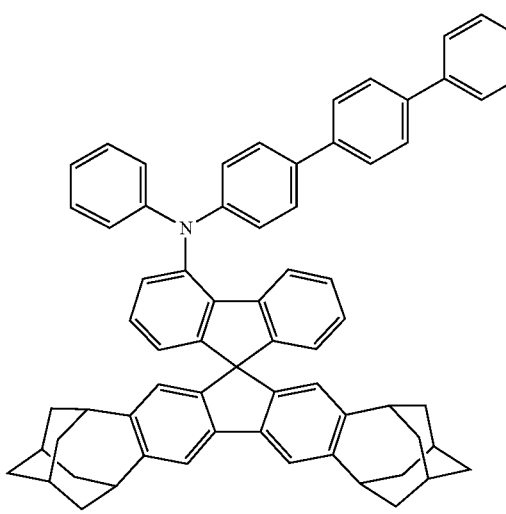 [897671-81-7] | 72% |

| Ex. | Reactants | Product | Yield |
|---|---|---|---|
| A17 | S7 | 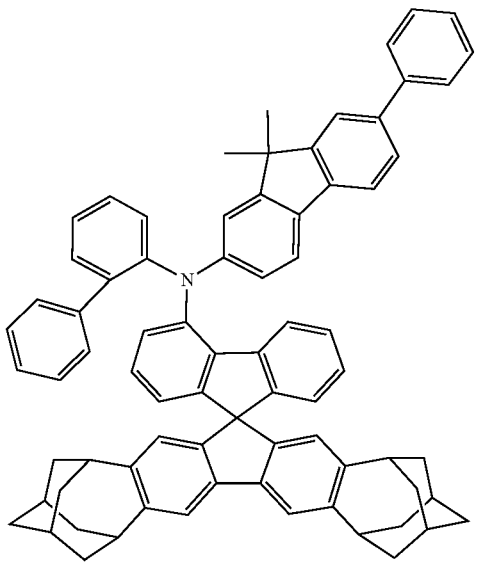 [SMILES: CC1(C)c2cc(-c3ccccc3)ccc2-c2ccc(N(c3ccccc3-c3ccccc3)c3cccc4c3-c3ccccc3C43c4cc5c(cc4-c4cc6c(cc43)C3CC4CC(CC6C4)C3)C3CC4CC(C3)CC5C4)cc21] [1372775-93-9] | 70% |
| A18 | S7 | 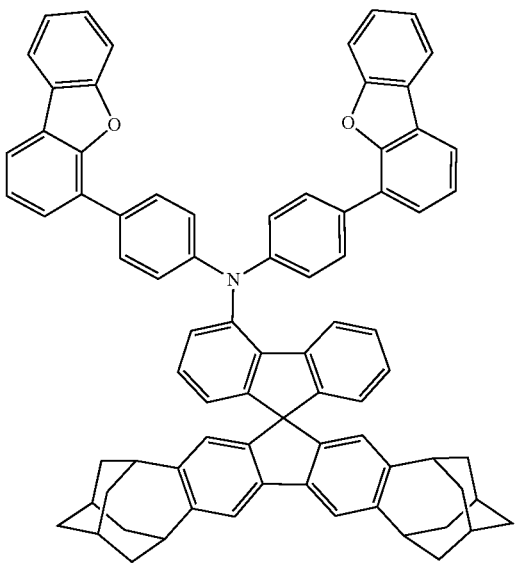 [SMILES: c1ccc2c(c1)-c1c(N(c3ccc(-c4cccc5c4oc4ccccc45)cc3)c3ccc(-c4cccc5c4oc4ccccc45)cc3)cccc1C21c2cc3c(cc2-c2cc4c(cc21)C1CC2CC(CC4C2)C1)C1CC2CC(C1)CC3C2] [955959-91-8] | 76% |

| Ex. | Reactants | Product | Yield |
|---|---|---|---|
| A19 | S8 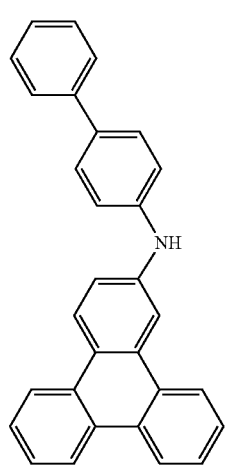 [1314527-06-4] | 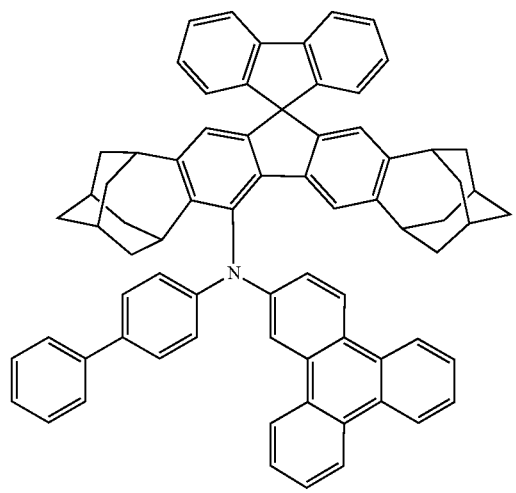 [SMILES: c1ccc(-c2ccc(N(c3ccc4c5ccccc5c5ccccc5c4c3)c3c4c(cc5c3C3CC6CC(CC5C6)C3)C3(c5ccccc5-c5ccccc53)c3cc5c(cc3-4)C3CC4CC(C3)CC5C4)cc2)cc1] | 44% |
| A20 | S8 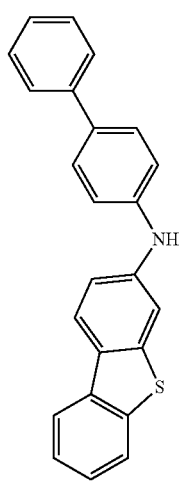 [1290037-87-0] | 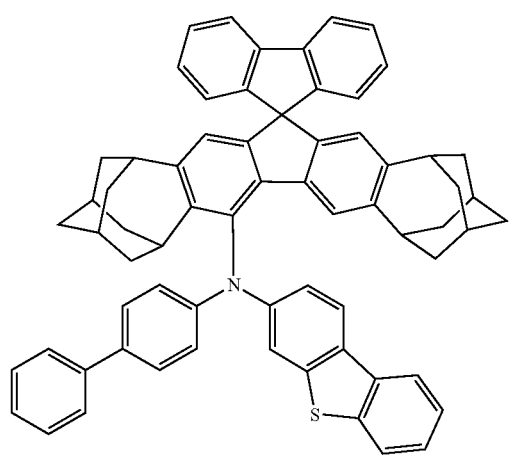 [SMILES: c1ccc(-c2ccc(N(c3ccc4c(c3)sc3ccccc34)c3c4c(cc5c3C3CC6CC(CC5C6)C3)C3(c5ccccc5-c5ccccc53)c3cc5c(cc3-4)C3CC4CC(C3)CC5C4)cc2)cc1] | 41% |

-continued
| Ex. | Reactants | Product | Yield |
|---|---|---|---|
| A21 | S9 | 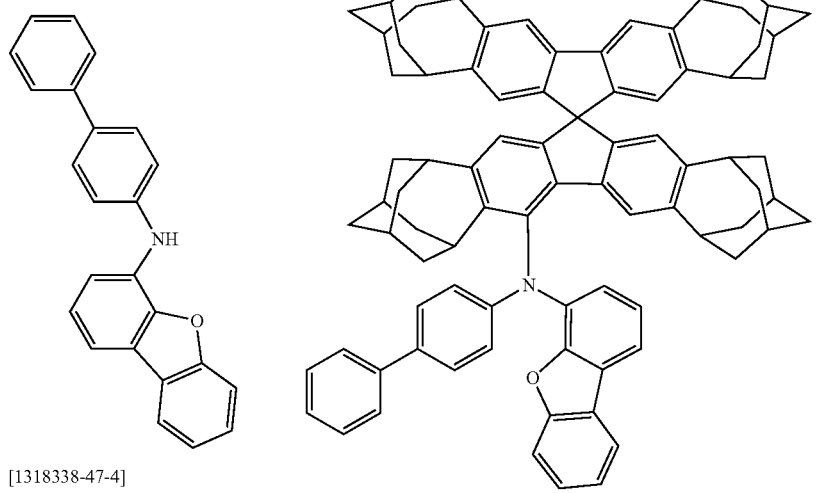 | 48% |
| | [1318338-47-4] | | |
| A30 | S15 | 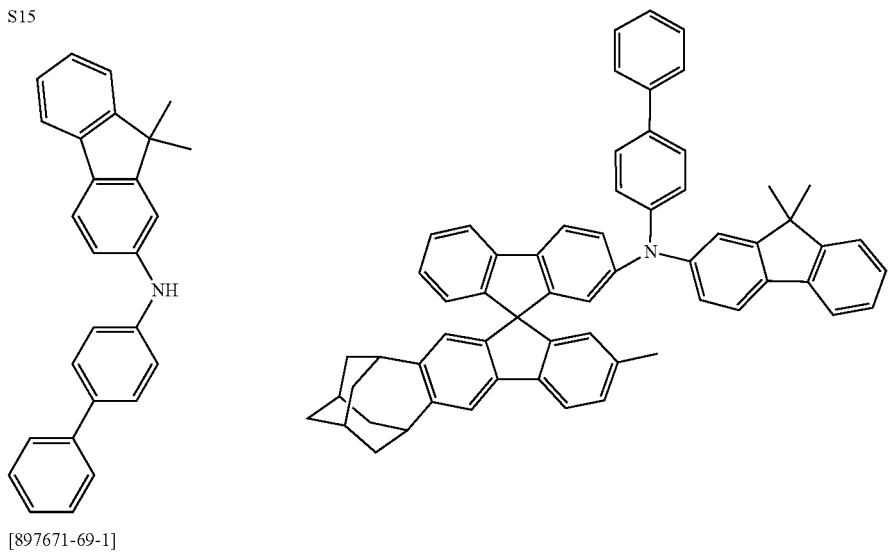 | 67% |
| | [897671-69-1] | | |

-continued

| Ex. | Reactants | Product | Yield |
|---|---|---|---|
| A31 | S15 [102113-98-4] | | 65% |
| S40 | S13 (50 mmol) [102113-98-4] | | 56% |

Example A22

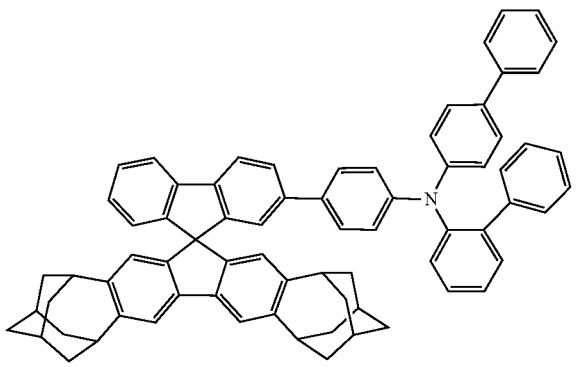 [SMILES: c1ccc(-c2ccc(N(c3ccc(-c4ccc5c(c4)C4(c6ccccc6-5)c5cc6c(cc5-c5cc7c(cc54)C4CC5CC(CC7C5)C4)C4CC5CC(C4)CC6C5)cc3)c3ccccc3-c3ccccc3)cc2)cc1]

A well-stirred mixture of 63.6 g (100 mmol) of S5, 57.6 g (110 mmol) of N-[1,1'-biphenyl]-2-yl-N-[4-(4,4,5,5-tetramethyl-1,3,2-dioxaborolan-2-yl)phenyl]-[1,1'-biphenyl]-4-amine [1608462-54-9], 63.7 g (300 mmol) of tripotassium phosphate, 1.83 g (6 mmol) of tri-o-tolylphosphine, 225 mg (1 mmol) of palladium(II) acetate, 500 ml of toluene, 100 ml of dioxane and 400 ml of water is heated under reflux for 16 h. After cooling, the organic phase is separated from the aqueous phase and washed once with 300 ml of water and once with 300 ml of saturated sodium chloride solution, and then dried over magnesium sulfate. The desiccant is filtered off using a silica gel bed in the form of a toluene slurry, and the filtrate is concentrated to dryness. The glassy residue is recrystallized from ethyl acetate/iso-propanol. The crude product is extracted three times with hot toluene and purified by zone sublimation under reduced pressure twice (p~$10^{-5}$ mbar, T~330° C.). Yield: 86.8 g (70 mmol), 70%. Purity by HPLC>99.9%.

The following compounds can be prepared analogously:
| Ex. | Reactants | Product | Yield |
|---|---|---|---|
| A23 | S5 | 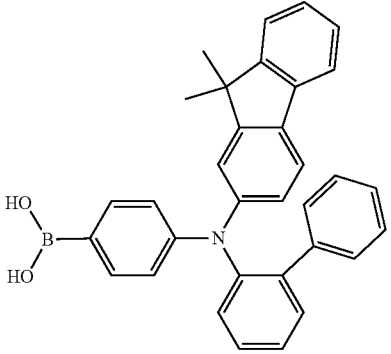 [1959599-90-6] 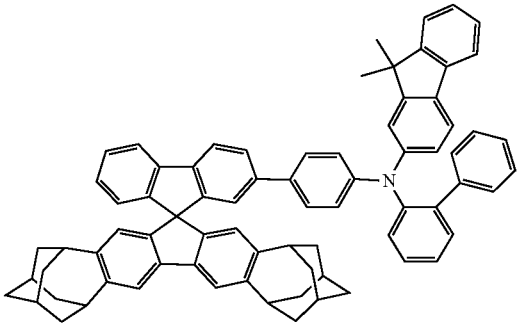 [SMILES: CC1(C)c2ccccc2-c2ccc(N(c3ccc(-c4ccc5c(c4)C4(c6ccccc6-5)c5cc6c(cc5-c5cc7c(cc54)C4CC5CC(CC7C5)C4)C4CC5CC(C4)CC6C5)cc3)c3ccccc3-c3ccccc3)cc21] | 68% |
| A24 | S5 | 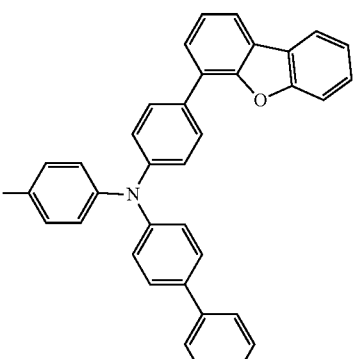 [1609381-12-5] 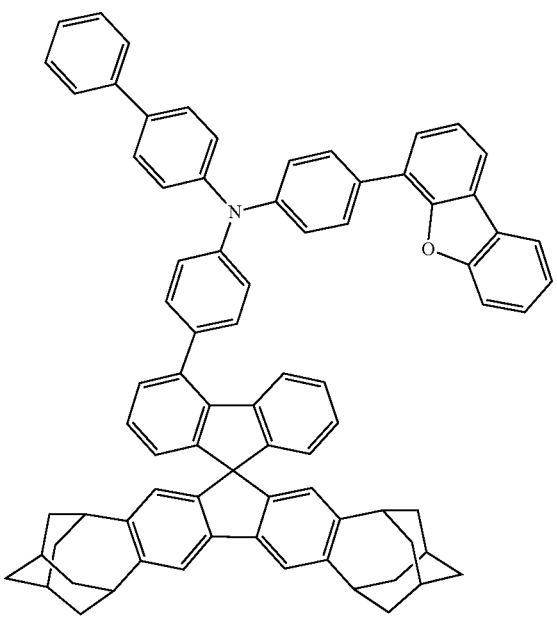 [SMILES: c1ccc(-c2ccc(N(c3ccc(-c4cccc5c4-c4ccccc4C54c5cc6c(cc5-c5cc7c(cc54)C4CC5CC(CC7C5)C4)C4CC5CC(C4)CC6C5)cc3)c3ccc(-c4cccc5c4oc4ccccc45)cc3)cc2)cc1] | 71% |

| Ex. | Reactants | Product | Yield |
|---|---|---|---|
| A25 | S5 | 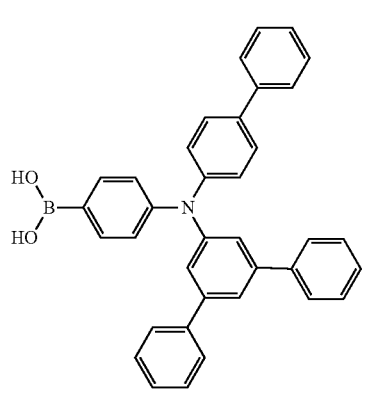 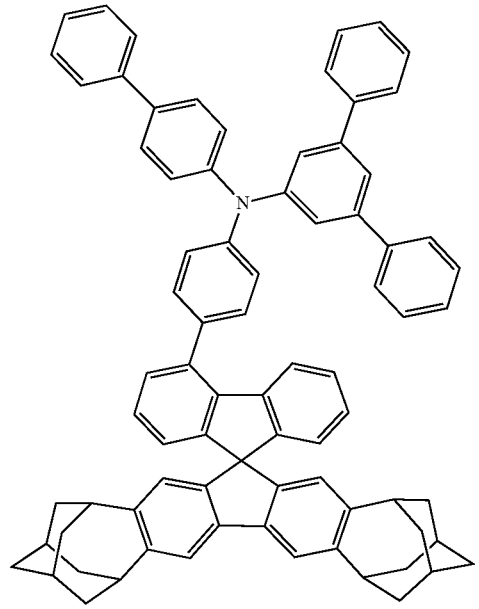 [SMILES: c1ccc(-c2ccc(N(c3ccc(-c4cccc5c4-c4ccccc4C54c5cc6c(cc5-c5cc7c(cc54)C4CC5CC(CC7C5)C4)C4CC5CC(C4)CC6C5)cc3)c3cc(-c4ccccc4)cc(-c4ccccc4)c3)cc2)cc1]<br>[1942032-55-4] | 75% |
| A26 | S8 | 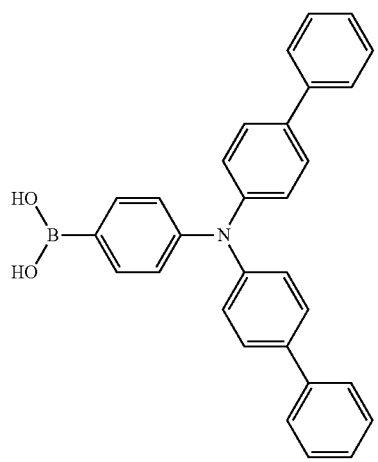 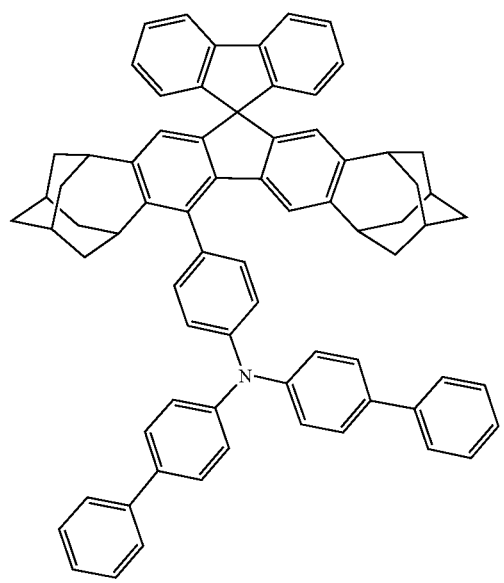 [SMILES: c1ccc(-c2ccc(N(c3ccc(-c4ccccc4)cc3)c3ccc(-c4c5c(cc6c4C4CC7CC(CC6C7)C4)C4(c6ccccc6-c6ccccc64)c4cc6c(cc4-5)C4CC5CC(C4)CC6C5)cc3)cc2)cc1]<br>[943836-24-6] | 73% |

| Ex. | Reactants | Product | Yield |
|---|---|---|---|
| A27 | S15 | 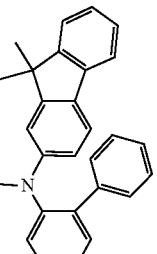 [1959599-90-6] | 69% |
| A28 | S15 | 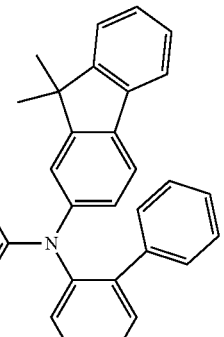 [1609381-12-5] | 73% |

3) Synthesis of the Carbazoles C

Example C1

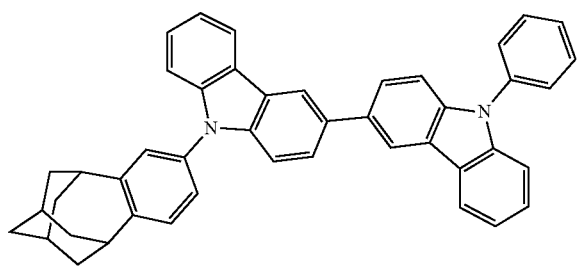 [SMILES: c1ccc(-n2c3ccccc3c3cc(-c4ccc5c(c4)c4ccccc4n5-c4ccc5c(c4)C4CC6CC(CC5C6)C4)ccc32)cc1]

A well-stirred mixture of 44.2 g (100 mmol) of S26, 36.9 g (100 mmol) of 9-phenyl-3-(4,4,5,5-tetramethyl-1,3,2-dioxaborolan-2-yl)-9H-carbazole [1126522-69-7], 63.7 g (300 mmol) of tripotassium phosphate, 1.83 g (6 mmol) of tri-o-tolylphosphine, 225 mg (1 mmol) of palladium(II) acetate, 350 ml of toluene, 80 ml of dioxane and 300 ml of water is heated under reflux for 16 h. After cooling, the aqueous phase is separated off and the organic phase is concentrated to dryness. The residue is taken up in 500 ml of DCM, and the organic phase is washed once with 300 ml of water and once with 300 ml of sat. sodium chloride solution, and then dried over magnesium sulfate. The desiccant is filtered off using a silica gel bed in the form of a DCM slurry, and the filtrate is concentrated to dryness. The residue is extracted by stirring with hot butyl acetate/isopropanol, then extracted three times with hot toluene and purified by zone sublimation under reduced pressure (p~$10^{-5}$ mbar, T~320° C.). Yield: 40.0 g (66 mmol), 66%. Purity by HPLC>99.9%.

The following compounds can be prepared analogously:
| Ex. | Reactants | Product | Yield |
|---|---|---|---|
| C2 | S26 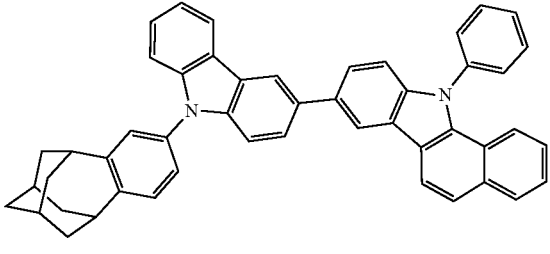 [SMILES: c1ccc(-n2c3ccc(-c4ccc5c(c4)c4ccccc4n5-c4ccc5c(c4)C4CC6CC(CC5C6)C4)cc3c3ccc4ccccc4c32)cc1] [1493715-55-1] | | 64% |
| C3 | S26 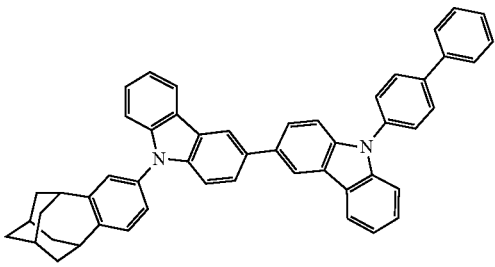 [SMILES: c1ccc(-c2ccc(-n3c4ccccc4c4cc(-c5ccc6c(c5)c5ccccc5n6-c5ccc6c(c5)C5CC7CC(CC6C7)C5)ccc43)cc2)cc1] [1391729-66-0] | | 70% |
| C4 | S26 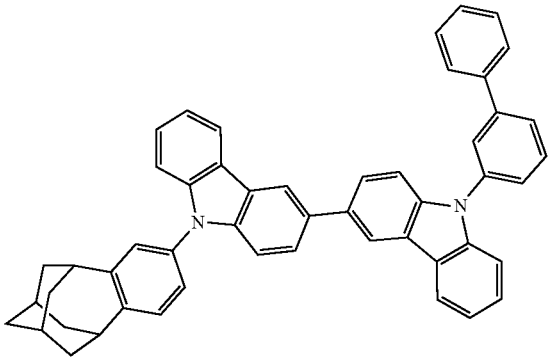 [SMILES: c1ccc(-c2cccc(-n3c4ccccc4c4cc(-c5ccc6c(c5)c5ccccc5n6-c5ccc6c(c5)C5CC7CC(CC6C7)C5)ccc43)c2)cc1] [1533406-38-0] | | 65% |
| C5 | S26 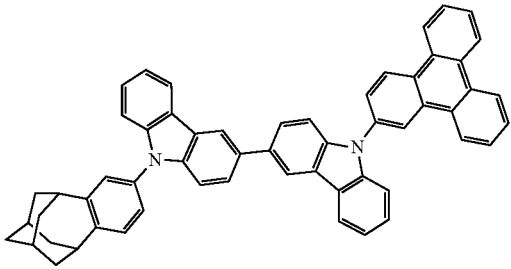 [SMILES: c1ccc2c(c1)c1ccccc1c1cc(-n3c4ccccc4c4cc(-c5ccc6c(c5)c5ccccc5n6-c5ccc6c(c5)C5CC7CC(CC6C7)C5)ccc43)ccc21] [1351870-14-8] | | 73% |

| Ex. | Reactants | Product | Yield |
|---|---|---|---|
| C6 | S26<br>[1357150-79-8] | 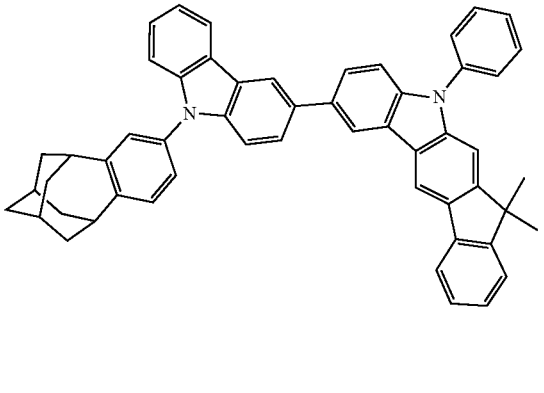 [SMILES: CC1(C)c2ccccc2-c2cc3c4cc(-c5ccc6c(c5)c5ccccc5n6-c5ccc6c(c5)C5CC7CC(CC6C7)C5)ccc4n(-c4ccccc4)c3cc21] | 71% |
| C7 | S26<br>[1846559-20-3] | 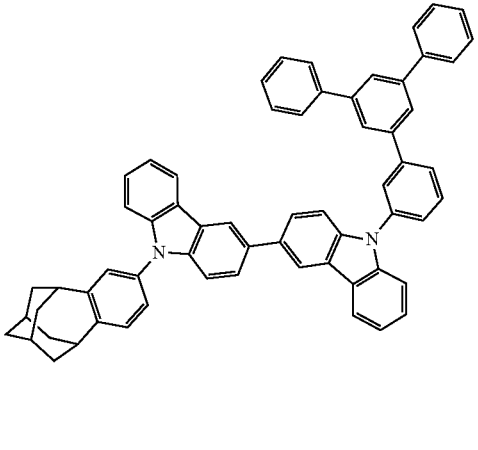 [SMILES: c1ccc(-c2cc(-c3ccccc3)cc(-c3cccc(-n4c5ccccc5c5cc(-c6ccc7c(c6)c6ccccc6n7-c6ccc7c(c6)C6CC8CC(CC7C8)C6)ccc54)c3)c2)cc1] | 51% |
| C8 | S20<br>Use of 2 mmol S-Phos rather than tri-o-tolylphosphine<br>[1622875-90-4] | 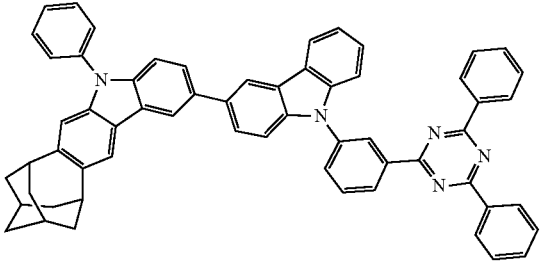 [SMILES: c1ccc(-c2nc(-c3ccccc3)nc(-c3cccc(-n4c5ccccc5c5cc(-c6ccc7c(c6)c6cc8c(cc6n7-c6ccccc6)C6CC7CC(CC8C7)C6)ccc54)c3)n2)cc1] | 57% |

| Ex. | Reactants | Product | Yield |
|---|---|---|---|
| C9 | S20<br>Use of 2 mmol S-Phos<br>rather than tri-o-tolylphosphine<br>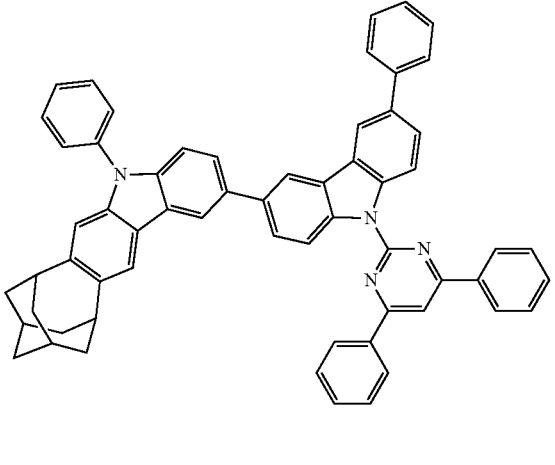 [SMILES: c1ccc(-c2ccc3c(c2)c2cc(-c4ccc5c(c4)c4cc6c(cc4n5-c4ccccc4)C4CC5CC(CC6C5)C4)ccc2n3-c2nc(-c3ccccc3)cc(-c3ccccc3)n2)cc1]<br>[1446005-91-9] | | 64% |
| C10 | S20<br>Use of 2 mmol S-Phos<br>rather than tri-o-tolylphosphine<br>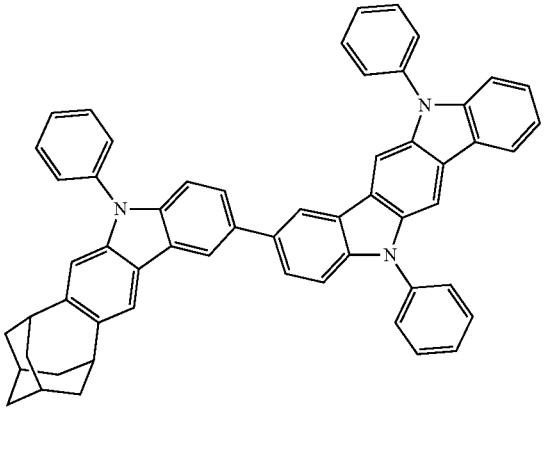 [SMILES: c1ccc(-n2c3ccc(-c4ccc5c(c4)c4cc6c(cc4n5-c4ccccc4)c4ccccc4n6-c4ccccc4)cc3c3cc4c(cc32)C2CC3CC(CC4C3)C2)cc1]<br>[1338068-90-8] | | 70% |
| C11 | S20<br>Use of 2 mmol S-Phos<br>rather than tri-o-tolylphosphine<br>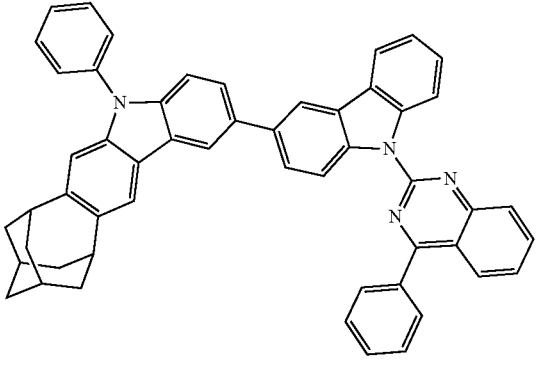 [SMILES: c1ccc(-c2nc(-n3c4ccccc4c4cc(-c5ccc6c(c5)c5cc7c(cc5n6-c5ccccc5)C5CC6CC(CC7C6)C5)ccc43)nc3ccccc23)cc1]<br>[1656982-71-6] | | 68% |

-continued

| Ex. | Reactants | Product | Yield |
|---|---|---|---|
| C12 | S20<br>Use of 2 mmol S-Phos<br>rather than tri-o-tolylphosphine<br>S31 | 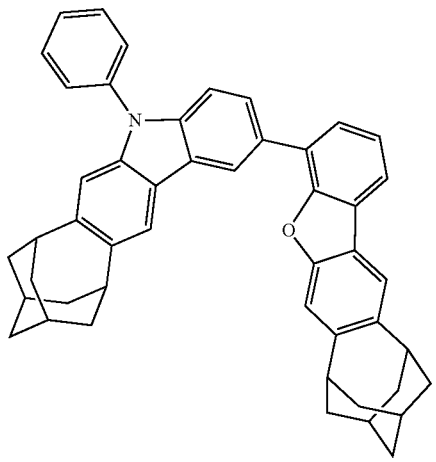 [SMILES: c1ccc(-n2c3ccc(-c4cccc5c4oc4cc6c(cc45)C4CC5CC(CC6C5)C4)cc3c3cc4c(cc32)C2CC3CC(CC4C3)C2)cc1] | 59% |

4) Synthesis of the Triazines T

Example T1

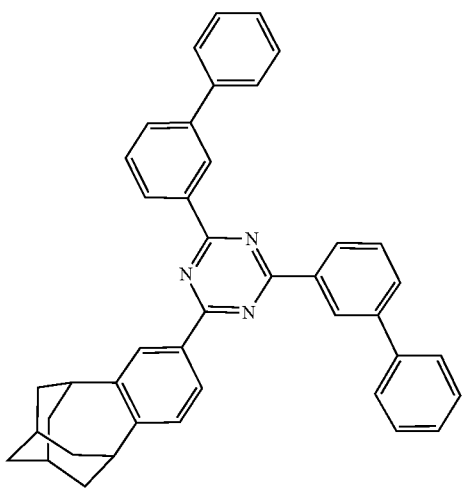 [SMILES: c1ccc(-c2cccc(-c3nc(-c4cccc(-c5ccccc5)c4)nc(-c4ccc5c(c4)C4CC6CC(CC5C6)C4)n3)c2)cc1]

A well-stirred mixture of 42.0 g (100 mmol) of (2,4-bis([1,1'-biphenyl]-3-yl)-6-chloro-1,3,5-triazine [1205748-61-3], 32.4 g (100 mmol) of 2-(6,7,8,9,10,11-hexahydro-5,9:7,11-dimethano-5H-benzocyclononen-2-yl)-4,4,5,5-tetramethyl-1,3,2-dioxaborolane [1801624-63-4], 31.9 g (150 mmol) of tripotassium phosphate, 821 mg (2 mmol) of S-Phos, 225 mg (1 mmol) of palladium(II) acetate, 400 ml of toluene, 80 ml of dioxane and 300 ml of water is heated under reflux for 16 h. After cooling, the organic phase is separated from the aqueous phase and washed once with 300 ml of water and once with 300 ml of saturated sodium chloride solution, and then dried over magnesium sulfate. The desiccant is filtered off using a silica gel bed in the form of a toluene slurry, and the filtrate is concentrated to dryness. The residue is extracted by stirring with hot iso-propanol, then extracted five times with hot acetonitrile and purified by zone sublimation under reduced pressure (p~ $10^{-5}$ mbar, T~310° C.). Yield: 37.8 g (65 mmol), 65%. Purity by HPLC>99.9%.

The following compounds can be prepared analogously:

| Ex. | Reactants | Product | Yield |
|---|---|---|---|
| T2 | S26 [2170382-97-3] | | 64% |
| T3 | S26 [1699739-82-6] | | 55% |
| T4 | S26 [2047632-07-6] | | 57% |

| Ex. | Reactants | Product | Yield |
|---|---|---|---|
| T5 | S26 | 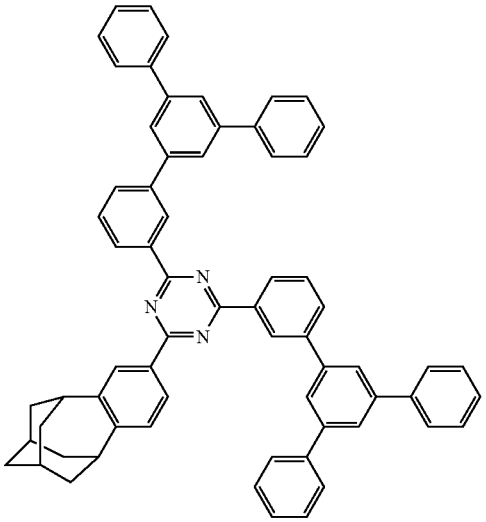 [SMILES: c1ccc(-c2cc(-c3ccccc3)cc(-c3cccc(-c4nc(-c5cccc(-c6cc(-c7ccccc7)cc(-c7ccccc7)c6)c5)nc(-c5ccc6c(c5)C5CC7CC(CC6C7)C5)n4)c3)c2)cc1] [1233200-61-7] | 49% |

5) Synthesis of the Host Materials for Singlet Emitters SH

Example SH1

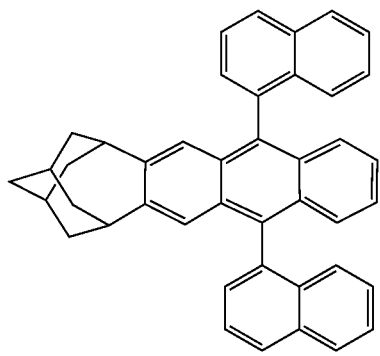 [SMILES: c1ccc2c(-c3c4ccccc4c(-c4cccc5ccccc45)c4cc5c(cc34)C3CC4CC(C3)CC5C4)cccc2c1]

A well-stirred mixture of 45.6 g (100 mmol) of S41, 37.8 g (220 mmol) of 1-naphthylboronic acid [13922-41-3], 63.7 g (300 mmol) of tripotassium phosphate, 1.83 g (6 mmol) of tri-o-tolylphosphine, 225 mg (1 mmol) of palladium(II) acetate, 400 ml of toluene, 80 ml of dioxane and 300 ml of water is heated under reflux for 16 h. After cooling, the aqueous phase is separated off and the organic phase is concentrated to dryness. The residue is taken up in 500 ml of DCM, and the organic phase is washed once with 300 ml of wafer and once with 300 ml of sat. sodium chloride solution, and then dried over magnesium sulfate. The desiccant is filtered off using a silica gel bed in the form of a DCM slurry, and the filtrate is concentrated to dryness. The residue is extracted by stirring with hot butyl acetate/isopropanol, then extracted five times with hot toluene and purified by zone sublimation under reduced pressure (p~$10^{-5}$ mbar, T~320° C.). Yield: 31.9 g (58 mmol) 58%, syn/anti isomer mixture. Purity by HPLC>99.9%.

6) Synthesis of the Singlet Emitters S

Example SE1

Procedure analogous to A1, except that, rather than S5, 28.8 g (50 mmol) of S40 and 31.0 g (110 mmol) of 4-(1,1-dimethylethyl)-N-[4-(1,1-dimethylethyl)phenyl]phenylamine [4627-22-9] is used. Purification by hot extraction with cyclohexane five times and zone sublimation under reduced pressure (p~$10^{-5}$ mbar, T~330° C.). Yield: 26.0 g (53 mmol) 53%. Purity by HPLC>99.9%.

The following compounds can be prepared analogously:
| Ex. | Reactants | Product | Yield |
|---|---|---|---|
| SE2 | S40 [37055-49-5] | 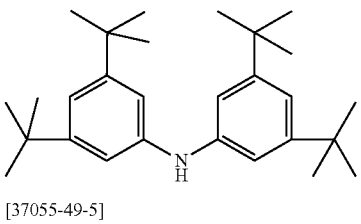 [SMILES: CC(C)(C)c1cc(Nc2cc(C(C)(C)C)cc(C(C)(C)C)c2)cc(C(C)(C)C)c1] | 48% |
7) Synthesis of the Spiro Materials H
The following compounds can be prepared analogously to S5:
| Ex. | Reactants Bromide Ketone/electrophile | Product | Yield |
|---|---|---|---|
| H1 | S2 S4 | 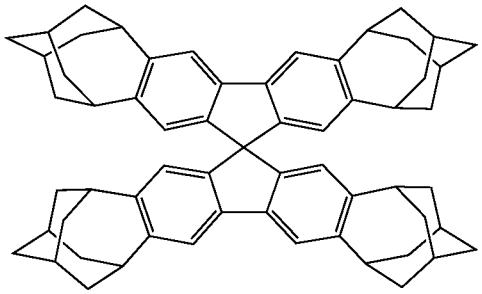 [SMILES: c1c2c(cc3c1C1CC4CC(C1)CC3C4)C1(c3cc4c(cc3-2)C2CC3CC(C2)CC4C3)c2cc3c(cc2-c2cc4c(cc21)C1CC2CC(CC4C2)C1)C1CC2CC(C1)CC3C2] | 91% |
| H2 | S2 50 mmol [84-65-1] | 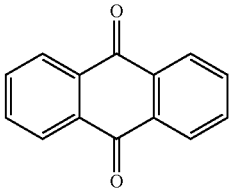 | 78% |

-continued

| Ex. | Reactants Bromide Ketone/electrophile | Product | Yield |
|---|---|---|---|
| H3 | S3, 25 mmol<br>SiCl$_4$, 12 mmol<br>[10026-04-7] | (structure) | 54% |

Production of the OLED Devices
1) Vacuum-Processed Devices:

OLEDs of the invention and OLEDs according to the prior art are produced by a general method according to WO 2004/058911, which is adapted to the circumstances described here (variation in layer thickness, materials used).

In the examples which follow, the results for various OLEDs are presented. Cleaned glass plaques (cleaning in Miele laboratory glass washer, Merck Extran detergent) coated with structured ITO (indium tin oxide) of thickness 50 nm are pretreated with UV ozone for 25 minutes (PR-100 UV ozone generator from UVP) and, within 30 mln, for improved processing, coated 50 with 20 nm of PEDOT:PSS (poly(3,4-ethylenedioxythiophene) poly(styrenesulfonate), purchased as CLEVIOS™ P VP Al 4083 from Heraeus Precious Metals GmbH Deutschland, spun on from aqueous solution) and then baked at 180° C. for 10 min. These coated glass plaques form the substrates to which the OLEDs are applied.

The OLEDs basically have the following layer structure: substrate/hole injection layer 1 (HIL1) consisting of HTM1 doped with 5% NDP-9 (commercially available from Novaled), 20 nm/hole transport layer 1 (HTL1)/hole transport layer 2 (HTL2)/emission layer (EML)/hole blocker layer (HBL)/electron transport layer (ETL)/optional electron injection layer (EIL) and finally a cathode. The cathode is formed by an aluminum layer of thickness 100 nm.

First of all, vacuum-processed OLEDs are described. For this purpose, all the materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as TMM1:TMM2:Ir(L1) (55%:35%: 10%) mean here that the material TMM1 is present in the layer in a proportion by volume of 55%, TMM2 in a proportion of 35% and Ir(L1) in a proportion of 10%. Analogously, the electron transport layer may also consist of a mixture of two materials. The exact structure of the OLEDs can be found in table 1. The materials used for production of the OLEDs are shown in table 4.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian emission characteristics, and also the lifetime are determined. The electroluminescence spectra are determined at a luminance of 1000 cd/m$^2$, and the CIE 1931 x and y color coordinates are calculated therefrom. The lifetime LT90 is defined as the time after which the luminance in operation has dropped to 90% of the starting luminance with a starting brightness of 10 000 cd/m$^2$.

The OLEDs can initially also be operated at different starting luminances. The values for the lifetime can then be converted to a figure for other starting luminances with the aid of conversion formulae known to those skilled in the art.

Use of Compounds of the Invention as Materials in Phosphorescent OLEDs

The compounds of the invention can be used inter alia as HTM (hole transport material), TMM (triplet matrix material), ETM (electron transport material) and as emitter materials in the emission layer in OLEDs. The compounds according to table 4 are used as a comparison according to the prior art. The results for the OLEDs are collated in table 2.

TABLE 1

Structure of the OLEDs

| Ex | HTL1 thickness | HTL2 thickness | EML thickness | HBL thickness | ETL thickness |
|---|---|---|---|---|---|
| Ref. D1 | HTM1 210 nm | HTM2 10 nm | TMM1:TMM2:Ir-Ref.1 (45%:40%:15%) 30 nm | ETM1 10 nm | ETM1:ETM2 (50%:50%) 30 nm |
| Ref. D2 | HTM1 210 nm | HTM2 10 nm | TMM1:TMM2:Ir-Ref2 (40%:50%:10%) 30 nm | ETM1 10 nm | ETM1:ETM2 (50%:50%) 30 nm |
| D1 | HTM1 210 nm | A1 10 nm | TMM1:TMM2:Ir-Ref.1 (45%:40%:15%) 30 nm | ETM1 10 nm | ETM1:ETM2 (50%:50%) 30 nm |
| D2 | HTM1 210 nm | A2 10 nm | TMM1:TMM2:Ir-Ref.1 (45%:40%:15%) 30 nm | ETM1 10 nm | ETM1:ETM2 (50%:50%) 30 nm |
| D3 | HTM1 210 nm | A3 10 nm | TMM1:TMM2:Ir-Ref.1 (45%:40%:15%) 30 nm | ETM1 10 nm | ETM1:ETM2 (50%:50%) 30 nm |
| D4 | HTM1 210 nm | A4 10 nm | TMM1:TMM2:Ir-Ref.1 (45%:40%:15%) 30 nm | ETM1 10 nm | ETM1:ETM2 (50%:50%) 30 nm |

TABLE 1-continued

Structure of the OLEDs

| Ex | HTL1 thickness | HTL2 thickness | EML thickness | HBL thickness | ETL thickness |
|---|---|---|---|---|---|
| D5 | HTM1 210 nm | A5 10 nm | TMM1:TMM2:Ir-Ref.1 (45%:40%:15%) 30 nm | ETM1 10 nm | ETM1:ETM2 (50%:50%) 30 nm |
| D6 | HTM1 210 nm | A6 10 nm | TMM1:TMM2:Ir-Ref.1 (45%:40%:15%) 30 nm | ETM1 10 nm | ETM1:ETM2 (50%:50%) 30 nm |
| D7 | HTM1 210 nm | A7 10 nm | TMM1:TMM2:Ir-Ref.1 (45%:40%:15%) 30 nm | ETM1 10 nm | ETM1:ETM2 (50%:50%) 30 nm |
| D8 | HTM1 210 nm | A8 10 nm | TMM1:TMM2:Ir-Ref.1 (45%:40%:15%) 30 nm | ETM1 10 nm | ETM1:ETM2 (50%:50%) 30 nm |
| D9 | HTM1 210 nm | A10 10 nm | TMM1:TMM2:Ir-Ref.1 (45%:40%:15%) 30 nm | ETM1 10 nm | ETM1:ETM2 (50%:50%) 30 nm |
| D10 | HTM1 210 nm | A13 10 nm | TMM1:TMM2:Ir-Ref.1 (45%:40%:15%) 30 nm | ETM1 10 nm | ETM1:ETM2 (50%:50%) 30 nm |
| D11 | HTM1 210 nm | A14 10 nm | TMM1:TMM2:Ir-Ref.1 (45%:40%:15%) 30 nm | ETM1 10 nm | ETM1:ETM2 (50%:50%) 30 nm |
| D12 | HTM1 210 nm | A16 10 nm | TMM1:TMM2:Ir-Ref.1 (45%:40%:15%) 30 nm | ETM1 10 nm | ETM1:ETM2 (50%:50%) 30 nm |
| D13 | HTM1 210 nm | A17 10 nm | TMM1:TMM2:Ir-Ref.1 (45%:40%:15%) 30 nm | ETM1 10 nm | ETM1:ETM (50%:50%) 30 nm |
| D14 | HTM1 210 nm | A19 10 nm | TMM1:TMM2:Ir-Ref.1 (45%:40%:15%) 30 nm | ETM1 10 nm | ETM1:ETM2 (50%:50%) 30 nm |
| D15 | HTM1 210 nm | A20 10 nm | TMM1:TMM2:Ir-Ref.1 (45%:40%:15%) 30 nm | ETM1 10 nm | ETM1:ETM2 (50%:50%) 30 nm |
| D16 | HTM1 210 nm | A30 10 nm | TMM1:TMM2:Ir-Ref.1 (45%:40%:15%) 30 nm | ETM1 10 nm | ETM1:ETM2 (50%:50%) 30 nm |
| D17 | HTM1 210 nm | A31 10 nm | TMM1:TMM2:Ir-Ref.1 (45%:40%:15%) 30 nm | ETM1 10 nm | ETM1:ETM2 (50%:50%) 30 nm |
| D18 | A9 210 nm | HTM2 10 nm | TMM1:TMM2:Ir-Ref.1 (45%:40%:15%) 30 nm | ETM1 10 nm | ETM1:ETM2 (50%:50%) 30 nm |
| D19 | A11 210 nm | HTM2 10 nm | TMM1:TMM2:Ir-Ref.1 (45%:40%:15%) 30 nm | ETM1 10 nm | ETM1:ETM2 (50%:50%) 30 nm |
| D20 | A12 210 nm | HTM2 10 nm | TMM1:TMM2:Ir-Ref.1 (45%:40%:15%) 30 nm | ETM1 10 nm | ETM1:ETM2 (50%:50%) 30 nm |
| D21 | A40 210 nm | HTM2 10 nm | TMM1:TMM2:Ir-Ref.1 (45%:40%:15%) 30 nm | ETM1 10 nm | ETM1:ETM2 (50%:50%) 30 nm |
| D22 | HTM1 210 nm | A22 10 nm | TMM1:TMM2:Ir-Ref.2 (40%:50%:10%) 30 nm | ETM1 10 nm | ETM1:ETM2 (50%:50%) 30 nm |
| D23 | HTM1 210 nm | A23 10 nm | TMM1:TMM2:Ir-Ref.2 (40%:50%:10%) 30 nm | ETM1 10 nm | ETM1:ETM2 (50%:50%) 30 nm |
| D24 | HTM1 210 nm | A24 10 nm | TMM1:TMM2:Ir-Ref.2 (40%:50%:10%) 30 nm | ETM1 10 nm | ETM1:ETM2 (50%:50%) 30 nm |
| D25 | HTM1 210 nm | A25 10 nm | TMM1:TMM2:Ir-Ref.2 (40%:50%:10%) 30 nm | ETM1 10 nm | ETM1:ETM2 (50%:50%) 30 nm |
| D26 | HTM1 210 nm | A26 10 nm | TMM1:TMM2:Ir-Ref.2 (40%:50%:10%) 30 nm | ETM1 10 nm | ETM1:ETM2 (50%:50%) 30 nm |
| D27 | HTM1 210 nm | A27 10 nm | TMM1:TMM2:Ir-Ref.2 (40%:50%:10%) 30 nm | ETM1 10 nm | ETM1:ETM2 (50%:50%) 30 nm |
| D28 | HTM1 210 nm | A28 10 nm | TMM1:TMM2:Ir-Ref.2 (40%:50%:10%) 30 nm | ETM1 10 nm | ETM1:ETM2 (50%:50%) 30 nm |
| D29 | HTM1 210 nm | HTM2 10 nm | TMM1:C1:Ir-Ref.1 (45%:40%:15%) 30 nm | ETM1 10 nm | ETM1:ETM2 (50%:50%) 30 nm |
| D30 | HTM1 210 nm | HTM2 10 nm | TMM1:C3:Ir-Ref.1 (45%:40%:15%) 30 nm | ETM1 10 nm | ETM1:ETM2 (50%:50%) 30 nm |
| D31 | HTM1 210 nm | HTM2 10 nm | TMM1:C4:Ir-Ref.1 (45%:40%:15%) 30 nm | ETM1 10 nm | ETM1:ETM2 (50%:50%) 30 nm |
| D32 | HTM1 210 nm | HTM2 10 nm | TMM1:C5:Ir-Ref.1 (45%:40%:15%) 30 nm | ETM1 10 nm | ETM1:ETM2 (50%:50%) 30 nm |
| D33 | HTM1 210 nm | A13 10 nm | TMM1:C12:Ir-Ref.1 (45%:40%:15%) 30 nm | ETM1 10 nm | ETM1:ETM2 (50%:50%) 30 nm |
| D34 | HTM1 210 nm | HTM2 10 nm | TMM1:TMM2:Ir-Ref.1 (45%:40%:15%) 30 nm | T1 10 nm | T1:ETM2 (50%:50%) 30 nm |
| D35 | HTM1 210 nm | HTM2 10 nm | TMM1:TMM2:Ir-Ref.1 (45%:40%:15%) 30 nm | T2 10 nm | T2:ETM2 (50%:50%) 30 nm |
| D36 | HTM1 210 nm | HTM2 10 nm | TMM1:TMM2:Ir-Ref.1 (45%:40%:15%) 30 nm | T3 10 nm | T3:ETM2 (50%:50%) 30 nm |
| D37 | HTM1 210 nm | HTM2 10 nm | TMM1:TMM2:Ir-Ref.1 (45%:40%:15%) 30 nm | ETM1 10 nm | T4:ETM2 (50%:50%) 30 nm |
| D38 | HTM1 210 nm | HTM2 10 nm | TMM1:TMM2:Ir-Ref.1 (45%:40%:15%) 30 nm | T5 10 nm | T5:ETM2 (50%:50%) 30 nm |
| D39 | HTM1 160 nm | HTM2 10 nm | SH1:BD-Ref.1 (94%:6%) 20 nm | --- | ETM1:ETM2 (50%:50%) 30 nm |
| D40 | HTM1 200 nm | HTM2 10 nm | SH1:SE1 (94%:6%) 25 nm | --- | ETM1:ETM2 (50%:50%) 30 nm |

TABLE 2

Results for the vacuum-processed OLEDs

| Ex. | EQE (%) 1000 cd/m2 | Voltage (V) 1000 cd/m2 | CIE x/y 1000 cd/m2 | LT90 (h) 10000 cd/m2 |
|---|---|---|---|---|
| \multicolumn{5}{c}{Green and yellow OLEDs} | | | | |
| Ref.D1 | 19.2 | 3.3 | 0.33/0.62 | 310 |
| Ref.D2 | 18.1 | 3.2 | 0.41/0.58 | 440 |
| D1 | 19.4 | 3.3 | 0.33/0.62 | 330 |
| D2 | 20.0 | 3.2 | 0.32/0.62 | 310 |
| D3 | 19.5 | 3.2 | 0.33/0.62 | 340 |
| D4 | 19.0 | 3.1 | 0.33/0.63 | 330 |
| D5 | 19.4 | 3.3 | 0.33/0.62 | 350 |
| D6 | 20.3 | 3.3 | 0.33/0.62 | 300 |
| D7 | 18.7 | 3.1 | 0.32/0.61 | 360 |
| D8 | 19.7 | 3.1 | 0.33/0.62 | 330 |
| D9 | 19.5 | 3.3 | 0.33/0.62 | 340 |
| D10 | 20.0 | 3.1 | 0.32/0.62 | 330 |
| D11 | 19.2 | 3.0 | 0.33/0.62 | 350 |
| D12 | 19.4 | 3.2 | 0.33/0.62 | 340 |
| D13 | 19.2 | 3.3 | 0.33/0.62 | 370 |
| D14 | 19.7 | 3.2 | 0.32/0.61 | 320 |
| D15 | 18.9 | 3.3 | 0.33/0.62 | 350 |
| D16 | 20.1 | 2.9 | 0.33/0.62 | 380 |
| D17 | 19.7 | 3.0 | 0.33/0.62 | 390 |
| D18 | 19.3 | 3.5 | 0.33/0.62 | 320 |
| D19 | 20.0 | 2.8 | 0.33/0.62 | 310 |
| D20 | 20.4 | 2.9 | 0.33/0.62 | 380 |
| D21 | 20.2 | 2.8 | 0.32/0.62 | 370 |
| D22 | 18.2 | 3.0 | 0.41/0.58 | 450 |
| D23 | 18.0 | 2.8 | 0.41/0.58 | 470 |
| D24 | 19.1 | 2.9 | 0.41/0.58 | 510 |
| D25 | 18.7 | 2.9 | 0.41/0.58 | 470 |
| D26 | 19.0 | 3.0 | 0.41/0.58 | 450 |
| D27 | 19.3 | 2.8 | 0.41/0.58 | 460 |
| D28 | 19.2 | 2.9 | 0.41/0.58 | 500 |
| D29 | 19.7 | 3.1 | 0.33/0.62 | 390 |
| D30 | 19.6 | 3.1 | 0.33/0.62 | 380 |
| D31 | 19.7 | 3.1 | 0.33/0.62 | 370 |
| D32 | 20.0 | 3.2 | 0.32/0.62 | 420 |
| D33 | 19.3 | 3.1 | 0.32/0.62 | 360 |
| D34 | 19.4 | 3.2 | 0.33/0.62 | 340 |
| D35 | 19.3 | 3.1 | 0.33/0.62 | 350 |
| D36 | 19.4 | 3.2 | 0.33/0.62 | 340 |
| D37 | 19.5 | 3.4 | 0.33/0.62 | 360 |
| D38 | 19.7 | 3.2 | 0.33/0.62 | 370 |
| \multicolumn{5}{c}{Blue and green OLEDs} | | | | |
| D39 | 7.2 | 4.2 | 0.15/0.09 | 300h |
| D40 | 8.6 | 3.7 | 0.29/0.62 | --- |

2. Solution-Processed Devices:

A: From Soluble Functional Materials of Low Molecular Weight

The materials of the invention can also be processed from solution and in that case lead to OLEDs which are much simpler in terms of process technology compared to the vacuum-processed OLEDs, but nevertheless have good properties. The production of such components is based on the production of polymeric light-emitting diodes (PLEDs), which has already been described many times in the literature (for example in WO 2004/037887). The structure is composed of substrate/ITO/hole injection layer (60 nm)/interlayer (20 nm)/emission layer (60 nm)/hole blocker layer (10 nm)/electron transport layer (40 nm)/cathode. For this purpose, substrates from Technoprint (soda-lime glass) are used, to which the ITO structure (indium tin oxide, a transparent conductive anode) is applied. The substrates are cleaned in a cleanroom with DI water and a detergent (Deconex 15 PF) and then activated by a UV/ozone plasma treatment. Thereafter, likewise in a cleanroom, a 20 nm hole injection layer is applied by spin-coating. The required spin rate depends on the degree of dilution and the specific spin-coater geometry. In order to remove residual water from the layer, the substrates are baked on a hotplate at 200° C. for 30 minutes. The interlayer used serves for hole transport; in this case, HL-X from Merck is used. The interlayer may alternatively also be replaced by one or more layers which merely have to fulfill the condition of not being leached off again by the subsequent processing step of EML deposition from solution. For production of the emission layer, the triplet emitters of the invention are dissolved together with the matrix materials in toluene or chlorobenzene. The typical solids content of such solutions is between 16 and 25 g/l when, as here, the layer thickness of 60 nm which is typical of a device is to be achieved by means of spin-coating. The solution-processed devices contain an emission layer of Matrix1: Matrix2:Ir-Ref.3 and optionally Ir-Ref.4. Optionally, a Matrix3 is additionally used (see table 3). The emission layer is spun on in an inert gas atmosphere, argon in the present case, and baked at 160° C. for 10 min. Vapor-deposited atop the latter are the hole blocker layer (10 nm ETM1) and the electron transport layer (40 nm ETM1 (50%)/ETM2 (50%)) (vapor deposition systems from Lesker or the like, typical vapor deposition pressure 5×10⁻⁶ mbar). Finally, a cathode of aluminum (100 nm) (high-purity metal from Aldrich) is applied by vapor deposition. In order to protect the device from air and air humidity, the device is finally encapsulated and then characterized. The OLED examples cited are yet to be optimized; table 3 summarizes the data obtained. The lifetime LT50 is defined as the time after which the luminance in operation drops to 50% of the starting luminance with a starting brightness of 1000 cd/m².

TABLE 3

Results with materials processed from solution

| Ex. | Matrix1 Matrix2 Matrix3 Ir-Ref.3 | EQE (%) 1000 cd/m² | Voltage (V) 1000 cd/m² | CIE x/y | LT50 (h) 1000 cd/m² |
|---|---|---|---|---|---|
| Sol-D1 | TMM3(20%) TMM4(60%) Ir-Ref.3 (20%) | 21.0 | 4.3 | 0.34/0.62 | 310000 |
| Sol-D2 | TMM3(26%) TMM4(50%) A15 (8%) Ir-Ref.3 (16%) | 20.9 | 3.9 | 0.34/0.62 | 330000 |
| Sol-D3 | TMM3(30%) TMM4(48%) A18 (6%) Ir-Ref.3 (16%) | 21.2 | 3.9 | 0.35/0.62 | 350000 |
| Sol-D4 | TMM3(30%) TMM4(48%) A21 (6%) Ir-Ref.3 (16%) | 21.5 | 3.8 | 0.34/0.62 | 330000 |
| Sol-D5 | TMM3(30%) TMM4(48%) C6 (6%) Ir-Ref.3 (16%) | 21.3 | 4.2 | 0.35/0.62 | 340000 |
| Sol-D6 | TMM3(30%) TMM4(48%) C7 (6%) Ir-Ref.3 (16%) | 21.1 | 4.1 | 0.35/0.62 | 330000 |
| Sol-D7 | C8 (20%) TMM4(56%) Ir-Ref.3 (24%) | 21.4 | 4.1 | 0.35/0.62 | 370000 |
| Sol-D8 | C9 (20%) TMM4(56%) Ir-Ref.3 (24%) | 21.0 | 4.0 | 0.34/0.62 | 350000 |
| Sol-D9 | TMM3(38%) TMM4(40%) C10 (6%) Ir-Ref.3 (16%) | 20.8 | 3.9 | 0.35/0.62 | 340000 |

TABLE 3-continued
Results with materials processed from solution
| Ex. | Matrix1 Matrix2 Matrix3 Ir-Ref.3 | EQE (%) 1000 cd/m² | Voltage (V) 1000 cd/m² | CIE x/y | LT50 (h) 1000 cd/m² |
|---|---|---|---|---|---|
| Sol-D10 | TMM3(20%) C11(20%) TMM4(52%) H1 (8%) Ir-Ref.3 (20%) | 21.6 | 4.2 | 0.34/0.62 | 360000 |
| Sol-D11 | TMM3(10%) C11(20%) TMM4(34%) Ir-Ref.3 (30%) Ir-Ref.4 (6%) | 18.1 | 5.7 | 0.67/0.33 | 300000 |
TABLE 4
Structural formulae of the materials used
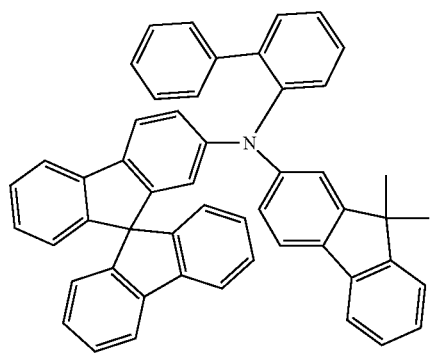 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
HTM1
[136463-07-5]
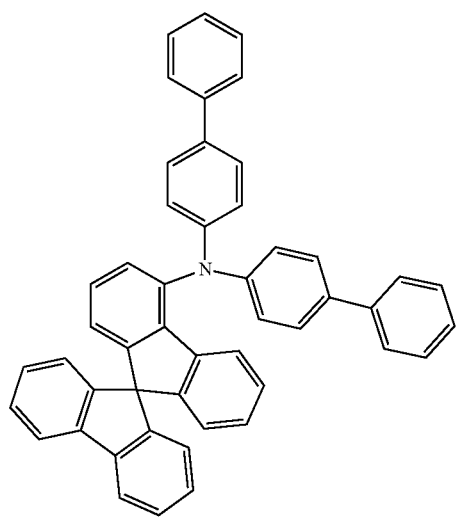 [SMILES: c1ccc(-c2ccc(N(c3ccc(-c4ccccc4)cc3)c3cccc4c3-c3ccccc3C43c4ccccc4-c4ccccc43)cc2)cc1]
HTM2
[1450933-43-3]

TABLE 4-continued
Structural formulae of the materials used
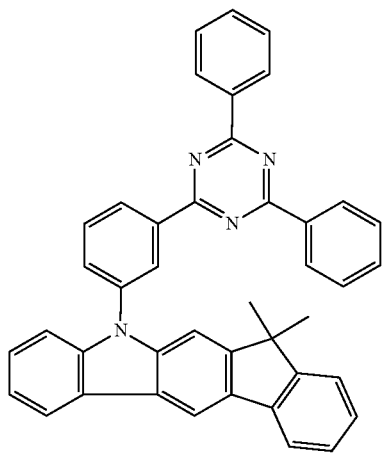 [SMILES: CC1(C)c2ccccc2-c2cc3c4ccccc4n(-c4cccc(-c5nc(-c6ccccc6)nc(-c6ccccc6)n5)c4)c3cc21]
TMM1
[1257248-13-7]
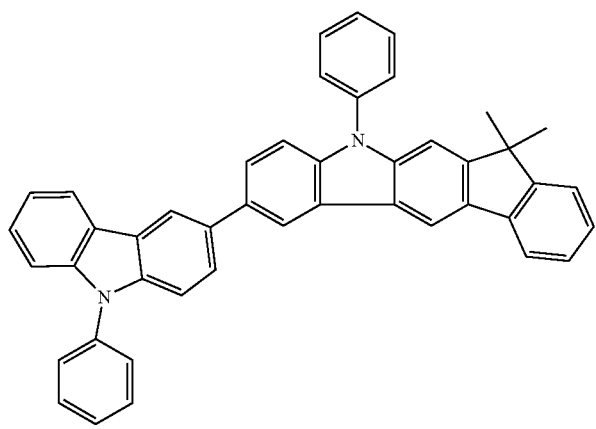 [SMILES: CC1(C)c2ccccc2-c2cc3c4cc(-c5ccc6c(c5)c5ccccc5n6-c5ccccc5)ccc4n(-c4ccccc4)c3cc21]
TMM1
[1357150-54-9]
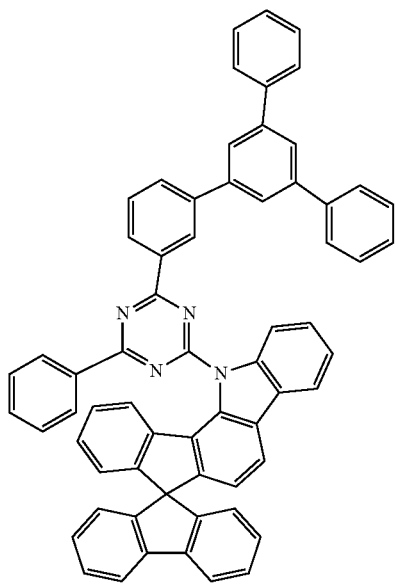 [SMILES: c1ccc(-c2cc(-c3ccccc3)cc(-c3cccc(-c4nc(-c5ccccc5)nc(-n5c6ccccc6c6ccc7c(c65)-c5ccccc5C75c6ccccc6-c6ccccc65)n4)c3)c2)cc1]
TMM3
[1616231-60-7]

TABLE 4-continued
Structural formulae of the materials used
| | |
|---|---|
| 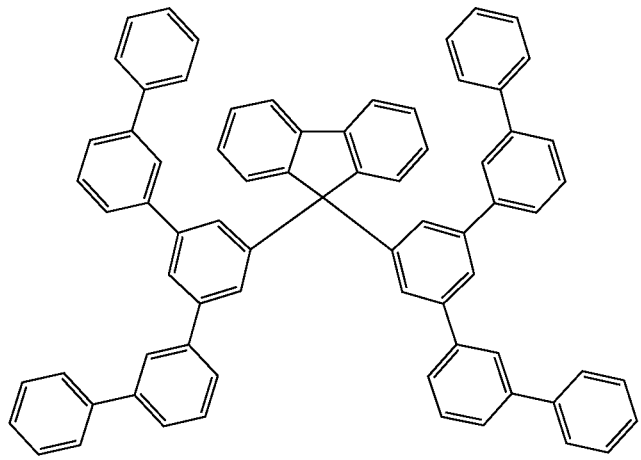 [SMILES: c1ccc(-c2cccc(-c3cc(-c4cccc(-c5ccccc5)c4)cc(C4(c5cc(-c6cccc(-c7ccccc7)c6)cc(-c6cccc(-c7ccccc7)c6)c5)c5ccccc5-c5ccccc54)c3)c2)cc1] | TMM4<br>[1246496-85-4] |
| 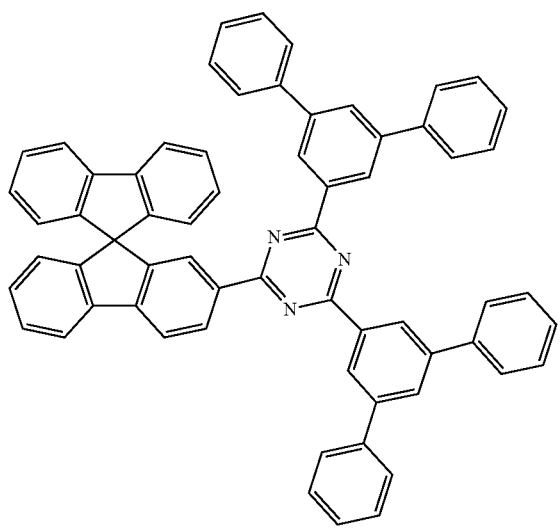 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1] | ETM1 = M10<br>[1233200-52-6] |
| 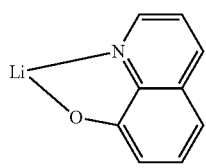 | ETM2<br>[25387-93-3] |

TABLE 4-continued
Structural formulae of the materials used
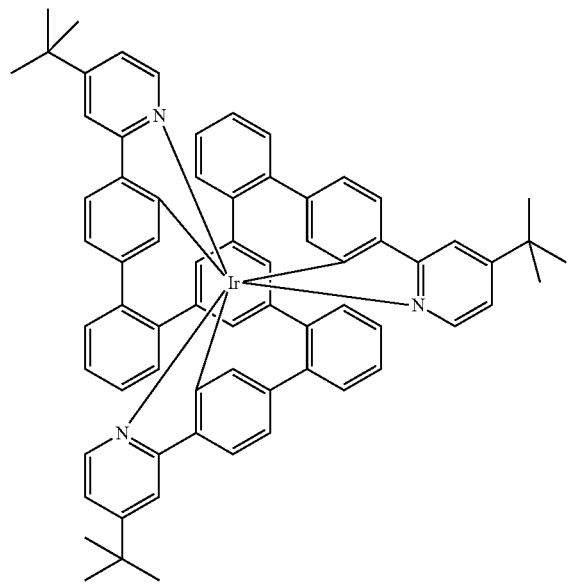
Ir-Ref.1
[1989606-01-0]
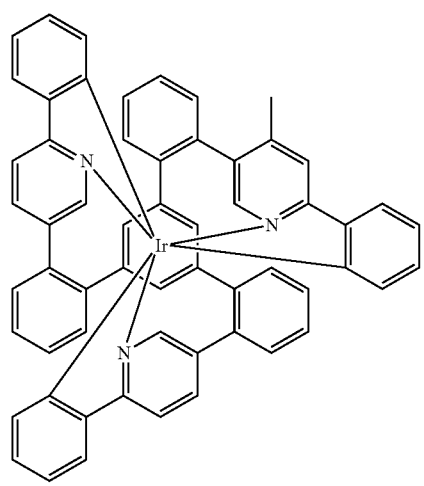
Ir-Ref.2
[1989605-56-2]

TABLE 4-continued
Structural formulae of the materials used
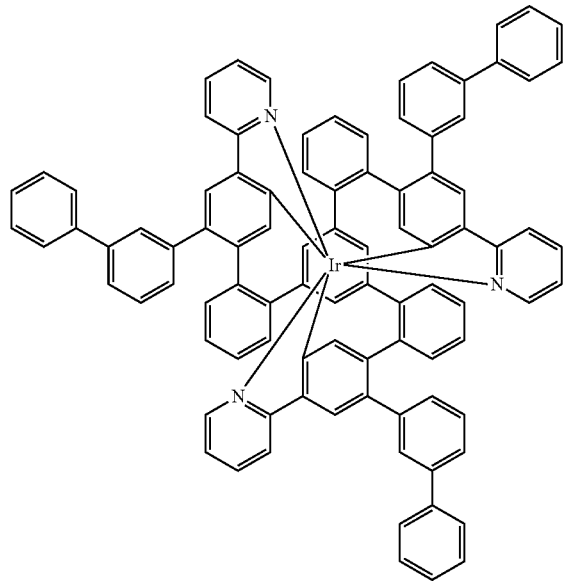
Ir-Ref.3
[2170173-12-1]
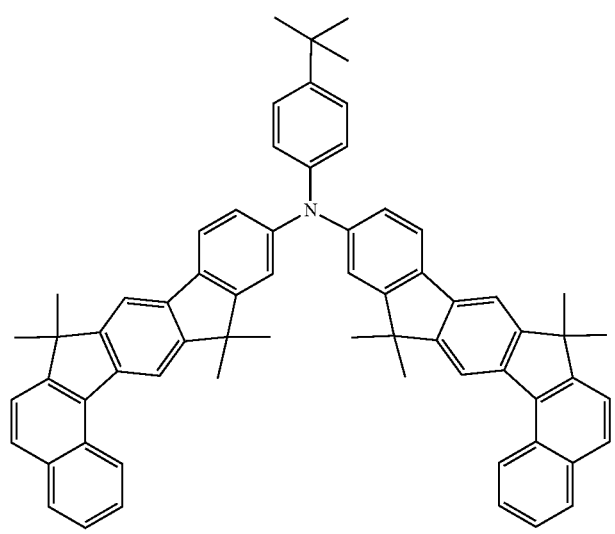 [SMILES: CC(C)(C)c1ccc(N(c2ccc3c(c2)C(C)(C)c2cc4c(cc2-3)C(C)(C)c2ccc3ccccc3c2-4)c2ccc3c(c2)C(C)(C)c2cc4c(cc2-3)C(C)(C)c2ccc3ccccc3c2-4)cc1]
BD-Ref.1
[1883835-29-7]
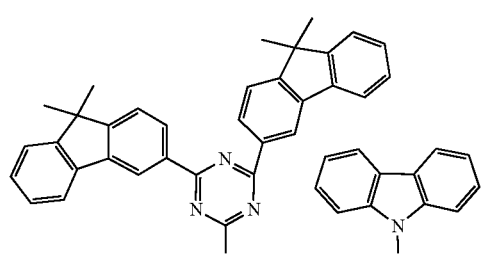
Ir-Ref.4
[1989604-92-3]

TABLE 4-continued

Structural formulae of the materials used

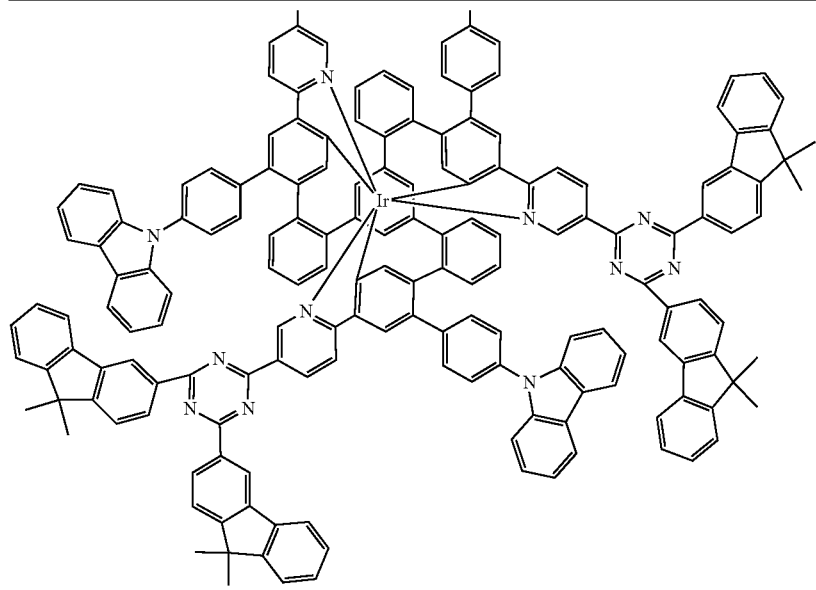

The invention claimed is:

1. A compound usable with preference as active compound in an organic electronic device, wherein the compound has at least one aromatic or heteroaromatic ring system which has 5 to 60 carbon atoms and is fused to an aliphatic polycyclic ring system having at least 3 rings, wherein the aliphatic polycyclic ring system which has at least 3 rings and is fused to the aromatic or heteroaromatic ring system having 5 to 60 carbon atoms forms a substructure of the formulae (N-1) to (N-6)

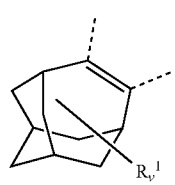

Formula (N-1)

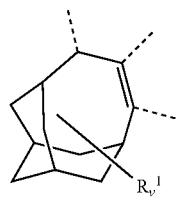

Formula (N-2)

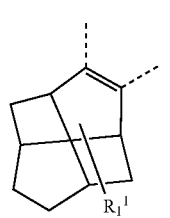

Formula (N-3)

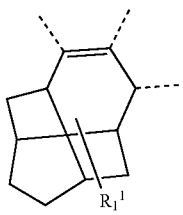

Formula (N-4)

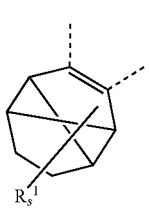

Formula (N-5)

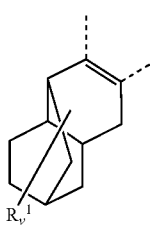

Formula (N-6)

wherein $R^1$ is the same or different at each instance and is H, D, OH, F, Cl, Br, I, CN, $NO_2$, $N(Ar^1)_2$, $N(R^2)_2$, $C(=O)Ar^1$, $C(=O)R^2$, $P(=O)(Ar^1)_2$, $P(Ar^1)_2$, $B(Ar^1)_2$, $B(OR^2)_2$, $Si(Ar^1)_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl or alkynyl group having 2 to 40 carbon atoms, each of which may be substituted by one or more $R^2$ radicals, where one or more nonadjacent $CH_2$ groups may be replaced by —R²C=CR²—, —C≡C—, Si(R²)₂, Ge(R²)₂, Sn(R²)₂, C=O, C=S, C=Se, C=NR², —C(=O)O—, —C(=O)NR²—, NR², P(=O)(R²), —O—, —S—, SO or SO₂ and where one or more hydrogen atoms may be replaced by D, F, Cl, Br, I, CN or NO₂, or an aromatic or heteroaromatic ring system which has 5 to 40 aromatic ring atoms, each of which may be substituted by one or more R² radicals, or an aryloxy or heteroaryloxy group which has 5 to 40 aromatic ring atoms and may be substituted by one or more R² radicals, or an aralkyl or heteroaralkyl group which has 5 to 40 aromatic ring atoms and may be substituted by one or more R² radicals, or a combination of these systems;

Ar¹ is the same or different at each instance and is an aromatic or heteroaromatic ring system which has 5 to 30 aromatic ring atoms and may be substituted by one or more, nonaromatic R² radicals; at the same time, it is possible for two Ar¹ radicals bonded to the same silicon atom, nitrogen atom, phosphorus atom or boron atom also to be joined to one another by a single bond or a bridge selected from B(R²), C(R²)₂, Si(R²)₂, C=O, C=NR², C=C(R²)₂, O, S, S=O, SO₂, N(R²), P(R²) and P(=O)R²;

R² is the same or different at each instance and is H, D, F, Cl, Br, I, CN, B(OR³)₂, NO₂, C(=O)R³, CR³=C(R³)₂, C(=O)OR³, C(=O)N(R³)₂, Si(R³)₃, P(R³)₂, B(R³)₂, N(R³)₂, NO₂, P(=O)(R³)₂, OSO₂R³, OR³, S(=O)R³, S(=O)₂R³, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R³ radicals, where one or more nonadjacent CH₂ groups may be replaced by —R³C=CR³—, —C≡C—, Si(R³)₂, Ge(R³)₂, Sn(R³)₂, C=O, C=S, C=NR³, —C(=O)O—, —C(=O)NR³—, NR³, P(=O)(R³), —O—, —S—, SO or SO₂ and where one or more hydrogen atoms may be replaced by D, F, Cl, Br, I, CN or NO₂, or an aromatic or heteroaromatic ring system which has 5 to 40 aromatic ring atoms and may be substituted in each case by one or more R³ radicals, or an aryloxy or heteroaryloxy group which has 5 to 40 aromatic ring atoms and may be substituted by one or more R³ radicals, or a combination of these systems; at the same time, two or more, adjacent substituents R² together may also form a mono- or polycyclic, aliphatic or aromatic or heteroaromatic ring system;

R³ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, two or more adjacent substituents R³ together may also form a mono- or polycyclic, aliphatic or aromatic or heteroaromatic ring system;

the index s is 0, 1, 2, 3, 4, 5 or 6;
the index t is 0, 1, 2, 3, 4, 5, 6, 7 or 8;
the index v is 0, 1, 2, 3, 4, 5, 6, 7, 8 or 9;
and the dotted lines represent the bonds of the aromatic or heteroaromatic ring system having 5 to 60 carbon atoms to which the aliphatic polycyclic ring system having at least 3 rings is fused, and wherein the aromatic or heteroaromatic ring system having 5 to 60 carbon atoms to which the aliphatic polycyclic ring system having at least 3 rings is fused forms a substructure of the formulae (Ar-2) to (Ar-11) and (Ar-13) to (Ar-66)

(Ar-2)

(Ar-3)

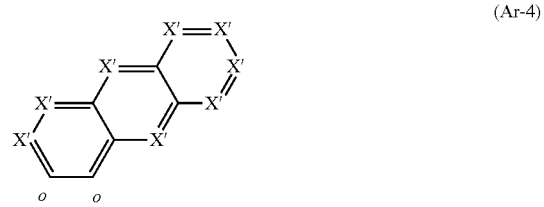

(Ar-4)

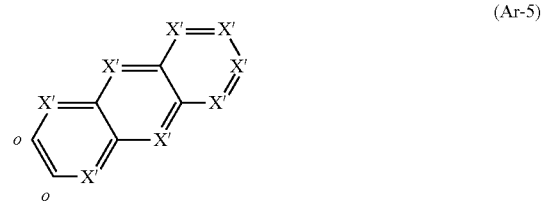

(Ar-5)

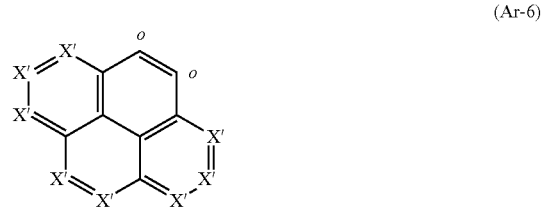

(Ar-6)

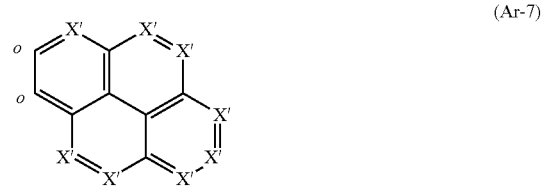

(Ar-7)

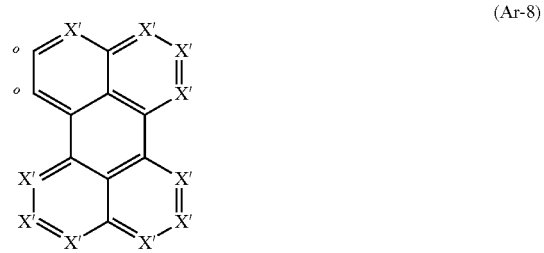

(Ar-8)

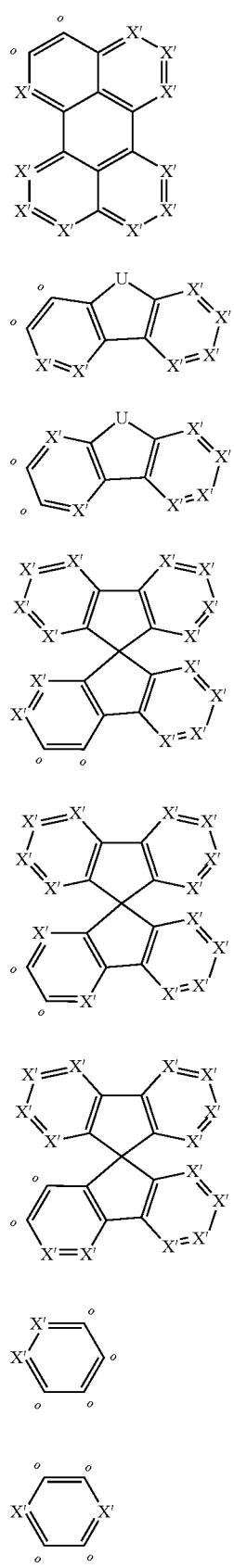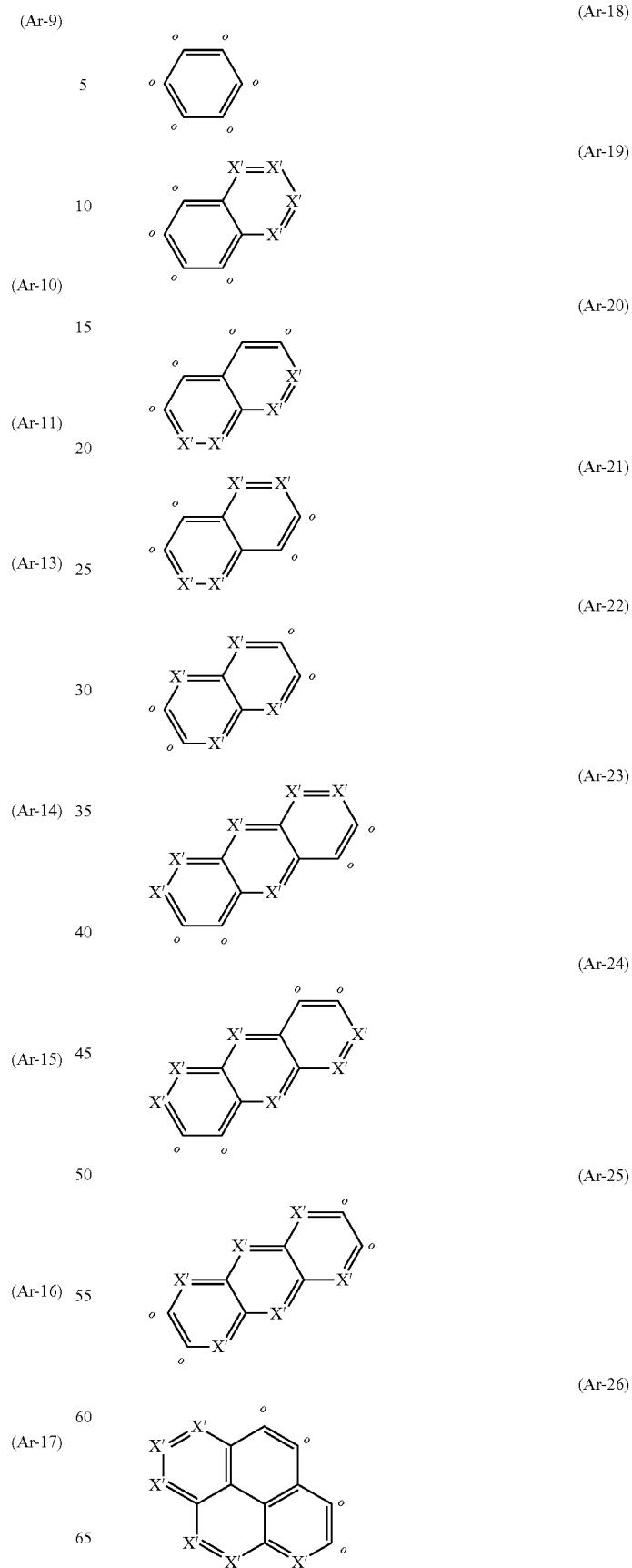

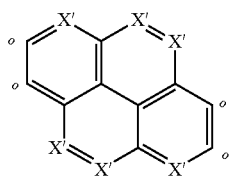 (Ar-27)
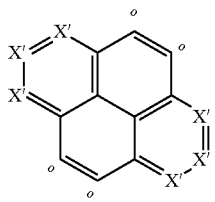 (Ar-28)
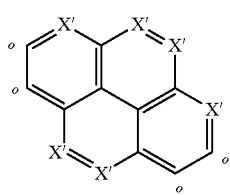 (Ar-29)
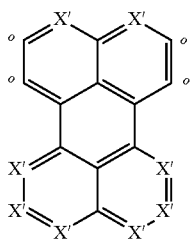 (Ar-30)
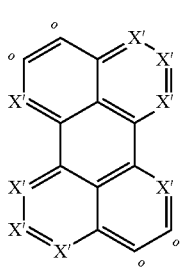 (Ar-31)
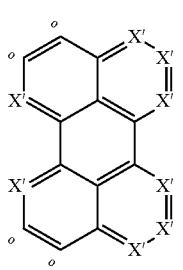 (Ar-32)
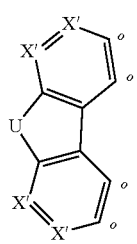 (Ar-33)
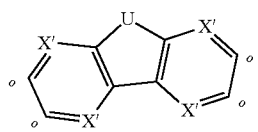 (Ar-34)
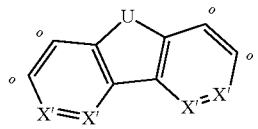 (Ar-35)
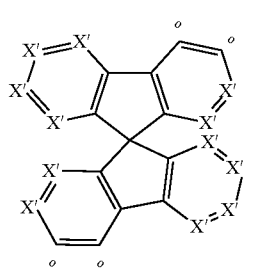 (Ar-36)
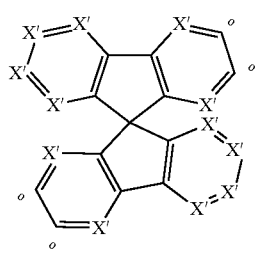 (Ar-37)
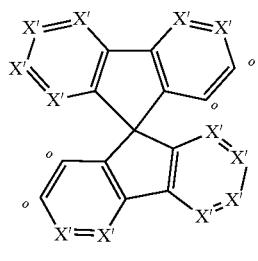 (Ar-38)
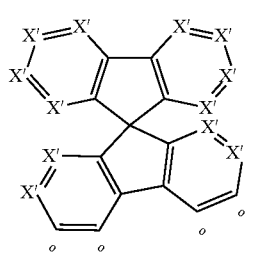 (Ar-39)

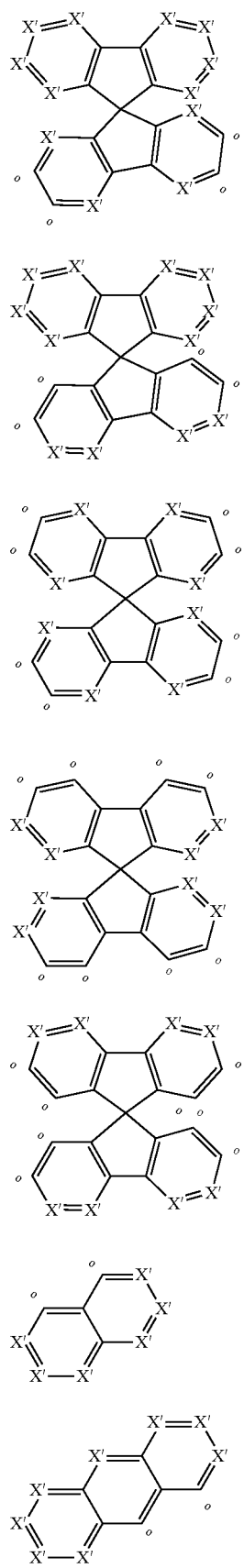
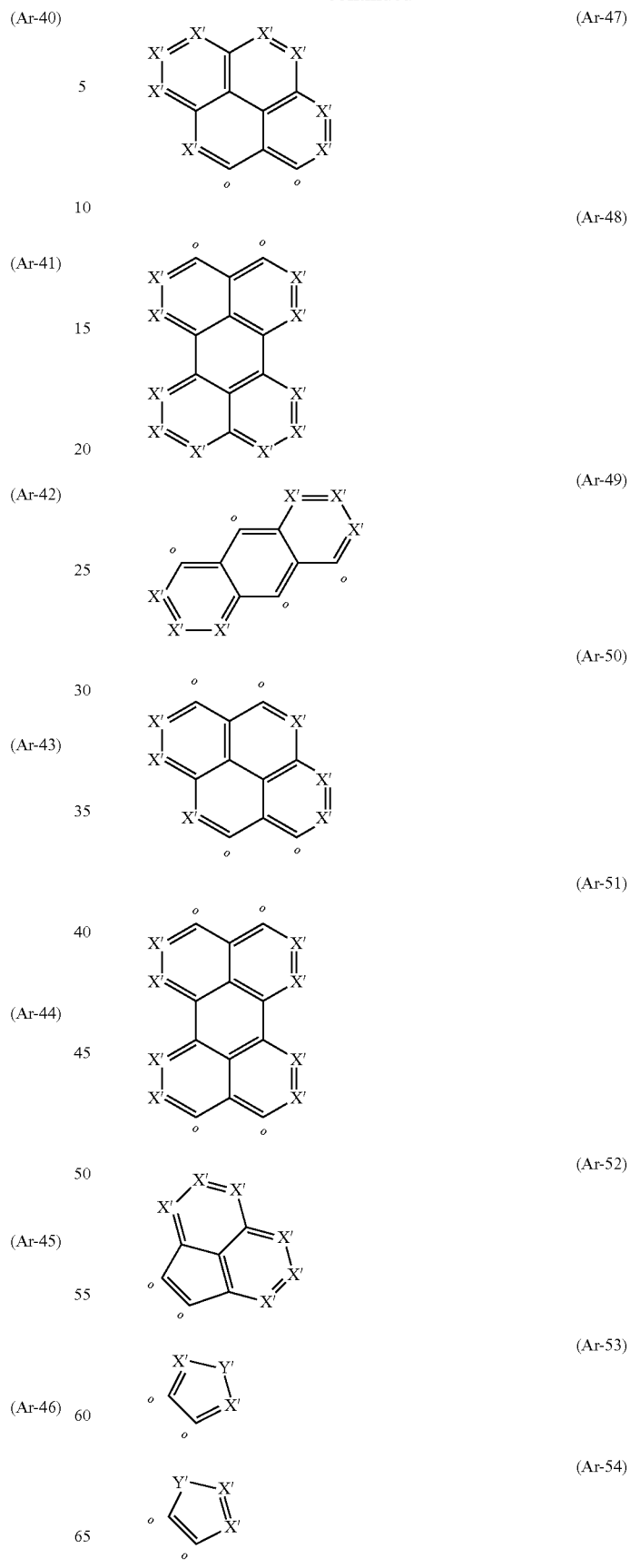

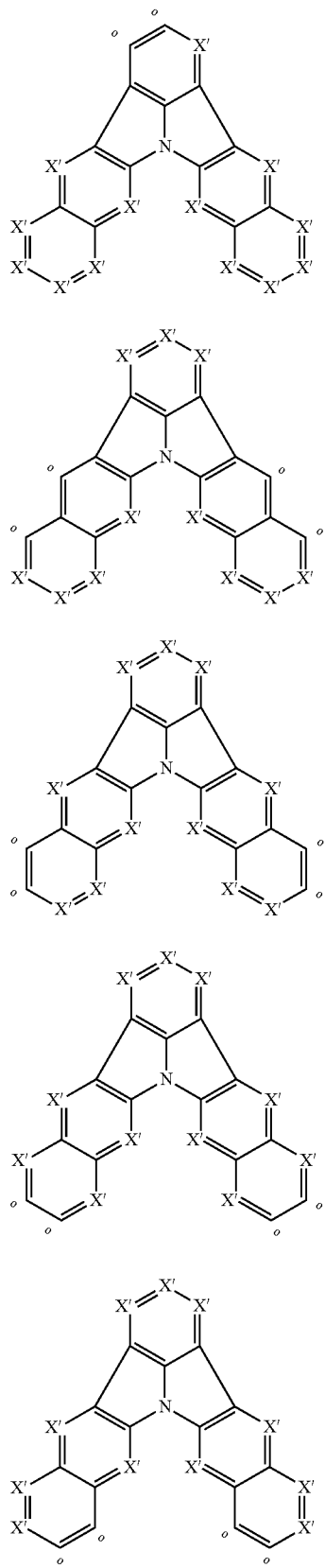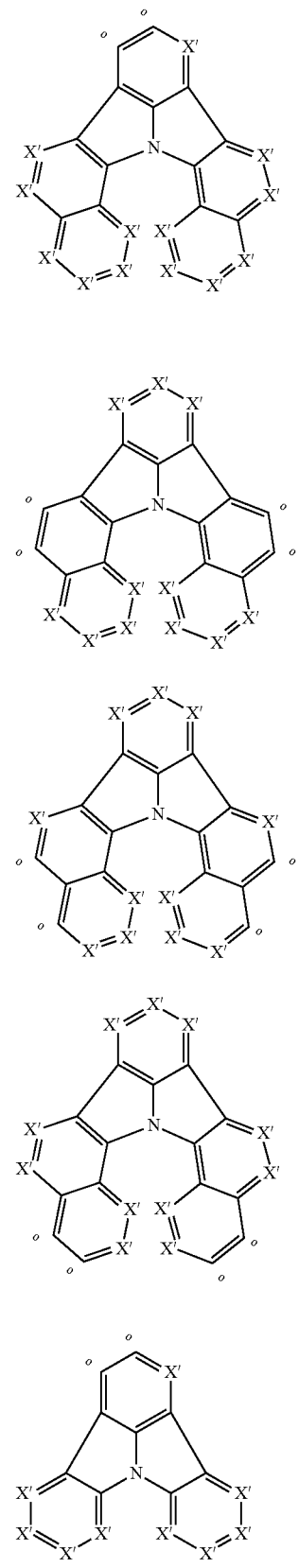

-continued (Ar-65)

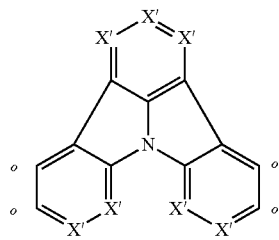

(Ar-66)

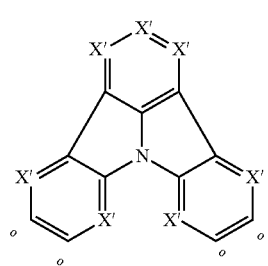

wherein X' is N or CR$^1$;
Y' is selected from O, S, C(R$^1$)$_2$, Si(R$^1$)$_2$, NR$^1$ and NAr$^1$;
U is selected from O, S, C(R$^1$)$_2$, N(R$^1$), B(R$^1$), Si(R$^1$)$_2$, C=O, S=O, SO$_2$, P(R$^1$) and P(=O)R$^1$;
R$^1$ is the same or different at each instance and is H, D, OH, F, Cl, Br, I, CN, NO$_2$, N(Ar$^1$)$_2$, N(R$^2$)$_2$, C(=O)Ar$^1$, C(=O)R$^2$, P(=O)(Ar$^1$)$_2$, P(Ar$^1$)$_2$, B(Ar$^1$)$_2$, B(OR$^2$)$_2$, Si(Ar$^1$)$_3$, Si(R$^2$)$_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl or alkynyl group having 2 to 40 carbon atoms, each of which may be substituted by one or more R$^2$ radicals, where one or more nonadjacent CH$_2$ groups may be replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, —C(=O)O—, —C(=O)NR$^2$—, NR$^2$, P(=O)(R$^2$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more R$^2$ radicals, or an aryloxy or heteroaryloxy group which has 5 to 40 aromatic ring atoms and may be substituted by one or more R$^2$ radicals, or an aralkyl or heteroaralkyl group which has 5 to 40 aromatic ring atoms and may be substituted by one or more R$^2$ radicals, or a combination of these systems;
Ar$^1$ is the same or different at each instance and is an aromatic or heteroaromatic ring system which has 5 to 30 aromatic ring atoms and may be substituted by one or more, nonaromatic R$^2$ radicals; at the same time, it is possible for two Ar$^1$ radicals bonded to the same silicon atom, nitrogen atom, phosphorus atom or boron atom also to be joined to one another by a single bond or a bridge selected from B(R$^2$), C(R$^2$)$_2$, Si(R$^2$)$_2$, C=O, C=NR$^2$, C=C(R$^2$)$_2$, O, S, S=O, SO$_2$, N(R$^2$), P(R$^2$) and P(=O)R$^2$;
R$^2$ is the same or different at each instance and is H, D, F, Cl, Br, I, CN, B(OR$^3$)$_2$, NO$_2$, C(=O)R$^3$, CR$^3$=C(R$^3$)$_2$, C(=O)OR$^3$, C(=O)N(R$^3$)$_2$, Si(R$^3$)$_3$, P(R$^3$)$_2$, B(R$^3$)$_2$, N(R$^3$)$_2$, NO$_2$, P(=O)(R$^3$)$_2$, OSO$_2$R$^3$, OR$^3$, S(=O)R$^3$, S(=O)$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^3$ radicals, where one or more nonadjacent CH$_2$ groups may be replaced by —R$^3$C=CR$^3$—, —C≡C—, Si(R$^3$)$_2$, Ge(R$^3$)$_2$, Sn(R$^3$)$_2$, C=O, C=S, C=NR$^3$, —C(=O)O—, —C(=O)NR$^3$—, NR$^3$, P(=O)(R$^3$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^3$ radicals, or an aryloxy or heteroaryloxy group which has 5 to 40 aromatic ring atoms and may be substituted by one or more R$^3$ radicals, or a combination of these systems; at the same time, two or more, adjacent substituents R$^2$ together may also form a mono- or polycyclic, aliphatic or aromatic or heteroaromatic ring system;

R$^3$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, two or more adjacent substituents R$^3$ together may also form a mono- or polycyclic, aliphatic or aromatic or heteroaromatic ring system;

and the aliphatic polycyclic ring system having at least 3 rings binds to the aromatic or heteroaromatic ring system having 5 to 60 carbon atoms at the respective positions identified by o to form a ring.

2. The compound as claimed in claim 1, wherein the aromatic or heteroaromatic ring system having 5 to 60 carbon atoms to which an aliphatic polycyclic ring system having at least 3 rings is fused forms a substructure of the formulae (Ar'-2) to (Ar'-11), and (Ar'-13) to (Ar'-65)

(Ar'-2)

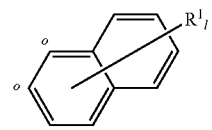

(Ar'-3)

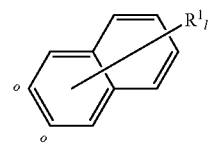

(Ar'-4)

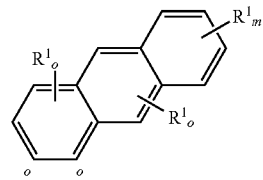

-continued
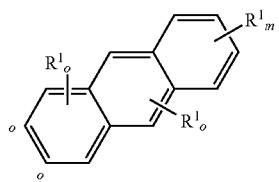
(Ar'-5)
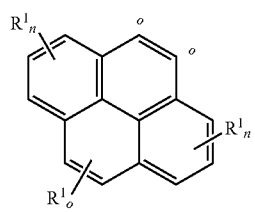
(Ar'-6)
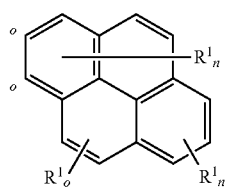
(Ar'-7)
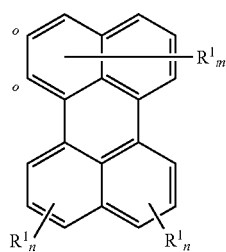
(Ar'-8)
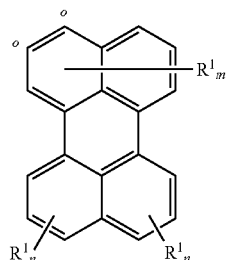
(Ar'-9)
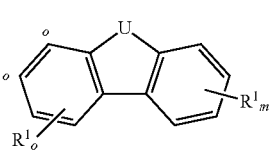
(Ar'-10)
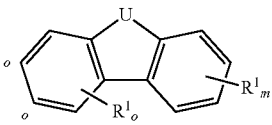
(Ar'-11)
-continued
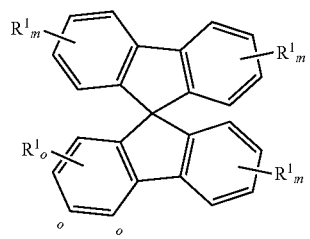
(Ar'-13)
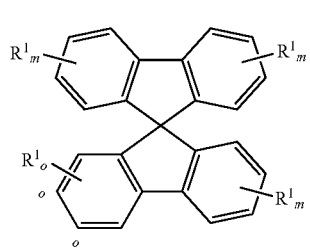
(Ar'-14)
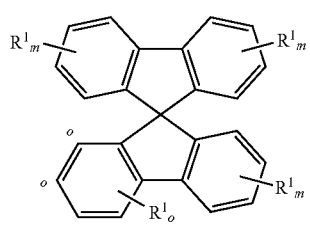
(Ar'-15)
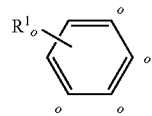
(Ar'-16)
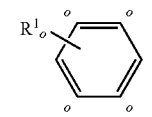
(Ar'-17)
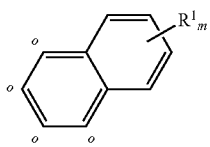
(Ar'-18)
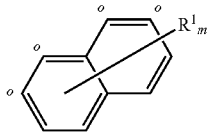
(Ar'-19)
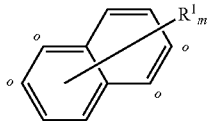
(Ar'-20)

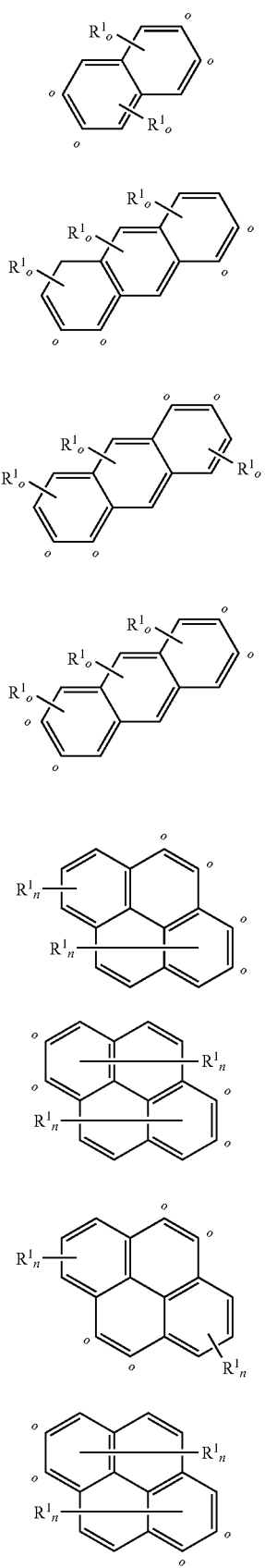
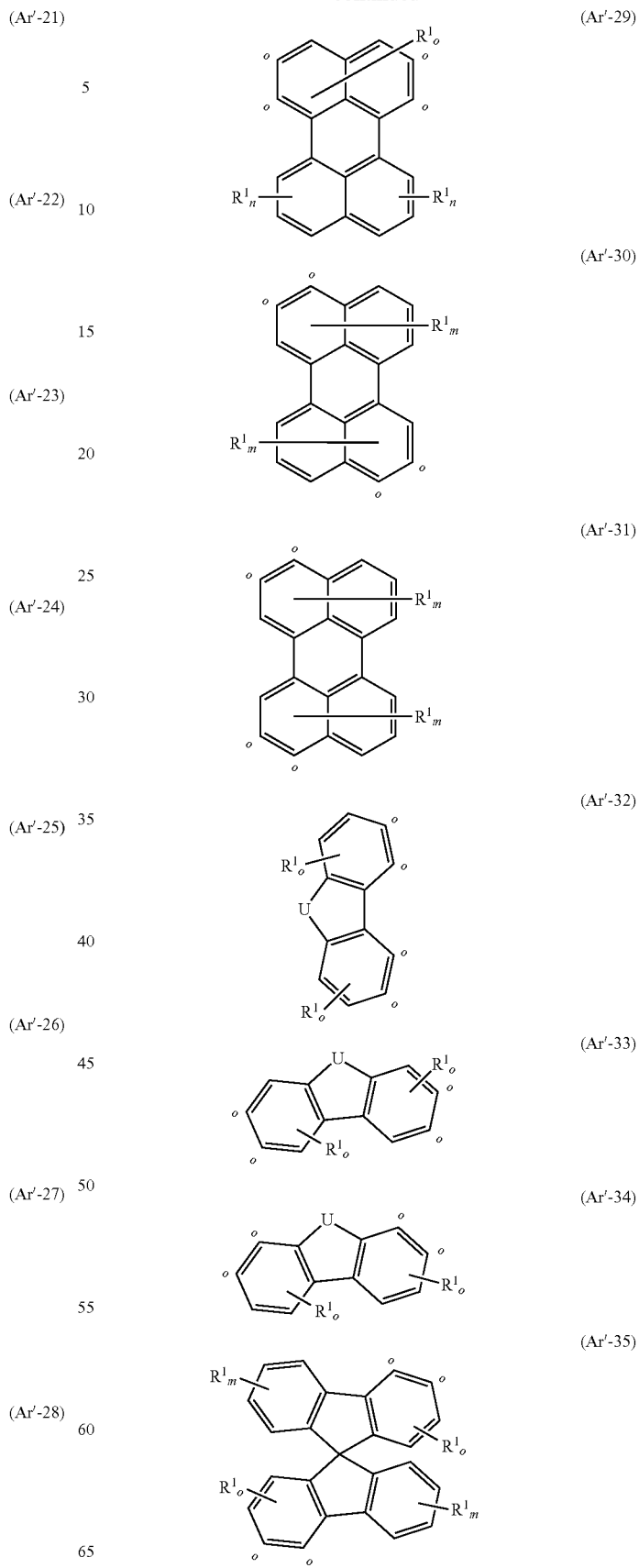

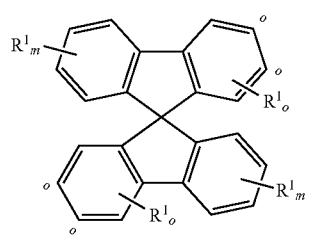 (Ar'-36)
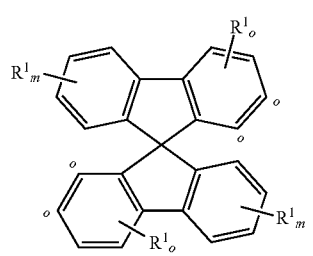 (Ar'-37)
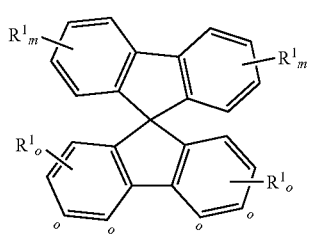 (Ar'-38)
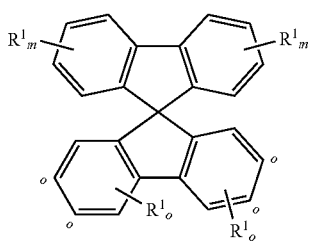 (Ar'-39)
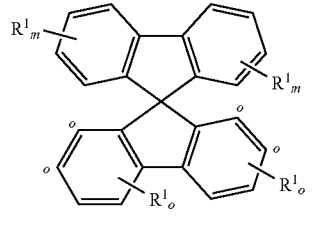 (Ar'-40)
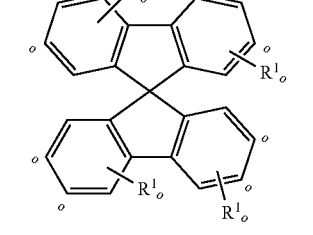 (Ar'-41)
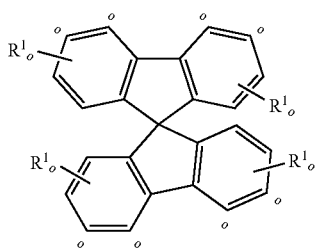 (Ar'-42)
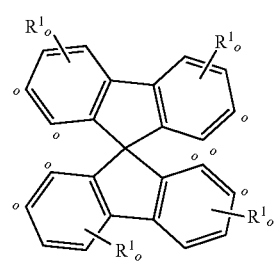 (Ar'-43)
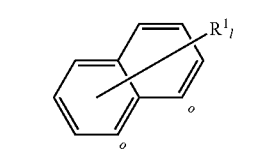 (Ar'-44)
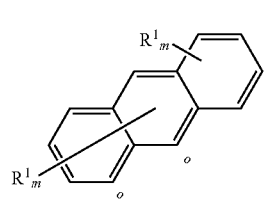 (Ar'-45)
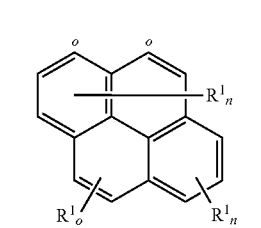 (Ar'-46)
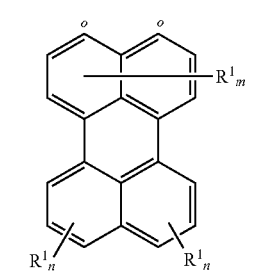 (Ar'-47)
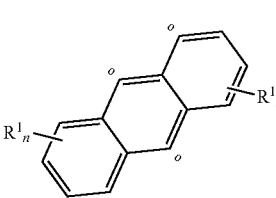 (Ar'-48)

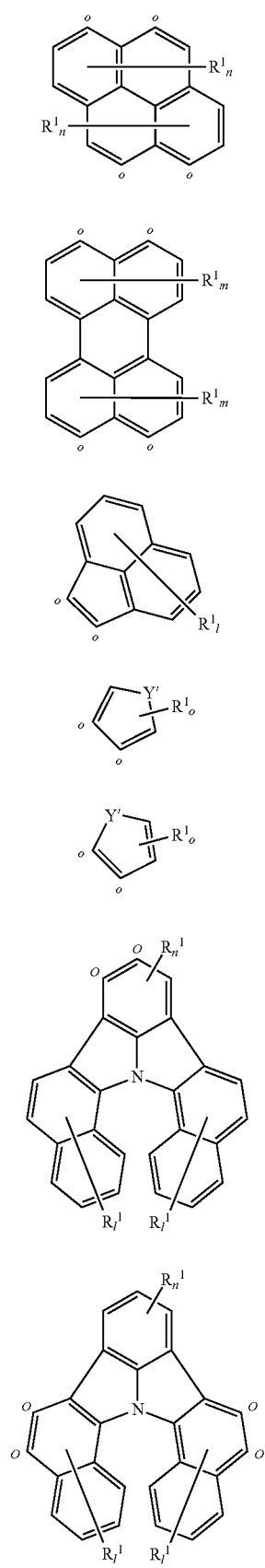
(Ar'-49)
(Ar'-50)
(Ar'-51)
(Ar'-52)
(Ar'-53)
(Ar'-54)
(Ar'-55)
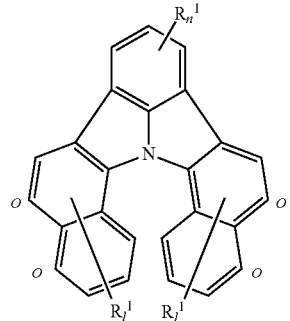
(Ar'-56)
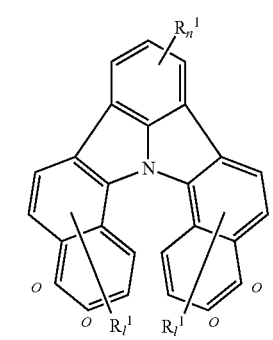
(Ar'-57)
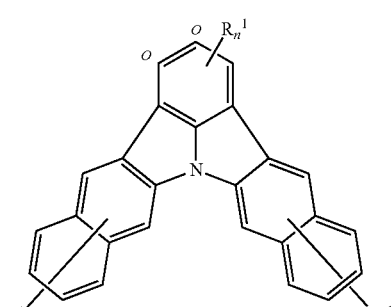
(Ar'-58)
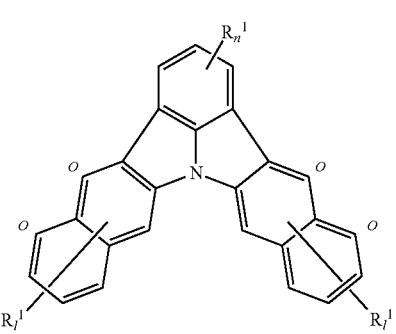
(Ar'-59)
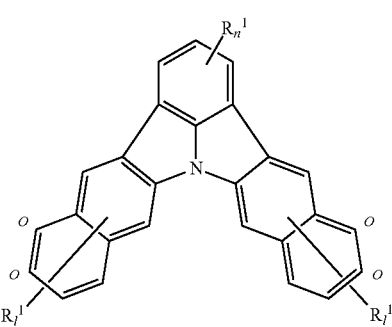
(Ar'-60)

-continued

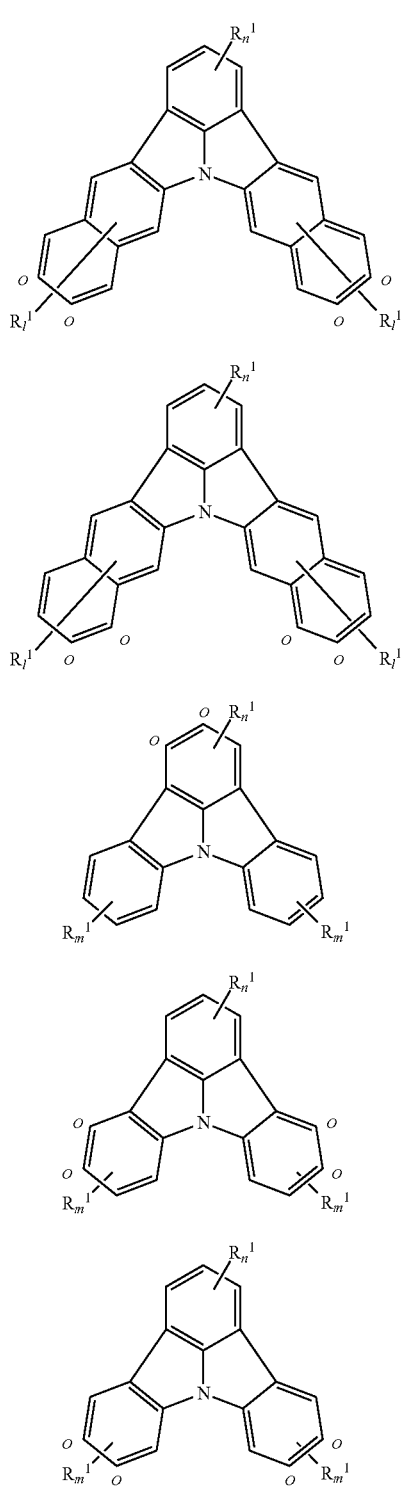

(Ar'-61)
(Ar'-62)
(Ar'-63)
(Ar'-64)
(Ar'-65)

wherein
R$^1$ is the same or different at each instance and is H, D, OH, F, Cl, Br, I, CN, NO$_2$, N(Ar$^1$)$_2$, N(R$^2$)$_2$, C(=O)Ar$^1$, C(=O)R$^2$, P(=O)(Ar$^1$)$_2$, P(Ar$^1$)$_2$, B(Ar$^1$)$_2$, B(OR$^2$)$_2$, Si(Ar$^1$)$_3$, Si(R$^2$)$_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl or alkynyl group having 2 to 40 carbon atoms, each of which may be substituted by one or more R$^2$ radicals, where one or more nonadjacent CH$_2$ groups may be replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, —C(=O)O—, —C(=O)NR$^2$—, NR$^2$, P(=O)(R$^2$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more R$^2$ radicals, or an aryloxy or heteroaryloxy group which has 5 to 40 aromatic ring atoms and may be substituted by one or more R$^2$ radicals, or an aralkyl or heteroaralkyl group which has 5 to 40 aromatic ring atoms and may be substituted by one or more R$^2$ radicals, or a combination of these systems;

Ar$^1$ is the same or different at each instance and is an aromatic or heteroaromatic ring system which has 5 to 30 aromatic ring atoms and may be substituted by one or more, nonaromatic R$^2$ radicals; at the same time, it is possible for two Ar$^1$ radicals bonded to the same silicon atom, nitrogen atom, phosphorus atom or boron atom also to be joined to one another by a single bond or a bridge selected from B(R$^2$), C(R$^2$)$_2$, Si(R$^2$)$_2$, C=O, C=NR$^2$, C=C(R$^2$)$_2$, O, S, S=O, SO$_2$, N(R$^2$), P(R$^2$) and P(=O)R$^2$;

R$^2$ is the same or different at each instance and is H, D, F, Cl, Br, I, CN, B(OR$^3$)$_2$, NO$_2$, C(=O)R$^3$, CR$^3$=C(R$^3$)$_2$, C(=O)OR$^3$, C(=O)N(R$^3$)$_2$, Si(R$^3$)$_3$, P(R$^3$)$_2$, B(R$^3$)$_2$, N(R$^3$)$_2$, NO$_2$, P(=O)(R$^3$)$_2$, OSO$_2$R$^3$, OR$^3$, S(=O)R$^3$, S(=O)$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^3$ radicals, where one or more nonadjacent CH$_2$ groups may be replaced by —R$^3$C=CR$^3$—, —C≡C—, Si(R$^3$)$_2$, Ge(R$^3$)$_2$, Sn(R$^3$)$_2$, C=O, C=S, C=NR$^3$, —C(=O)O—, —C(=O)NR$^3$—, NR$^3$, P(=O)(R$^3$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^3$ radicals, or an aryloxy or heteroaryloxy group which has 5 to 40 aromatic ring atoms and may be substituted by one or more R$^3$ radicals, or a combination of these systems; at the same time, two or more, adjacent substituents R$^2$ together may also form a mono- or polycyclic, aliphatic or aromatic or heteroaromatic ring system;

R$^3$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, two or more adjacent substituents R$^3$ together may also form a mono- or polycyclic, aliphatic or aromatic or heteroaromatic ring system;

Y' is selected from O, S, C(R$^1$)$_2$, Si(R$^1$)$_2$, N R$^1$ and NAr$^1$,
U is selected from O, S, C(R$^1$)$_2$, N(R$^1$), B(R$^1$), Si(R$^1$)$_2$, C=O, S=O, SO$_2$, P(R$^1$) and P(=O)R$^1$,
the index o is 0, 1 or 2,
the index n is 0, 1, 2 or 3, the index m is 0, 1, 2, 3 or 4, and the index l is 0, 1, 2, 3, 4, 5 or 6, and the aliphatic polycyclic ring system having at least 3 rings binds to the aromatic or heteroaromatic ring system having 5 to 60 carbon atoms at the respective positions identified by o to form a ring.

3. The compound as claimed in claim 1, wherein the compound comprises a hole transport group, wherein the Ar group present in a Y group or an R group comprises and represents the hole transport group, or, in a structure of the formulae (N-1) to (N-6), (Ar-2) to (Ar-11), (Ar-13) to (Ar-54) and/or (Ar'-2) to (Ar'-11), (Ar'-13) to (Ar'-53), Formula (N-1)

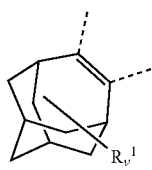

Formula (N-2)

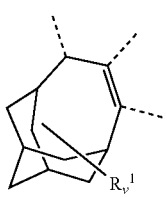

Formula (N-3)

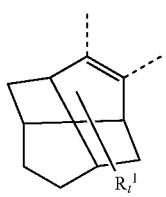

Formula (N-4)

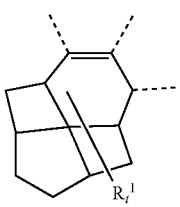

Formula (N-5)

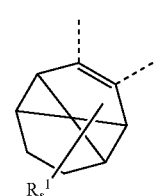

Formula (N-6)

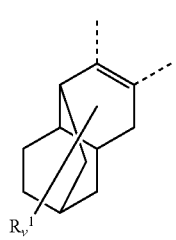

(Ar-2)

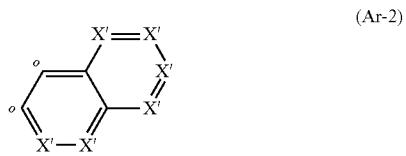

(Ar-3)

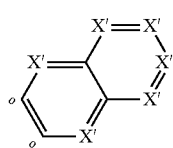

(Ar-4)

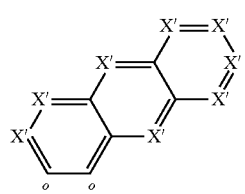

(Ar-5)

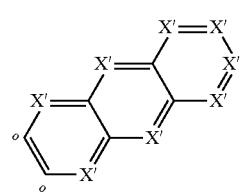

(Ar-6)

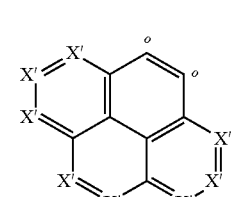

(Ar-7)

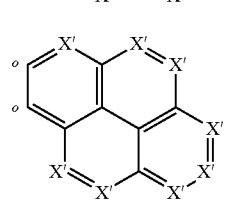

(Ar-8)

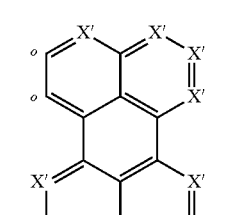

(Ar-9)

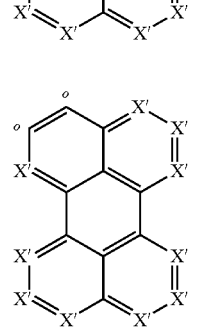

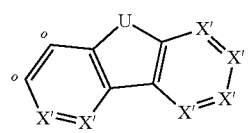 (Ar-10)
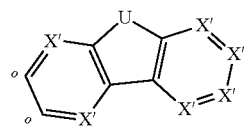 (Ar-11)
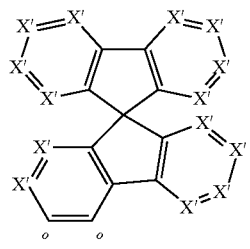 (Ar-13)
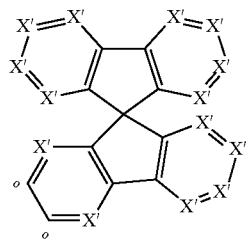 (Ar-14)
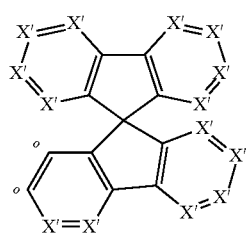 (Ar-15)
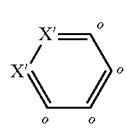 (Ar-16)
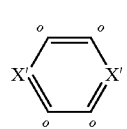 (Ar-17)
 (Ar-18)
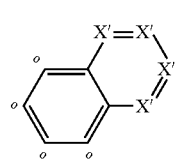 (Ar-19)
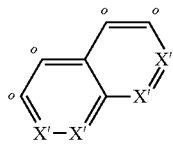 (Ar-20)
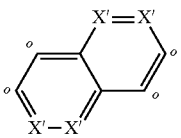 (Ar-21)
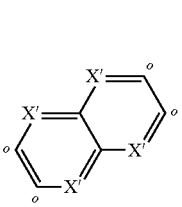 (Ar-22)
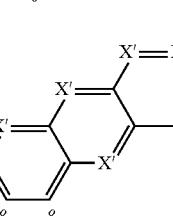 (Ar-23)
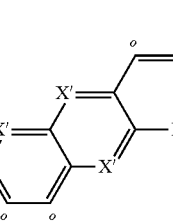 (Ar-24)
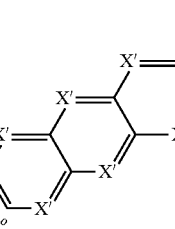 (Ar-25)
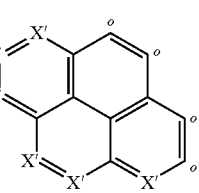 (Ar-26)
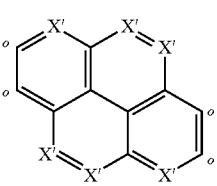 (Ar-27)

-continued
(Ar-28)
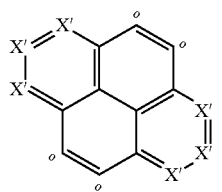
(Ar-29)
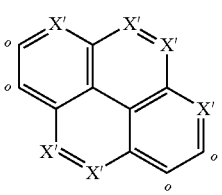
(Ar-30)
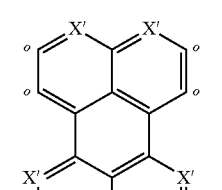
(Ar-31)
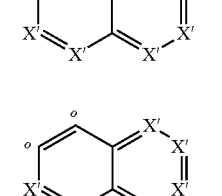
(Ar-32)
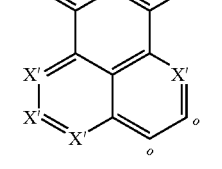
(Ar-33)
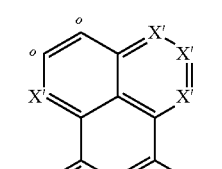
(Ar-34)
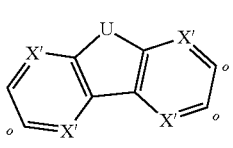
-continued
(Ar-35)
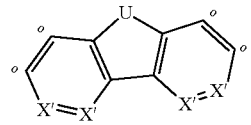
(Ar-36)
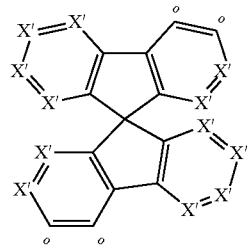
(Ar-37)
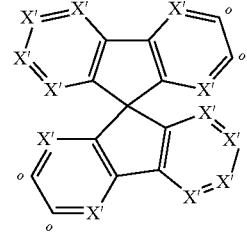
(Ar-38)
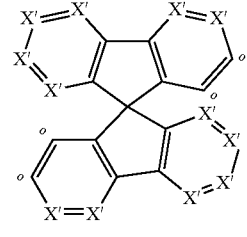
(Ar-39)
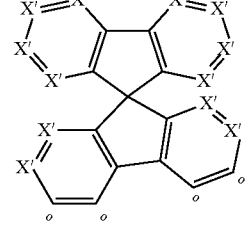
(Ar-40)
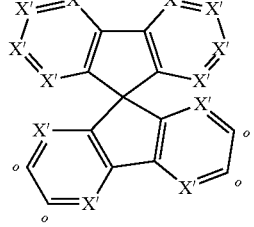

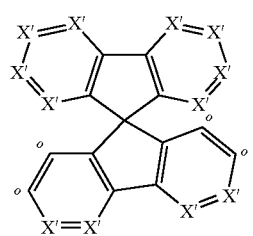 (Ar-41)
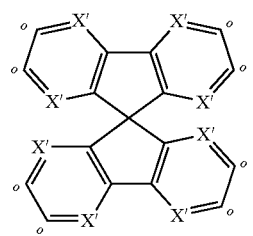 (Ar-42)
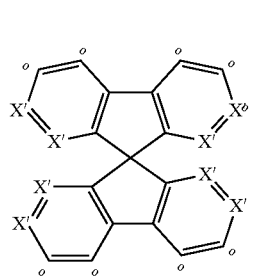 (Ar-43)
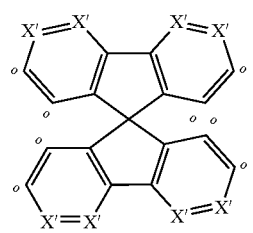 (Ar-44)
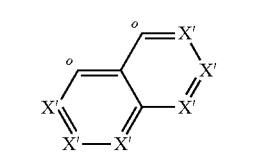 (Ar-45)
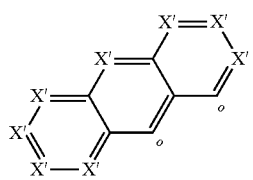 (Ar-46)
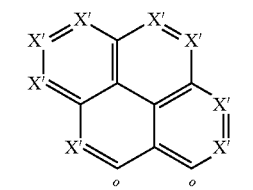 (Ar-47)
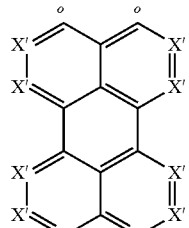 (Ar-48)
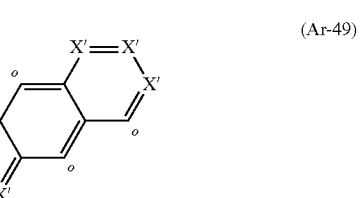 (Ar-49)
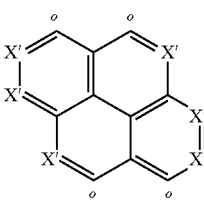 (Ar-50)
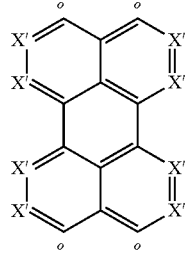 (Ar-51)
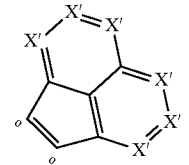 (Ar-52)
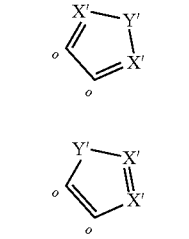 (Ar-53)
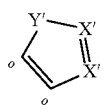 (Ar-54)

(Ar-55) 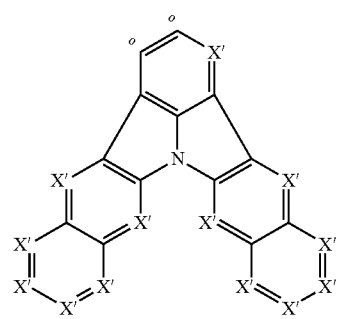
(Ar-56) 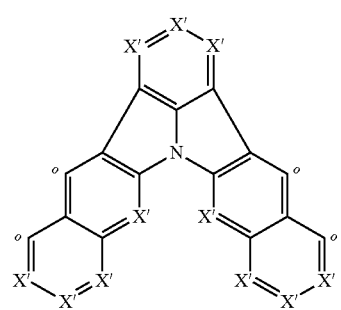
(Ar-57) 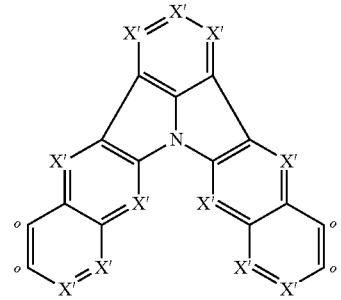
(Ar-58) 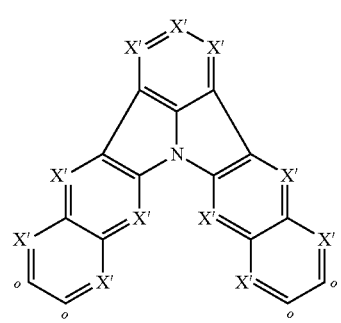
(Ar-59) 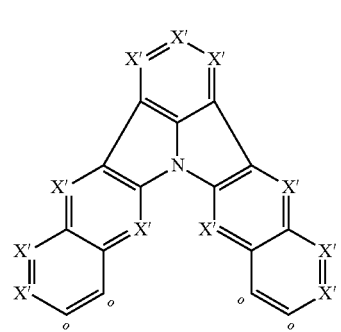
(Ar-60) 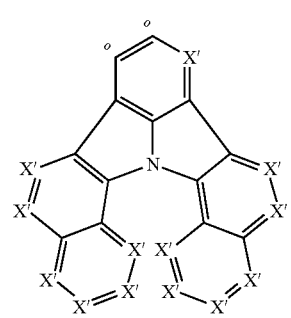
(Ar-61) 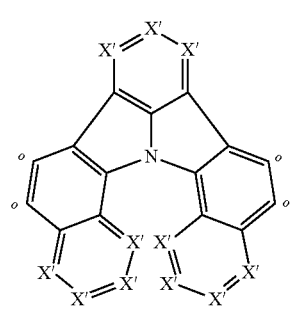
(Ar-62) 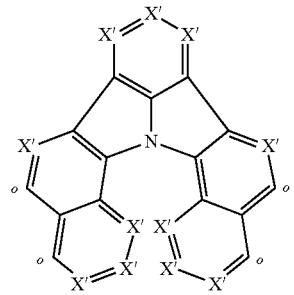
(Ar-63) 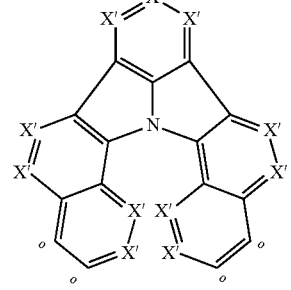
(Ar-64) 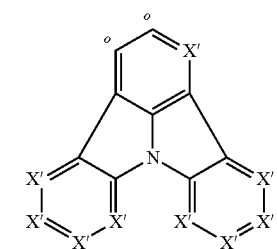

-continued
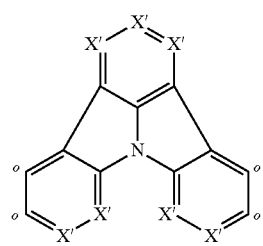
(Ar-65)
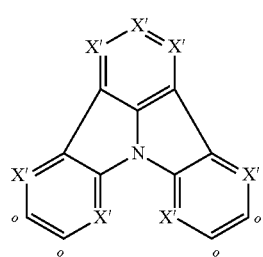
(Ar-66)
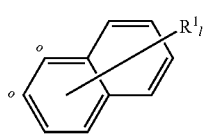
(Ar'-2)
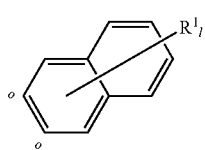
(Ar'-3)
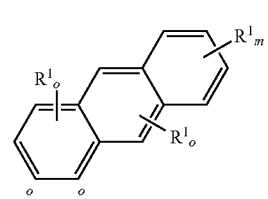
(Ar'-4)
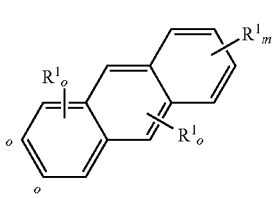
(Ar'-5)
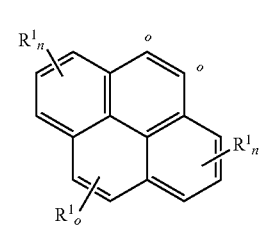
(Ar'-6)
-continued
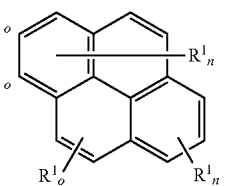
(Ar'-7)
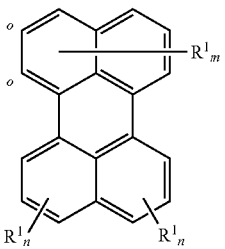
(Ar'-8)
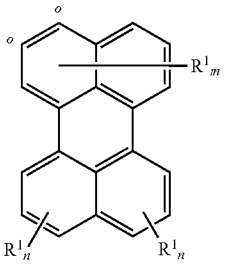
(Ar'-9)
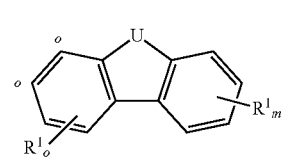
(Ar'-10)
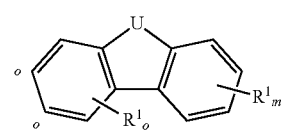
(Ar'-11)
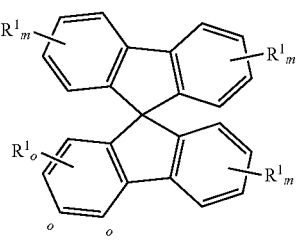
(Ar'-13)
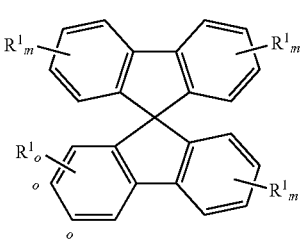
(Ar'-14)

-continued
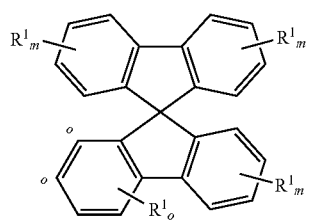 (Ar'-15)
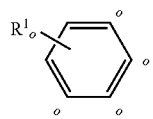 (Ar'-16)
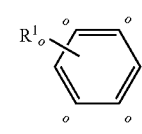 (Ar'-17)
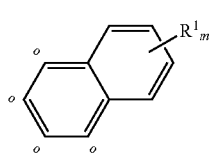 (Ar'-18)
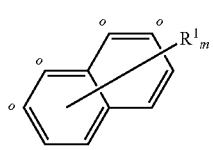 (Ar'-19)
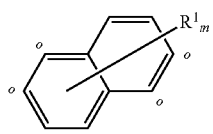 (Ar'-20)
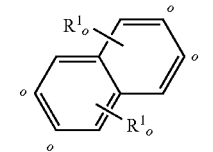 (Ar'-21)
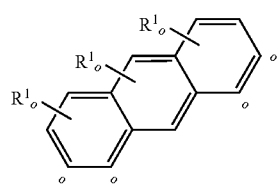 (Ar'-22)
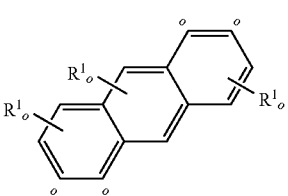 (Ar'-23)
-continued
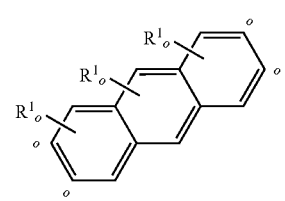 (Ar'-24)
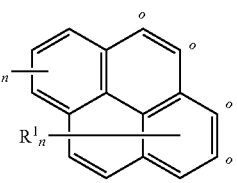 (Ar'-25)
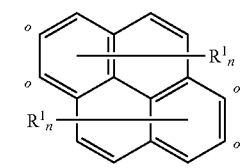 (Ar'-26)
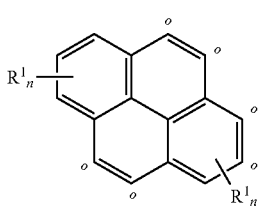 (Ar'-27)
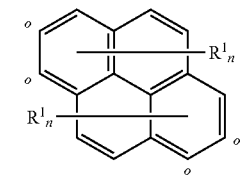 (Ar'-28)
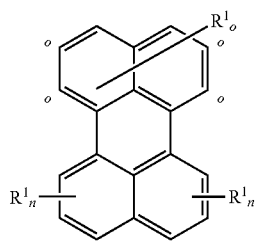 (Ar'-29)
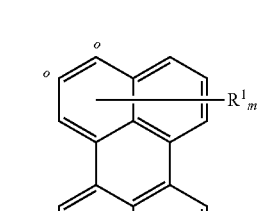 (Ar'-30)
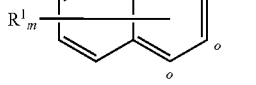

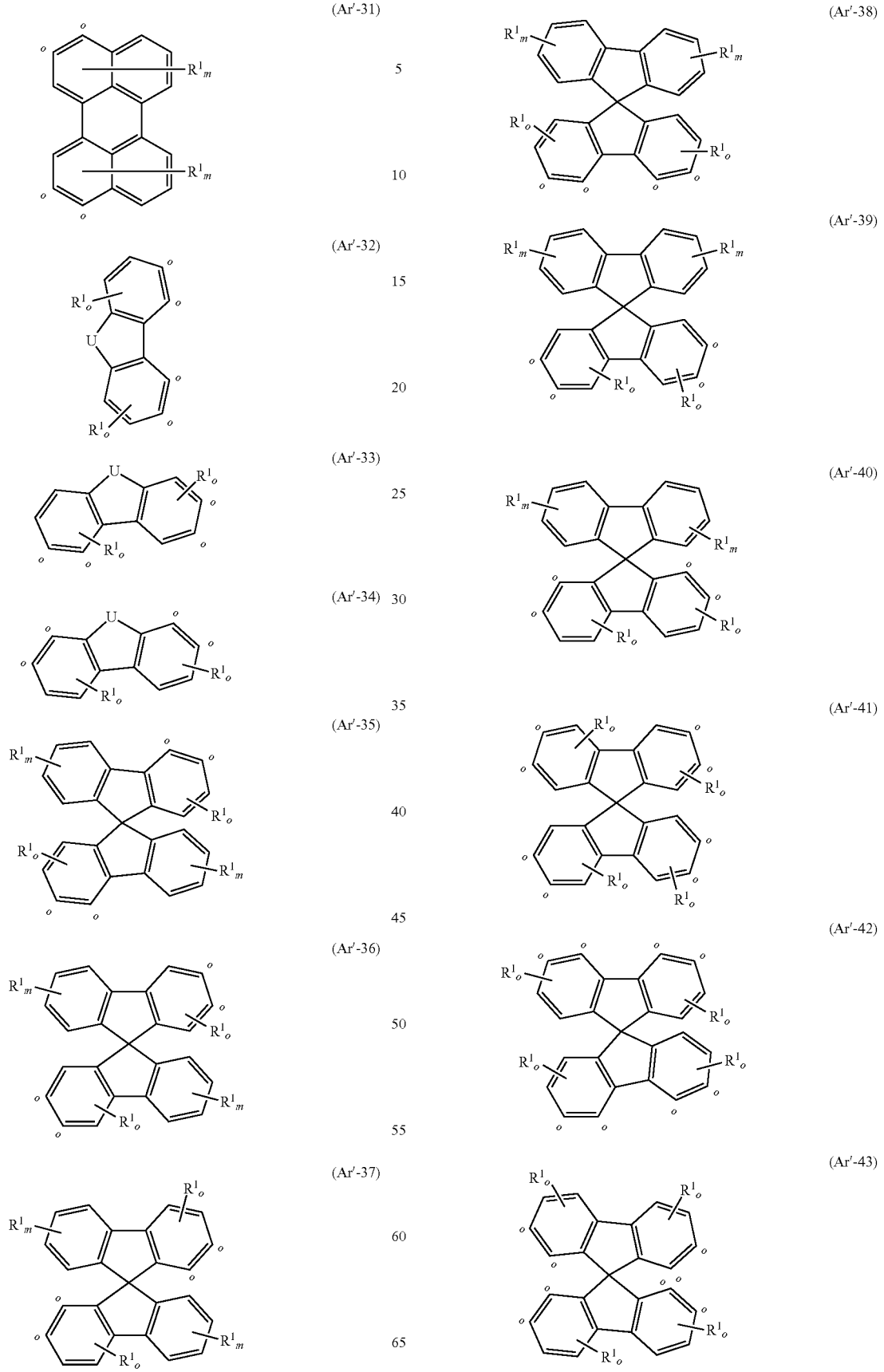

-continued
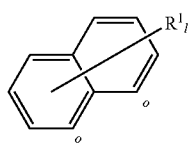
(Ar'-44)
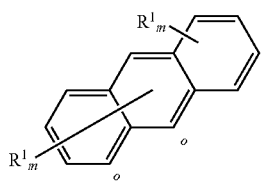
(Ar'-45)
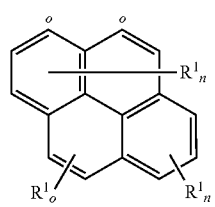
(Ar'-46)
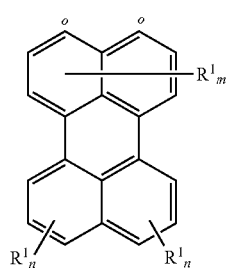
(Ar'-47)
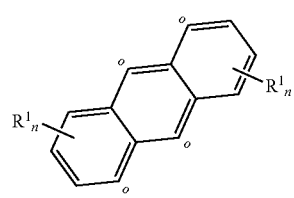
(Ar'-48)
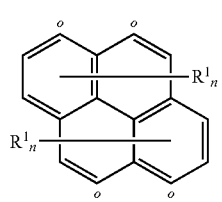
(Ar'-49)
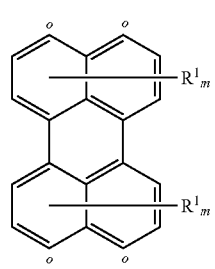
(Ar'-50)
-continued
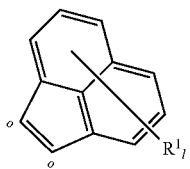
(Ar'-51)
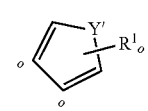
(Ar'-52)
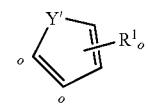
(Ar'-53)
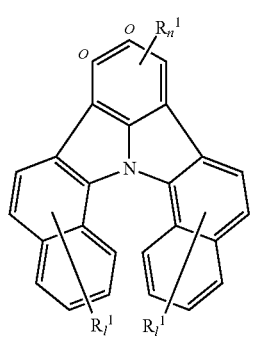
(Ar'-54)
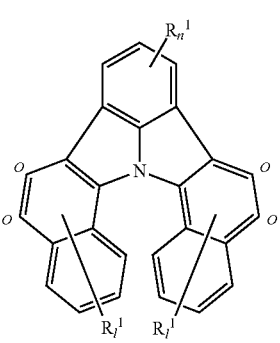
(Ar'-55)
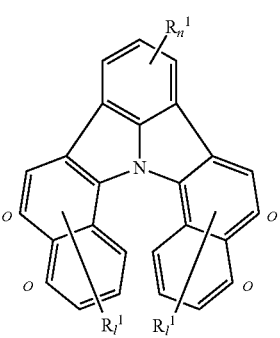
(Ar'-56)

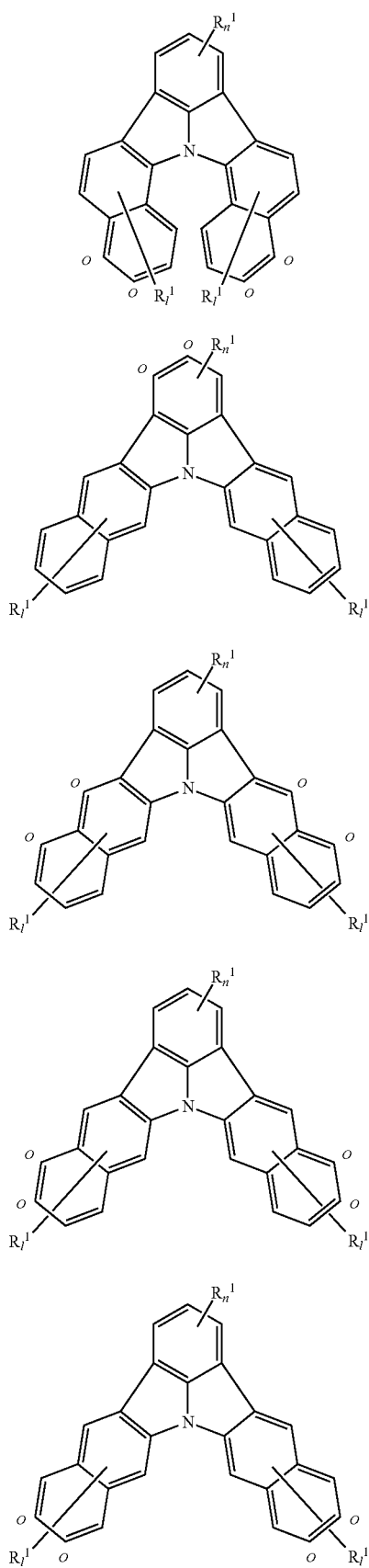
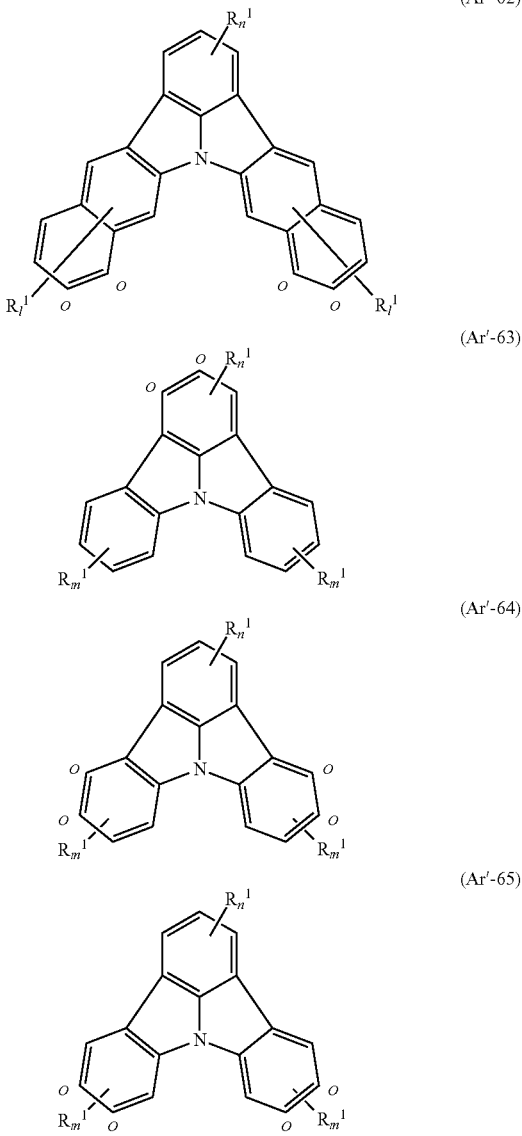

wherein
X' is N or CR$^1$;
Y' is selected from O, S, C(R$^1$)$_2$, Si(R$^1$)$_2$, N R$^1$ and NAr$^1$;
U is selected from O, S, C(R$^1$)$_2$, N(R$^1$), B(R$^1$), Si(R$^1$)$_2$, C=O, S=O, SO$_2$, P(R$^1$) and P(=O)R$^1$;
R$^1$ is the same or different at each instance and is H, D, OH, F, Cl, Br, I, CN, NO$_2$, N(Ar$^1$)$_2$, N(R$^2$)$_2$, C(=O)Ar$^1$, C(=O)R$^2$, P(=O)(Ar$^1$)$_2$, P(Ar$^1$)$_2$, B(Ar$^1$)$_2$, B(OR$^2$)$_2$, Si(Ar$^1$)$_3$, Si(R$^2$)$_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl or alkynyl group having 2 to 40 carbon atoms, each of which may be substituted by one or more R$^2$ radicals, where one or more nonadjacent CH$_2$ groups may be replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, —C(=O)O—, —C(=O)NR$^2$—, NR$^2$, P(=O)(R$^2$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a combination of these systems;

$Ar^1$ is the same or different at each instance and is an aromatic or heteroaromatic ring system which has 5 to 30 aromatic ring atoms and may be substituted by one or more, nonaromatic $R^2$ radicals; at the same time, it is possible for two $Ar^1$ radicals bonded to the same silicon atom, nitrogen atom, phosphorus atom or boron atom also to be joined to one another by a single bond or a bridge selected from $B(R^2)$, $C(R^2)_2$, $Si(R^2)_2$, $C=O$, $C=NR^2$, $C=C(R^2)_2$, O, S, $S=O$, $SO_2$, $N(R^2)$, $P(R^2)$ and $P(=O)R^2$;

$R^2$ is the same or different at each instance and is H, D, F, Cl, Br, I, CN, $B(OR^3)_2$, $NO_2$, $C(=O)R^3$, $CR^3=C(R^3)_2$, $C(=O)OR^3$, $C(=O)N(R^3)_2$, $Si(R^3)_3$, $P(R^3)_2$, $B(R^3)_2$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by —$R^3C=CR^3$—, —$C\equiv C$—, $Si(R^3)_2$, $Ge(R^3)_2$, $Sn(R^3)_2$, $C=O$, $C=S$, $C=NR^3$, —$C(=O)O$—, —$C(=O)NR^3$—, $NR^3$, $P(=O)(R^3)$, —O—, —S—, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^3$ radicals, or an aryloxy or heteroaryloxy group which has 5 to 40 aromatic ring atoms and may be substituted by one or more $R^3$ radicals, or a combination of these systems; at the same time, two or more, adjacent substituents $R^2$ together may also form a mono- or polycyclic, aliphatic or aromatic or heteroaromatic ring system;

R is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, two or more adjacent substituents $R^3$ together may also form a mono- or polycyclic, aliphatic or aromatic or heteroaromatic ring system;

Y' is selected from O, S, $C(R^1)_2$, $Si(R^1)_2$, N $R^1$ and $NAr^1$;
U is selected from O, S, $C(R^1)_2$, $N(R^1)$, $B(R^1)$, $Si(R^1)_2$, $C=O$, $S=O$, $SO_2$, $P(R^1)$ and $P(=O)R^1$,
the index s is 0, 1, 2, 3, 4, 5 or 6;
the index t is 0, 1, 2, 3, 4, 5, 6, 7 or 8;
the index v is 0, 1, 2, 3, 4, 5, 6, 7, 8 or 9;
the index o is 0, 1 or 2,
the index n is 0, 1, 2, or 3,
the index m is 0, 1, 2, 3 or 4, and
the index l is 0, 1, 2, 3, 4, 5 or 6;
and
the aliphatic polycyclic ring system having at least 3 rings binds to the aromatic or heteroaromatic ring system having 5 to 60 carbon atoms at the respective positions identified by o to form a ring.

4. The compound as claimed in claim 2, wherein the compound comprises an electron transport group, wherein, in the structure of the formulae (N-1) to (N-6), (Ar-2) to (Ar-11), (Ar-13) to (Ar-54) and (Ar'-2) to (Ar'-11) and (Ar'-13) to (Ar'-53),

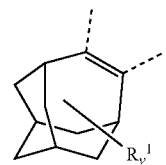

Formula (N-1)

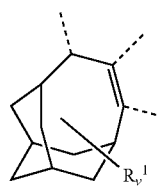

Formula (N-2)

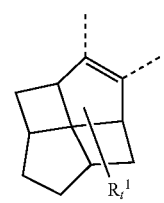

Formula (N-3)

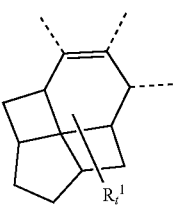

Formula (N-4)

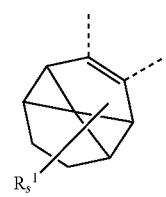

Formula (N-5)

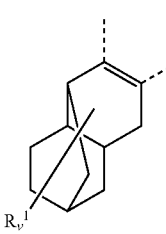

Formula (N-6)

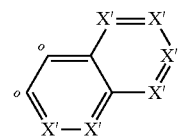

(Ar-2)

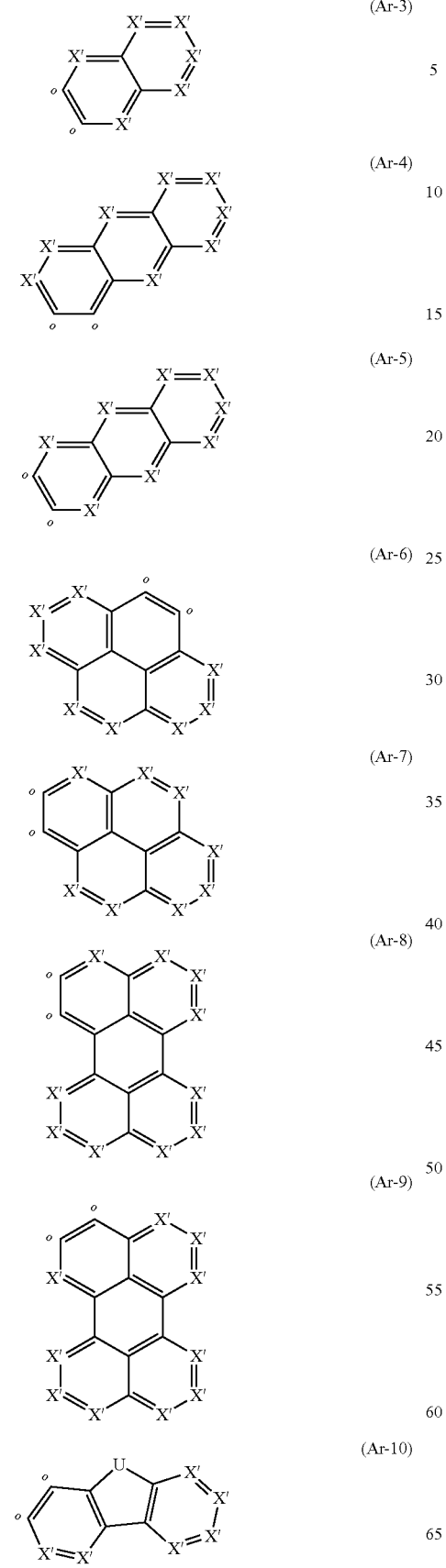
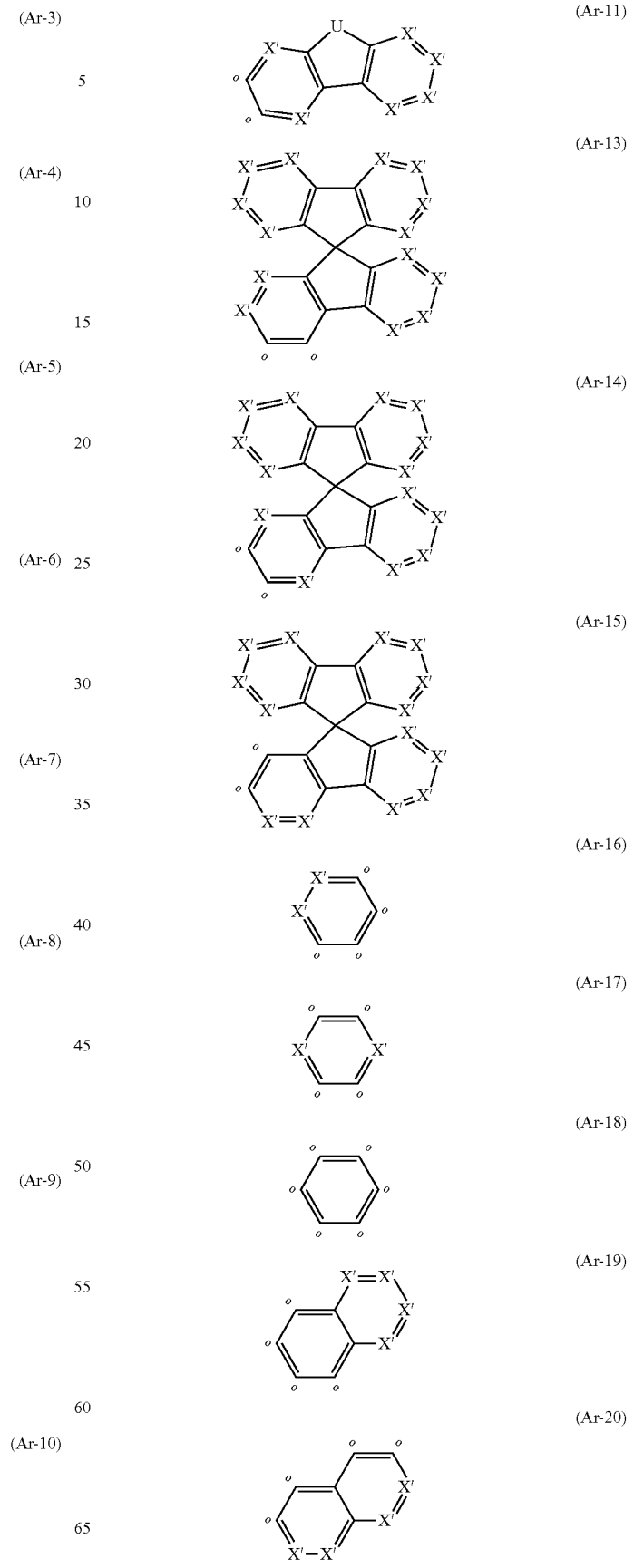

-continued
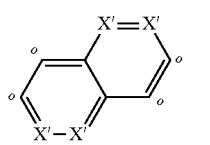
(Ar-21)
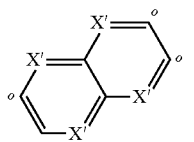
(Ar-22)
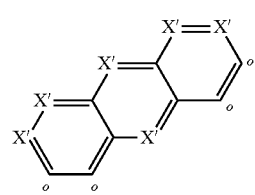
(Ar-23)
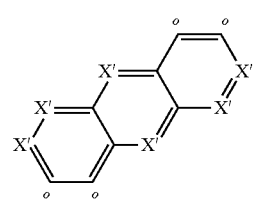
(Ar-24)
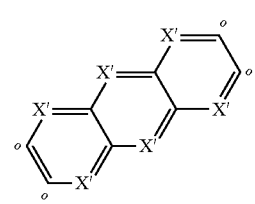
(Ar-25)
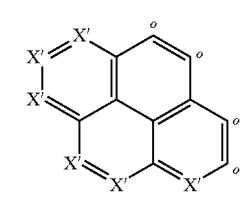
(Ar-26)
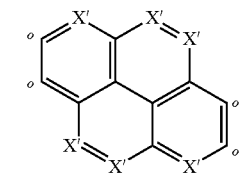
(Ar-27)
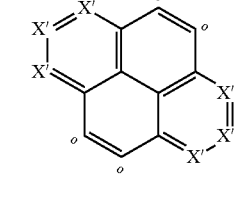
(Ar-28)
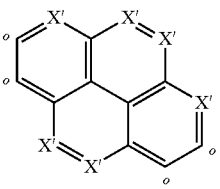
(Ar-29)
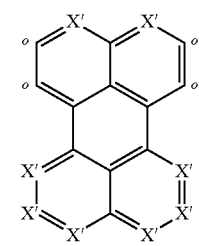
(Ar-30)
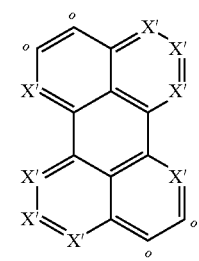
(Ar-31)
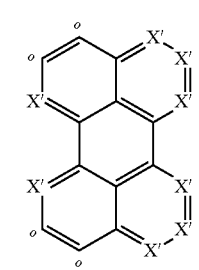
(Ar-32)
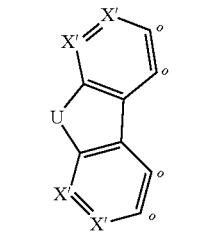
(Ar-33)
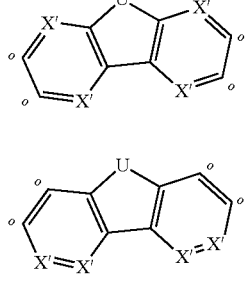
(Ar-34)
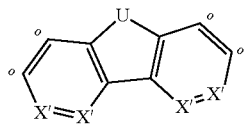
(Ar-35)

-continued
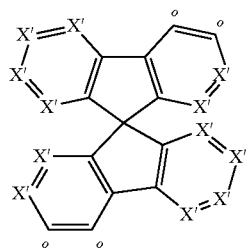 (Ar-36)
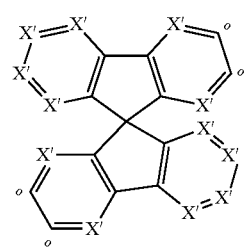 (Ar-37)
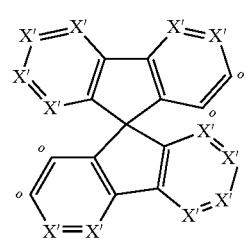 (Ar-38)
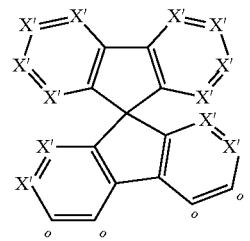 (Ar-39)
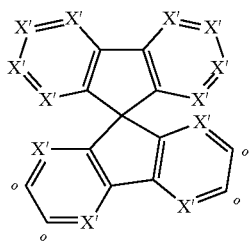 (Ar-40)
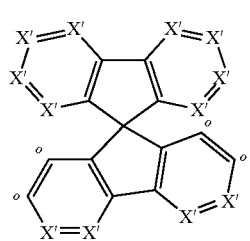 (Ar-41)
-continued
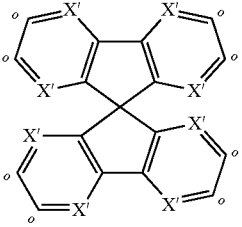 (Ar-42)
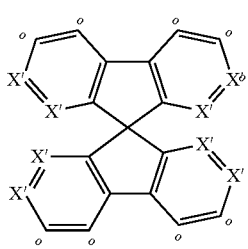 (Ar-43)
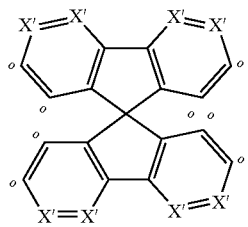 (Ar-44)
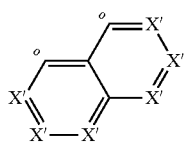 (Ar-45)
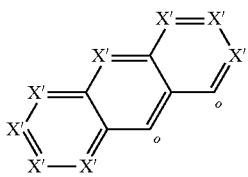 (Ar-46)
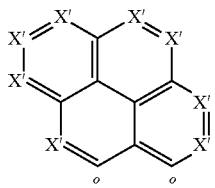 (Ar-47)
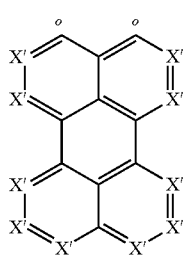 (Ar-48)

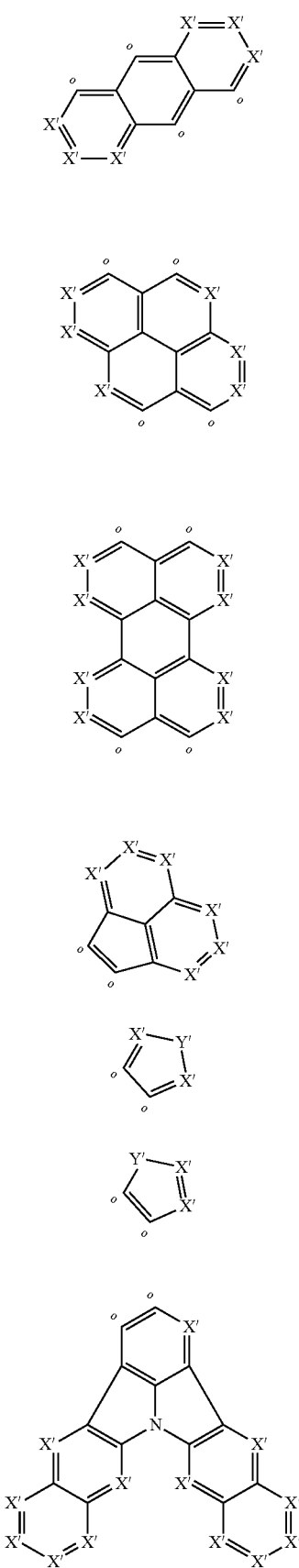
(Ar-49)
(Ar-50)
(Ar-51)
(Ar-52)
(Ar-53)
(Ar-54)
(Ar-55)
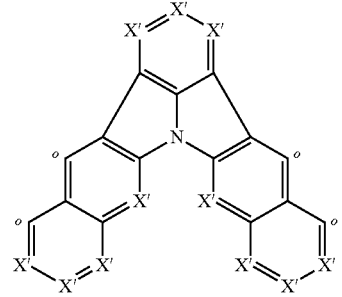
(Ar-56)
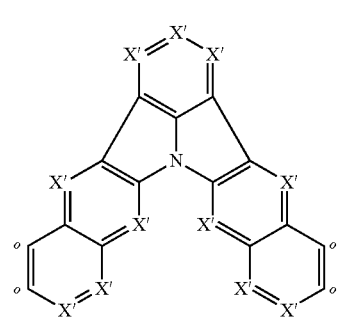
(Ar-57)
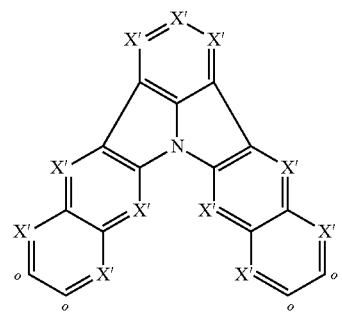
(Ar-58)
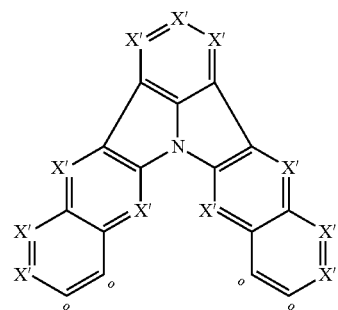
(Ar-59)
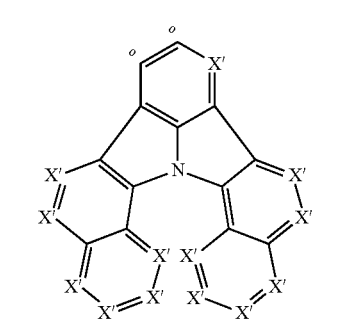
(Ar-60)

(Ar-61)
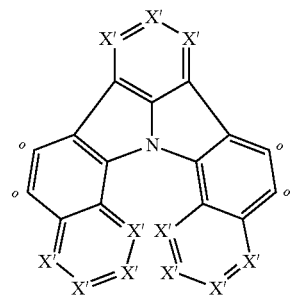
(Ar-62)
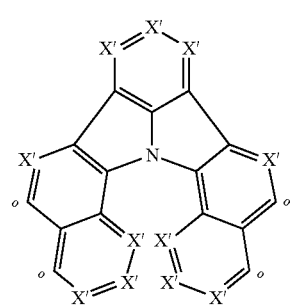
(Ar-63)
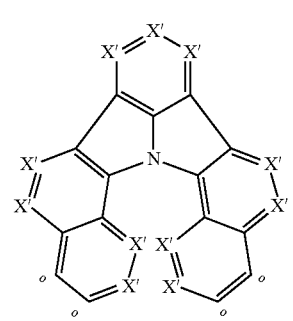
(Ar-64)
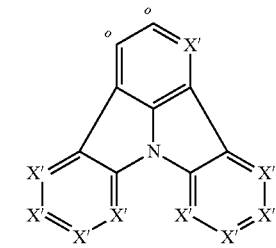
(Ar-65)
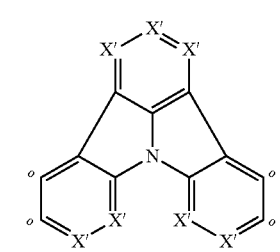
(Ar-66)
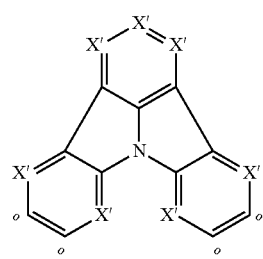
(Ar'-2)
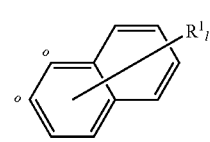
(Ar'-3)
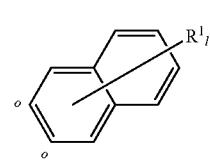
(Ar'-4)
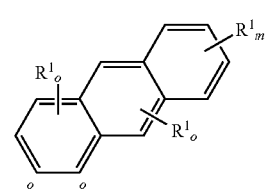
(Ar'-5)
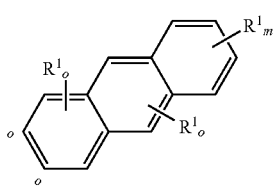
(Ar'-6)
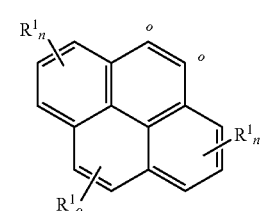
(Ar'-7)
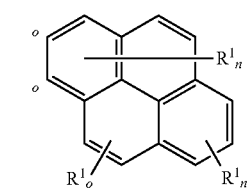

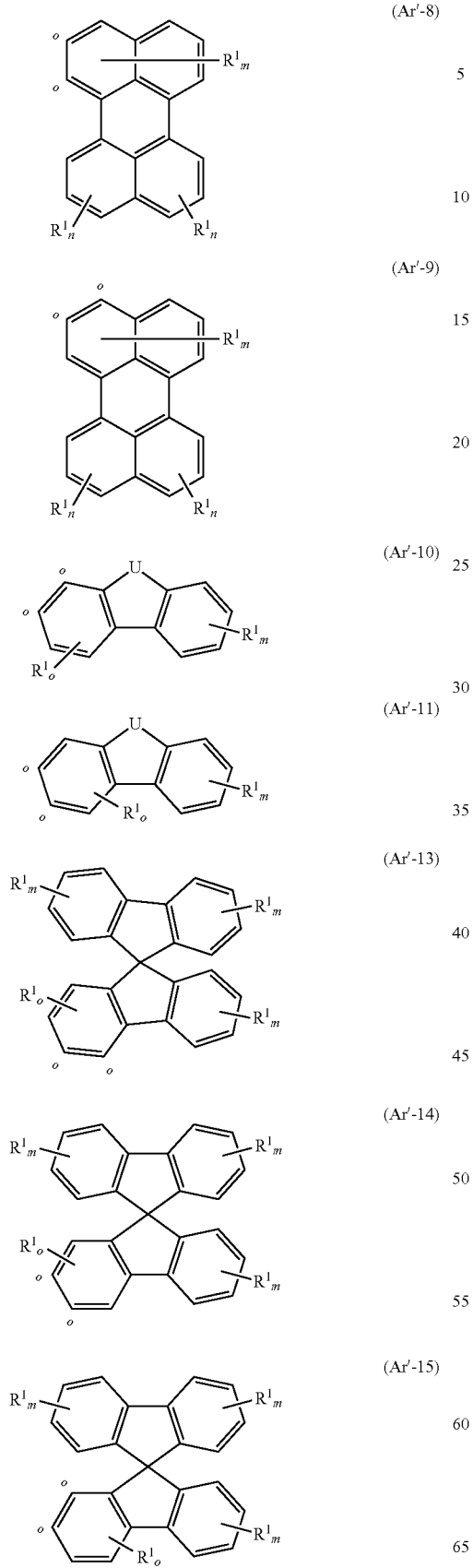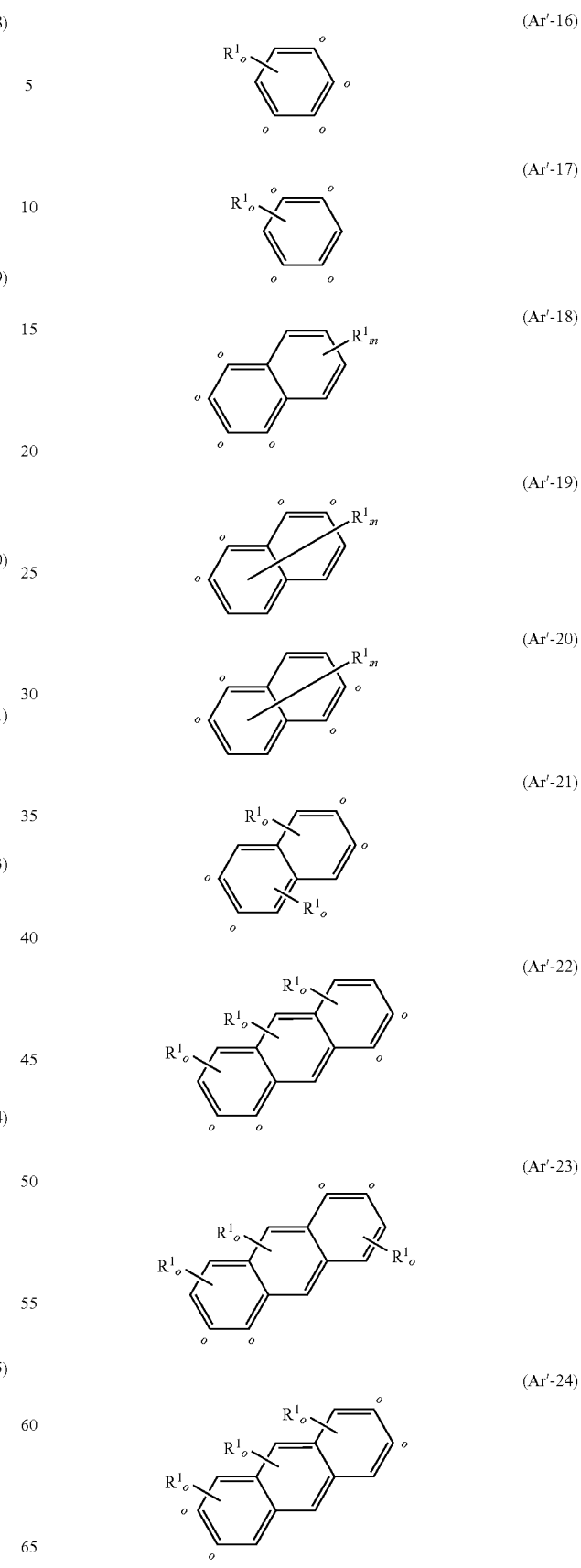

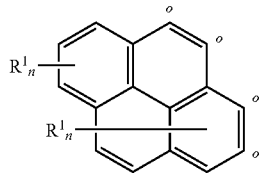
(Ar'-25)
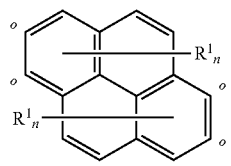
(Ar'-26)
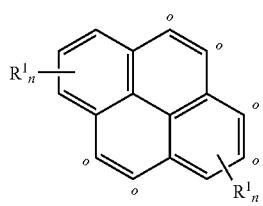
(Ar'-27)
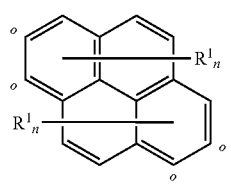
(Ar'-28)
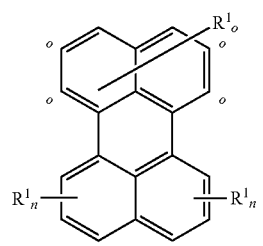
(Ar'-29)
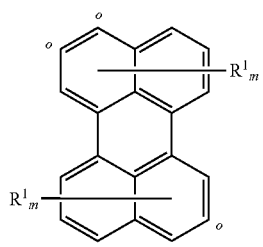
(Ar'-30)
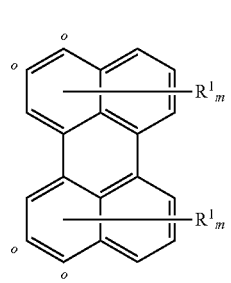
(Ar'-31)
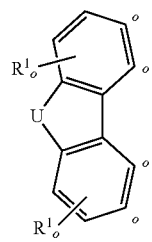
(Ar'-32)
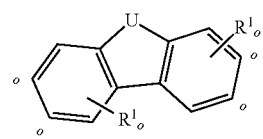
(Ar'-33)
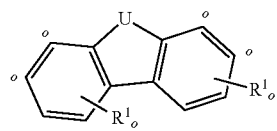
(Ar'-34)
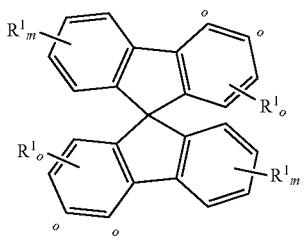
(Ar'-35)
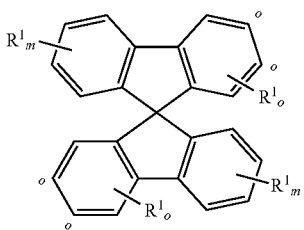
(Ar'-36)
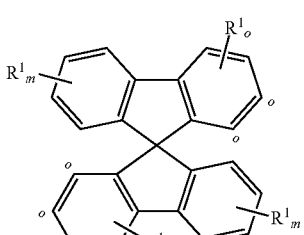
(Ar'-37)
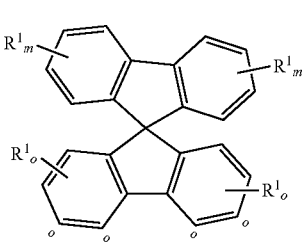
(Ar'-38)

-continued
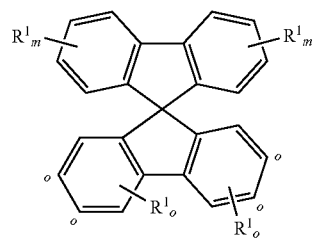 (Ar'-39)
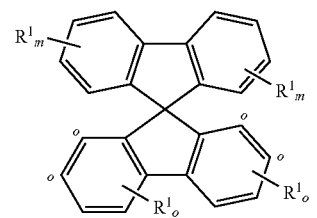 (Ar'-40)
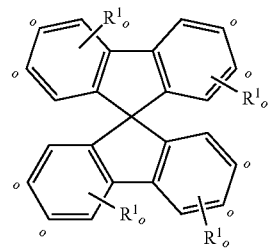 (Ar'-41)
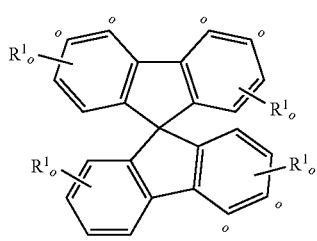 (Ar'-42)
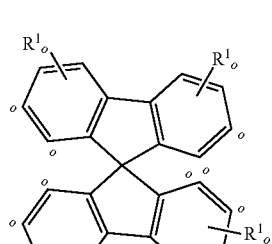 (Ar'-43)
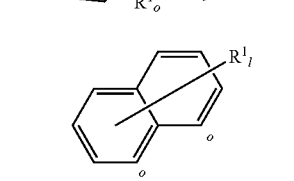 (Ar'-44)
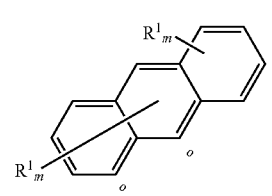 (Ar'-45)
-continued
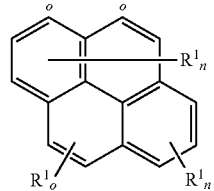 (Ar'-46)
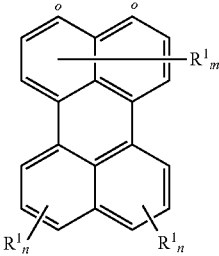 (Ar'-47)
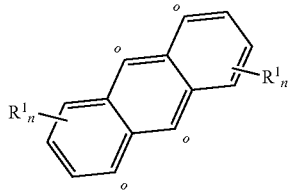 (Ar'-48)
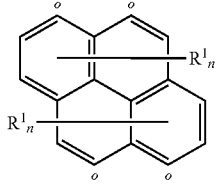 (Ar'-49)
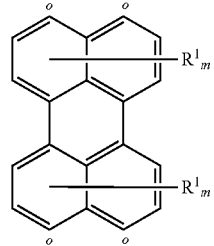 (Ar'-50)
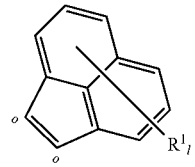 (Ar'-51)
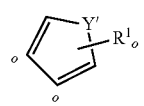 (Ar'-52)

(Ar'-53) 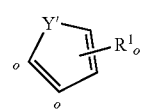
(Ar'-54) 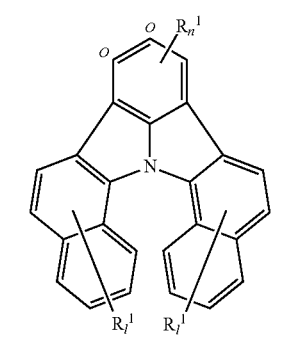
(Ar'-55) 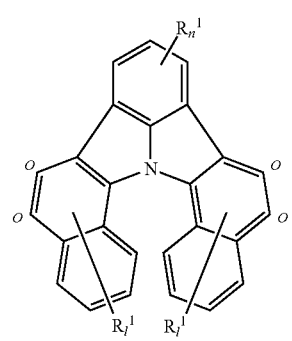
(Ar'-56) 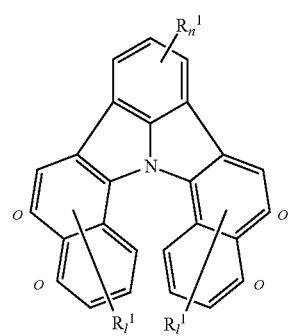
(Ar'-57) 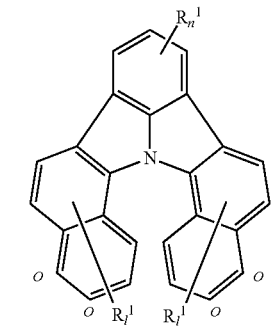
(Ar'-58) 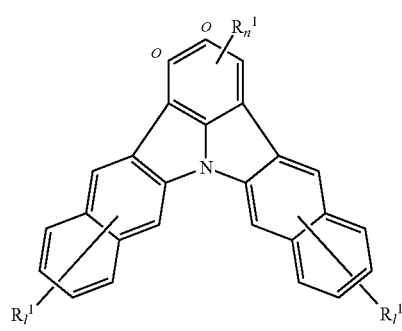
(Ar'-59) 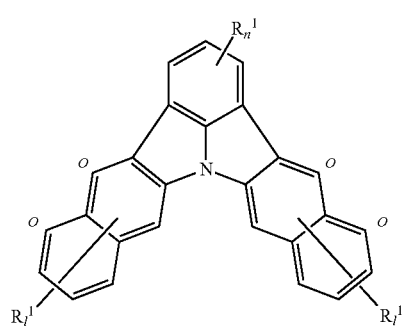
(Ar'-60) 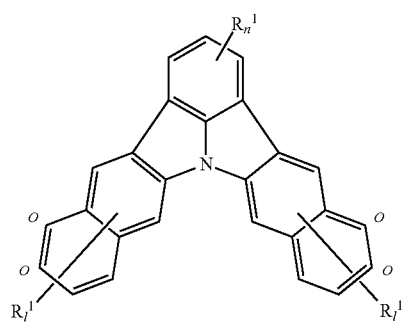
(Ar'-61) 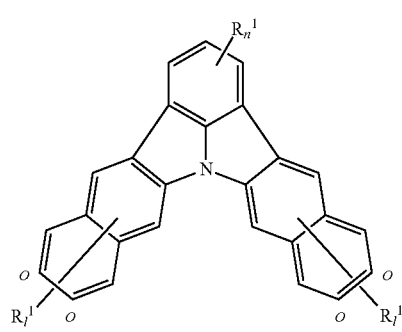
(Ar'-62) 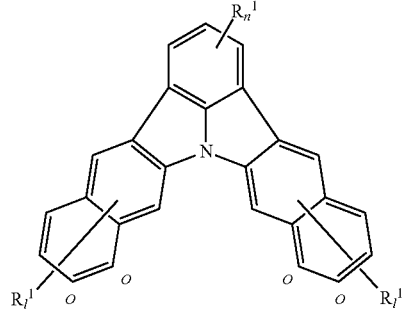

-continued

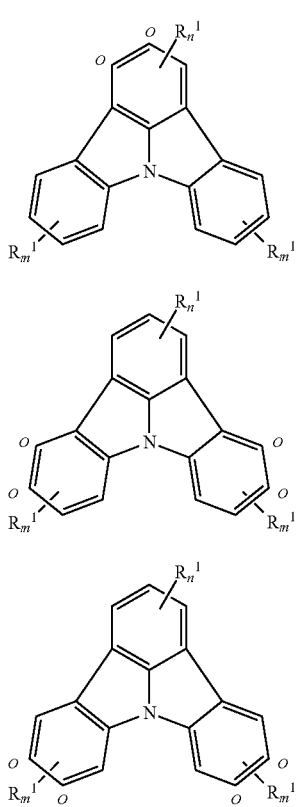

(Ar'-63)

(Ar'-64)

(Ar'-65)

wherein X' is N or CR$^1$;
Y' is O, S, C(R$^1$)$_2$, Si(R$^1$)$_2$, NR$^1$ or NAr$^1$;
U is O, S, C(R$^1$)$_2$, N(R$^1$), B(R$^1$), Si(R$^1$)$_2$, C=O, S=O, SO$_2$, P(R$^1$) or P(=O)R$^1$;
Y is the same or different at each instance and is O, S, C(R)$_2$, CArR, C(Ar)$_2$, Si(Ar)$_2$, SiArR or Si(R)$_2$, NR or NAr;
X is the same or different at each instance and is N or CR;
R is the same or different at each instance and is H, D, OH, F, Cl, Br, I, CN, NO$_2$, N(Ar)$_2$, N(R$^1$)$_2$, C(=O)N(Ar)$_2$, C(=O)N(R$^1$)$_2$, Si(Ar)$_3$, Si(R$^1$)$_3$, B(OAr)$_2$, B(OR$^1$)$_2$, C(=O)Ar, C(=O)R$^1$, P(=O)(Ar)$_2$, P(=O)(R$^1$)$_2$, S(=O)Ar, S(=O)R$^1$, S(=O)$_2$Ar, S(=O)$_2$R$^1$, OSO$_2$Ar, OSO$_2$R$^1$, a straight-chain alkyl, alkoxy or thioalkoxy group having 1 to 20 carbon atoms or an alkenyl or alkynyl group having 2 to 20 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more R$^1$ radicals, where one or more nonadjacent CH$_2$ groups may be replaced by R$^1$C=CR$^1$, C≡C, Si(R$^1$)$_2$, C=O, NR$^1$, O, S or CONR$^1$, or an aromatic or heteroaromatic ring system which has 5 to 40 aromatic ring atoms and may be substituted in each case by one or more R$^1$ radicals, or an aryloxy or heteroaryloxy group which has 5 to 40 aromatic ring atoms and may be substituted by one or more R$^1$ radicals;
the index o is 0, 1 or 2;
the index n is 0, 1, 2, or 3;
the index m is 0, 1, 2, 3 or 4; and
the index l is 0, 1, 2, 3, 4, 5 or 6;
and the aliphatic polycyclic ring system having at least 3 rings binds to the aromatic or heteroaromatic ring system having 5 to 60 carbon atoms at the respective positions identified by o to form a ring;
and R$^1$ group comprises and represents an electron transport group, where the electron conductor groups comprise at least 2 nitrogen atoms in one six-membered ring or in two fused six-membered rings.

5. The compound as claimed in claim 1, wherein the ring via which the aliphatic polycyclic ring system having at least 3 rings is fused to the aromatic or heteroaromatic ring system having 5 to 60 carbon atoms comprises six ring atoms and at least two nonadjacent nitrogen atoms.

6. The compound as claimed in claim 1, wherein the ring via which the aliphatic polycyclic ring system having at least 3 rings is fused to the aromatic or heteroaromatic ring system having 5 to 60 carbon atoms comprises six ring atoms and at least one nitrogen atom and no further ring system is fused to that ring.

7. An oligomer, polymer or dendrimer containing one or more compounds as claimed in claim 1, wherein, rather than a hydrogen atom or a substituent, there are one or more bonds of the compounds to the polymer, oligomer or dendrimer.

8. A composition comprising at least one compound as claimed in claim 1 and at least one further compound selected from the group consisting of fluorescent emitters, phosphorescent emitters, emitters that exhibit TADF (thermally activated delayed fluorescence), host materials, electron transport materials, electron injection materials, hole conductor materials, hole injection materials, electron blocker materials and hole blocker materials.

9. A formulation comprising at least one compound as claimed in claim 1 and at least one solvent.

10. An electronic device fluorescent emitter, emitter that exhibits TADF (thermally activated delayed fluorescence), host material, electron transport material, electron injection material, hole-conducting material, hole injection material, electron blocker material, hole blocker material and/or wide bandgap material which comprises at least one compound as claimed in claim 1.

11. A fluorescent emitter (singlet emitter), host material, hole-conducting material and/or electron transport material which comprises at least one compound as claimed in claim 1.

12. A process for preparing the compound as claimed in claim 1 which comprises a coupling reaction, a compound comprising at least one aliphatic polycyclic ring system having at least 3 rings is joined to a compound comprising at least one aromatic or heteroaromatic group.

13. An electronic device comprising at least one compound as claimed in claim 1, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells and organic laser diodes.

* * * * *